US011312723B2

United States Patent
Ponda et al.

(10) Patent No.: US 11,312,723 B2
(45) Date of Patent: Apr. 26, 2022

(54) PYRANOPYRAZOLE AND PYRAZOLOPYRIDINE IMMUNOMODULATORS FOR TREATMENT OF AUTOIMMUNE DISEASES

(71) Applicant: The Rockefeller University, New York, NY (US)

(72) Inventors: Manish P. Ponda, New York, NY (US); Harold Selnick, Ambler, PA (US); Melissa Egbertson, Ambler, PA (US); Jan L. Breslow, Scarsdale, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 0 days.

(21) Appl. No.: 16/767,936

(22) PCT Filed: Nov. 28, 2018

(86) PCT No.: PCT/US2018/062702
§ 371 (c)(1),
(2) Date: May 28, 2020

(87) PCT Pub. No.: WO2019/108565
PCT Pub. Date: Jun. 6, 2019

(65) Prior Publication Data
US 2020/0369677 A1 Nov. 26, 2020

Related U.S. Application Data

(60) Provisional application No. 62/592,003, filed on Nov. 29, 2017.

(51) Int. Cl.
C07D 491/052 (2006.01)
C07D 471/04 (2006.01)
C07D 519/00 (2006.01)

(52) U.S. Cl.
CPC ....... C07D 491/052 (2013.01); C07D 471/04 (2013.01); C07D 519/00 (2013.01)

(58) Field of Classification Search
CPC .............................................. C07D 491/052
See application file for complete search history.

(56) References Cited

U.S. PATENT DOCUMENTS

| 8,835,444 | B2 | 9/2014 | Beattie et al. |
| 10,538,512 | B2 * | 1/2020 | Ponda .................. A61P 29/00 |
| 2007/0265256 | A1 | 11/2007 | Arrington et al. |
| 2017/0247375 | A1 | 8/2017 | Sattler et al. |

FOREIGN PATENT DOCUMENTS

WO 2017123518 A1 7/2017

OTHER PUBLICATIONS

Silverman, R.B. The Organic Chemistry of Drug Design and Drug Action 1992, Academic: New York, p. 19.*
STN-Chemical Database Registry entry # 1908794-86-4 for 3-amino-2,4,5,7-tetrahydro-2-(1H-indol-2-ylcarbonyl)-6H-Pyrazolo[3,4-c]pyridine-6-carboxylicacid, 1,1-dimethylethyl ester ED Entered STN: May 12, 2016.*
STN-Chemical Database Registry entry # 1908794-65-9 for 3-amino-2-[(2,3-dihydro-1H-inden-5-yl)carbonyl]-2,4,5,7-tetrahydro-6H-Pyrazolo[3,4-c]pyridine-6-carboxylic acid, 1,1-dimethylethyl ester ED Entered STN: May 12, 2016.*
STN-Chemical Database Registry entry # 1901986-31-9 for 3-amino-2-(1,3-benzodioxol-5-ylcarbonyl)-2,4,5,7-tetrahydro-6H-Pyrazolo[3,4-c]pyridine-6-carboxylic acid, 1,1-dimethylethyl ester ED Entered STN: May 2, 2016.*
Online: "http://web.archive.org/web/20070406205858/http://www.aurorafinechemicals.com/english/order.html" dated Apr. 6, 2007, accessed Feb. 19, 2015.*
Maas "Coagulation factor XII in thrombosis and inflammation" Blood Apr. 26, 2018 | vol. 131, No. 17 1903-1909.*
Mailer "An update on factor XII-driven vascular inflammation" BBA—Molecular Cell Research 1869 (2022), Available online Oct. 24, 2021, 119166.*
International Search Report and Written Opinion issued in PCT/US2018/62702, dated Jan. 22, 2019.
RN 802030-95-1, CAS Registry, Dec. 23, 2004.
RN 802301-49-1, CAS Registry, Dec. 25, 2004.

* cited by examiner

*Primary Examiner* — David K O'Dell
(74) *Attorney, Agent, or Firm* — Heslin Rothenberg Farley & Mesiti, P.C.

(57) ABSTRACT

Pyranoyrazoles and pyrazolopyridines of formula I or formula II are disclosed:

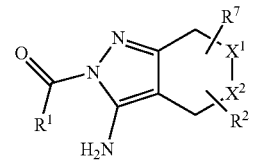

Formula I

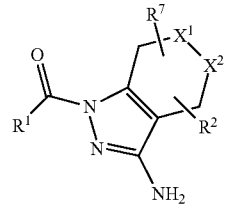

Formula II

These compounds inhibit Coagulation Factor XIIa in the presence of thrombin and other coagulation factors. They are useful to treat autoimmune diseases.

23 Claims, No Drawings

PYRANOPYRAZOLE AND PYRAZOLOPYRIDINE IMMUNOMODULATORS FOR TREATMENT OF AUTOIMMUNE DISEASES

CROSS-REFERENCE TO RELATED APPLICATIONS

This application is a U.S. National Phase filing under 35 U.S.C. § 371 of International Application PCT/US2018/62702, filed Nov. 28, 2018, and published as WO2019/108565 A1 on Jun. 6, 2019. PCT/US2018/62702 claims priority from U.S. provisional application 62/592,003, filed Nov. 29, 2017. Both are incorporated herein by reference in their entirety.

FIELD OF THE INVENTION

The invention relates to 3-amino-(7H)-4,5-dihydropyranopyrazoles and 3-amino-4,5,6,7-tetrahydro-5-methylpyrazolopyridines that inhibit Coagulation Factor XIIa. Those that selectively inhibit Coagulation Factor XIIa in the presence of thrombin and other coagulation factors possess particular advantages. These compounds are useful to treat autoimmune diseases.

BACKGROUND

Chemotaxis is directional movement in response to a specific chemical gradient. This cellular ability is necessary for immune homeostasis and the response to inflammation, among other critical biologic processes. Several chemokines have been identified along with their receptors, providing a molecular mechanism to orchestrate movement of distinct cell types in response to diverse stimuli. For example, chemokine receptor 7 (CCR7) and its ligands, CCL19 and CCL21, comprise a signaling axis required for chemotaxis of T-cells into and within lymphoid organs. CCR7-mediated chemotaxis is important in developing adaptive immunity, as well as maintaining tolerance and memory.

Chemokines are broadly grouped as homeostatic or inflammatory. For the latter, acutely increasing production may be sufficient to control a chemotactic response. For homeostatic chemokines, such as CCL19/21, signal modulation occurs by altering receptor density or effective ligand concentration. This is achieved either directly (e.g. increased receptor expression) or indirectly (e.g. atypical chemokine receptor scavenging of ligands). Indeed, for CCR7, exposure to serum promotes cell migration, and there is an enhanced chemotactic response of T-cells to CCL19/21 in the presence of serum.

PCT WO 2017/123518 discloses that a fragment from high molecular weight kininogen (HK) is a potent cofactor that accelerates CCL19-mediated chemotaxis. This HK fragment is necessary and sufficient for accelerated chemotaxis towards CCL19, and for serum or plasma, the activity is dependent on coagulation factor XIIa. High molecular weight kininogen (HK) is well-known for a role in inflammation, particularly as the parent molecule of the nonapeptide bradykinin.

Mechanistically, serum-accelerated chemotaxis is dependent on active coagulation factor XII (FXIIa), which is known to promote cleavage of HK. Pre-treatment of native murine lymphocytes with this HK-derived fragment peptide enhances in vivo homing of T-cells to lymph nodes. A circulating cofactor that is activated at sites of inflammation and injury to enhance lymphocyte chemotaxis represents a powerful mechanism coupling inflammation to adaptive immunity. In particular, small molecule therapeutic agents that can modulate FXIIa function—and thereby production of the HK fragment—without significantly affecting thrombin activation offer a means of safely regulating immune cell chemotaxis through humoral cofactors.

BRIEF SUMMARY OF THE INVENTION

In one aspect, the invention relates to compounds of formula I or formula II:

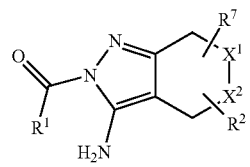

Formula I

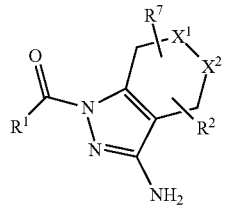

Formula II wherein
$R^1$ is an optionally substituted bicyclic ring system;
$R^2$ is chosen from hydrogen, halogen, hydroxy, amino, cyano, $(C_1-C_4)$alkyl, $(C_1-C_4)$alkoxy, $(C_1-C_4)$alkylamino, di$(C_1-C_4)$alkylamino, $(C_1-C_4)$acylamino, $(C_1-C_4)$fluoroalkyl, $(C_1-C_4)$fluoroalkoxy, and $(C_1-C_6)$oxaalkyl;
one of $X^1$ and $X^2$ is chosen from —O—, and —N(QR$^5$)—, and the other is —CR$^3$R$^4$—;
Q is chosen from a direct bond, —CH$_2$—, —C(=O)—, —C(=O)O—, —C(=O)NR$^6$—, —SO$_2$—, and —SO$_2$NR$^6$—;
$R^3$, $R^4$, $R^6$ and $R^7$ are independently chosen from hydrogen and $(C_1-C_6)$alkyl; and
$R^5$ is chosen from hydrogen, $(C_1-C_6)$alkyl, hydroxy$(C_2-C_6)$alkyl, a three- to seven-membered carbocycle, and a three- to seven-membered heterocycle.

In another aspect, the invention relates to a method for inhibiting Factor XIIa in a subject including, for example, administering to the subject an inhibitory amount of a compound of formula I or formula II described above.

In another aspect, the invention relates to a method for selectively inhibiting Factor XIIa in the presence of thrombin and kallikrein including, for example, contacting an inhibitory amount of a compound of formula I or formula II described above with Factor XIIa.

In another aspect, the invention relates to a method for treating inflammation in a patient including, for example, administering to the patient a therapeutically effective amount of a compound of formula I or formula II as described above.

In another aspect, the invention relates to a method for treating an immunological disorder in a patient including, for example, administering to the patient a therapeutically effective amount of a compound of formula I or formula II as described above.

In another aspect, the invention relates to a method for treating vasodilatation in a patient including, for example, administering to the patient a therapeutically effective amount of a compound of formula I or formula II as described above.

In another aspect, the invention relates to a method for treating thrombosis in a patient including, for example, administering to the patient a therapeutically effective amount of a compound of formula I or formula II as described above.

These and other objects, features, and advantages of the invention will become apparent from the following detailed description of the various aspects of the invention.

DETAILED DESCRIPTION OF THE INVENTION

In one aspect, the invention relates to compounds of formula I or formula II:

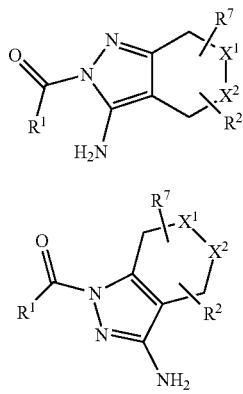

Formula I

Formula II

In the compounds of formula I or formula II, $R^1$ is an optionally substituted bicyclic ring system. Optional substituents include: halogen, hydroxy, amino, cyano, oxo, $(C_1-C_6)$aliphatic hydrocarbyl, $(C_1-C_4)$alkoxy, $(C_1-C_4)$alkylamino, di$(C_1-C_4)$alkylamino, $(C_1-C_4)$acylamino, $(C_1-C_4)$alkylsulfonyl, [$(C_1-C_4)$alkylsulfonyl]amino, $(C_1-C_4)$fluoroalkyl, $(C_1-C_4)$fluoroalkoxy, $(C_1-C_6)$oxaalkyl, aryl, and heteroaryl. In some embodiments, $R^1$ is a 6:6 or 6:5 bicycle. Examples of bicyclic ring systems that may be optionally substituted, include indole, isoindole, oxindole, tetrahydroindole, tetralin, indoline, isoindoline, tetrahydroquinoline, tetrahydroisoquinoline, 3,4-dihydro-1H-isochromene, 3,4-dihydro-2H-chromene, benzofuran, dihydrobenzofuran, tetrahydrobenzofuran, benzothiophene, tetrahydrobenzothiophene, indazole, tetrahydroindazole, 2,3-dihydro-1H-indene, naphthalene, tetrahydronaphthalene, naphthyridine, tetrahydronaphthyridine, and isochroman. For instance, in some embodiments, $R^1$ may be a nitrogenous bicycle such as an optionally substituted tetrahydroquinoline, indole, tetrahydronaphthyridine or tetrahydroindole.

In some embodiments, $R^1$ may be a bicyclic ring system optionally substituted with one or more of halogen, hydroxy, amino, cyano, oxo, $(C_1-C_8)$hydrocarbyl, $(C_1-C_8)$hydrocarbyloxy, $(C_1-C_4)$alkoxy, $(C_1-C_4)$alkylamino, di$(C_1-C_4)$alkylamino, $(C_1-C_4)$acylamino, $(C_1-C_4)$alkylsulfonyl, [$(C_1-C_4)$alkylsulfonyl]amino, $(C_1-C_4)$fluoroalkyl, $(C_1-C_4)$fluoroalkoxy, $(C_1-C_6)$oxaalkyl, $(C_3-C_6)$carbocycle, aryl, heteroaryl and $(C_1-C_4)$alkenyl. In certain embodiments, the $(C_1-C_8)$hydrocarbyl substituent may be chosen from straight chain $(C_1-C_8)$alkyl, branched $(C_1-C_8)$alkyl, $(C_3-C_6)$cycloalkyl, and $(C_3-C_6)$cycloalkyl$(C_1-C_3)$alkyl. In some embodiments, $R^1$ is optionally substituted with one to three substituents chosen from halogen, hydroxy, amino, cyano, oxo, $(C_1-C_6)$aliphatic hydrocarbyl, $C_4$)alkoxy, $(C_1-C_4)$alkylamino, di$(C_1-C_4)$alkylamino, $(C_1-C_4)$acylamino, $(C_1-C_4)$alkylsulfonyl, [$(C_1-C_4)$alkylsulfonyl]amino, $(C_1-C_4)$fluoroalkyl, $(C_1-C_4)$fluoroalkoxy, $(C_1-C_6)$oxaalkyl, aryl, and heteroaryl. In some embodiments, $R^1$ is optionally substituted with one or more of halogen, $(C_1-C_6)$aliphatic hydrocarbyl, $(C_1-C_4)$fluoroalkyl, $(C_1-C_4)$alkoxy, $(C_1-C_4)$acylamino, $(C_1-C_4)$alkylsulfonyl, phenyl, and pyridinyl, and, in particular, with one or two fluoro, chloro, bromo, methyl, ethyl, propyl, trifluoromethyl, methoxy, methanesulfonyl, acetamido, phenyl, and pyridinyl.

An exemplary embodiment of the optionally substituted bicyclic ring system includes a compound of formula I or formula II, wherein $R^1$ may be one of

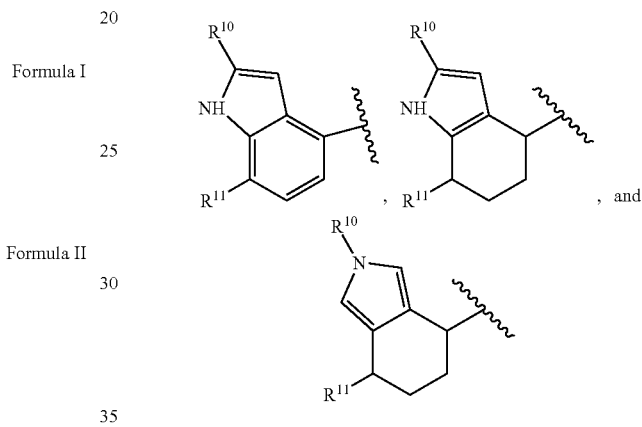

, and wherein
$R^{10}$ is chosen from H, halogen, $(C_1-C_4)$alkyl, and $(C_3-C_6)$cycloalkyl;
$R^{11}$ is chosen from H and methoxy; and
$R^{12}$ is chosen from H and $(C_1-C_4)$alkyl.

Another exemplary embodiment of the optionally substituted bicyclic ring system includes a compound of formula I or formula II, wherein $R^1$ may be:

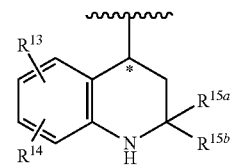

wherein
$R^{13}$ and $R^{14}$ are chosen independently from H, halogen, $(C_1-C_4)$alkyl, fluoro$(C_1-C_4)$alkyl, $(C_1-C_4)$alkoxy, $(C_1-C_4)$acylamino $(C_1-C_4)$alkylsulfonyl, phenyl, and pyridinyl; and
$R^{15a}$ and $R^{15b}$ are chosen independently from —H, and —$(C_1-C_4)$alkyl or, taken together, $R^{15a}$ and $R^{15b}$ are oxo.

In these embodiments, the carbon marked with an asterisk may be racemic or >90% e.e. in the (R) absolute configuration or >90% e.e. in the (S) absolute configuration.

In some embodiments, $R^1$ may be an optionally substituted naphthyridine, particularly a tetrahydro-1,8-naphthyridine or tetrahydro-1,6-naphthyridine In one subgenus, the compound of formula I or formula II is a 3-amino-(7H)-4,5-dihydropyranopyrazole:

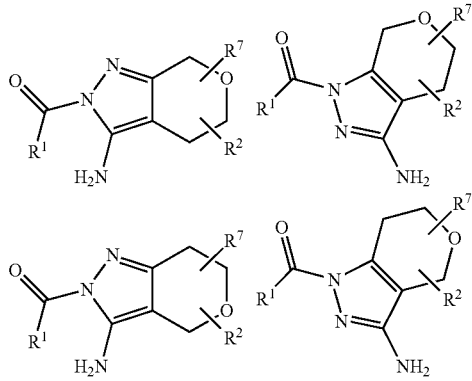

In another subgenus, the compound of formula I or formula II is a 3-amino-4,5,6,7-tetrahydro-5-methylpyrazolopyridine:

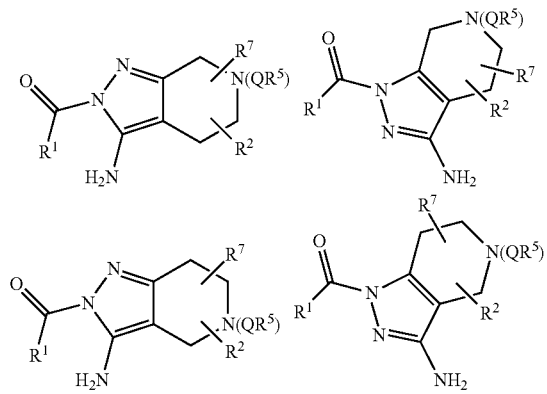

In some embodiments, Q is chosen from a direct bond, —CH$_2$—, —C(=O)—, —C(=O)O—, —C(=O)NR$^6$—, —SO$_2$—, and —SO$_2$NR$^6$—; and R$^6$ is hydrogen or methyl.

In some embodiments, R$^2$ and R$^7$ are chosen independently from hydrogen and methyl. In some R$^2$ and R$^7$ are both hydrogen; in others R$^2$ is hydrogen and R$^7$ is methyl. As will be clear from the examples, R$^2$ and R$^7$ may be attached at any carbon of the six-membered ring—including both at the same carbon.

In some embodiments R$^3$ and R$^4$ are both hydrogen.

In some embodiments, R$^5$ is chosen from H, (C$_1$-C$_4$)alkyl, (C$_3$-C$_6$)cycloalkyl, hydroxy(C$_2$-C$_6$)alkyl, fluoromethyl, difluoromethyl, phenyl, pyridinyl, oxetanyl, tetrahydrofuranyl, and tetrahydropyranyl.

Of the two main genera, formula I (the 2-acyl-3-amines) and formula II (the 1-acyl-3-amines), the compounds of formula I are, as a class, generally more selective and potent than their 1-acyl-3-amine congeners. Within the class of 2-acyl-3-amines, preferred compounds include those in which R$^3$ and R$^4$ are both hydrogen; Q is chosen from a direct bond, —CH$_2$—, —C(=O)—, —C(=O)O—, —C(=O)NR$^6$—, —SO$_2$—, and —SO$_2$NR$^6$—; R$^6$ is hydrogen or methyl and R$^5$ is chosen from H, (C$_1$-C$_4$)alkyl, (C$_3$-C$_6$)cycloalkyl, fluoromethyl, difluoromethyl, phenyl, pyridinyl, oxetanyl, tetrahydrofuranyl, and tetrahydropyranyl.

Throughout this specification the terms and substituents retain their definitions.

C$_1$ to C$_{20}$ hydrocarbyl (or any subset thereof, e.g. (C$_1$-C$_6$) hydrocarbyl), includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cy-propyl, cy-butyl, cy-pentyl, norbornyl and the like.

Unless otherwise specified, the term "carbocycle" is intended to include ring systems in which the ring atoms are all carbon but of any oxidation state. Thus (C$_3$-C$_7$) carbocycle refers to both non-aromatic and aromatic systems, including such systems as cyclopropane, benzene and cyclohexene; carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, naphthyridine, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, naphthyridinyl, tetrahydrofuryl, tetrahydropyranyl, thienyl (also historically called thiophenyl), benzothienyl, thiamorpholinyl, oxadiazolyl, triazolyl and tetrahydroquinolinyl.

Hydrocarbyloxy refers to groups of from 1 to 20 carbon atoms, preferably 1 to 10 carbon atoms, more preferably 1 to 6 carbon atoms attached to the parent structure through an oxygen. Alkoxy is a subset of hydrocarbyloxy and includes groups of a straight or branched configuration. Examples include methoxy, ethoxy, propoxy, isopropoxy and the like. Lower-alkoxy refers to groups containing one to four carbons. The term "halogen" means fluorine, chlorine, bromine or iodine atoms.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Loweracyl refers to groups containing one to four carbons.

The double bonded oxygen, when referred to as a substituent itself is called "oxo". It will be appreciated by persons of skill in the art that, because oxo is a divalent radical, there are circumstances in which it will not be appropriate as a substituent (e.g. on phenyl) and other circumstances, such as examples 43 and 44 below, where it can be accommodated.

As used herein, the term "optionally substituted" may be used interchangeably with the phrase "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, hydrocarbyl, acyl, alkoxyalkyl, hydroxy lower alkyl, carbonyl, phenyl, heteroaryl, benzenesulfonyl, hydroxy, hydrocarbyloxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

In some embodiments, the substituent R$^1$ may be an optionally substituted 6,5- 5,6- or 6,6 bicycle AB, in which ring A is non-aromatic and the carbon at its point of attachment is of a specific absolute configuration as shown in the depiction:

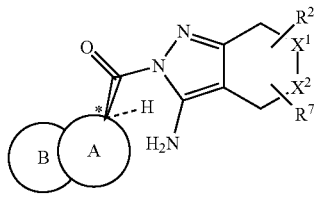

The configuration at the chiral center * is such that the ring A is in the plane of the paper and the substituents H and carbonyl are disposed above and below that plane. (As would be understood by the person of skill in the art, the nomenclature (R) or (S) may vary according to the hierarchy of the atoms adjacent to the chiral carbon in the ring.)

The graphic representations of racemic, ambiscalemic and scalemic or enantiomerically pure compounds used herein are taken from Maehr *J. Chem. Ed.* 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. For nomenclature in the text corresponding to wedge outlines and dotted or broken lines, we define R* and S* as indicating single enantiomers of uncertain absolute configuration. Thus, for example, in Examples 18 and 19 below, the syntheses of (S*)-(3-amino-6-(methylsulfonyl)-4,5,6,7-tetrahydropyrazolo[3,4-c]pyridin-2-yl)(6-fluoro-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(6-fluoro-1,2,3,4-tetrahydroquinolin-4-yl)methanone are described. The (R*) and (S*) are intended to indicate that the product is a single enantiomer possessing the characteristics described (e.g. NMR, HPLC retention time, etc.), in which each of the chiral centers is believed on the basis of circumstantial evidence to be of the configuration shown, but the absolute configuration has not been confirmed. Thus, the depiction:

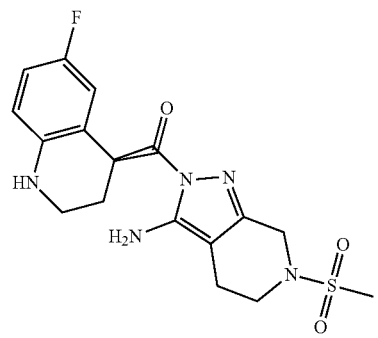 [SMILES: CS(=O)(=O)N1CCc2c(nn(C(=O)[C@H]3CCNc4ccc(F)cc43)c2N)C1]

means that the product is a single one of the two following isomers, probably the first:

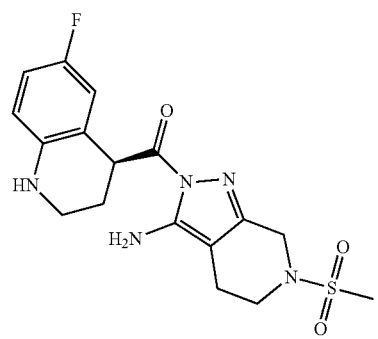

-continued

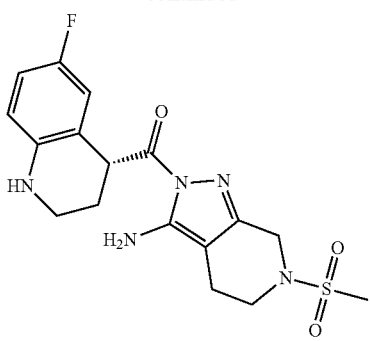

When a compound possesses a center of asymmetry, its depiction in the claims of this patent with simple lines,

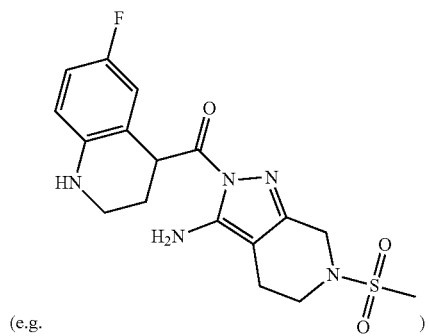 [SMILES: CS(=O)(=O)N1CCc2c(nn(C(=O)C3CCNc4ccc(F)cc43)c2N)C1]

(e.g.

is intended to indicate that the structure includes any and all isomers without regard to enantiomeric purity. When its depiction in the claims of this patent includes wedges, dashed lines etc.

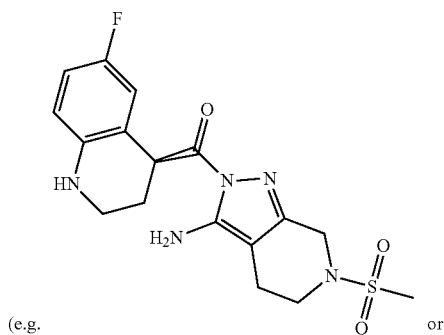

(e.g.                                             or

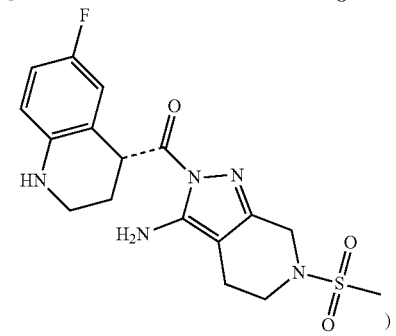

)

it is intended to indicate that the structure encompasses isomers of that relative or absolute configuration of at least 80% ee, preferably >90% ee.

Substituents Rn are generally defined when introduced and retain that definition throughout the specification and claims.

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in Protecting Group Chemistry, 1st Ed., Oxford University Press, 2000; and in March's Advanced Organic chemistry: Reactions, Mechanisms, and Structure, 5th Ed., Wiley-Interscience Publication, 2001.

In general, compounds of formula I or formula II can be prepared as shown in Schemes I-XVI. The appropriately substituted starting materials and intermediates used in the preparation of compounds of the invention are either commercially available or readily prepared by methods known in the literature to those skilled in the art.

All solvents used were commercially available and were used without further purification. Reactions were typically run using anhydrous solvents under an inert atmosphere of nitrogen. Proton spectra were recorded at 300 or 400 MHz for proton on a Bruker Mercury Plus 400 NMR Spectrometer equipped with a Bruker 400 BBO probe. All deuterated solvents contained typically 0.03% to 0.05% v/v tetramethylsilane, which was used as the reference signal (set at d 0.00 for both 1H and 13C).

LCMS analyses were performed on a SHIMADZU LCMS consisting of an UFLC 20-AD and LCMS 2020 MS detector. The column used was a Shim-pack XR-ODS, 2.2 µm, 3.0×50 mm. A linear gradient was applied, starting at 95% A (A: 0.05% TFA in water) and ending at 100% B (B: 0.05% TFA in MeCN) over 2.2 min with a total run time of 3.6 min. The column temperature was at 40° C. with the flow rate of 1.0 mL/min. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 0.7 s.

HPLC analyses were performed on a SHIMADZU UFLC with two LC20 AD pump and a SPD-M20A Photodiiode Array Detector. The column used was an XBridge C18, 3.5 µm, 4 60×100 mm. A linear gradient was applied, starting at 90% A (A: 0.05% TFA in water) and ending at 95% B (B: 0.05% TFA in MeCN) over 10 min with a total run time of 15 min. The column temperature was at 40° C. with the flow rate of 1.5 mL/min. The Diode Array Detector was scanned from 200-400 nm.

Thin layer chromatography (TLC) was performed on Alugram® (Silica gel 60 F254) from Mancherey-Nagel and UV was typically used to visualize the spots. Additional visualization methods were also employed in some cases. In these cases the TLC plate was developed with iodine (generated by adding approximately 1 g of 12 to 10 g silica gel and thoroughly mixing), ninhydrin (available commercially from Aldrich), or Magic Stain (generated by thoroughly mixing 25 g $(NH4)_6Mo_7O_{24} \cdot 4H2O$, 5 g $(NH4)_2Ce(IV)(NO_3)_6$ in 450 mL water and 50 mL concentrated H2SO4) to visualize the compound. Flash chromatography was performed using 40-63 µm (230-400 mesh) silica gel from Silicycle following analogous techniques to those disclosed in Still, W. C.; Kahn, M.; and Mitra, M. Journal of Organic Chemistry, 1978, 43, 2923. Typical solvents used for flash chromatography or thin layer chromatography were mixtures of chloroform/methanol, dichloromethane/methanol, ethyl acetate/methanol and hexanes/ethyl acetate.

Intermediate 1. tert-butyl 3-amino-4,5,6,7-tetrahydro-2H-pyrazolo[4,3-c]pyridin-5-carboxylate

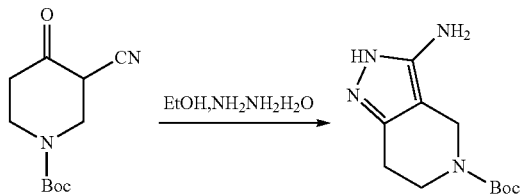 [SMILES: CC(C)(C)OC(=O)N1CCC(=O)C(C#N)C1 ; CC(C)(C)OC(=O)N1CCc2n[nH]c(N)c2C1]

Into a 250-mL round-bottom flask, was placed tert-butyl 3-cyano-4-oxopiperidine-1-carboxylate (5 g, 22.30 mmol, 1.00 equiv), NH2NH2H2O (11.1 g, 223 mmol, 10.00 equiv), EtOH (100 mL). The resulting solution was stirred overnight at 25° C. The resulting mixture was concentrated under vacuum. The residue was applied onto a silica gel column with chloroform/methanol (95/5). This resulted in 4.9 g (93%) of tert-butyl 3-amino-4,5,6,7-tetrahydro-2H-pyrazolo[4,3-c]pyridin-5-carboxylate as a white solid. MS (ES, m/z) [M+H]: 239.

Intermediate 2. 5-methyl-4,5,6,7-tetrahydro-2H-pyrazolo[4,3-c]pyridin-3-amine

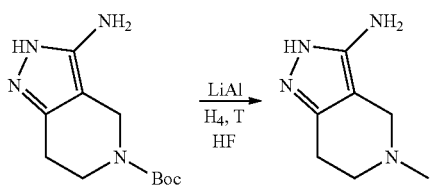 [SMILES: CC(C)(C)OC(=O)N1CCc2n[nH]c(N)c2C1 ; "LiAl" ; CN1CCc2n[nH]c(N)c2C1]

Into a 100-mL round-bottom flask purged and maintained with an inert atmosphere of nitrogen, was placed tert-butyl 3-amino-4,5,6,7-tetrahydro-2H-pyrazolo[4,3-c]pyridin-5-carboxylate (700 mg, 2.94 mmol, 1.00 equiv), tetrahydrofuran (15 mL), LiAlH$_4$ (334 mg, 8.80 mmol, 3.00 equiv) was added at 0° C. The resulting solution was stirred overnight at 60° C. The reaction was then quenched by the addition of water (2 ml) and NaOH (1M/1, 4 ml) and water (2 ml). The mixture was stirred for 30 min. The solids were filtered out. The crude product was purified by Prep-HPLC with the following conditions: Column, Atlantis Prep T3 OBD Column, 19×250 mm 10 u; mobile phase, water (0.1% FA) and ACN (0 up to 30.0% in 15 min); Detector, UV 254 nm. This resulted in 90 mg (20%) of 5-methyl-4,5,6,7-tetrahydro-2H-pyrazolo[4,3-c]pyridin-3-amine as a yellow solid. MS (ES, m/z) [M+H]: 153.

Intermediate 3. HCl salt of 4,5,6,7-tetrahydro-2H-pyrazolo[4,3-c]pyridin-3-amine

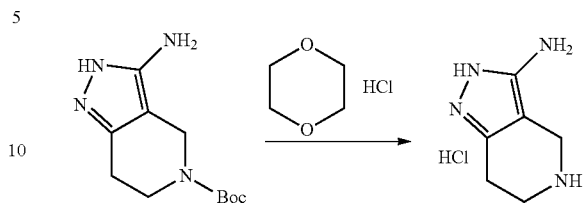

Into a 100-mL 3-necked round-bottom flask, was placed tert-butyl 3-amino-4,5,6,7-tetrahydro-2H-pyrazolo[4,3-c]pyridin-5-carboxylate (3 g, 12.59 mmol, 1.00 equiv). This was followed by the addition of HCl in 1,4-dioxane (10 mL) dropwise with stirring at 0° C. The resulting solution was stirred for 8 h at 25° C. The resulting mixture was concentrated under vacuum. This resulted in 1.5 g (68%) of HCl salt of 4,5,6,7-tetrahydro-2H-pyrazolo[4,3-c]pyridin-3-amine hydrochloride as a yellow solid. MS (ES, m/z) [M+H]$^+$: 139.

Intermediate 4. benzyl 3-amino-4,5,6,7-tetrahydro-2H-pyrazolo[4,3-c]pyridin-5-carboxylate

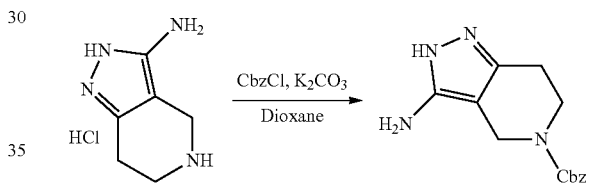

Into a 100-mL round-bottom flask, was placed 4,5,6,7-tetrahydro-2H-pyrazolo[4,3-c]pyridin-3-amine hydrochloride (200 mg, 1.15 mmol, 1.00 equiv), potassium carbonate (476 mg, 3.44 mmol, 3.00 equiv), water (2 mL), 1,4-dioxane (10 mL). This was followed by the addition of Cbz-Cl (165 mg, 0.97 mmol, 0.90 equiv) dropwise with stirring at 0° C. The resulting solution was stirred overnight at 25° C. The resulting solution was diluted with H$_2$O (10 mL). The resulting solution was extracted with dichloromethane (80 mL×3) and the organic layers combined and concentrated under vacuum. The residue was applied onto a silica gel column with dichloromethane/methanol (10/1). This resulted in 150 mg (48%) of benzyl 3-amino-4,5,6,7-tetrahydro-2H-pyrazolo[4,3-c]pyridin-5-carboxylate as yellow oil. MS (ES, m/z) [M+H]$^+$: 273.

Intermediate 5. 6-benzyl-4,5,6,7-tetrahydro-2H-pyrazolo[3,4-c]pyridin-3-amine

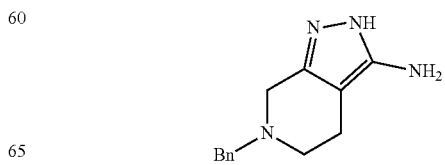

Step 1. Ethyl 2-(benzyl(3-cyanopropyl)amino)acetate

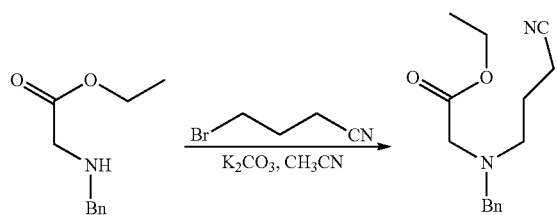 [SMILES: CCOC(=O)CNCc1ccccc1 ; N#CCCCBr ; CCOC(=O)CN(CCCC#N)Cc1ccccc1]

Into a 500-mL round-bottom flask, was placed CH₃CN (300 mL), ethyl 2-(benzylamino)acetate (32 g, 167.40 mmol, 1.00 equiv), potassium carbonate (64.4 g, 465.96 mmol, 3.00 equiv), 4-bromobutanenitrile (27.4 g, 185.13 mmol, 1.20 equiv). The resulting solution was stirred overnight at 80° C. After cooled to room temperature, the solids were filtered out. The filtrate was concentrated under vacuum. The residue was applied onto a silica gel column with ethyl acetate/petroleum ether (0-100%). This resulted in 40 g (97%) of ethyl2-[benzyl(3-cyanopropyl)amino]acetate as yellow oil. MS (ES, m/z) [M+H]⁺: 261.

Step 2. 1-benzyl-3-oxopiperidine-4-carbonitrile

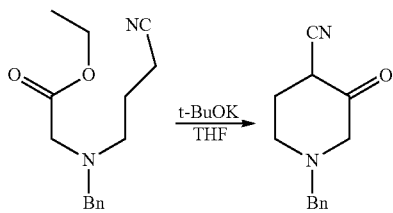 [SMILES: "t-BuOK" ; CCOC(=O)CN(CCCC#N)Cc1ccccc1 ; N#CC1CCN(Cc2ccccc2)CC1=O ; "THF"]

Into a 500-mL 3-necked round-bottom flask purged and maintained with an inert atmosphere of nitrogen, was placed ethyl 2-[benzyl(3-cyanopropyl)amino]acetate (20 g, 76.83 mmol, 1.00 equiv), tetrahydrofuran (300 mL). This was followed by the addition of t-BuOK (12.9 g, 114.96 mmol, 1.50 equiv) in several batches at 0° C. The resulting solution was stirred overnight at room temperature. The resulting solution was diluted with DCM:MeOH (4:1, 1000 mL). The resulting mixture was washed with brine (1000 mL×3). The organic phase was dried over anhydrous sodium sulfate and concentrated under vacuum. This resulted in 13.6 g (83%) of 1-benzyl-3-oxopiperidine-4-carbonitrile as red oil. MS (ES, m/z) [M+H]⁺: 215.

Step 3. 6-benzyl-4,5,6,7-tetrahydro-2H-pyrazolo[3,4-c]pyridin-3-amine

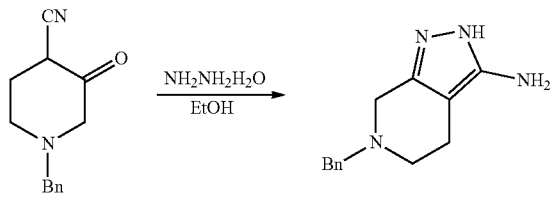

Into a 250-mL round-bottom flask, was placed 1-benzyl-3-oxopiperidine-4-carbonitrile (13.6 g, 63.47 mmol, 1.00 equiv), ethanol (100 mL), NH₂NH₂H₂O (14 mL). The resulting solution was stirred overnight at room temperature. The resulting mixture was concentrated under vacuum. The residue was applied onto a silica gel column with methanol/dichloromethane (0-10%). This resulted in 8.5 g (59%) of 6-benzyl-4,5,6,7-tetrahydro-2H-pyrazolo[4,3-c]pyridin-3-amine as yellow oil. MS (ES, m/z) [M+H]⁺: 229.

Intermediate 6

Step 1. 4,5,6,7-tetrahydro-2H-pyrazolo[3,4-c]pyridin-3-amine

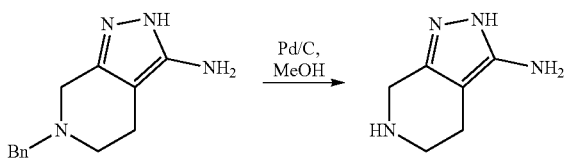 [SMILES: Nc1[nH]nc2c1CCN(Cc1ccccc1)C2 ; "Pd/C,MeOH" ; Nc1[nH]nc2c1CCNC2]

Into a 250-mL round-bottom flask, was placed 6-benzyl-4,5,6,7-tetrahydro-2H-pyrazolo[3,4-c]pyridin-3-amine (15 g, 65.71 mmol, 1.00 equiv), methanol (100 mL), palladium carbon (10%, 10 g). To the above hydrogen was introduced in. The resulting solution was stirred for 38 h at room temperature. The solids were filtered out. The filtrate was concentrated under vacuum. This resulted in 8.2 g (90%) of 4,5,6,7-tetrahydro-2H-pyrazolo[4,3-c]pyridin-3-amine as a yellow solid. MS (ES, m/z) [M+H]⁺: 139

Intermediate 7. tert-butyl 3-amino-4,5,6,7-tetrahydro-2H-pyrazolo[3,4-c]pyridin-6-carboxylate

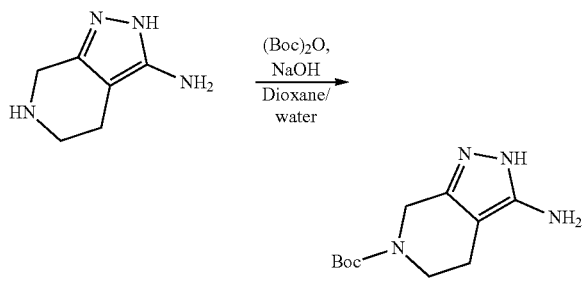

Into a 50-mL round-bottom flask, was placed 4,5,6,7-tetrahydro-2H-pyrazolo[3,4-c]pyridin-3-amine (350 mg, 2.53 mmol, 1.00 equiv), dioxane (8 mL), a solution of sodium hydroxide (203 mg, 5.08 mmol, 2.00 equiv) in water (2 mL). This was followed by the addition of a solution of (Boc)₂O (442 mg, 2.03 mmol, 0.80 equiv) in dioxane (3 mL) dropwise with stirring at 0° C. The resulting solution was stirred for 3 h at room temperature. The resulting mixture was concentrated under vacuum. The residue was purified by preparative TLC (EA:PE=1:1). This resulted in 410 mg (68%) of tert-butyl 3-amino-4,5,6,7-tetrahydro-2H-pyrazolo[3,4-c]pyridin-6-carboxylate as a yellow solid. MS (ES, m/z) [M+H]⁺: 239.

Intermediate 8. 6-methyl-4,5,6,7-tetrahydro-2H-pyrazolo[3,4-c]pyridin-3-amine

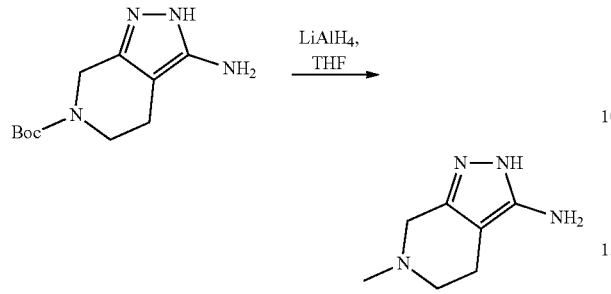

Into a 100-mL 3-necked round-bottom flask purged and maintained with an inert atmosphere of nitrogen, was placed tert-butyl 3-amino-4,5,6,7-tetrahydro-2H-pyrazolo[3,4-c]pyridine-6-carboxylate (320 mg, 1.34 mmol, 1.00 equiv), tetrahydrofuran (40 mL). This was followed by the addition of LiAlH$_4$ (102 mg, 2.69 mmol, 2.00 equiv) in several batches at 0° C. The resulting solution was stirred overnight at 70° C. The resulting mixture was concentrated under vacuum. The residue was purified by preparative TLC (DCM:MeOH=10:1). This resulted in 50 mg (24%) of 6-methyl-4,5,6,7-tetrahydro-2H-pyrazolo[3,4-c]pyridin-3-amine as a white solid. MS (ES, m/z) [M+H]$^+$: 153.

Intermediate 9. 6-(methylsulfonyl)-4,5,6,7-tetrahydro-2H-pyrazolo[3,4-c]pyridin-3-amine

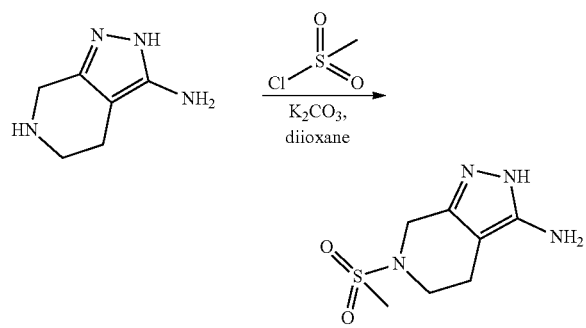

Into a 250-mL round-bottom flask, was placed 4,5,6,7-tetrahydro-2H-pyrazolo[3,4-c]pyridin-3-amine (5 g, 36.19 mmol, 1.00 equiv), 1,4-dioxane (40 mL), a solution of potassium carbonate (10 g, 72.35 mmol, 2.00 equiv) in water (10 mL). This was followed by the addition of a solution of methanesulfonyl chloride (2 g, 17.46 mmol, 0.50 equiv) in dioxane (5 mL) dropwise with stirring at 0° C. The resulting solution was stirred for 2 h at room temperature. The resulting mixture was concentrated under vacuum. The residue was applied onto a silica gel column with methanol/dichloromethane (0-10%). This resulted in 3.2 g (41%) of 6-methanesulfonyl-4,5,6,7-tetrahydro-2H-pyrazolo[3,4-c]pyridin-3-amine as a white solid. MS (ES, m/z) [M+H]$^+$: 217.

Example 1: tert-butyl 3-amino-2-[(2-methyl-1H-indol-4-yl)carbonyl]-4,5,6,7-tetrahydro-2H-pyrazolo[4,3-c]pyridin-5-carboxylate

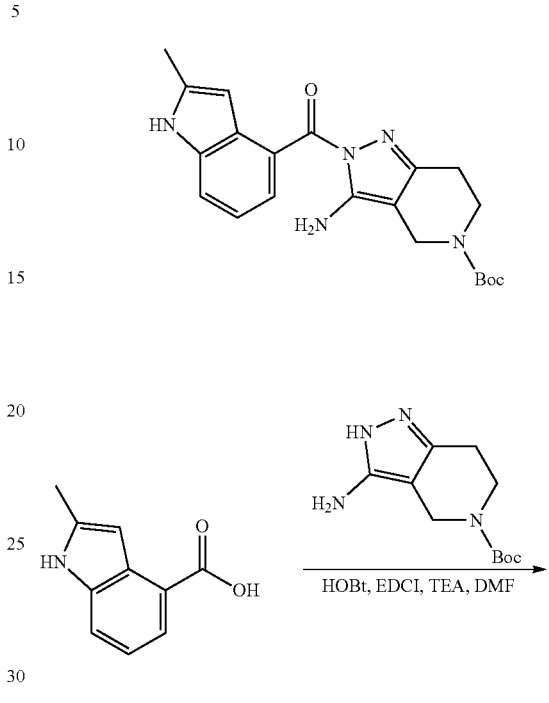

Into a 50-mL round-bottom flask, was placed 2-methyl-1H-indole-4-carboxylic acid (52 mg, 0.30 mmol, 1.00 equiv), tert-butyl 3-amino-4,5,6,7-tetrahydro-2H-pyrazolo[4,3-c]pyridine-5-carboxylate (85 mg, 0.36 mmol, 1.20 equiv), HOBt (61 mg, 0.45 mmol, 1.50 equiv), EDCI (86 mg, 0.45 mmol, 1.50 equiv), N,N-dimethylformamide (3 mL), TEA (194 mg, 1.92 mmol, 5.00 equiv). The resulting solution was stirred overnight at 25° C. The reaction mixture was diluted with DCM (80 mL), washed with H$_2$O (50 mL×3) and brine (50 mL×3) and dried with Na$_2$SO$_4$. After filtration, the filtrate was concentrated under reduced pressure. The crude product was purified by Prep-HPLC with the following conditions: Column, XSelect CSH Prep C18 OBD Column, 5 um, 19×150 mm; mobile phase, water (0.1% FA) and ACN (30.0% ACN up to 49.0% in 9 min); Detector, UV 254 nm. The collected fraction was lyophilized to give 1.4 mg (2%) of tert-butyl 3-amino-2-[(2-methyl-1H-indol-4-yl)carbonyl]-4,5,6,7-tetrahydro-2H-pyrazolo[4,3-c]pyridin-5-carboxylate as an off-white solid. MS (ES, m/z) [M+H]$^+$: 396; (300 MHz, DMSO-d$_6$, ppm): δ 11.22 (s, 1H), 7.57 (d, J=7.5 Hz, 1H), 7.48 (d, J=7.8 Hz, 1H), 7.09-7.04 (m, 1H), 6.65 (s, 2H), 6.29 (s, 1H), 4.27 (s, 2H), 3.58-2.54 (m, 2H), 2.49-2.45 (m, 2H), 2.41 (s, 3H), 1.44 (s, 9H).

Example 2: (3-amino-4,5,6,7-tetrahydropyrazolo[4,3-c]pyridin-2-yl)(2-methyl-1H-indol-4-yl)methanone

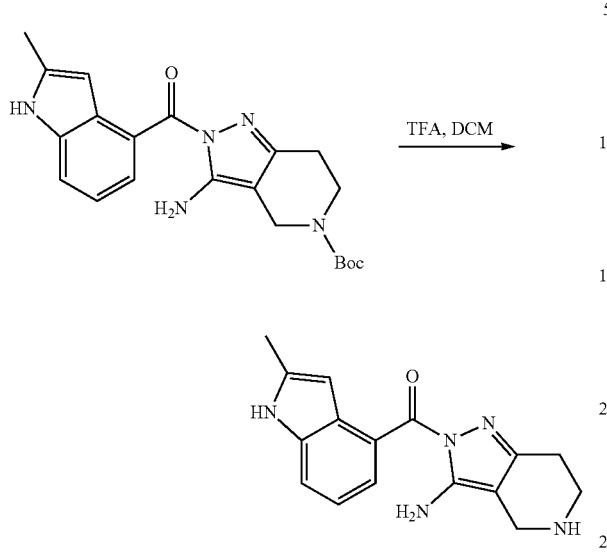

Into a 50-mL round-bottom flask, was placed tert-butyl 3-amino-2-[(2-methyl-1H-indol-4-yl)carbonyl]-4,5,6,7-tetrahydro-2H-pyrazolo[4,3-c]pyridine-5-carboxylate (70 mg, 0.18 mmol, 1.00 equiv), dichloromethane (8 mL), TFA (2 mL). The resulting solution was stirred for 20 min at 25° C. The resulting solution was diluted with 2 mL of H$_2$O. The pH value of the solution was adjusted to 8 with sodium bicarbonate (1 mol/L). The solution was extracted with ethyl acetate, washed with water and brine and concentrated. The crude product was purified by Prep-HPLC with the following conditions: Column, XBridge C18 OBD Prep Column, 5 μm, 19 mm×250 mm; mobile phase, water (0.1% FA) and ACN (38.0% ACN up to 58.0% in 7 min); Detector, UV/mass 254& 220 nm. The collected fraction was lyophilized to give 1.8 mg (3%) of (3-amino-4,5,6,7-tetrahydropyrazolo[4,3-c]pyridin-2-yl)(2-methyl-1H-indol-4-yl)methanone as a pink solid. MS (ES, m/z) [M+H]$^+$: 296; (400 MHz, DMSO-d$_6$, ppm): δ 11.30 (s, 1H), 8.25-8.23 (m, 1H), 7.56-7.46 (m, 2H), 7.08-7.04 (m, 1H), 6.53 (d, J=12.0 Hz, 2H), 6.27 (s, 1H), 3.67-3.64 (m, 2H), 3.09-2.96 (m, 2H), 2.51-2.50 (m, 2H), 2.40 (s, 3H).

Example 3: (3-amino-5-methyl-4,5,6,7-tetrahydropyrazolo[4,3-c]pyridin-2-yl)(2-chloro-4,5,6,7-tetrahydro-1H-indol-4-yl)methanone

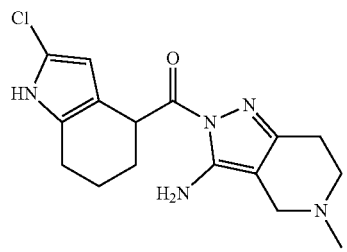 [SMILES: CN1CCc2nn(C(=O)C3CCCc4[nH]c(Cl)cc43)c(N)c2C1]

Step 1. 1-[(4-methylbenzene)sulfonyl]-4,5,6,7-tetrahydro-1H-indol-4-one

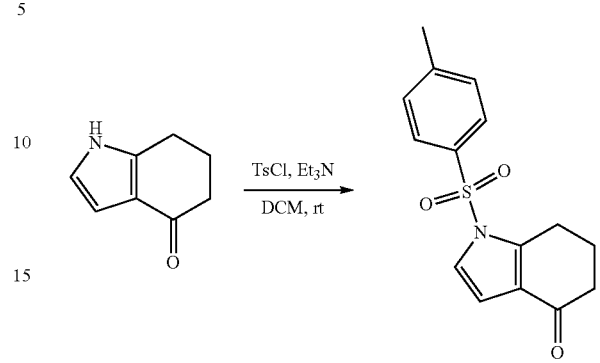

Into a 5000-mL round-bottom flask, was placed a solution of 4,5,6,7-tetrahydro-1H-indol-4-one (200 g, 1.48 mol, 1.00 equiv) in dichloromethane (3000 mL), 4-methylbenzene-1-sulfonyl chloride (290 g, 1.52 mol, 1.03 equiv), TEA (600 mL), 4-dimethylaminopyridine (18 g, 147.34 mmol, 0.10 equiv). The resulting solution was stirred for 16 h at 25° C. The reaction was then quenched by the addition of water. The resulting solution was extracted with ethyl acetate (4000 ml). The organic layer was washed with brine (1000 mL×4) and concentrated under vacuum. The isolated solid was collected and purified by crystallization with PE/EA. This resulted in 130 g (30%) of 1-[(4-methylbenzene)sulfonyl]-4,5,6,7-tetrahydro-1H-indol-4-one as a white solid. MS [M+H]$^+$ (ES, m/z): 290.

Step 2. 1-[(4-methylbenzene)sulfonyl]-4-[(trimethylsilyl)oxy]-4,5,6,7-tetrahydro-1H-indole-4-carbonitrile

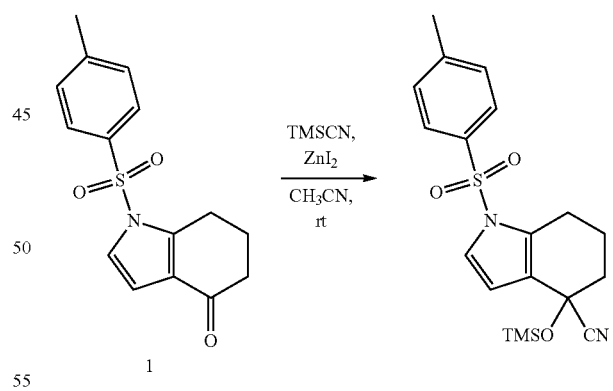

Into a 2000-mL round-bottom flask purged and maintained with an inert atmosphere of nitrogen, was placed a solution of 1-[(4-methylbenzene)sulfonyl]-4,5,6,7-tetrahydro-1H-indol-4-one (130 g, 449.28 mmol, 1.00 equiv) in CH$_3$CN (1000 mL), TMSCN (120 mL), ZnI$_2$ (13 g, 40.72 mmol, 0.09 equiv). The resulting solution was stirred for 3 h at 25° C. The reaction was then quenched by the addition of water.

The resulting solution was extracted with ethyl acetate (4000 mL). The resulting mixture was washed with brine (1000 mL×4). The mixture was dried over anhydrous sodium sulfate. The solids were filtered out. The resulting mixture was concentrated. This resulted in 170 g of 1-[(4-methylbenzene)sulfonyl]-4-[(trimethylsilyl)oxy]-4,5,6,7-tetrahydro-1H-indole-4-carbonitrile as yellow oil. MS [M+H]+ (ES, m/z): 389.

Step 3. 1-[(4-methylbenzene)sulfonyl]-6,7-dihydro-1H-indole-4-carbonitrile

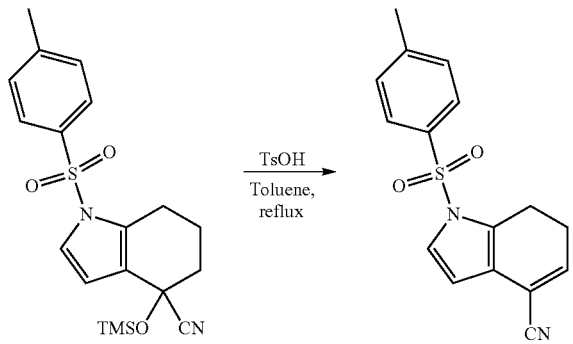

Into a 3000-mL round-bottom flask, was placed a solution of 1-[(4-methylbenzene)sulfonyl]-4-[(trimethylsilyl)oxy]-4,5,6,7-tetrahydro-1H-indole-4-carbonitrile (170 g, crude) in toluene (2000 mL), 4-methylbenzene-1-sulfonic acid (5 g). The resulting solution was stirred for 5 h at 110° C. The reaction was then quenched by the addition of water. The resulting solution was extracted with ethyl acetate (4000 mL). The resulting mixture was washed with brine (1000 mL×4). The mixture was dried over anhydrous sodium sulfate. The solids were filtered out. The resulting mixture was concentrated. The isolated solid was collected and purified by crystallization with PE/EA. This resulted in 110 g (crude) of 1-[(4-methylbenzene)sulfonyl]-6,7-dihydro-1H-indole-4-carbonitrile as a yellow solid. MS [M+H]+ (ES, m/z):

Step 4. 1-[(4-methylbenzene)sulfonyl]-4,5,6,7-tetrahydro-1H-indole-4-carbonitrile

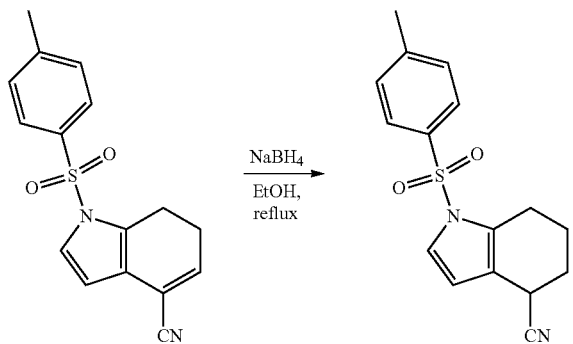 [SMILES: Cc1ccc(S(=O)(=O)n2ccc3c2CCC=C3C#N)cc1 ; "NaBH4" ; Cc1ccc(S(=O)(=O)n2ccc3c2CCCC3C#N)cc1]

Into a 2 L round-bottom flask, was placed a solution of 1-[(4-methylbenzene)sulfonyl]-6,7-dihydro-1H-indole-4-carbonitrile (110 g, crude) in ethanol (1000 mL), sodium borohydride (45 g, 1.22 mol). The resulting solution was stirred for 6 h at 80° C. The reaction was then quenched by the addition of water/ice. The resulting solution was extracted with ethyl acetate (4000 mL). The organic layer was washed with brine (1 L×4) and dried over anhydrous sodium sulfate. The solids were filtered out and concentrated under vacuum. The isolated solid was collected and purified by crystallization with PE/EA. This resulted in 89 g of 1-[(4-methylbenzene)sulfonyl]-4,5,6,7-tetrahydro-1H-indole-4-carbonitrile as a white solid. MS [M+H]+ (ES, m/z): 301.

Step 5. Ethyl 1-[(4-methylbenzene)sulfonyl]-4,5,6,7-tetrahydro-1H-indole-4-carboxylate

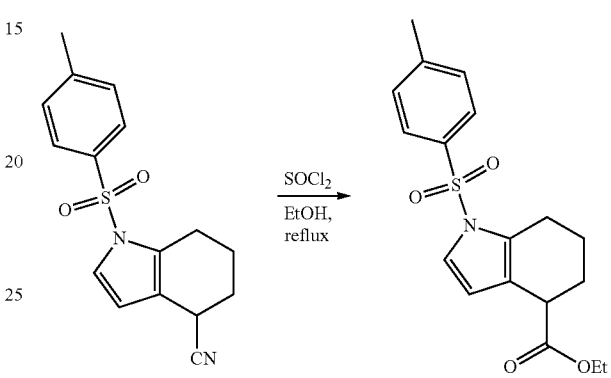

Into a 2 L round-bottom flask, was placed a solution of 1-[(4-methylbenzene)sulfonyl]-4,5,6,7-tetrahydro-1H-indole-4-carbonitrile (89 g, 296.30 mmol, 1.00 equiv) in ethanol (1000 mL), sulfuryl dichloride (350 g, 2.94 mol, 9.93 equiv). The resulting solution was stirred for 16 h at 90° C. The reaction was then quenched by the addition of water/ice. The resulting solution was extracted with of ethyl acetate (4000 mL). The resulting mixture was washed with brine (1 L×4). The resulting mixture was concentrated under vacuum. The residue was applied onto a silica gel column (PE/EA) to afford 70 g (68%) of ethyl 1-[(4-methylbenzene)sulfonyl]-4,5,6,7-tetrahydro-1H-indole-4-carboxylate as a white solid. MS [M+H]+ (ES, m/z): 348.

Step 6. 4,5,6,7-tetrahydro-1H-indole-4-carboxylic acid

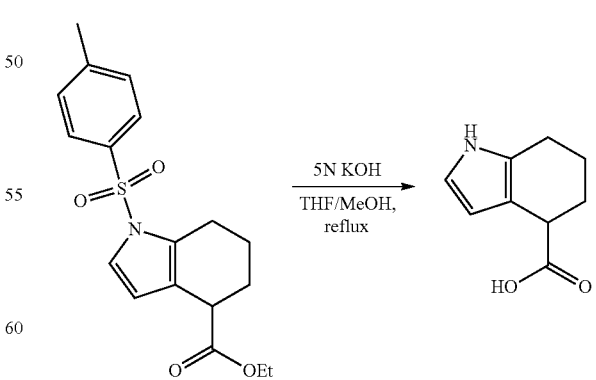

Into a 2 L round-bottom flask, was placed ethyl 1-[(4-methylbenzene)sulfonyl]-4,5,6,7-tetrahydro-1H-indole-4-carboxylate (60 g, 172.70 mmol, 1.00 equiv), methanol (240 mL), tetrahydrofuran (240 mL), potassium hydroxide (5N)

(420 mL). The resulting solution was stirred for 26 h at 85° C. The resulting mixture was concentrated under vacuum to remove the MeOH and THF. The resulting solution was extracted with of ethyl acetate (1 L×3). The pH value of the aqueous phase was adjusted to 6 with HCl (1 N). The resulting mixture was washed with brine (1 L×4) and dried over anhydrous sodium sulfate. The solids were filtered out and concentrated under vacuum. The isolated solid was collected and purified by crystallization with PE/EA. This resulted in 26 g (91%) of 4,5,6,7-tetrahydro-1H-indole-4-carboxylic acid as a white solid. MS [M+H]⁺ (ES, m/z): 166.

Step 7.
2-chloro-4,5,6,7-tetrahydro-1H-indole-4-carboxylic acid

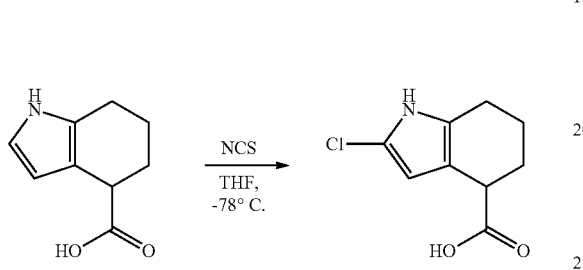

Into a 500-mL round-bottom flask purged and maintained with an inert atmosphere of nitrogen, was placed a solution of 4,5,6,7-tetrahydro-1H-indole-4-carboxylic acid (7.5 g, 45.40 mmol, 1.00 equiv) in tetrahydrofuran (210 mL). This was followed by the addition of 1-chloropyrrolidine-2,5-dione (6.6 g, 49.43 mmol, 1.09 equiv) in THF (20 mL) dropwise with stirring at −78° C. The resulting solution was stirred for 3 h at −78° C. The reaction was then quenched by the addition of water. The resulting solution was extracted with ethyl acetate (800 mL×3) and the organic layers combined and dried over anhydrous sodium sulfate. The solids were filtered out. The resulting solution was diluted with DMF (150 mL). The resulting mixture was concentrated under vacuum (out of EA). This resulted in 9 g (conversion) of 2-chloro-4,5,6,7-tetrahydro-1H-indole-4-carboxylic acid. MS [M+H]⁺ (ES, m/z): 200 and 202.

Step 8. 5-methyl-4,5,6,7-tetrahydro-2H-pyrazolo[4,3-c]pyridin-3-amine

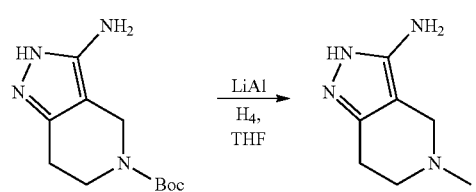 [SMILES: CC(C)(C)OC(=O)N1CCc2n[nH]c(N)c2C1 ; "LiAl" ; CN1CCc2n[nH]c(N)c2C1]

Into a 100-mL round-bottom flask purged and maintained with an inert atmosphere of nitrogen, was placed tert-butyl 3-amino-4,5,6,7-tetrahydro-2H-pyrazolo[4,3-c]pyridin-5-carboxylate (700 mg, 2.94 mmol, 1.00 equiv), tetrahydrofuran (15 mL), LiAlH₄ (334 mg, 8.80 mmol, 3.00 equiv) was added at 0° C. The resulting solution was stirred overnight at 60° C. The reaction was then quenched by the addition of water (2 ml) and NaOH (1M/1, 4 ml) and water (2 ml). The mixture was stirred for 30 min. The solids were filtered out. The crude product was purified by Prep-HPLC with the following conditions: Column, Atlantis Prep T3 OBD Column, 19×250 mm 10 u; mobile phase, water (0.1% FA) and ACN (0 up to 30.0% in 15 min); Detector, UV 254 nm. This resulted in 90 mg (20%) of 5-methyl-4,5,6,7-tetrahydro-2H-pyrazolo[4,3-c]pyridin-3-amine as a yellow solid. MS (ES, m/z) [M+H]: 153.

Step 9. (3-amino-5-methyl-4,5,6,7-tetrahydropyrazolo[4,3-c]pyridin-2-yl)(2-chloro-4,5,6,7-tetrahydro-1H-indol-4-yl)methanone

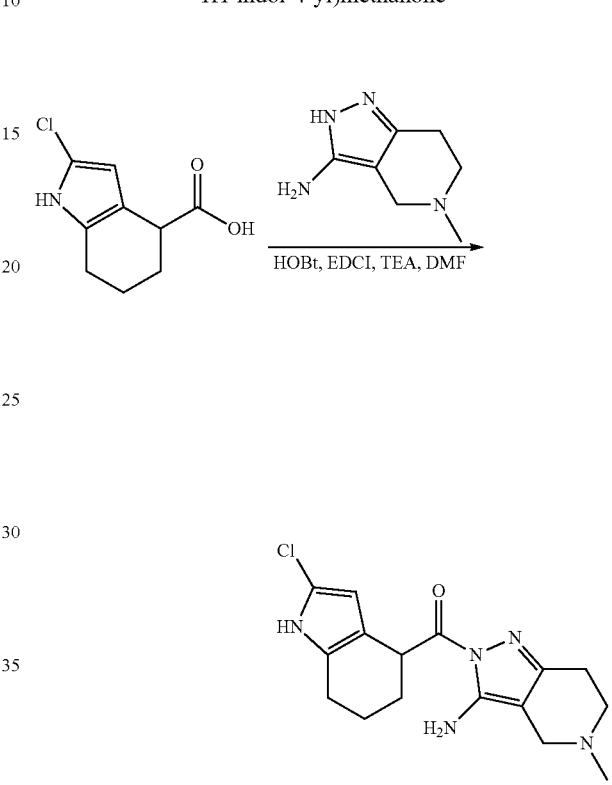

Into a 50-mL round-bottom flask, was placed 2-chloro-4,5,6,7-tetrahydro-1H-indole-4-carboxylic acid (60 mg, 0.30 mmol, 1.00 equiv), 5-methyl-4,5,6,7-tetrahydro-2H-pyrazolo[4,3-c]pyridin-3-amine (50 mg, 0.33 mmol, 1.10 equiv), HOBT (61 mg, 0.45 mmol, 1.50 equiv), EDCI (86 mg, 0.45 mmol, 1.50 equiv), TEA (92 mg, 0.91 mmol, 3.00 equiv), N,N-dimethylformamide (8 mL). The resulting solution was stirred overnight at room temperature. The reaction was then quenched by the addition of water (30 mL). The resulting solution was extracted with ethyl acetate (30 mL×3), washed with brine (80 mL×2), dried over anhydrous sodium sulfate and concentrated under vacuum. The crude product was purified by Prep-HPLC with the following conditions: Column: XBridge C18 OBD Prep Column 5 µm, 19 mm×250 mm; Mobile Phase A: water (10 MMOL/L NH₄HCO₃), Mobile Phase B: ACN; Flow rate: 20 mL/min; Gradient: 5% B to 20% B in 7 min; 254& 220 nm; Rt: 7 min. The collected fraction was lyophilized to give 2.3 mg (2%) of (3-amino-5-methyl-4,5,6,7-tetrahydropyrazolo[4,3-c]pyridin-2-yl)(2-chloro-4,5,6,7-tetrahydro-1H-indol-4-yl)methanone as a yellow solid. MS (ES, m/z) [M+H]⁺: 334; (DMSO-d₆, 300 MHz, ppm): δ 11.07 (s, 1H), 6.50 (s, 2H), 5.54 (s, 1H), 4.70-4.67 (m, 1H), 3.42-3.40 (m, 2H), 2.79-2.70 (m, 2H), 2.66-2.65 (s, 2H), 2.48-2.45 (m, 2H), 1.99-1.81 (m, 3H), 1.70-1.68 (m, 1H).

Example 4 & 5: Benzyl 3-amino-2-(2-ethyl-4,5,6,7-tetrahydro-1H-indole-4-carbonyl)-6,7-dihydro-2H-pyrazolo[4,3-c]pyridine-5(4H)-carboxylate and benzyl 3-amino-1-(2-ethyl-4,5,6,7-tetrahydro-1H-indole-4-carbonyl)-6,7-dihydro-1H-pyrazolo[4,3-c]pyridine-5(4H)-carboxylate

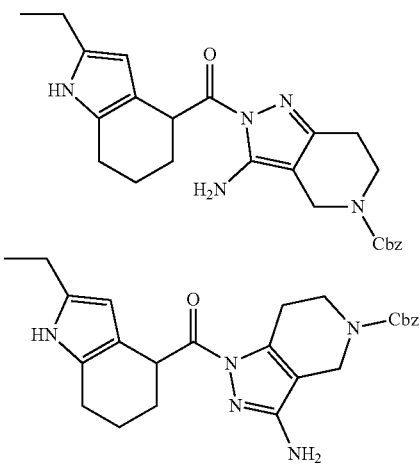

Step 1. tert-butyl 2-ethyl-5-formyl-1H-pyrrole-1-carboxylate

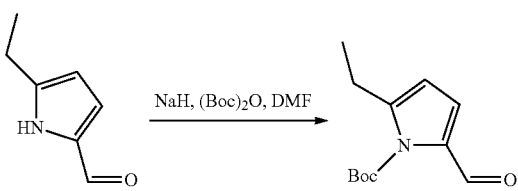

Into a 250-mL 3-necked round-bottom flask purged and maintained with an inert atmosphere of nitrogen, was placed 5-ethyl-1H-pyrrole-2-carbaldehyde (2.0 g, 16.24 mmol, 1.00 equiv), N,N-dimethylformamide (150 mL). This was followed by the addition of sodium hydride (780 mg, 19.50 mmol, 1.20 equiv, 60%) in several batches at 0° C. To this was added a solution of (Boc)$_2$O (3.9 g, 17.87 mmol, 1.10 equiv) in N,N-dimethylformamide (8 mL) dropwise with stirring at 5° C. The resulting solution was stirred overnight at 25° C. The reaction was then quenched by the addition of ice/water (250 mL). The resulting solution was extracted with ethyl acetate (250 mL×2) and the organic layers combined. The resulting mixture was washed with saturated brine (200 mL×3). The mixture was dried over anhydrous sodium sulfate. The solids were filtered out. The resulting mixture was concentrated under vacuum. The residue was applied onto a silica gel column and eluted with ethyl acetate/petroleum ether (1:10). The collected fraction was concentrated to give 3.7 g (97.2%) of tert-butyl 2-ethyl-5-formyl-1H-pyrrole-1-carboxylate as yellow oil. MS (ES, m/z) [M+H]$^+$: 224.

Step 2. tert-butyl 2-ethyl-5-vinyl-1H-pyrrole-1-carboxylate

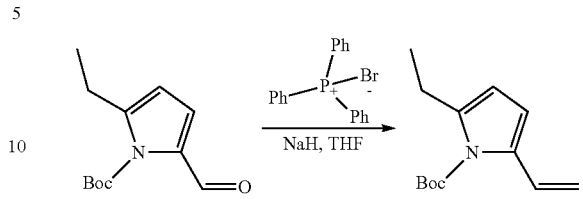

Into a 250-mL 3-necked round-bottom flask purged and maintained with an inert atmosphere of nitrogen, was placed tetrahydrofuran (80 mL). This was followed by the addition of sodium hydride (1.0 g, 41.67 mmol, 1.50 equiv) at 5° C. To this was added methyltriphenylphosphonium bromide (8.9 g, 24.91 mmol, 1.50 equiv) at 5° C. The mixture was stirred for 1.5 hour at 70° C., then cooled to below 35° C., the mixture was added a solution of tert-butyl 2-ethyl-5-formyl-1H-pyrrole-1-carboxylate (3.7 g, 16.57 mmol, 1.00 equiv) in tetrahydrofuran (8 mL). The resulting solution was stirred for 3 h at 70° C.

After cooled to room temperature, the solids were filtered out. The residue was applied onto a silica gel column with ethyl acetate/petroleum ether (1/7). This resulted in 2.6 g (71%) of tert-butyl 2-ethenyl-5-ethyl-1H-pyrrole-1-carboxylate as yellow oil. MS(ES, m/z) [M+H]$^+$: 222.

Step 3. 1-tert-butyl 4-methyl 2-ethyl-4,5,6,7-tetrahydroindole-1,4-dicarboxylate

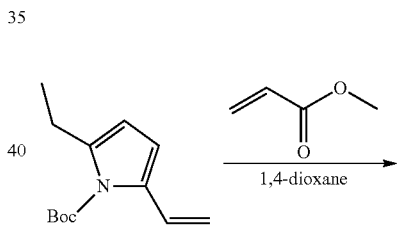

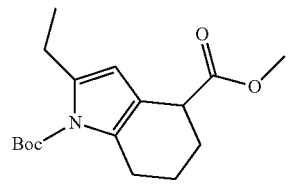

The tert-butyl 2-ethenyl-5-ethyl-1H-pyrrole-1-carboxylate (2.0 g, 9.04 mmol, 1.00 equiv), dioxane (60 mL), methyl prop-2-enoate (3.1 g, 36.01 mmol, 4.00 equiv) was placed into eight 25-mL sealed tube average, purged and maintained with an inert atmosphere of nitrogen. The resulting solution was stirred overnight at 120° C. After cooled to room temperature, the resulting mixture was concentrated under vacuum. This resulted in 500 mg (18%) of 1-tert-butyl 4-methyl 2-ethyl-4,5,6,7-tetrahydro-1H-indole-1,4-dicarboxylate as yellow oil. MS (ES, m/z) [M+H]$^+$: 308.

Step 4. methyl 2-ethyl-4,5,6,7-tetrahydro-1H-indole-4-carboxylate

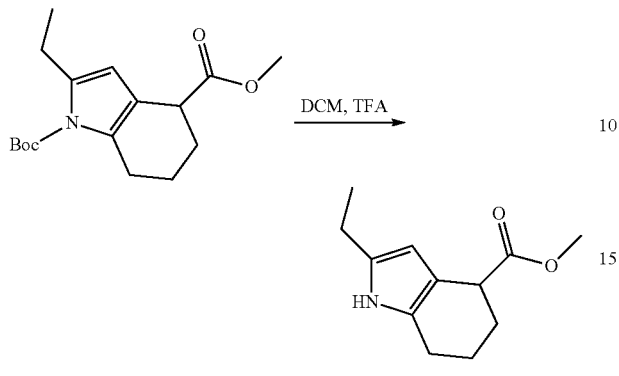

Into a 100-mL round-bottom flask, was placed 1-tert-butyl 4-methyl 2-ethyl-4,5,6,7-tetrahydro-1H-indole-1,4-dicarboxylate (300 mg, 0.98 mmol, 1.00 equiv), dichloromethane (10 g, 117.74 mmol, 120.64 equiv), $CF_3COOH$ (1.5 g, 13.16 mmol, 13.48 equiv). The resulting solution was stirred for 2 h at 25° C. The reaction was then quenched by the addition of water (80 mL). The resulting solution was extracted with dichloromethane (80 mL×2) and the organic layers combined and dried over anhydrous sodium sulfate. The solids were filtered out. The filtrate was concentrated under vacuum. This resulted in 200 mg (99%) of methyl 2-ethyl-4,5,6,7-tetrahydro-1H-indole-4-carboxylate as light yellow crude oil. MS (ES, m/z) [M+H]$^+$: 208.

Step 5. 2-ethyl-4,5,6,7-tetrahydro-1H-indole-4-carboxylic acid

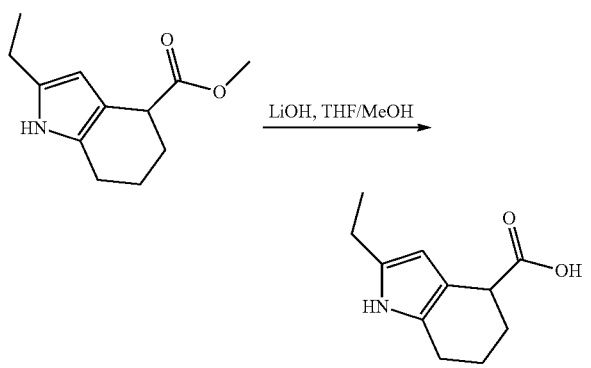

Into a 50-mL round-bottom flask, was placed methyl 2-ethyl-4,5,6,7-tetrahydro-1H-indole-4-carboxylate (200 mg, 0.96 mmol, 1.00 equiv), tetrahydrofuran (8 mL), methanol (4 mL), a solution of LiOH (139.1 mg, 5.81 mmol, 6.00 equiv) in H2O (3 mL). The resulting solution was stirred overnight at 15° C. The resulting mixture was concentrated under vacuum. The resulting solution was diluted with H2O (3 mL). The resulting solution was extracted with ethyl acetate (40 mL) and the aqueous layers combined. HCl (1 mol/L) was employed to adjust the pH to 5-6. The resulting solution was extracted with ethyl acetate (80 mL×2) and the organic layers combined and dried over anhydrous sodium sulfate. The solids were filtered out. The resulting mixture was concentrated under vacuum. This resulted in 170 mg (91%) of 2-ethyl-4,5,6,7-tetrahydro-1H-indole-4-carboxylic acid as a red crystal. (ES, m/z) [M+H]+: 194.

Step 6. benzyl 3-amino-2-(2-ethyl-4,5,6,7-tetrahydro-1H-indole-4-carbonyl)-6,7-dihydro-2H-pyrazolo[4,3-c]pyridine-5(4H)-carboxylate and benzyl 3-amino-1-(2-ethyl-4,5,6,7-tetrahydro-1H-indole-4-carbonyl)-6,7-dihydro-1H-pyrazolo[4,3-c]pyridine-5(4H)-carboxylate

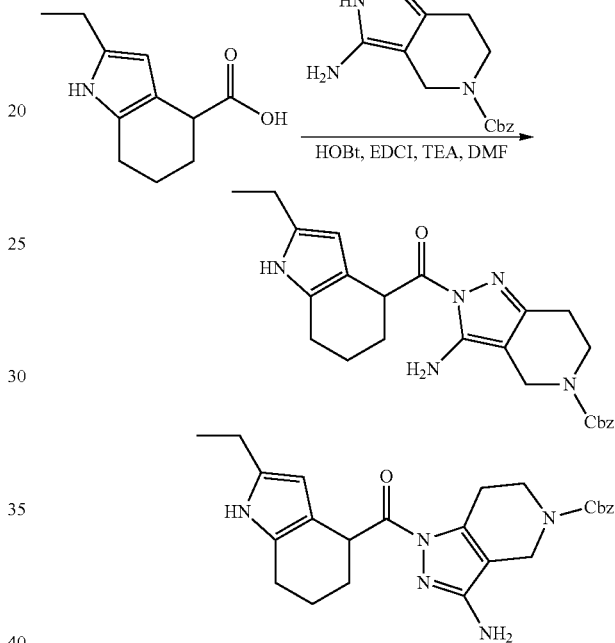

Into a 50-mL round-bottom flask, was placed 2-ethyl-4,5,6,7-tetrahydro-1H-indole-4-carboxylic acid (150 mg, 0.78 mmol, 1.20 equiv), benzyl 3-amino-4,5,6,7-tetrahydro-2H-pyrazolo[4,3-c]pyridine-5-carboxylate (90 mg, 0.33 mmol, 1.00 equiv), HOBT (90 mg, 0.67 mmol, 1.20 equiv), EDCI (190 mg, 0.99 mmol, 1.50 equiv), N,N-dimethylformamide (5 mL), TEA (140 mg, 1.38 mmol, 3.00 equiv). The resulting solution was stirred for 4 h at 25° C. The reaction mixture was diluted with DCM (80 mL), washed with H2O (50 mL×3) and brine (50 mL×3) and dried with Na2SO4. After filtration, the filtrate was concentrated under reduced pressure. The crude product was purified by Prep-HPLC with the following conditions: Column: XBridge Prep OBD C18 Column; 150 mm 5 um; Mobile Phase A: water (10 mM $NH_4HCO_3$), Mobile Phase B: ACN; Flow rate: 60 mL/min; Gradient: 25% B to 55% B in 7 min; 254 nm.

Fraction A: The collected fraction was lyophilized to give 2.0 mg (1%) of benzyl 3-amino-2-(2-ethyl-4,5,6,7-tetrahydro-1H-indole-4-carbonyl)-6,7-dihydro-2H-pyrazolo[4,3-c]pyridine-5(4H)-carboxylate as a white solid. Rt2: 6.32 min. MS (ES, m/z) [M+H]+: 448; (300 MHz, DMSO-d6, ppm): δ 10.10 (s, 1H), 7.40-7.38 (m, 5H), 6.60 (s, 2H), 5.28 (s, 1H), 5.13 (m, 2H), 4.74-4.69 (m, 1H), 4.30 (s, 2H), 3.32 (s, 2H), 2.51-2.50 (m, 2H), 2.41-2.39 (m, 3H), 1.98-1.61 (m, 5H), 1.09-1.04 (m, 3H).

Fraction B: The collected fraction was lyophilized to give 1.5 mg (1%) of benzyl 3-amino-1-(2-ethyl-4,5,6,7-tetrahydro-1H-indole-4-carbonyl)-6,7-dihydro-1H-pyrazolo[4,3-c]pyridine-5(4H)-carboxylate as a white solid. Rt1: 5.69 min. MS (ES, m/z) [M+H]+: 448; (300 MHz, DMSO-d6, ppm): δ 10.06 (s, 1H), 7.39-7.38 (m, 5H), 5.65 (s, 2H), 5.30 (d, J=2.1 Hz, 1H), 5.13 (m, 2H), 4.65-4.61 (m, 1H), 4.28 (s, 2H), 3.63 (s, 2H), 2.49-2.36 (m, 3H), 1.86-1.64 (m, 5H), 1.10-1.05 (m, 3H).

Example 6: (3-amino-4,5,6,7-tetrahydropyrazolo[4,3-c]pyridin-2-yl)(2-ethyl-4,5,6,7-tetrahydro-1H-indol-4-yl)methanone

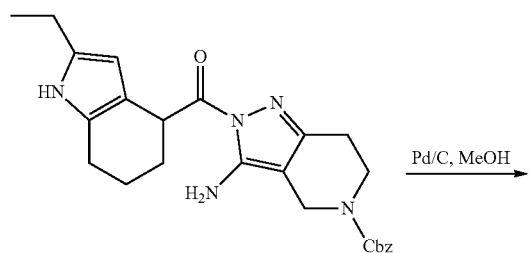

Into a 25-mL round-bottom flask, was placed benzyl 3-amino-2-[(2-ethyl-4,5,6,7-tetrahydro-1H-indol-4-yl)carbonyl]-4,5,6,7-tetrahydro-2H-pyrazolo[4,3-c]pyridine-5-carboxylate (30 mg, 0.07 mmol, 1.00 equiv), methanol (3 mL), AcOH (0.2 mL), Palladium carbon (10%, 30 mg). To the above hydrogen was introduced in. The resulting solution was stirred for 40 min at room temperature. The solids were filtered out. The filtrate was concentrated under vacuum. The crude product was purified by Prep-HPLC with the following conditions: Column: XBridge Prep OBD C18 Column 150 mm 5 um; Mobile Phase A: water (10 mM NH4HCO3), Mobile Phase B: ACN; Flow rate: 60 mL/min; Gradient: 25% B to 55% B in 7 min; 254 nm; Rt: 6.32 min. The collected fraction was lyophilized to give 1.3 mg (6%) of (3-amino-4,5,6,7-tetrahydropyrazolo[4,3-c]pyridin-2-yl)(2-ethyl-4,5,6,7-tetrahydro-1H-indol-4-yl)methanone as a white solid. MS (ES, m/z) [M+H]+: 314. (DMSO-d6, 400 MHz, ppm): δ 10.11 (s, 1H), 6.37 (s, 2H), 5.28 (s, 1H), 4.74-4.72 (m, 1H), 3.52-3.51 (m, 2H), 2.92-2.84 (m, 2H), 2.47-2.39 (m, 7H), 2.01-1.84 (m, 3H), 1.75-1.68 (m, 1H), 1.09-1.05 (m, 3H).

Example 7 & 8: Tert-butyl 3-amino-2-(2-methyl-1H-indole-4-carbonyl)-4,5-dihydro-2H-pyrazolo[3,4-c]pyridine-6(7H)-carboxylate and tert-butyl 3-amino-1-(2-methyl-1H-indole-4-carbonyl)-4,5-dihydro-1H-pyrazolo[3,4-c]pyridine-6(7H)-carboxylate

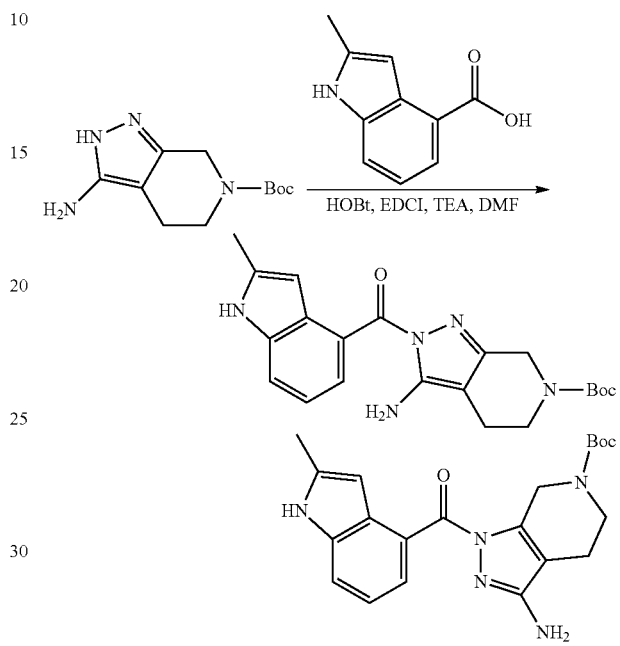

Into a 50-mL round-bottom flask, was placed tert-butyl 3-amino-4,5,6,7-tetrahydro-2H-pyrazolo[3,4-c]pyridin-6-carboxylate (30 mg, 0.13 mmol, 1.00 equiv), N,N-dimethylformamide (5 mL), HOBt (26 mg, 0.19 mmol, 1.50 equiv), EDCI (37 mg, 0.19 mmol, 1.50 equiv), TEA (64 mg, 0.63 mmol, 5.00 equiv), 2-methyl-1H-indole-4-carboxylic acid (27 mg, 0.15 mmol, 1.20 equiv). The resulting solution was stirred for 16 h at room temperature. The reaction was then quenched by the addition of water (30 mL). The resulting solution was extracted with ethyl acetate (30 mL×3), washed with brine (100 mL×3) and concentrated under vacuum. The crude product was purified by Prep-HPLC with the following conditions: Column, XBridge C18 OBD Prep Column, 19 mm×250 mm; mobile phase, water (0.1% FA) and ACN (10.0% ACN up to 30.0% in 7 min); Detector, UV/mass 254 & 220 nm.

Fraction A: The collected fraction was lyophilized to give 0.8 mg (2%) of tert-butyl 3-amino-2-(2-methyl-1H-indole-4-carbonyl)-4,5-dihydro-2H-pyrazolo[3,4-c]pyridine-6 (7H)-carboxylate as a yellow solid. Rt2: 6.42 min. MS (ES, m/z) [M+H]+: 396; (DMSO-d6, 300 MHz, ppm): δ 11.22 (s, 1H), 7.55 (d, J=6.9 Hz, 1H), 7.52 (d, J=12.9 Hz, 1H), 7.09-7.04 (m, 1H), 6.55 (s, 2H), 6.27 (s, 1H), 4.27 (s, 2H), 3.54-3.16 (m, 2H), 2.52-2.49 (m, 5H), 1.4 (s, 9H).

Fraction B: The collected fraction was lyophilized to give 2.5 mg (5%) of tert-butyl 3-amino-1-(2-methyl-1H-indole-4-carbonyl)-4,5-dihydro-1H-pyrazolo[3,4-c]pyridine-6 (7H)-carboxylate as a yellow solid. Rt1: 5.78 min. MS (ES, m/z) [M+H]+: 396; (DMSO-d6, 400 MHz, ppm): δ 11.16 (s, 1H), 7.56 (d, J=7.2 Hz, 1H); 7.44 (d, J=8.0 Hz, 1H), 7.06-7.02 (m, 1H), 6.27 (s, 1H), 5.53 (s, 2H), 4.78 (s, 2H), 3.60-3.57 (m, 2H), 2.51-2.49 (m, 3H), 2.39-2.38 (m, 2H), 1.44 (s, 9H).

Example 9: (3-amino-4,5,6,7-tetrahydropyrazolo[3,4-c]pyridin-2-yl)(2-methyl-1H-indol-4-yl)methanone

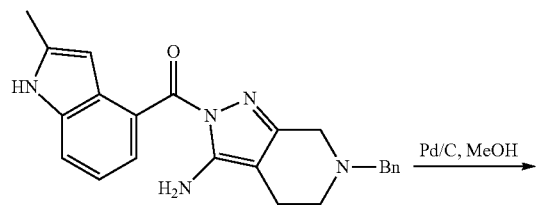

Into a 50-mL round-bottom flask, was placed 6-benzyl-2-[(2-methyl-1H-indol-4-yl)carbonyl]-4,5,6,7-tetrahydro-2H-pyrazolo[3,4-c]pyridin-3-amine (60 mg, 0.16 mmol, 1.00 equiv), Palladium carbon (10%, 60 mg), methanol (10 mL), AcOH (0.5 mL). The resulting solution was stirred for 1.5 h at room temperature. The solids were filtered out. The filtrate was concentrated under vacuum. The crude product was purified by Prep-HPLC with the following conditions: Column: XBridge Shield RP18 OBD Column, 5 um, 19×150 mm; Mobile Phase A: water (0.1% FA), Mobile Phase B: ACN; Flow rate: 20 mL/min; Gradient: 25% B to 50% B in 7 min; 254 nm; Rt: 6.3 min. The collected fraction was lyophilized to give 6 mg (13%) of (3-amino-4,5,6,7-tetrahydropyrazolo[3,4-c]pyridin-2-yl)(2-methyl-1H-indol-4-yl)methanone as a brown solid. MS (ES, m/z) [M+H]+: 295; (DMSO-d6, 300 MHz, ppm): δ 11.20 (s, 1H), 8.19 (s, 1H), 7.53 (d, J=7.5 Hz, 1H), 7.46 (d, J=7.8 Hz, 1H), 7.07-7.02 (m, 1H), 6.47 (s, 2H), 6.27 (s, 1H), 3.63 (s, 2H), 2.91-2.89 (m, 2H), 2.40-2.34 (m, 5H).

Example 10 & 11: (3-amino-6-benzyl-4,5,6,7-tetrahydropyrazolo[3,4-c]pyridin-2-yl)(2-methyl-1H-indol-4-yl)methanone and (3-amino-6-benzyl-4,5,6,7-tetrahydropyrazolo[3,4-c]pyridin-1-yl)(2-methyl-1H-indol-4-yl)methanone

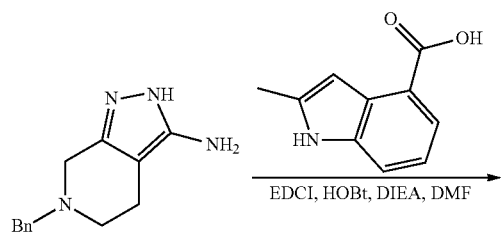

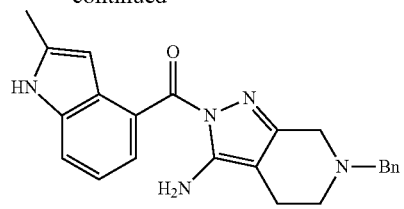

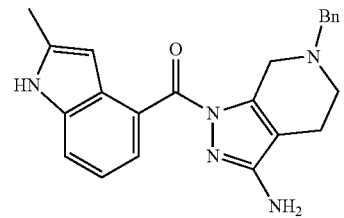

Into a 50-mL round-bottom flask, was placed 2-methyl-1H-indole-4-carboxylic acid (91 mg, 0.52 mmol, 1.00 equiv), 6-benzyl-4,5,6,7-tetrahydro-2H-pyrazolo[3,4-c]pyridin-3-amine (119 mg, 0.52 mmol, 1.00 equiv), N,N-dimethylformamide (5 mL), HOBT (135 mg, 1.00 mmol, 1.50 equiv), EDCI (150 mg, 0.78 mmol, 1.50 equiv), TEA (262 mg, 2.59 mmol, 5.00 equiv). The resulting solution was stirred for 18 h at 30° C. The reaction was then quenched by the addition of water (10 mL). The resulting solution was extracted with ethyl acetate (10 mL×3) and the organic layers combined and concentrated under vacuum. The crude product (10 mg) was purified by Prep-HPLC with the following conditions: Column, XBridge C18 OBD Prep Column, 100×5 μm, 19 mm×250 mm; mobile phase, water (10 mmoL/L NH4HCO3) and ACN (5.0% ACN up to 20.0% in 12 min); Detector, UV/mass 254 & 220 nm.

Fraction A: The collected fraction was lyophilized to give 4.1 mg (2%) of (3-amino-6-benzyl-4,5,6,7-tetrahydropyrazolo[3,4-c]pyridin-2-yl)(2-methyl-1H-indol-4-yl)methanone as a yellow solid. Rt2: 11.02 min. MS (ES, m/z) [M+H]+: 386; (DMSO-d6, 400 MHz, ppm): δ 11.21 (s, 1H), 7.54 (d, J=11.2 Hz, 1H), 7.46 (d, J=10.4 Hz, 1H), 7.38-7.26 (m, 5H), 7.06-7.00 (m, 1H), 6.49 (s, 2H), 6.26 (s, 1H), 3.63-3.61 (m, 2H), 3.35-3.34 (m, 2H), 2.52-2.49 (m, 2H), 2.40-2.38 (m, 5H).

Fraction B: The collected fraction was lyophilized to give 3.6 mg (2%) of (3-amino-6-benzyl-4,5,6,7-tetrahydropyrazolo[3,4-c]pyridin-1-yl)(2-methyl-1H-indol-4-yl)methanone as a white solid. Rt1: 10.13 min. MS (ES, m/z) [M+H]+: 386; (DMSO-d6, 400 MHz, ppm): δ 11.13 (s, 1H), 7.52 (d, J=9.6 Hz, 1H), 7.42-7.35 (m, 5H), 7.42-7.35 (m, 1H); 7.05-7.02 (m, 1H), 6.20 (s, 1H), 5.46 (s, 2H), 3.82-3.80 (m, 2H), 3.74-3.72 (m, 2H), 2.73-2.71 (m, 2H), 2.51-2.47 (m, 5H).

Example 12 & 13: (3-amino-6-(methylsulfonyl)-4,5,6,7-tetrahydropyrazolo[3,4-c]pyridin-2-yl)(6-methyl-1,2,3,4-tetrahydroquinolin-4-yl)methanone and (3-amino-6-(methylsulfonyl)-4,5,6,7-tetrahydropyrazolo[3,4-c]pyridin-1-yl)(6-methyl-1,2,3,4-tetrahydroquinolin-4-yl)methanone

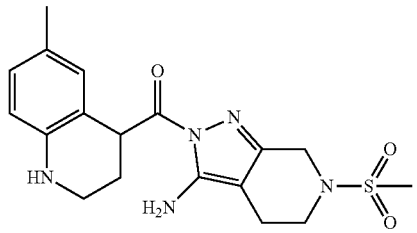

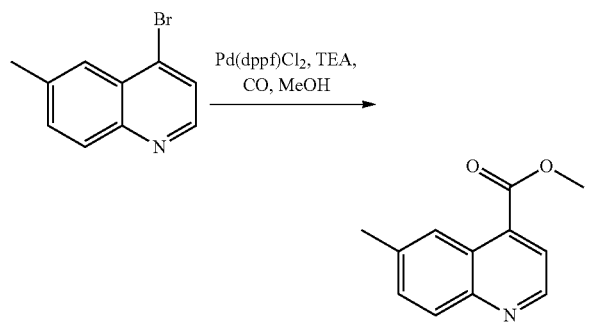

Step 1. methyl 6-methylquinoline-4-carboxylate

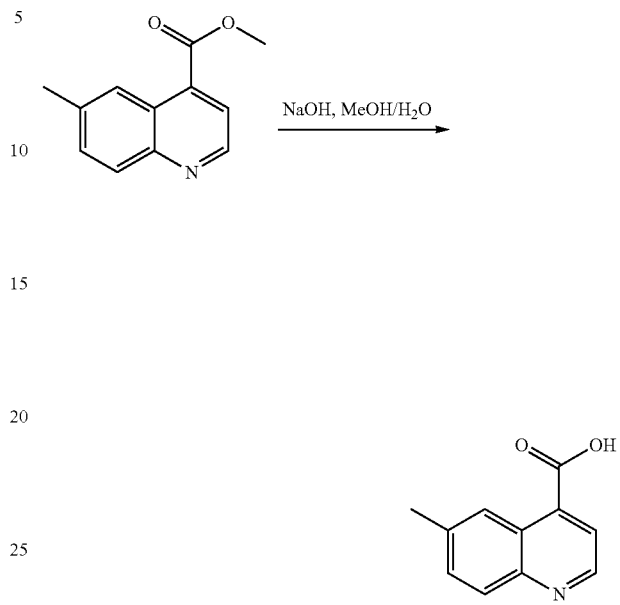

Into a 30-mL pressure tank reactor (60 atm) purged and maintained with an inert atmosphere of argon, was placed 4-bromo-6-methylquinoline (1 g, 4.50 mmol, 1.00 equiv), Pd(dppf)Cl2CH2Cl2 (1.84 g, 2.25 mmol, 0.50 equiv), TEA (2.86 g, 28.26 mmol, 1.50 equiv), methanol (20 mL). The resulting solution was stirred overnight at 70° C. After cooled to room temperature, the resulting mixture was concentrated under vacuum. The residue was applied onto a silica gel column with ethyl acetate/petroleum ether (1/1). This resulted in 610 mg (67%) of methyl 6-methylquinoline-4-carboxylate as a yellow solid. MS (ES, m/z) [M+H]+: 202.

Step 2. 6-methylquinoline-4-carboxylic acid

Into a 50-mL round-bottom flask, was placed methyl 6-methylquinoline-4-carboxylate (200 mg, 0.99 mmol, 1.00 equiv), sodium hydroxide (200 mg, 6.24 mmol, 5.00 equiv), water (2 mL), methanol (10 mL). The resulting solution was stirred overnight at 25° C. The resulting mixture was concentrated under vacuum. The resulting mixture was washed with EA (50 mL×2). The pH value of the solution was adjusted to 6 with hydrochloric acid (1 mol/L). The resulting solution was extracted with dichloromethane (50 mL×2) and concentrated. This resulted in 145 mg (78%) of 6-methylquinoline-4-carboxylic acid as a yellow solid. MS (ES, m/z) [M+H]+: 188.

Step 3. 6-methyl-1,2,3,4-tetrahydroquinoline-4-carboxylic acid

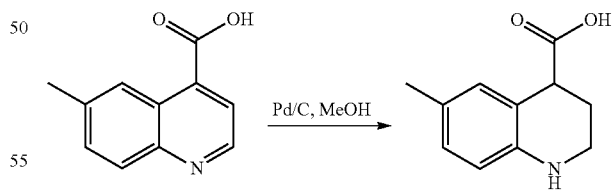

Into a 100-mL round-bottom flask purged and maintained with an inert atmosphere of H2, was placed 6-methylquinoline-4-carboxylic acid (145 mg, 0.77 mmol, 1.00 equiv), Palladium carbon (10%, 100 mg), methanol (10 mL). The resulting solution was stirred overnight at 25° C. The solids were filtered out. The filtrate was concentrated under vacuum. This resulted in 120 mg (81%) of 6-methyl-1,2,3,4-tetrahydroquinoline-4-carboxylic acid as white oil. MS (ES, m/z) [M+H]+: 192.

Step 4. (3-amino-6-(methylsulfonyl)-4,5,6,7-tetrahydropyrazolo[3,4-c]pyridin-2-yl)(6-methyl-1,2,3,4-tetrahydroquinolin-4-yl)methanone and (3-amino-6-(methylsulfonyl)-4,5,6,7-tetrahydropyrazolo[3,4-c]pyridin-1-yl)(6-methyl-1,2,3,4-tetrahydroquinolin-4-yl)methanone

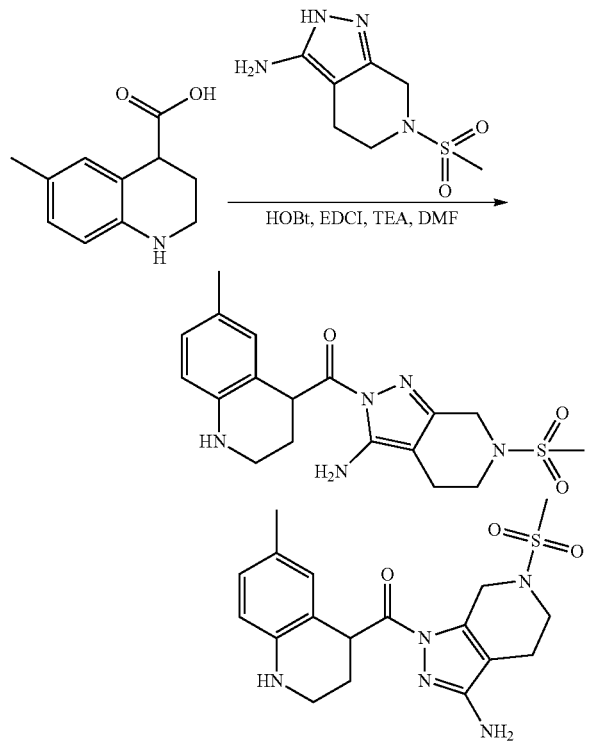

Into a 100-mL round-bottom flask, was placed 6-methyl-1,2,3,4-tetrahydroquinoline-4-carboxylic acid (54 mg, 0.28 mmol, 1.00 equiv), 6-methanesulfonyl-4,5,6,7-tetrahydro-2H-pyrazolo[3,4-c]pyridin-3-amine (60 mg, 0.28 mmol, 1.00 equiv), EDCI (80.6 mg, 0.42 mmol, 1.50 equiv), HOBt (56.7 mg, 0.42 mmol, 1.50 equiv), N,N-dimethylformamide (10 mL), TEA (141.4 mg, 1.40 mmol, 5.00 equiv). The resulting solution was stirred for 3 h at room temperature. The resulting mixture was diluted with H2O (50 mL). The resulting solution was extracted with ethyl acetate (100 mL×3) and concentrated under vacuum. The crude product was purified by Prep-HPLC with the following conditions: Column: XBridge C18 OBD Prep Column 100 10 µm, 19 mm×250 mm; Mobile Phase A: water (0.1% FA), Mobile Phase B: ACN; Flow rate: 20 mL/min; Gradient: 20% B to 45% B in 7 min; 254& 220 nm.

Fraction A: The collected fraction was lyophilized to give 2.8 mg (3%) of (3-amino-6-(methylsulfonyl)-4,5,6,7-tetrahydropyrazolo[3,4-c]pyridin-2-yl)(6-methyl-1,2,3,4-tetrahydroquinolin-4-yl)methanone as a white solid. Rt2: 6.77 min. MS (ES, m/z) [M+H]+: 390. (DMSO-d6, 400 MHz, ppm): δ 6.74-6.70 (m, 1H), 6.63-6.57 (m, 3H), 6.44-6.42 (d, J=8.4, 1H), 5.63 (s, 1H), 4.98-4.97 (m, 1H), 4.23 (s, 2H), 3.42-3.40 (m, 2H), 3.23-3.27 (m, 1H), 3.13-3.18 (m, 1H), 2.97 (s, 3H), 2.47-2.45 (m, 2H), 2.09-2.06 (m, 3H), 2.02-2.01 (m, 2H).

Fraction B: The collected fraction was lyophilized to give 4.7 mg (5%) of (3-amino-6-(methylsulfonyl)-4,5,6,7-tetrahydropyrazolo[3,4-c]pyridin-1-yl)(6-methyl-1,2,3,4-tetrahydroquinolin-4-yl)methanone as a white solid. Rt1: 6.19 min. MS (ES, m/z) [M+H]+: 390. (DMSO-d6, 400 MHz, ppm): δ 6.73-6.70 (m, 1H), 6.59 (s, 1H), 6.42-6.40 (d, J=8.0, 1H), 5.81-5.78 (m, 2H), 5.60 (s, 1H), 4.90-4.87 (m, 1H), 4.56-4.52 (m, 2H), 3.47-3.45 (m, 3H), 3.39-3.37 (m, 1H), 3.16-3.13 (m, 1H), 2.96 (s, 3H), 2.47-2.41 (m, 1H), 2.09-2.07 (m, 3H), 2.00-1.99 (m, 2H).

Example 14 & 15: (3-amino-6-(methylsulfonyl)-4,5,6,7-tetrahydropyrazolo[3,4-c]pyridin-2-yl)(6-chloro-1,2,3,4-tetrahydroquinolin-4-yl)methanone and (3-amino-6-(methylsulfonyl)-4,5,6,7-tetrahydropyrazolo[3,4-c]pyridin-1-yl)(6-chloro-1,2,3,4-tetrahydroquinolin-4-yl)methanone

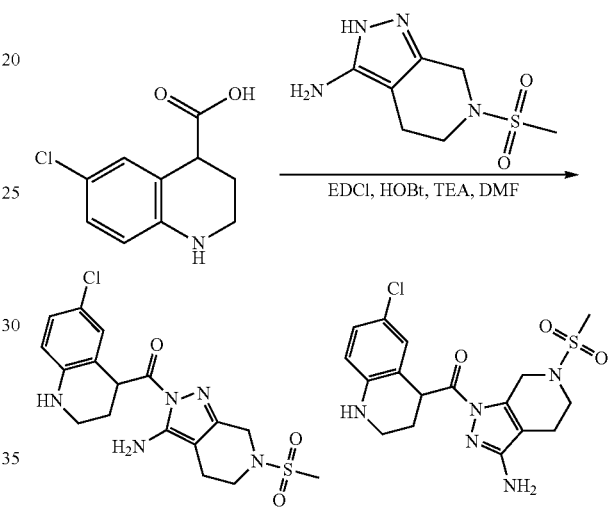

Into a 40-mL round-bottom flask, was placed 6-chloro-1,2,3,4-tetrahydroquinoline-4-carboxylic acid (28 mg, 0.13 mmol, 1.00 equiv) (prepared by a method similar to that described for 6-methyl-1,2,3,4-tetrahydroquinoline-4-carboxylic acid (example 12) starting from commercially available 6-chloroquinoline-4-carboxylic acid and utilizing Pt2O), HOBt (27 mg, 0.20 mmol, 1.50 equiv), EDCI (38 mg, 0.20 mmol, 1.50 equiv), TEA (100 mg, 0.99 mmol, 7.50 equiv), N,N-dimethylformamide (6.0 mL), 6-methanesulfonyl-4,5,6,7-tetrahydro-2H-pyrazolo[3,4-c]pyridin-3-amine (29 mg, 0.13 mmol, 1.00 equiv). The resulting solution was stirred for 5 h at 20 degree C. The reaction was then quenched by the addition of water/ice (20 mL). The resulting solution was extracted with ethyl acetate (30 ml×3) and the organic layers combined and dried over anhydrous sodium sulfate and concentrated under vacuum. The crude product was purified by Prep-HPLC with the following conditions: Column, XBridge Shield RP18 OBD Column, 5 um, 19×150 mm; mobile phase, water (0.1% FA) and ACN (35.0% ACN up to 55.0% in 7 min); Detector, UV 254 nm.

Fraction A: The collected fraction was lyophilized to give 0.9 mg (2%) of (3-amino-6-(methylsulfonyl)-4,5,6,7-tetrahydropyrazolo[3,4-c]pyridin-2-yl)(6-chloro-1,2,3,4-tetrahydroquinolin-4-yl)methanone as a gray solid. MS (ES, m/z) [M+H]+: 410; (400 MHz, DMSO-d6, ppm) δ 6.95-6.93 (m, 1H), 6.84 (d, J=2.5 Hz, 1H), 6.67 (s, 2H), 6.53 (d, J=8.7 Hz, 1H), 6.12 (s, 1H), 4.98-4.97 (m, 1H), 4.24 (s, 2H), 3.42-3.39 (m, 2H), 3.22-3.20 (m, 2H), 2.98 (s, 3H), 2.50-2.43 (m, 2H), 2.04-1.98 (m, 2H).

Fraction B: The collected fraction was lyophilized to give 5.1 mg (9%) of (3-amino-6-(methylsulfonyl)-4,5,6,7-tetrahydropyrazolo[3,4-c]pyridin-1-yl)(6-chloro-1,2,3,4-tetrahydroquinolin-4-yl)methanone as a white solid. MS (ES, m/z) [M+H]+: 410; (400 MHz, DMSO-d6, ppm) δ 6.94-6.92 (m, 1H), 6.86 (d, J=2.5 Hz, 1H), 6.52 (d, J=8.6 Hz, 1H), 6.09 (s, 1H), 5.83 (s, 2H), 4.89-4.86 (m, 1H), 4.57-4.51 (m, 2H), 3.52-3.34 (m, 2H), 3.19-3.17 (m, 2H), 2.97 (s, 3H), 2.11-1.94 (m, 2H).

Example 16 & 17 & 18 & 19: (3-amino-6-(methylsulfonyl)-4,5,6,7-tetrahydropyrazolo[3,4-c]pyridin-2-yl)(6-fluoro-1,2,3,4-tetrahydroquinolin-4-yl)methanone and (3-amino-6-(methylsulfonyl)-4,5,6,7-tetrahydropyrazolo[3,4-c]pyridin-1-yl)(6-fluoro-1,2,3,4-tetrahydroquinolin-4-yl)methanone and (S*)-(3-amino-6-(methylsulfonyl)-4,5,6,7-tetrahydropyrazolo[3,4-c]pyridin-2-yl)(6-fluoro-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(6-fluoro-1,2,3,4-tetrahydroquinolin-4-yl)methanone

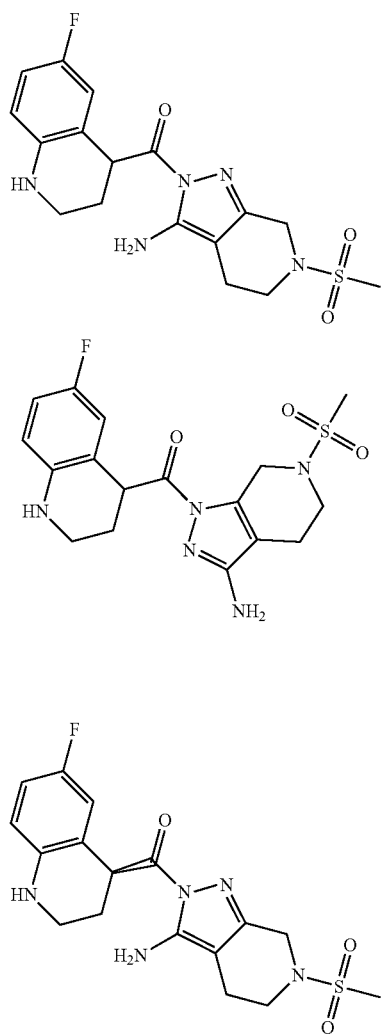

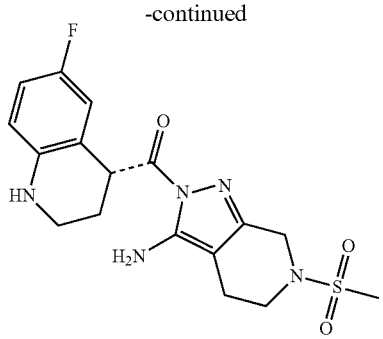

Step 1. Methyl 6-fluoroquinoline-4-carboxylate

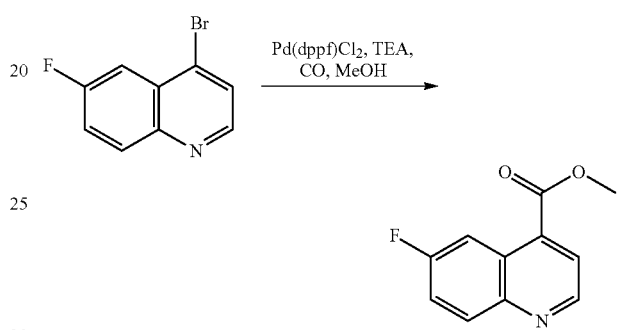

Into a 300-mL pressure tank reactor (60 atm), was placed 4-bromo-6-fluoroquinoline (10 g, 44.24 mmol, 1.00 equiv), Pd(dppf)Cl$_2$CH$_2$Cl$_2$ (3.3 g, 4.04 mmol, 0.10 equiv), methanol (100 mL). To the above CO (g) was introduced in. The resulting solution was stirred overnight at 120° C. After cooled to room temperature, the resulting mixture was concentrated under vacuum. The residue was applied onto a silica gel column with ethyl acetate/petroleum ether (0-20%). This resulted in 7.5 g (83%) of methyl 6-fluoroquinoline-4-carboxylate as a yellow solid. MS (ES, m/z) [M+H]+: 206.

Step 2. Methyl 6-fluoro-1,2,3,4-tetrahydroquinoline-4-carboxylate

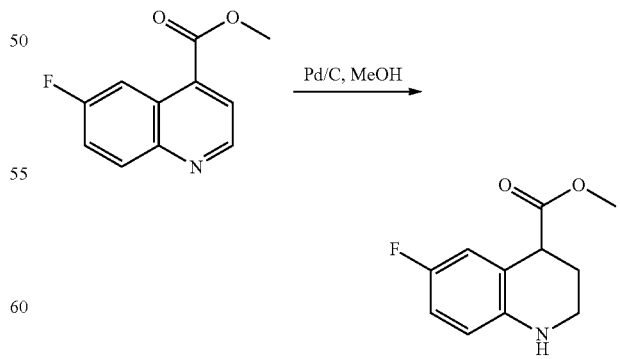

Into a 250-mL round-bottom flask, was placed methyl 6-fluoroquinoline-4-carboxylate (4 g, 19.49 mmol, 1.00 equiv), methanol (50 mL), Palladium carbon (10%, 3 g). The flask was evacuated and flushed three times with nitrogen, followed by flushing with hydrogen. The mixture was stirred 2 h at room temperature under an atmosphere of hydrogen (balloon). The solid was filtered out. The filtrate was concentrated under vacuum. This resulted in 3.5 g (86%) of methyl 6-fluoro-1,2,3,4-tetrahydroquinoline-4-carboxylate as yellow oil. MS (ES, m/z) [M+H]+: 210.

Step 3.
6-fluoro-1,2,3,4-tetrahydroquinoline-4-carboxylic acid

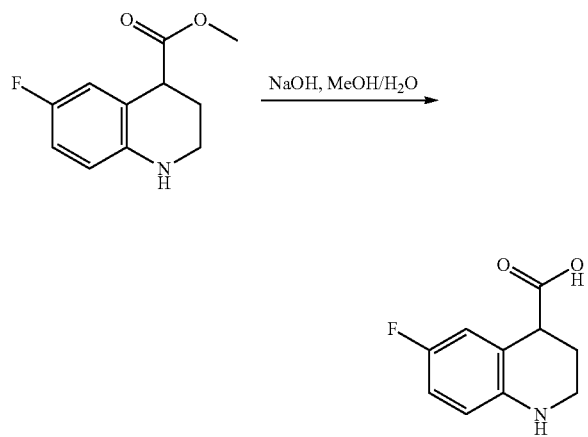

Into a 250-mL round-bottom flask, was placed methyl 6-fluoro-1,2,3,4-tetrahydroquinoline-4-carboxylate (3.5 g, 16.73 mmol, 1.00 equiv), sodium hydroxide (2 g, 50.00 mmol, 3.00 equiv), CH₃OH (30 mL), H₂O (30 mL). The resulting solution was stirred for 12 h at room temperature. The pH value of the solution was adjusted to 6 with hydrochloric acid (1 mol/L). The resulting solution was extracted with EA (150 mL×3) and the organic layers combined and dried over anhydrous sodium sulfate and concentrated under vacuum. This resulted in 2.3 g (70%) of 6-fluoro-1,2,3,4-tetrahydroquinoline-4-carboxylic acid as yellow oil. MS (ES, m/z) [M+H]+: 196.

Step 4. (3-amino-6-(methylsulfonyl)-4,5,6,7-tetrahydropyrazolo[3,4-c]pyridin-2-yl)(6-fluoro-1,2,3,4-tetrahydroquinolin-4-yl)methanone and (3-amino-6-(methylsulfonyl)-4,5,6,7-tetrahydropyrazolo[3,4-c]pyridin-1-yl)(6-fluoro-1,2,3,4-tetrahydroquinolin-4-yl)methanone

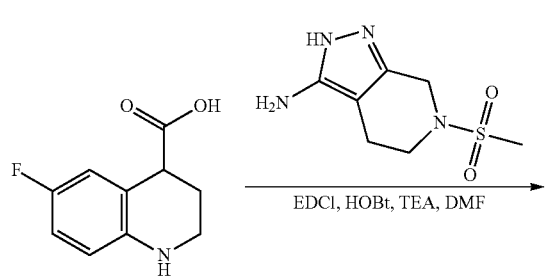

-continued

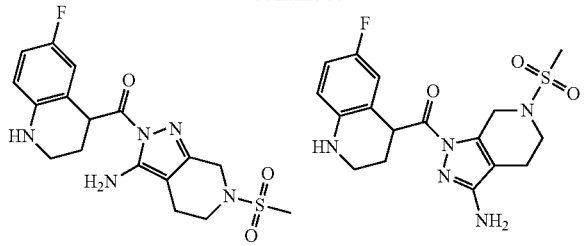

Into a 100-mL round-bottom flask, was placed 6-fluoro-1,2,3,4-tetrahydroquinoline-4-carboxylic acid (60 mg, 0.31 mmol, 1.00 equiv), 6-methanesulfonyl-4,5,6,7-tetrahydro-2H-pyrazolo[3,4-c]pyridin-3-amine (80 mg, 0.37 mmol, 1.20 equiv), DECl (88 mg, 1.50 equiv), HOBt (62 mg, 0.46 mmol, 1.50 equiv), N,N-dimethylformamide (10 mL), TEA (156 mg, 1.54 mmol, 5.00 equiv). The resulting solution was stirred for 3 h at room temperature. The resulting solution was stirred for 12 h at room temperature. The reaction was then quenched by the addition of water (50 mL). The resulting solution was extracted with ethyl acetate (100 mL×2) and concentrated under vacuum. The crude product was purified by Prep-HPLC with the following conditions: Column: XBridge Shield RP18 OBD Column, 5 um, 19×150 mm; Mobile Phase A: water (0.1% FA), Mobile Phase B: ACN; Flow rate: 20 mL/min; Gradient: 25% B to 65% B in 10 min; 254 nm.

First eluting compound: The collected fraction was lyophilized to give 8.2 mg (7%) of (3-amino-6-(methylsulfonyl)-4,5,6,7-tetrahydropyrazolo[3,4-c]pyridin-2-yl)(6-fluoro-1,2,3,4-tetrahydroquinolin-4-yl)methanone as a white solid. Rt2: 9.78 min. MS (ES, m/z) [M+H]+: 394. (DMSO-d6, 400 MHz, ppm): δ 6.79-6.78 (m, 1H), 6.68-6.64 (m, 3H), 6.52-6.49 (m, 1H), 5.80 (s, 1H), 4.98-4.97 (m, 1H), 4.24 (s, 2H), 3.43-3.40 (m, 2H), 3.27-3.15 (m, 2H), 2.97 (s, 3H), 2.47-2.45 (m, 2H), 2.06-1.98 (m, 2H).

Second eluting compound: The collected fraction was lyophilized to give 16.7 mg (14%) of (3-amino-6-(methylsulfonyl)-4,5,6,7-tetrahydropyrazolo[3,4-c]pyridin-1-yl)(6-fluoro-1,2,3,4-tetrahydroquinolin-4-yl)methanone as a white solid. Rt1: 8.35 min. MS (ES, m/z) [M+H]+: 394. (DMSO-d6, 400 MHz, ppm): δ 6.77-6.74 (m, 1H), 6.70-6.67 (m, 1H), 6.51-6.48 (m, 1H), 5.81-5.78 (m, 3H), 4.89-4.86 (m, 1H), 4.52 (s, 2H), 3.44-3.40 (m, 2H), 3.27-3.15 (m, 2H), 2.95 (s, 3H), 2.51-2.47 (m, 2H), 2.07-2.04 (m, 2H).

Step 5. (S*)-(3-amino-6-(methylsulfonyl)-4,5,6,7-tetrahydropyrazolo[3,4-c]pyridin-2-yl)(6-fluoro-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(6-fluoro-1,2,3,4-tetrahydroquinolin-4-yl)methanone

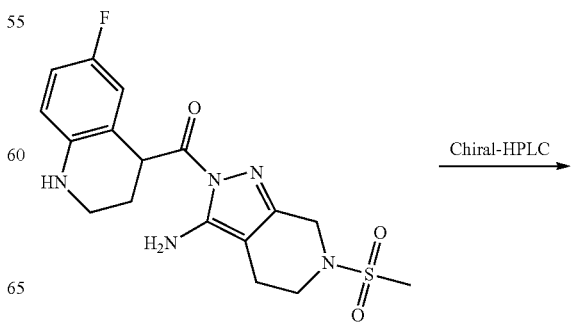

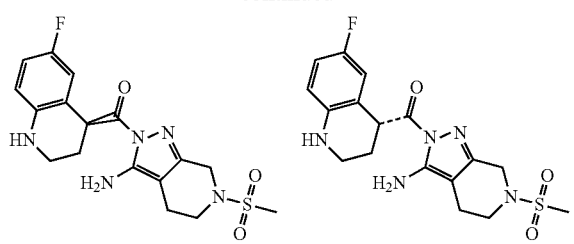

(3-amino-6-(methylsulfonyl)-4,5,6,7-tetrahydropyrazolo[3,4-c]pyridin-2-yl)(6-fluoro-1,2,3,4-tetrahydroquinolin-4-yl)methanone (50 mg, 0.13 mmol, 1.00 equiv) was separated by Prep-chiral-HPLC with the following conditions: Column: Chiralpak IA, 2×25 cm, 5 um; Mobile Phase A: Hex-HPLC, Mobile Phase B: EtOH-HPLC; Flow rate: 17 mL/min; Gradient: 50 B to 50 B in 24 min; 220/254 nm;

Enantiomer A, first eluting compound. Example 19: This resulted in 17.0 mg (34%) of (R*)-(3-amino-6-(methylsulfonyl)-4,5,6,7-tetrahydropyrazolo[3,4-c]pyridin-2-yl)(6-fluoro-1,2,3,4-tetrahydroquinolin-4-yl)methanone as a white solid. Rt1: 9.64 min. MS (ES, m/z) [M+H]+: 394; (DMSO-d6, 400 MHz, ppm): δ 6.82-6.77 (m, 1H), 6.69-6.65 (m, 3H), 6.54-6.49 (m, 1H), 5.82 (s, 1H), 4.99-4.96 (m, 1H), 4.24 (s, 2H), 3.42-3.40 (m, 2H), 3.25-3.14 (m, 2H), 2.97 (s, 3H), 2.47-2.45 (m, 2H), 2.09-1.99 (m, 2H).

Enantiomer B, second eluting compound. Example 18: This resulted in 13.9 mg (28%) of (S*)-(3-amino-6-(methylsulfonyl)-4,5,6,7-tetrahydropyrazolo[3,4-c]pyridin-2-yl)(6-fluoro-1,2,3,4-tetrahydroquinolin-4-yl)methanone as a white solid. Rt2: 11.58 min. MS (ES, m/z) [M+H]+: 394; (DMSO-d6, 400 MHz, ppm): δ 6.82-6.77 (m, 1H), 6.69-6.65 (m, 3H), 6.53-6.49 (m, 1H), 5.82 (s, 1H), 4.99-4.96 (m, 1H), 4.24 (s, 2H), 3.43-3.41 (m, 2H), 3.26-3.14 (m, 2H), 2.97 (s, 3H), 2.47-2.45 (m, 2H), 2.10-1.98 (m, 2H).

Example 20 & 21: (3-amino-6-ethyl-4,5,6,7-tetrahydropyrazolo[3,4-c]pyridin-2-yl)(1,2,3,4-tetrahydroquinolin-4-yl)methanone and (3-amino-6-ethyl-4,5,6,7-tetrahydropyrazolo[3,4-c]pyridin-1-yl)(1,2,3,4-tetrahydroquinolin-4-yl)methanone

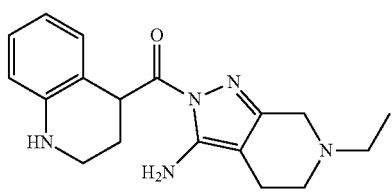

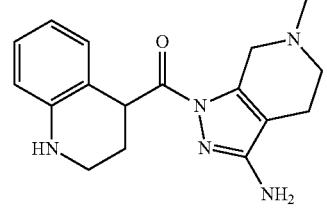

Step 1. Tert-butyl 3-amino-6-benzyl-4,5,6,7-tetrahydropyrazolo[3,4-c]pyridine-2-carboxylate

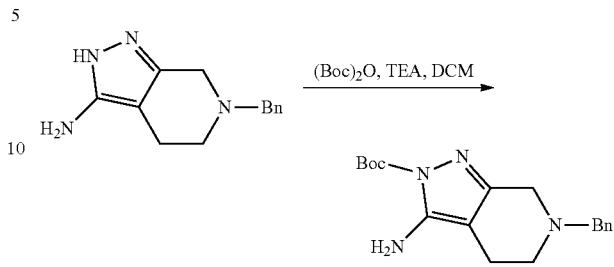

Into a 50-mL round-bottom flask, was placed 6-benzyl-4,5,6,7-tetrahydro-2H-pyrazolo[3,4-c]pyridin-3-amine (500 mg, 2.19 mmol, 1.00 equiv), dichloromethane (10 mL), TEA (665 mg, 6.60 mmol, 3.00 equiv), di-tert-butyl dicarbonate (478 mg, 2.19 mmol, 1.00 equiv). The resulting solution was stirred for 16 h at room temperature. The resulting mixture was concentrated under vacuum. The residue was purified by preparative TLC (EA:PE=1:1). This resulted in 548 mg (76%) of tert-butyl 3-amino-6-benzyl-4,5,6,7-tetrahydropyrazolo[3,4-c]pyridine-2-carboxylate as yellow oil. MS (ES, m/z) [M+H]+: 329.

Step 2. Tert-butyl 3-amino-4,5,6,7-tetrahydropyrazolo[3,4-c]pyridine-2-carboxylate

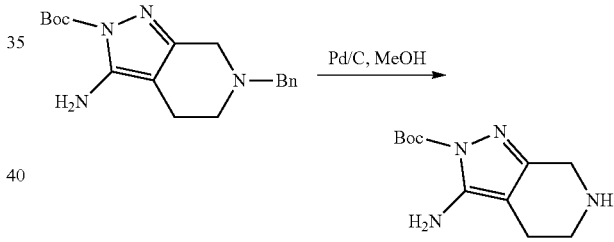

Into a 50-mL round-bottom flask, was placed tert-butyl 3-amino-6-benzyl-4,5,6,7-tetrahydropyrazolo[3,4-c]pyridine-2-carboxylate (548 mg, 1.67 mmol, 1.00 equiv), methanol (20 mL), Palladium carbon (10%, 500 mg). The flask was evacuated and flushed three times with nitrogen, followed by flushing with hydrogen. The mixture was stirred 16 h at room temperature under an atmosphere of hydrogen (balloon). The solid was filtered out. The resulting mixture was concentrated under vacuum. This resulted in 392 mg (99%) of tert-butyl 3-amino-4,5,6,7-tetrahydropyrazolo[3,4-c]pyridine-2-carboxylate as yellow oil. MS (ES, m/z) [M+H]+: 239.

Step 3. tert-butyl 3-amino-6-ethyl-4,5,6,7-tetrahydropyrazolo[3,4-c]pyridine-2-carboxylate

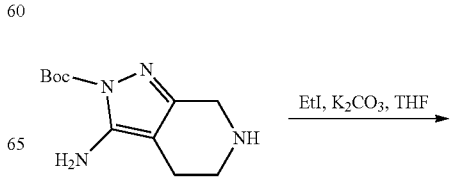

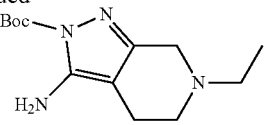

Into a 50-mL round-bottom flask, was placed tert-butyl 3-amino-4,5,6,7-tetrahydro-2H-pyrazolo[3,4-c]pyridine-2-carboxylate (150 mg, 0.63 mmol, 1.00 equiv), tetrahydrofuran (10 mL), potassium carbonate (148 mg, 1.07 mmol, 1.10 equiv). This was followed by the addition of a solution of iodoethane (261 mg, 1.67 mmol, 3.00 equiv) in tetrahydrofuran (5 mL) at room temperature. The resulting solution was stirred for 16 h at 40° C. The resulting mixture was concentrated under vacuum. The residue was purified by preparative TLC (PE:EA=1:1). This resulted in 78 mg (47%) of tert-butyl 3-amino-6-ethyl-4,5,6,7-tetrahydropyrazolo[3,4-c]pyridine-2-carboxylate as yellow oil. MS (ES, m/z) [M+H]+: 267.

Step 4. 6-ethyl-4,5,6,7-tetrahydro-2H-pyrazolo[3,4-c]pyridin-3-amine

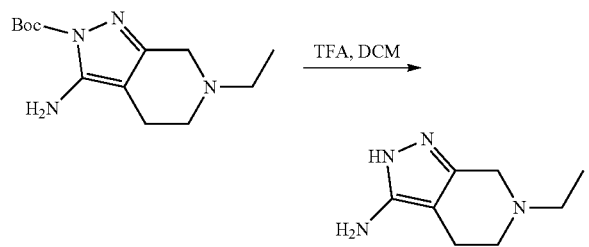

Into a 50-mL round-bottom flask, was placed tert-butyl 3-amino-6-ethyl-4,5,6,7-tetrahydropyrazolo[3,4-c]pyridine-2-carboxylate (61 mg, 0.23 mmol, 1.00 equiv), dichloromethane (4 mL), trifluoroacetic acid (1 mL). The resulting solution was stirred for 2.5 h at room temperature. The resulting mixture was concentrated under vacuum. After add water (30 ml), hydrochloric acid (1 moL/L) (0.2 mL). The mixture was sent to freeze. This resulted in 57.9 mg (152%) of 6-ethyl-4,5,6,7-tetrahydro-2H-pyrazolo[3,4-c]pyridin-3-amine salt as a white solid. MS (ES, m/z) [M+H]+: 167.

Step 5. (3-amino-6-ethyl-4,5,6,7-tetrahydropyrazolo[3,4-c]pyridin-2-yl)(1,2,3,4-tetrahydroquinolin-4-yl)methanone and (3-amino-6-ethyl-4,5,6,7-tetrahydropyrazolo[3,4-c]pyridin-1-yl)(1,2,3,4-tetrahydroquinolin-4-yl)methanone

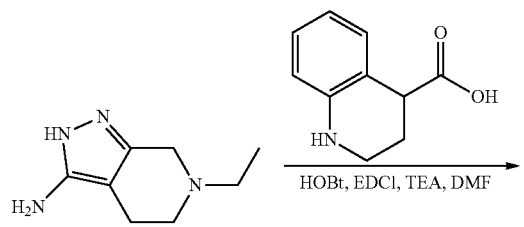

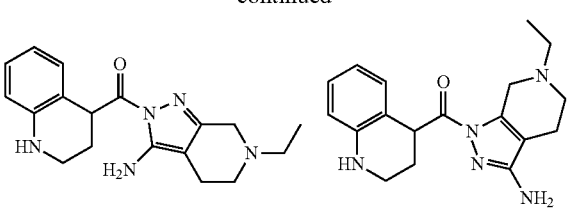

Into a 100-mL round-bottom flask, was placed 6-ethyl-4,5,6,7-tetrahydro-2H-pyrazolo[3,4-c]pyridin-3-amine salt (57 mg, 0.34 mmol, 1.00 equiv), N,N-dimethylformamide (10 mL), HOBt (36 mg, 0.27 mmol, 1.50 equiv), EDCI (50 mg, 0.26 mmol, 1.50 equiv), TEA (89 mg, 0.88 mmol, 5.00 equiv), 1,2,3,4-tetrahydroquinoline-4-carboxylic acid (37 mg, 0.21 mmol, 1.20 equiv). The resulting solution was stirred for 7 h at room temperature. The reaction was then quenched by the addition of water (30 mL). The resulting solution was extracted with ethyl acetate (30 mL×3) and the organic layers combined. The resulting mixture was washed with Brine (100 mL×3). The mixture was concentrated under vacuum. The crude product was purified by Prep-HPLC with the following conditions: Column, XBridge C18 OBD Prep Column, 5 μm, 19 mm×250 mm; mobile phase, water (0.1% FA) and ACN (30.0% ACN up to 55.0% in 10 min); Detector, UV 254 nm.

Fraction A: The collected fraction was lyophilized to give 3.2 mg (3%) of (3-amino-6-ethyl-4,5,6,7-tetrahydropyrazolo[3,4-c]pyridin-2-yl)(1,2,3,4-tetrahydroquinolin-4-yl)methanone as a white solid. Rt2: 7.07 min. MS (ES, m/z) [M+H]+: 326. (300 MHz, DMSO-d6, ppm): δ 6.93-6.90 (m, 1H), 6.87 (d, J=1.2 Hz, 1H), 6.77-6.75 (m, 2H), 6.52-6.49 (m, 1H), 5.84 (s, 1H), 5.01-5.00 (m, 1H), 3.32-3.20 (m, 6H), 2.79-2.28 (m, 3H), 2.09 (s, 2H), 1.09 (s, 3H).

Fraction B: The collected fraction was lyophilized to give 2.8 mg (3%) of (3-amino-6-ethyl-4,5,6,7-tetrahydropyrazolo[3,4-c]pyridin-1-yl)(1,2,3,4-tetrahydroquinolin-4-yl)methanone as a white solid. Rt2: 6.73 min. MS (ES, m/z) [M+H]+: 326. (300 MHz, DMSO-d6, ppm): δ 6.94-6.88 (m, 1H), 6.76 (d, J=7.2 Hz, 1H), 6.50 (d, J=0.9 Hz, 1H), 5.78-5.80 (m, 1H), 5.64 (s, 1H), 4.90-4.91 (m, 1H), 3.67 (s, 2H), 3.32 (s, 2H), 3.30 (s, 2H), 2.73-2.27 (m, 4H), 2.02-1.99 (m, 2H), 1.12-1.04 (m, 3H).

Example 22 & 23: (3-amino-6-(methylsulfonyl)-4,5,6,7-tetrahydropyrazolo[3,4-c]pyridin-2-yl)(6-methoxy-1,2,3,4-tetrahydroquinolin-4-yl)methanone and (3-amino-6-(methylsulfonyl)-4,5,6,7-tetrahydropyrazolo[3,4-c]pyridin-1-yl)(6-methoxy-1,2,3,4-tetrahydroquinolin-4-yl)methanone

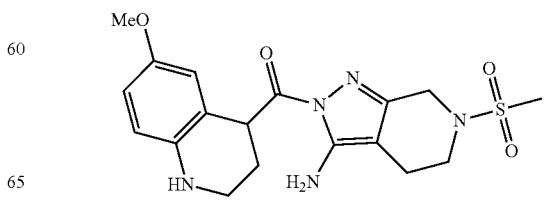

-continued

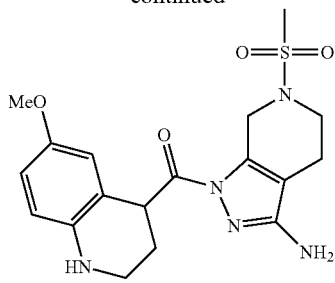

Step 1. Methyl 6-methoxyquinoline-4-carboxylate

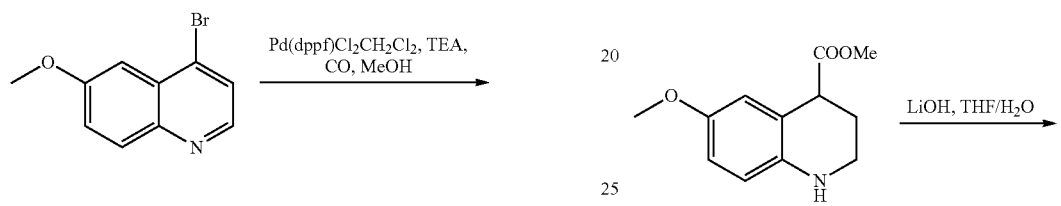

Into a 50-mL pressure tank reactor (60 atm) purged and maintained with an inert atmosphere of CO, was placed 4-bromo-6-methoxyquinoline (4 g, 16.80 mmol, 1.00 equiv), TEA (5.11 g, 50.50 mmol, 3.00 equiv), Pd(dppf)Cl$_2$CH$_2$Cl$_2$ (4.13 g, 5.05 mmol, 0.30 equiv), methanol (30 mL). The resulting solution was stirred overnight at 120° C. After cooled to room temperature, the resulting mixture was concentrated under vacuum. The residue was applied onto a silica gel column with ethyl acetate/petroleum ether (1/5). This resulted in 2 g (55%) of methyl 6-methoxyquinoline-4-carboxylate as a white solid. MS (ES, m/z) [M+H]+: 218.

Step 2. Methyl 6-methoxy-1,2,3,4-tetrahydroquinoline-4-carboxylate

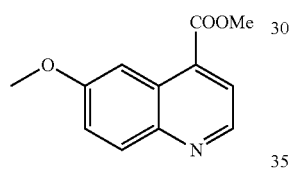

Into a 100-mL maintained with an inert atmosphere of H2, was placed methyl 6-methoxyquinoline-4-carboxylate (217 mg, 1.00 mmol, 1.00 equiv), Palladium carbon (10%, 217 mg), methanol (12 mL), AcOH (2 mL). The resulting solution was stirred overnight at 20° C. The solids were filtered out. The resulting mixture was concentrated under vacuum. This resulted in 230 mg (crude) of methyl 6-methoxy-1,2,3,4-tetrahydroquinoline-4-carboxylate as brown oil. MS (ES, m/z) [M+H]+: 222.

Step 3.
6-methoxy-1,2,3,4-tetrahydroquinoline-4-carboxylic acid

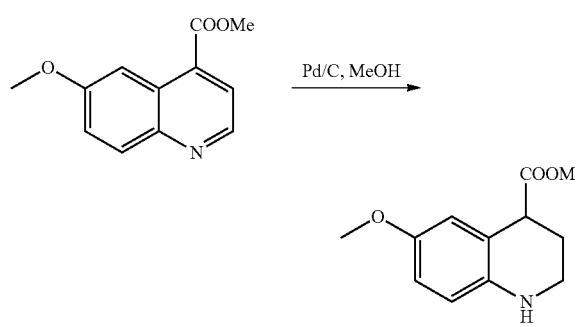

Into a 100-mL round-bottom flask, was placed methyl 6-methoxy-1,2,3,4-tetrahydroquinoline-4-carboxylate (221 mg, 1.00 mmol, 1.00 equiv), methanol (8 mL), tetrahydrofuran (2 mg, 0.03 mmol, 0.03 equiv), LiOH (120 mg, 5.01 mmol, 5.00 equiv), water (1 ml). The resulting solution was stirred overnight at 25° C. The resulting mixture was concentrated under vacuum. The resulting solution was diluted with H2O (20 mL). The pH value of the solution was adjusted to 4 with hydrochloric acid (1 mol/L). The resulting solution was extracted with ethyl acetate (20 mL×3) and the organic layers combined and concentrated under vacuum. The residue was applied onto a silica gel column with dichloromethane/methanol (10/1). This resulted in 40 mg (19%) of 6-methoxy-1,2,3,4-tetrahydroquinoline-4-carboxylate as a brown solid. MS (ES, m/z) [M+H]+: 208.

Step 4. (3-amino-6-(methylsulfonyl)-4,5,6,7-tetrahydropyrazolo[3,4-c]pyridin-2-yl)(6-methoxy-1,2,3,4-tetrahydroquinolin-4-yl)methanone and (3-amino-6-(methylsulfonyl)-4,5,6,7-tetrahydropyrazolo[3,4-c]pyridin-1-yl)(6-methoxy-1,2,3,4-tetrahydroquinolin-4-yl)methanone

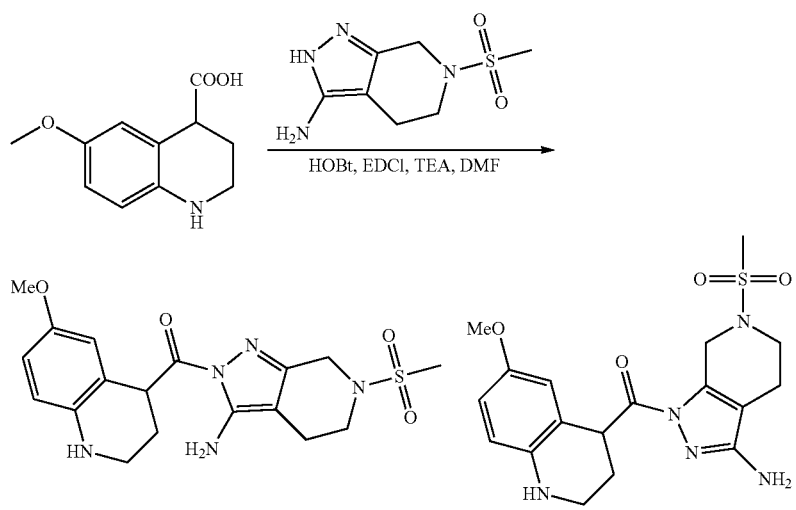

Into a 50-mL round-bottom flask, was placed 6-methoxy-1,2,3,4-tetrahydroquinoline-4-carboxylic acid (60 mg, 0.29 mmol, 1.00 equiv), HOBt (59 mg, 0.44 mmol, 1.50 equiv), EDCI (84 mg, 0.44 mmol, 1.50 equiv), N,N-dimethylformamide (3 mL), 6-methanesulfonyl-4,5,6,7-tetrahydro-2H-pyrazolo[3,4-c]pyridin-3-amine (75 mg, 0.35 mmol, 1.20 equiv), TEA (88 mg, 0.87 mmol, 3.00 equiv). The resulting solution was stirred for 3 h at 25° C. The reaction mixture was diluted with DCM (80 mL), washed with H2O (50 mL×3) and brine (50 mL×3) and dried with Na2SO4. After filtration, the filtrate was concentrated under reduced pressure. The crude product was purified by Prep-HPLC with the following conditions (Analyse HPLC-SHIMADZU): Column: XBridge Prep C18 OBD Column 19×150 mm 5 um; Mobile Phase A: water (10 mM NH4HCO3), Mobile Phase B: ACN; Flow rate: 20 mL/min; Gradient: 25% B to 25% B in 11 min; 254/220 nm;

Fraction A: The collected fraction was lyophilized to give 1.3 mg (1%) of (3-amino-6-(methylsulfonyl)-4,5,6,7-tetrahydropyrazolo[3,4-c]pyridin-2-yl)(6-methoxy-1,2,3,4-tetrahydroquinolin-4-yl)methanone as a white solid. Rt2:10.27 min. MS (ES, m/z) [M+H]+: 406. (300 MHz, DMSO-d6, ppm): δ 6.61-6.57 (m, 3H), 6.48 (s, 2H), 5.42 (s, 1H), 4.98-4.95 (m, 1H), 4.23 (s, 2H), 3.54 (s, 3H), 3.43- 3.41 (m, 2H), 3.22-3.09 (m, 2H), 2.95 (s, 3H), 2.49-2.44 (s, 2H), 2.03-1.97 (m, 2H).

Fraction B: The collected fraction was lyophilized to give 4.5 mg (4%) of (3-amino-6-(methylsulfonyl)-4,5,6,7-tetrahydropyrazolo[3,4-c]pyridin-1-yl)(6-methoxy-1,2,3,4-tetrahydroquinolin-4-yl)methanone as a white solid. Rt1: 7.13 min. MS (ES, m/z) [M+H]+: 406. (300 MHz, DMSO-d6, ppm): δ 6.60-6.56 (m, 1H), 6.46-6.43 (m, 2H), 5.77 (s, 2H), 5.39 (s, 1H), 4.89-4.86 (m, 1H), 4.51 (s, 2H), 3.54 (s, 3H), 3.43-3.41 (m, 2H), 3.22-3.10 (m, 2H), 2.94 (s, 3H), 2.49-2.44 (s, 2H), 2.03-1.97 (m, 2H).

Example 24 & 25: (3-amino-6-(methylsulfonyl)-4,5,6,7-tetrahydropyrazolo[3,4-c]pyridin-2-yl)(6-(trifluoromethyl)-1,2,3,4-tetrahydroquinolin-4-yl)methanone and (3-amino-6-(methylsulfonyl)-4,5,6,7-tetrahydropyrazolo[3,4-c]pyridin-1-yl)(6-(trifluoromethyl)-1,2,3,4-tetrahydroquinolin-4-yl)methanone

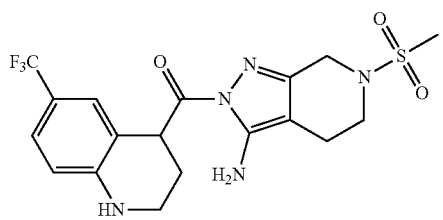

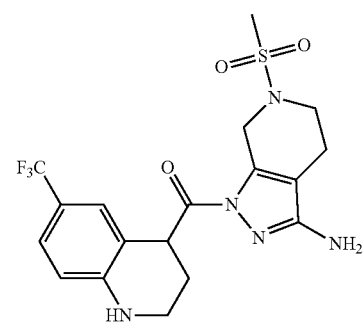

Step 1. 6-(trifluoromethyl)quinolin-4-yl trifluoromethanesulfonate

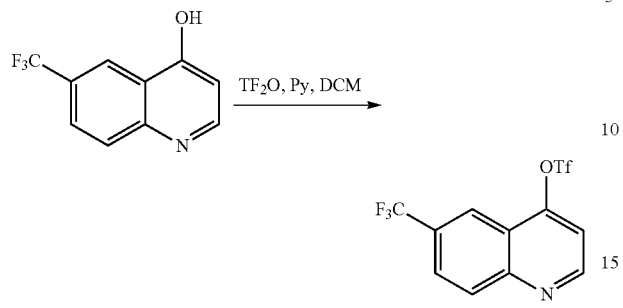

Into a 500-mL round-bottom flask, was placed 6-(trifluoromethyl)quinolin-4-ol (2.0 g, 9.38 mmol, 1.00 equiv), dichloromethane (150 mL), pyridine (1.5 g, 18.96 mmol, 2.00 equiv), This was followed by the addition of (trifluoromethane)sulfonyl trifluoromethanesulfonate (3.18 g, 11.27 mmol, 1.20 equiv), which was added dropwise with stirring at 0 degree C. The resulting solution was stirred overnight at room temperature. The resulting solution was extracted with hydrochloric acid (1 mol/L, 100 mL×2) and the organic layers combined and dried over anhydrous sodium sulfate. The residue was applied onto a silica gel column with ethyl acetate/petroleum ether (0-20%). This resulted in 0.8 g (25%) of 6-(trifluoromethyl)quinolin-4-yl trifluoromethanesulfonate as a white solid. MS (ES, m/z) [M+H]+: 346.

Step 2. Methyl 6-(trifluoromethyl)quinoline-4-carboxylate

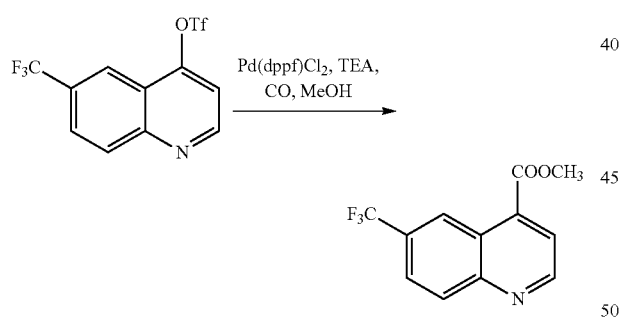

Into a 50-mL pressure tank reactor (60 atm) purged and maintained with an inert atmosphere of CO, was placed 6-(trifluoromethyl)quinolin-4-yl trifluoromethanesulfonate (820 mg, 2.38 mmol, 1.00 equiv), Pd(dppf)Cl2.CH2Cl2 (388 mg, 0.47 mmol, 0.20 equiv), TEA (1.2 g, 11.88 mmol, 5.00 equiv), methanol (10 mL). The resulting solution was stirred overnight at 80° C. in an oil bath. After cooled to room temperature, the reaction was then quenched by the addition of DCM (50 mL). The resulting solution was washed with water (50 mL×3), the organic layers combined and dried over anhydrous sodium sulfate. After filtration, the filtrate was concentrated under reduced pressure. The residue was purified by preparative TLC (EtOAc:PE=1:2). This resulted in 210 mg (35%) of methyl 6-(trifluoromethyl) quinoline-4-carboxylate as a white solid. MS (ES, m/z) [M+H]+: 256.

Step 3. Methyl 6-(trifluoromethyl)-1,2,3,4-tetrahydroquinoline-4-carboxylate

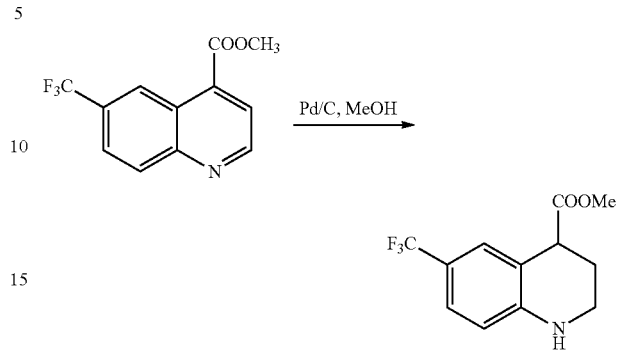

Into a 100-mL round-bottom flask, was placed methyl 6-(trifluoromethyl)quinoline-4-carboxylate (100 mg, 0.39 mmol, 1.00 equiv), methanol (10 mL), Palladium carbon (10%, 100 mg). The flask was evacuated and flushed three times with nitrogen, followed by flushing with hydrogen. The mixture was stirred 4 h at room temperature under an atmosphere of hydrogen (balloon). The solids were filtered out. The resulting mixture was concentrated under vacuum. This resulted in 98.2 mg (97%) of methyl 6-(trifluoromethyl)-1,2,3,4-tetrahydroquinoline-4-carboxylate as colorless oil. MS (ES, m/z) [M+H]+: 260.

Step 4. 6-(trifluoromethyl)-1,2,3,4-tetrahydroquinoline-4-carboxylic acid

Into a 100-mL round-bottom flask, was placed methyl 6-(trifluoromethyl)-1,2,3,4-tetrahydroquinoline-4-carboxylate (98 mg, 0.38 mmol, 1.00 equiv), tetrahydrofuran (20 mL), water (5 mL), LiOH (45 mg, 1.88 mmol, 5.00 equiv). The resulting solution was stirred overnight at room temperature. The reaction was then quenched by the addition of water/ice (20 mL). The resulting solution was extracted with dichloromethane (25 mL×3) and the aqueous layers combined. The pH value of the solution was adjusted to 4-6 with hydrochloric acid (1 mol/L). The resulting solution was extracted with dichloromethane (40 mL×3) and the organic layers combined and dried over anhydrous sodium sulfate and concentrated under vacuum. This resulted in 87 mg (94%) of 6-(trifluoromethyl)-1,2,3,4-tetrahydroquinoline-4-carboxylic acid as a red solid. MS (ES, m/z) [M+H]+: 246.

Step 5. (3-amino-6-(methylsulfonyl)-4,5,6,7-tetrahydropyrazolo[3,4-c]pyridin-2-yl) (6-(trifluoromethyl)-1,2,3,4-tetrahydroquinolin-4-yl)methanone and (3-amino-6-(methylsulfonyl)-4,5,6,7-tetrahydropyrazolo[3,4-c]pyridin-1-yl)(6-(trifluoromethyl)-1,2,3,4-tetrahydroquinolin-4-yl)methanone

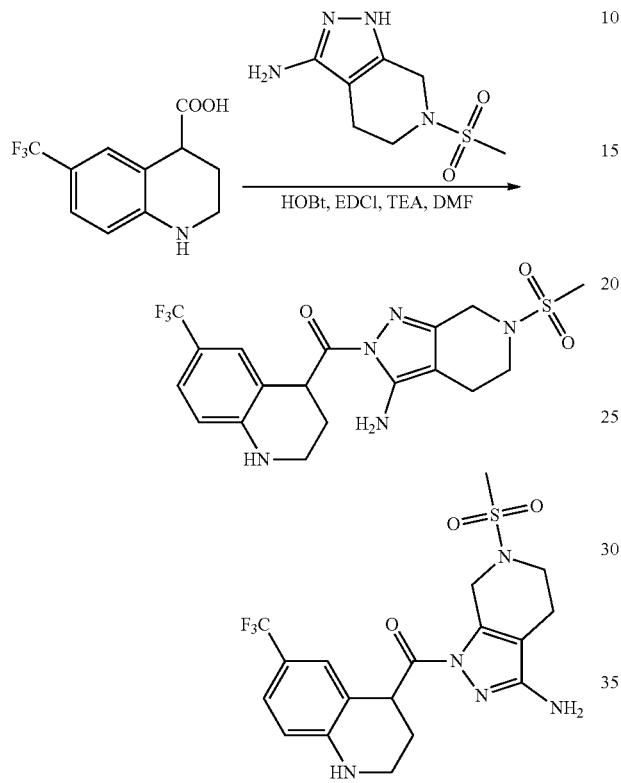

Into a 40-mL round-bottom flask, was placed 6-(trifluoromethyl)-1,2-dihydroquinoline-4-carboxylic acid (60 mg, 0.25 mmol, 1.00 equiv), HOBt (49 mg, 0.36 mmol, 1.50 equiv), EDCI (70.2 mg, 0.37 mmol, 1.50 equiv), TEA (185 mg, 1.83 mmol, 7.50 equiv), N,N-dimethylformamide (8.0 mL), 6-methanesulfonyl-4,5,6,7-tetrahydro-2H-pyrazolo[3,4-c]pyridin-3-amine (53 mg, 0.25 mmol, 1.00 equiv). The resulting solution was stirred for 4 h at 20° C. The reaction was then quenched by the addition of water/ice (30 mL). The resulting solution was extracted with ethyl acetate (30 mL×3) and the organic layers combined and dried over anhydrous sodium sulfate. The solids were filtered out. The resulting mixture was concentrated under vacuum. The crude product was purified by Prep-HPLC with the following conditions: Column, XSelect CSH Prep C18 OBD Column, 5 um, 19×150 mm; mobile phase, water (0.1% FA) and ACN (30.0% ACN up to 60.0% in 10 min); Detector, UV 254/220 nm.

Fraction A: The collected fraction was lyophilized to give 2.8 mg (3%) of (3-amino-6-(methylsulfonyl)-4,5,6,7-tetrahydropyrazolo[3,4-c]pyridin-2-yl)(6-(trifluoromethyl)-1,2,3,4-tetrahydroquinolin-4-yl)methanone as a white solid. Rt2: 9.65 min. MS (ES, m/z) [M+H]+: 444. (400 MHz, DMSO-d6, ppm) δ 7.23-7.21 (m, 1H), 7.16-7.15 (m, 1H), 6.69-6.61 (m, 4H), 5.03-5.00 (m, 1H), 4.24 (s, 2H), 3.43-3.40 (m, 2H), 3.28-3.26 (m, 2H), 2.97 (s, 3H), 2.46-2.42 (m, 2H), 2.11-2.08 (m, 1H), 2.03-1.99 (m, 1H).

Fraction B: The collected fraction was lyophilized to give 9.8 mg (9%) of (3-amino-6-(methylsulfonyl)-4,5,6,7-tetrahydropyrazolo[3,4-c]pyridin-1-yl)(6-(trifluoromethyl)-1,2,3,4-tetrahydroquinolin-4-yl)methanone as a white solid. Rt1: 8.78 min. MS (ES, m/z): [M+H]+ 0.444. (300 MHz, DMSO-d6, ppm) δ 7.23-7.15 (m, 2H), 6.67-6.60 (m, 2H), 5.85 (s, 2H), 4.94-4.90 (m, 1H), 4.53 (s, 2H), 3.50-3.36 (m, 2H), 3.27-3.22 (m, 2H), 2.96 (s, 3H), 2.47-2.43 (m, 2H), 2.15-2.09 (m, 1H), 2.03-1.96 (m, 1H).

Example 26 & 27: (3-amino-6-(methylsulfonyl)-4,5,6,7-tetrahydropyrazolo[3,4-c]pyridin-2-yl)(2-methyl-4,5,6,7-tetrahydro-2H-isoindol-4-yl)methanone and (3-amino-6-(methylsulfonyl)-4,5,6,7-tetrahydropyrazolo[3,4-c]pyridin-1-yl)(2-methyl-4,5,6,7-tetrahydro-2H-isoindol-4-yl)methanone Step 1. 6,7-dihydro-2H-isoindol-4(5H)-one Into a 500-mL 3-necked round-bottom flask purged and maintained with an inert atmosphere of nitrogen, was placed a solution of sodium hydride (5.1 g, 1.50 equiv, 60%) in tetrahydrofuran (50 mL), cyclohex-2-en-1-one (7.8 g, 81.14 mmol, 1.00 equiv) and TosMic (16 g, 1.00 equiv) in tetrahydrofuran (50 mL) and DMSO (80 mL) was added with stirring at 0° C. The resulting solution was stirred for 15 h at room temperature. The reaction was then quenched by the addition of water/ice (100 mL). The resulting solution was extracted with ethyl acetate (150 mL×3) and the organic layers combined and concentrated under vacuum. The residue was applied onto a silica gel column with ethyl acetate/hexane (1:10). This resulted in 6.1 g (56%) of 6,7-dihydro-2H-isoindol-4(5H)-one as a light yellow solid. MS (ES, m/z) [M+H]+: 136.

Step 2.
2-methyl-6,7-dihydro-2H-isoindol-4(5H)-one

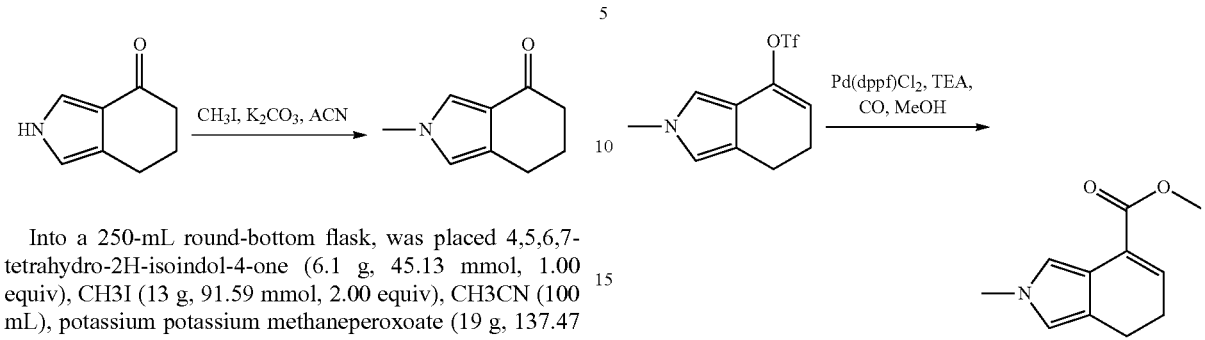

Into a 250-mL round-bottom flask, was placed 4,5,6,7-tetrahydro-2H-isoindol-4-one (6.1 g, 45.13 mmol, 1.00 equiv), CH3I (13 g, 91.59 mmol, 2.00 equiv), CH3CN (100 mL), potassium potassium methaneperoxoate (19 g, 137.47 mmol, 3.00 equiv). The resulting solution was stirred for 15 h at 85° C. After cooled to room temperature, the solids were filtered out. The resulting mixture was concentrated under vacuum. The residue was applied onto a silica gel column with ethyl acetate/hexane (1:3). This resulted in 5 g (74%) of 2-methyl-6,7-dihydro-2H-isoindol-4(5H)-one as a yellow liquid. MS (ES, m/z) [M+H]+: 150.

Step 3. 2-methyl-6,7-dihydro-2H-isoindol-4-yl trifluoromethanesulfonate

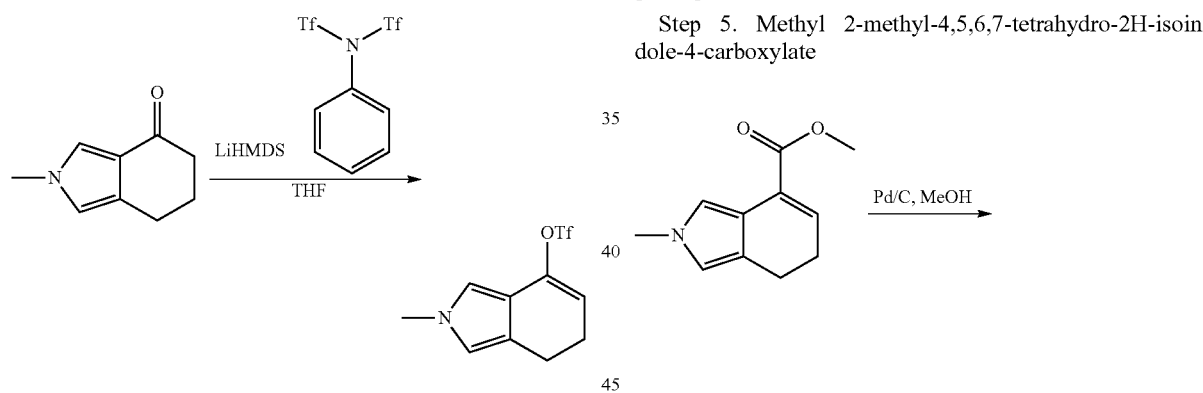

Into a 250-mL 3-necked round-bottom flask purged and maintained with an inert atmosphere of nitrogen, was placed 2-methyl-4,5,6,7-tetrahydro-2H-isoindol-4-one (2 g, 13.41 mmol, 1.00 equiv), tetrahydrofuran (80 mL), LiHMDS (25 mL, 25.48 mmol, 1.90 equiv) was added with stirring at −78° C.

The above mixture was stirred for 5 min at −78° C. A solution of 1,1,1-trifluoro-N-phenyl-N-(trifluoromethane) sulfonyl methanesulfonamide (4.5 g, 25.50 mmol, 1.90 equiv) in tetrahydrofuran (10 mL) was added slowly at −78° C. The temperature was increased to room temperature naturally. The resulting solution was stirred for 15 h at room temperature. The reaction was then quenched by the addition of water/ice (100 mL). The resulting solution was extracted with ethyl acetate (100 mL×3) and the organic layers combined and dried over anhydrous sodium sulfate and concentrated under vacuum. This resulted in 6 g (crude) of 2-methyl-6,7-dihydro-2H-isoindol-4-yl trifluoromethanesulfonate as brown oil. MS (ES, m/z) [M+H]+: 282.

Step 4. Methyl 2-methyl-6,7-dihydro-2H-isoindole-4-carboxylate

Into a 30-mL pressure tank reactor (CO, 60 atm), was placed 2-methyl-6,7-dihydro-2H-isoindol-4-yl trifluoromethanesulfonate (6 g, 21.33 mmol, 1.00 equiv), pd(dppf)Cl2CH2Cl2 (0.46 g, 0.10 equiv), methanol (10 mL), TEA (7.3 mg, 5.00 equiv). The resulting solution was stirred for 15 h at 75° C. After cooled to room temperature, the reaction mixture was concentrated and the residue was applied onto a silica gel column with ethyl acetate/PE (1:10). This resulted in 3 g (74%) of methyl 2-methyl-6,7-dihydro-2H-isoindole-4-carboxylate as brown oil. MS (ES, m/z) [M+H]+: 192.

Step 5. Methyl 2-methyl-4,5,6,7-tetrahydro-2H-isoindole-4-carboxylate

Into a 100-mL round-bottom flask, was placed methyl 2-methyl-6,7-dihydro-2H-isoindole-4-carboxylate (100 mg, 0.52 mmol, 1.00 equiv), methanol (10 mL), Palladium carbon (10%, 50 mg). The flask was evacuated and flushed three times with nitrogen, followed by flushing with hydrogen. The mixture was stirred 4 h at room temperature under an atmosphere of hydrogen (balloon). The solids were filtered out. The filtrate was concentrated under vacuum. This resulted in 100 mg (99%) of methyl 2-methyl-4,5,6,7-tetrahydro-2H-isoindole-4-carboxylate as yellow oil. MS (ES, m/z) [M+H]+: 194.

Step 6. 2-methyl-4,5,6,7-tetrahydro-2H-isoindole-4-carboxylic acid

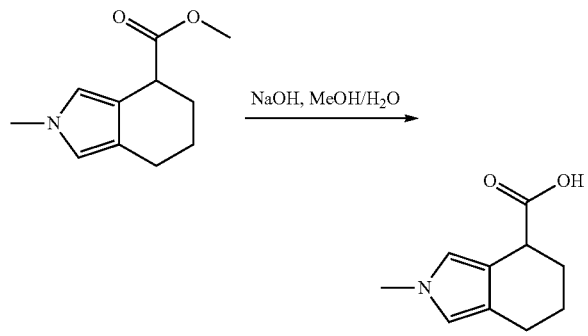

Into a 100-mL round-bottom flask, was placed methyl 2-methyl-4,5,6,7-tetrahydro-2H-isoindole-4-carboxylate (110 mg, 0.57 mmol, 1.00 equiv), sodium hydroxide (45.6 mg, 1.14 mmol, 2.00 equiv), water (10 mL), methanol (20 mL). The resulting solution was stirred for 15 h at room temperature. The pH value of the solution was adjusted to 6 with hydrochloric acid (1 mol/L). The resulting solution was extracted with ethyl acetate (80 mL×3) and the organic layers combined and concentrated under vacuum. This resulted in 30 mg (29%) of 2-methyl-4,5,6,7-tetrahydro-2H-isoindole-4-carboxylic acid as a yellow solid. MS (ES, m/z) [M+H]+: 180.

Step 7. (3-amino-6-(methylsulfonyl)-4,5,6,7-tetrahydropyrazolo[3,4-c]pyridin-2-yl)(2-methyl-4,5,6,7-tetrahydro-2H-isoindol-4-yl)methanone and (3-amino-6-(methylsulfonyl)-4,5,6,7-tetrahydropyrazolo[3,4-c]pyridin-1-yl)(2-methyl-4,5,6,7-tetrahydro-2H-isoindol-4-yl)methanone

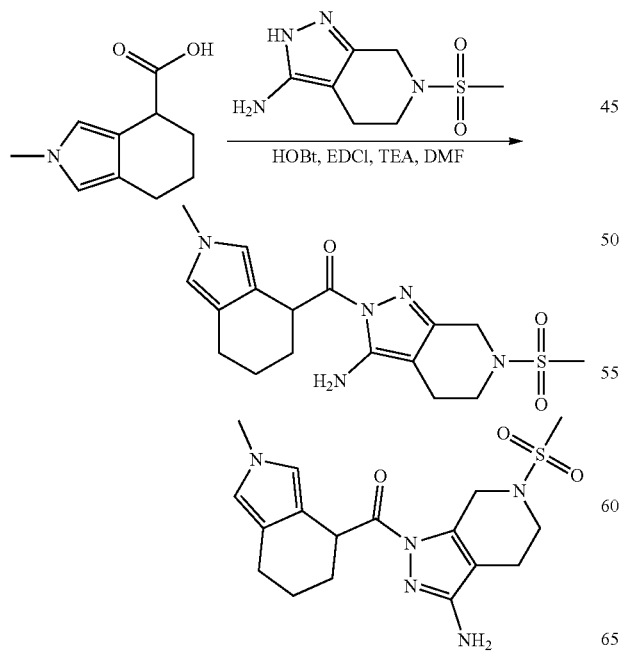

Into a 100-mL round-bottom flask, was placed 2-methyl-4,5,6,7-tetrahydro-2H-isoindole-4-carboxylic acid (30 mg, 0.17 mmol, 1.00 equiv), 6-methanesulfonyl-4,5,6,7-tetrahydro-2H-pyrazolo[3,4-c]pyridin-3-amine (36.2 mg, 0.17 mmol, 1.00 equiv), EDCI (48.3 mg, 0.25 mmol, 1.50 equiv), HOBt (33.8 mg, 0.25 mmol, 1.50 equiv), N,N-dimethylformamide (10 mL), TEA (85.9 mg, 0.85 mmol, 5.00 equiv). The resulting solution was stirred for 6 h at room temperature. The reaction was then quenched by the addition of water (100 mL). The resulting solution was extracted with ethyl acetate (150 mL×3) and the organic layers combined and concentrated under vacuum. The crude product was purified by Prep-HPLC with the following conditions: Column, XBridge Shield RP18 OBD Column, 5 um, 19×150 mm; mobile phase, water (0.1% FA) and ACN (25.0% ACN up to 60.0% in 7 min); Detector, UV 254 nm.

Fraction A: The collected fraction was lyophilized to give 2.8 mg (4%) of (3-amino-6-(methylsulfonyl)-4,5,6,7-tetrahydropyrazolo[3,4-c]pyridin-2-yl)(2-methyl-4,5,6,7-tetrahydro-2H-isoindol-4-yl)methanone as a white solid. Rt2: 6.20 min. MS (ES, m/z) [M+H]+: 378. (DMSO-d6, 300 MHz, ppm): δ 6.59 (s, 1H), 6.37-6.36 (m, 1H), 6.18-6.17 (m, 1H), 4.75-4.76 (m, 1H), 4.23-4.22 (m, 2H), 3.46 (s, 3H), 3.43-3.40 (m, 2H), 2.97 (s, 3H), 2.47-2.43 (m, 4H), 1.91-1.88 (m, 3H), 1.63-1.57 (m, 1H).

Fraction B: The collected fraction was lyophilized to give 1.1 mg (2%) of (3-(3-amino-6-(methylsulfonyl)-4,5,6,7-tetrahydropyrazolo[3,4-c]pyridin-1-yl)(2-methyl-4,5,6,7-tetrahydro-2H-isoindol-4-yl)methanone as a white solid. Rt1: 5.60 min. MS (ES, m/z) [M+H]+: 378. (DMSO-d6, 300 MHz, ppm): δ 6.36-6.35 (m, 1H), 6.20-6.19 (m, 1H), 5.70 (s, 2H), 4.68-4.63 (m, 1H), 4.52 (s, 2H), 3.47 (s, 3H), 3.46-3.36 (m, 2H), 2.96 (s, 3H), 2.53-2.52 (m, 1H), 2.47-2.43 (m, 3H), 1.93-1.82 (m, 3H), 1.58-1.55 (m, 1H).

Example 28 & 29: (3-amino-6-phenyl-4,5,6,7-tetrahydropyrazolo[3,4-c]pyridin-2-yl)(6-fluoro-1,2,3,4-tetrahydroquinolin-4-yl)methanone and (3-amino-6-phenyl-4,5,6,7-tetrahydropyrazolo[3,4-c]pyridin-1-yl)(6-fluoro-1,2,3,4-tetrahydroquinolin-4-yl)methanone

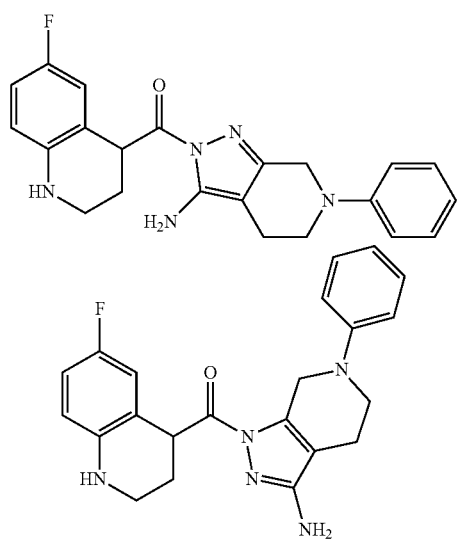

Step 1. Tert-butyl 3-amino-6-phenyl-4,5,6,7-tetrahydropyrazolo[3,4-c]pyridine-2-carboxylate

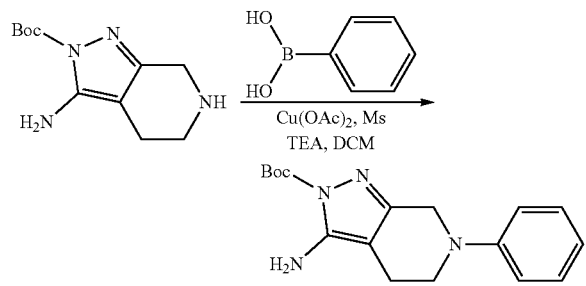

Into a 100-mL round-bottom flask, was placed tert-butyl 3-amino-4,5,6,7-tetrahydro-2H-pyrazolo[3,4-c]pyridine-2-carboxylate (720 mg, 3.02 mmol, 1.00 equiv), phenylboronic acid (293 mg, 2.40 mmol, 0.80 equiv), dichloromethane (20 mL), TEA (1.53 g, 15.12 mmol, 5.00 equiv), Cu(OAc)2 (821 mg, 4.52 mmol, 1.50 equiv), MS (1.4 g). The resulting solution was stirred for 16 h at room temperature. The resulting mixture was concentrated under vacuum. The residue was applied onto a silica gel column with dichloromethane/methanol (10:1). This resulted in 72 mg (8%) of tert-butyl 3-amino-6-phenyl-4,5,6,7-tetrahydropyrazolo[3,4-c]pyridine-2-carboxylate as yellow oil. MS (ES, m/z) [M+H]+: 315.

Step 2. HCl salt of 6-phenyl-4,5,6,7-tetrahydro-2H-pyrazolo[3,4-c]pyridin-3-amine

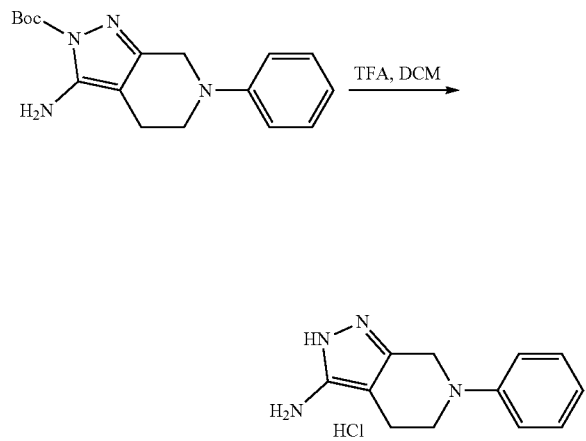

Into a 50-mL round-bottom flask, was placed tert-butyl 3-amino-6-phenyl-4,5,6,7-tetrahydro-2H-pyrazolo[3,4-c]pyridine-2-carboxylate (72 mg, 0.33 mmol, 1.00 equiv), dichloromethane (4 mL), trifluoroacetic acid (1 mL). The resulting solution was stirred for 1 h at room temperature. The resulting mixture was concentrated under vacuum. The resulting solution was diluted with 3 mL of ACN, 10 ml of H2O and 2 ml of hydrochloric acid (1 mol/L). The resulting mixture was lyophilized to give 15 mg (49%) of HCl salt of 6-phenyl-4,5,6,7-tetrahydro-2H-pyrazolo[3,4-c]pyridin-3-amine as a yellow solid. MS (ES, m/z) [M+H]+: 215.

Step 3. (3-amino-6-phenyl-4,5,6,7-tetrahydropyrazolo[3,4-c]pyridin-2-yl)(6-fluoro-1,2,3,4-tetrahydroquinolin-4-yl)methanone and (3-amino-6-phenyl-4,5,6,7-tetrahydropyrazolo[3,4-c]pyridin-1-yl)(6-fluoro-1,2,3,4-tetrahydroquinolin-4-yl)methanone

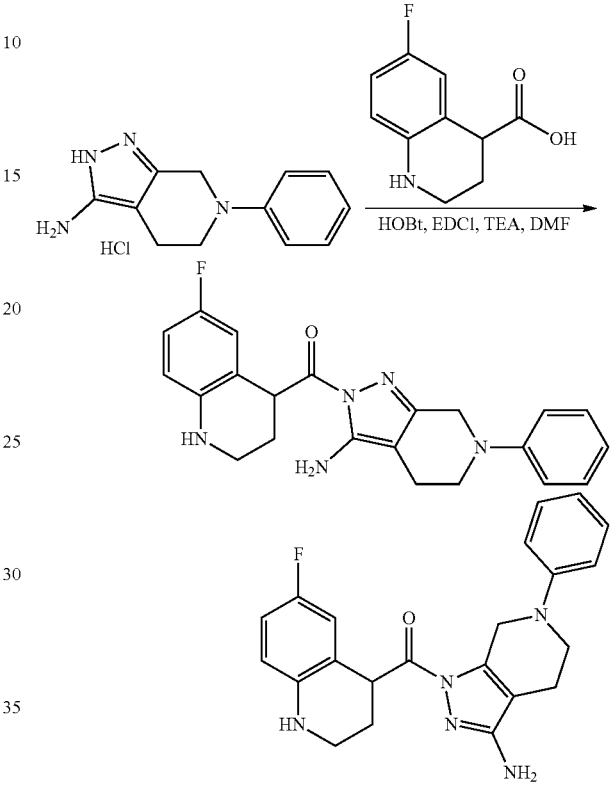

Into a 25-mL round-bottom flask, was placed HCl salt of 6-phenyl-4,5,6,7-tetrahydro-2H-pyrazolo[3,4-c]pyridin-3-amine (15 mg, 0.07 mmol, 1.00 equiv), 6-fluoro-1,2,3,4-tetrahydroquinoline-4-carboxylic acid (15 mg, 0.08 mmol, 1.00 equiv), HOBt (14 mg, 0.10 mmol, 1.50 equiv), EDCI (20 mg, 0.10 mmol, 1.50 equiv), TEA (21 mg, 0.21 mmol, 3.00 equiv), N,N-dimethylformamide (3 mL). The resulting solution was stirred for 5 h at room temperature. The reaction was then quenched by the addition of water (10 mL). The resulting solution was extracted with ethyl acetate (10 mL×3) and the organic layers combined and concentrated under vacuum. The crude product was purified by Prep-HPLC with the following conditions: Column: XBridge C18 OBD Prep Column, 5 μm, 19 mm×250 mm; Mobile Phase A: water (0.1% FA), Mobile Phase B: ACN; Flow rate: 20 mL/min; Gradient: 25% B to 45% B in 15 min; 254/220 nm;

Fraction A: The collected fraction was lyophilized to give 1.1 mg (4%) of (3-amino-6-phenyl-4,5,6,7-tetrahydropyrazolo[3,4-c]pyridin-2-yl)(6-fluoro-1,2,3,4-tetrahydroquinolin-4-yl)methanone as a white solid. Rt2: 13.70 min. MS (ES, m/z) [M+H]+: 392; (DMSO-d6, 300 MHz, ppm): δ 7.24-7.18 (m, 2H), 7.03-7.01 (m, 2H), 6.82-6.66 (m, 3H), 6.53-6.48 (m, 3H), 5.79 (s, 1H), 5.03-4.99 (m, 1H), 4.27 (s, 2H), 3.58-3.55 (m, 2H), 3.31-3.18 (m, 2H), 2.45-2.42 (m, 2H), 2.11-2.00 (m, 2H).

Fraction B: The collected fraction was lyophilized to give 2.5 mg (9%) of (3-amino-6-phenyl-4,5,6,7-tetrahydropyrazolo[3,4-c]pyridin-1-yl)(6-fluoro-1,2,3,4-tetrahydroquinolin-4-yl)methanone as a white solid. Rt1: 12.50 min. MS (ES, m/z) [M+H]+: 392. (DMSO-d6, 300 MHz, ppm): δ 7.24-7.19 (m, 2H), 6.97-6.94 (m, 2H), 6.81-6.67 (m, 3H), 6.53-6.48 (m, 1H), 5.77 (s, 1H), 5.74 (s, 2H), 4.92-4.89 (m, 1H), 4.48 (s, 2H), 3.55-3.52 (m, 2H), 3.31-3.27 (m, 1H), 3.18-3.12 (m, 1H), 2.46-2.44 (m, 2H), 2.11-1.97 (m, 2H).

Example 30 & 31 & 32 & 33: (3-amino-6-(methylsulfonyl)-4,5,6,7-tetrahydropyrazolo[3,4-c]pyridin-2-yl)(6-ethyl-1,2,3,4-tetrahydroquinolin-4-yl)methanone and (3-amino-6-(methylsulfonyl)-4,5,6,7-tetrahydropyrazolo[3,4-c]pyridin-1-yl)(6-ethyl-1,2,3,4-tetrahydroquinolin-4-yl)methanone and (S*)-(3-amino-6-(methylsulfonyl)-4,5,6,7-tetrahydropyrazolo[3,4-c]pyridin-2-yl)(6-ethyl-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(6-ethyl-1,2,3,4-tetrahydroquinolin-4-yl)methanone

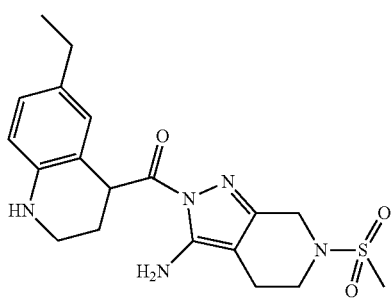

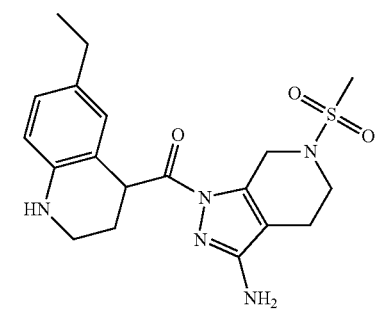

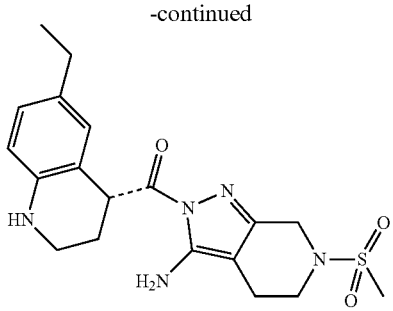

Step 1. 6-vinylquinoline-4-carboxylic acid

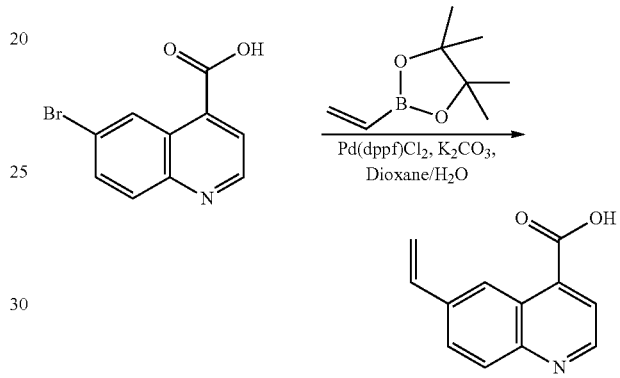

Into a 250-mL round-bottom flask purged and maintained with an inert atmosphere of nitrogen, was placed 6-bromoquinoline-4-carboxylic acid (2 g, 7.93 mmol, 1.00 equiv), 2-ethenyl-4,4,5,5-tetramethyl-1,3,2-dioxaborolane (1.8 g, 11.69 mmol, 1.50 equiv), Pd(dppf)Cl2CH2Cl2 (1.3 g, 0.20 equiv), potassium carbonate (3.3 g, 23.88 mmol, 3.00 equiv), water (6 mL), dioxane (60 mL). The resulting solution was stirred overnight at 100° C. The mixture was cooled to 20° C. The resulting solution was diluted with H₂O (60 mL). The resulting mixture was washed with DCM (100 mL×2). The pH value of the solution was adjusted to 3-4 with hydrochloric acid (1 mol/L). The resulting solution was extracted with dichloromethane (100 mL×5) and the organic layers combined and concentrated under vacuum. This resulted in 880 mg (56%) of 6-vinylquinoline-4-carboxylic acid as a brown solid. MS (ES, m/z) [M+H]+: 200.

Step 2. 6-ethyl-1,2,3,4-tetrahydroquinoline-4-carboxylic acid

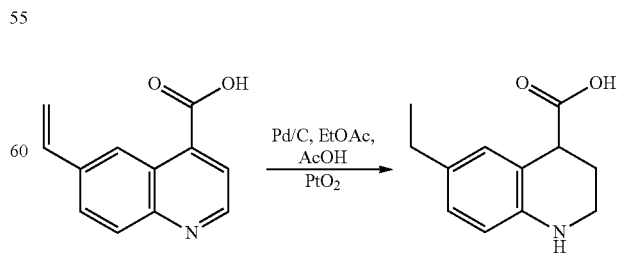

Into a 100-mL round-bottom flask purged and maintained with an inert atmosphere of H2, was placed 6-ethenylquinoline-4-carboxylic acid (620 mg, 3.11 mmol, 1.00 equiv), ethyl acetate (40 mL), Palladium carbon (10%, 600 mg), AcOH (0.25 mL), The resulting solution was stirred for 1 h at 25° C. The solids were filtered out. Pt2O (300 mg) was added. The resulting solution was stirred for 6 h at 25° C. The solids were filtered out. The filtrate was concentrated and the residue was applied onto a silica gel column with dichloromethane/methanol (10/1). This resulted in 100 mg (16%) of 6-ethyl-1,2,3,4-tetrahydroquinoline-4-carboxylic acid as a yellow solid. MS (ES, m/z) [M+H]+: 206.

Step 3. (3-amino-6-(methylsulfonyl)-4,5,6,7-tetrahydropyrazolo[3,4-c]pyridin-2-yl)(6-ethyl-1,2,3,4-tetrahydroquinolin-4-yl)methanone and (3-amino-6-(methylsulfonyl)-4,5,6,7-tetrahydropyrazolo[3,4-c]pyridin-1-yl)(6-ethyl-1,2,3,4-tetrahydroquinolin-4-yl)methanone Into a 50-mL round-bottom flask, was placed 6-ethyl-1,2,3,4-tetrahydroquinoline-4-carboxylic acid (150 mg, 0.72 mmol, 1.00 equiv), 1H-1,2,3-benzotriazol-1-ol (150 mg, 1.11 mmol, 1.50 equiv), EDCI (210 mg, 1.11 mmol, 1.50 equiv), TEA (222 mg, 2.19 mmol, 3.00 equiv), N,N-dimethylformamide (10 mL), 6-methanesulfonyl-4,5,6,7-tetrahydro-2H-pyrazolo[3,4-c]pyridin-3-amine (210 mg, 0.96 mmol, 1.30 equiv). The resulting solution was stirred for 2 h at 20° C. The reaction was then quenched by the addition of water (30 mL). The resulting solution was extracted with ethyl acetate (30 ml×3) and the organic layers combined and dried over anhydrous sodium sulfate. The solids were filtered out. The resulting mixture was concentrated under vacuum. The crude product was purified by Prep-HPLC with the following conditions: Column: XSelect CSH Prep C18 OBD Column, 5 um, 19×150 mm; Mobile Phase A: water (0.1% FA), Mobile Phase B: ACN; Flow rate: 20 mL/min; Gradient: 15% B to 50% B in 7 min; 254 nm;

Fraction A: The collected fraction was lyophilized to give 15 mg (13%) of (3-amino-6-(methylsulfonyl)-4,5,6,7-tetrahydropyrazolo[3,4-c]pyridin-2-yl)(6-ethyl-1,2,3,4-tetrahydroquinolin-4-yl)methanone as a white solid. Rt2: 6.05 min. MS (ES, m/z) [M+H]+: 404. (DMSO-d6, 300 MHz, ppm): δ 6.79-6.76 (m, 1H), 6.63-6.61 (m, 3H), 6.47-6.44 (m, 1H), 5.65 (s, 1H), 5.00-4.97 (m, 1H), 4.24 (s, 2H), 3.44-3.40 (m, 2H), 3.26-3.16 (m, 2H), 2.97 (s, 3H), 2.47-2.45 (m, 2H), 2.39-2.31 (m, 2H), 2.03-2.01 (m, 2H), 1.07-1.02 (m, 3H).

Fraction B: The collected fraction was lyophilized to give 9.4 mg (9%) of (3-amino-6-(methylsulfonyl)-4,5,6,7-tetrahydropyrazolo[3,4-c]pyridin-1-yl)(6-ethyl-1,2,3,4-tetrahydroquinolin-4-yl)methanone as a white solid. Rt1: 5.8 min. MS (ES, m/z) [M+H]+: 404. (DMSO-d6, 300 MHz, ppm): δ 6.78-6.75 (m, 1H), 6.62-6.61 (m, 1H), 6.46-6.43 (m, 1H), 5.79 (s, 2H), 5.65 (s, 1H), 4.91-4.88 (m, 1H), 4.53 (s, 2H), 3.44-3.39 (m, 3H), 3.27-3.23 (m, 2H), 3.15-3.11 (m, 1H), 2.96 (s, 3H), 2.39-2.31 (m, 2H), 2.01-1.99 (m, 2H), 1.07-1.02 (m, 3H).

Step 4. (S*)-(3-amino-6-(methylsulfonyl)-4,5,6,7-tetrahydropyrazolo[3,4-c]pyridin-2-yl)(6-ethyl-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(6-ethyl-1,2,3,4-tetrahydroquinolin-4-yl)methanone

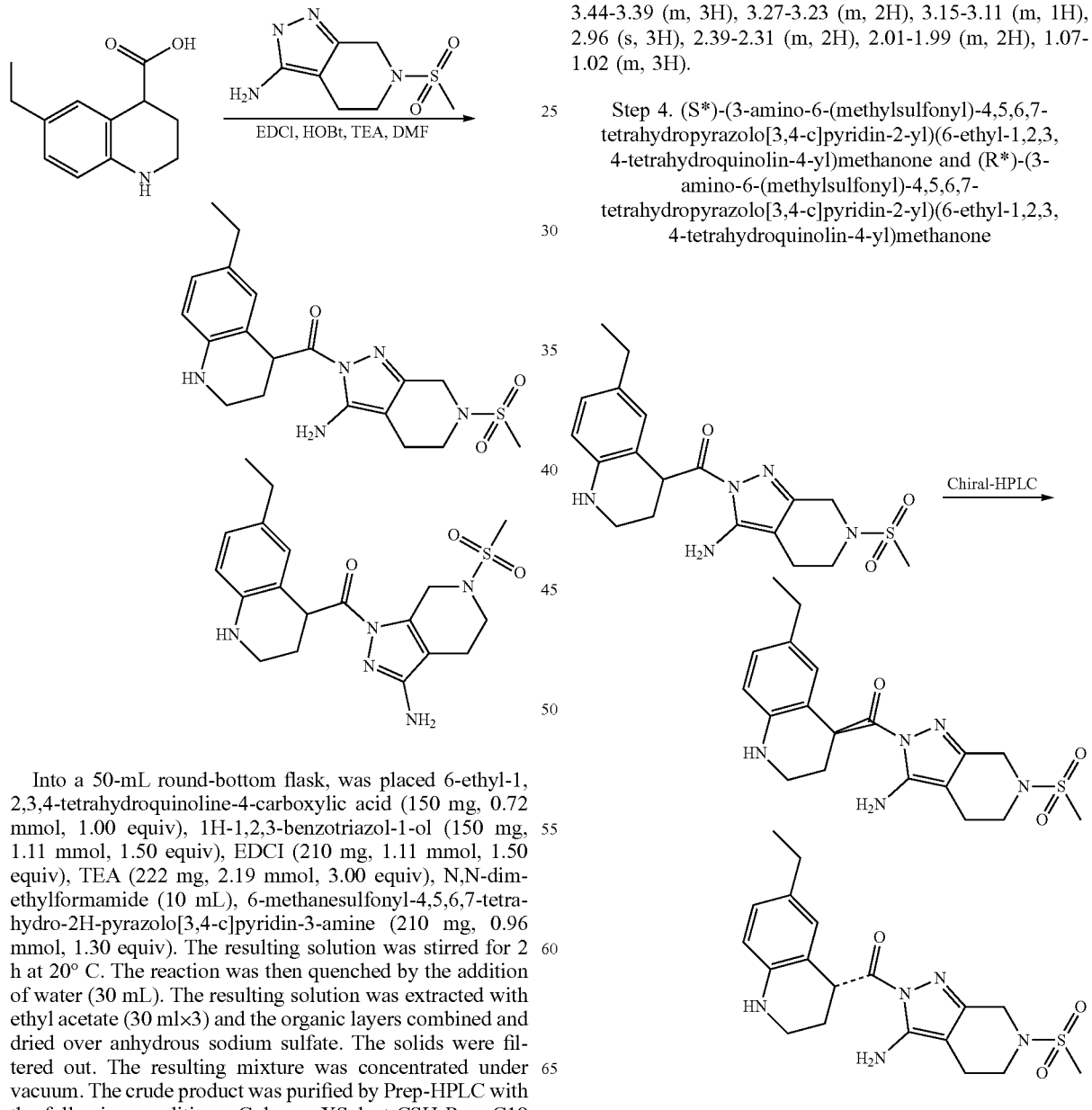

(3-amino-6-(methylsulfonyl)-4,5,6,7-tetrahydropyrazolo[3,4-c]pyridin-2-yl)(6-ethyl-1,2,3,4-tetrahydroquinolin-4-yl)methanone (15 mg, 0.05 mmol, 1.00 equiv) was separated by Prep-chiral-HPLC with the following conditions: Column: CHIRALPAK IA, 2.12×15 cm, 5 um; Mobile Phase A: Hex-HPLC, Mobile Phase B: EtOH-HPLC; Flow rate: 20 mL/min; Gradient: 50 B to 50 B in 15 min; 254/220 nm.

Enantiomer A. Example 32: This resulted in 2.8 mg (15%) of (S*)-(3-amino-6-(methylsulfonyl)-4,5,6,7-tetrahydropyrazolo[3,4-c]pyridin-2-yl)(6-ethyl-1,2,3,4-tetrahydroquinolin-4-yl)methanone as a white solid. Rt2:10.45 min. MS (ES, m/z) [M+H]+: 404. (DMSO-d6, 300 MHz, ppm): δ 6.77-6.74 (m, 1H), 6.61-6.59 (m, 3H), 6.45-6.42 (m, 1H), 5.62 (s, 1H), 4.98-4.97 (m, 1H), 4.22 (s, 2H), 3.42-3.39 (m, 2H), 3.26-3.14 (m, 2H), 2.95 (s, 3H), 2.37-2.29 (m, 4H), 2.02-1.98 (m, 2H), 1.06-1.00 (m, 3H).

Enantiomer B. Example 33: This resulted in 3.4 mg (18%) of (R*)-(3-amino-6-(methylsulfonyl)-4,5,6,7-tetrahydropyrazolo[3,4-c]pyridin-2-yl)(6-ethyl-1,2,3,4-tetrahydroquinolin-4-yl)methanone as a white solid. Rt1:6.36 min. MS (ES, m/z) [M+H]+: 404. (DMSO-d6, 300 MHz, ppm): δ 6.79-6.76 (m, 1H), 6.69-6.61 (m, 3H), 6.47-6.44 (m, 1H), 5.66 (s, 1H), 5.01-4.97 (m, 1H), 4.24 (s, 2H), 3.42-3.40 (m, 2H), 3.17-3.13 (m, 2H), 2.97 (s, 3H), 2.39-2.27 (m, 4H), 2.03-2.01 (m, 2H), 1.06-1.02 (m, 3H).

Example 34 & 35 & 36: (3-amino-6-(methylsulfonyl)-4,5,6,7-tetrahydropyrazolo[3,4-c]pyridine-2-yl)(8-methyl-1,2,3,4-tetrahydroquinolin-4-yl)methanone and (S*)-(3-amino-6-(methylsulfonyl)-4,5,6,7-tetrahydropyrazolo[3,4-c]pyridine-2-yl)(8-methyl-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(8-methyl-1,2,3,4-tetrahydroquinolin-4-yl)methanone

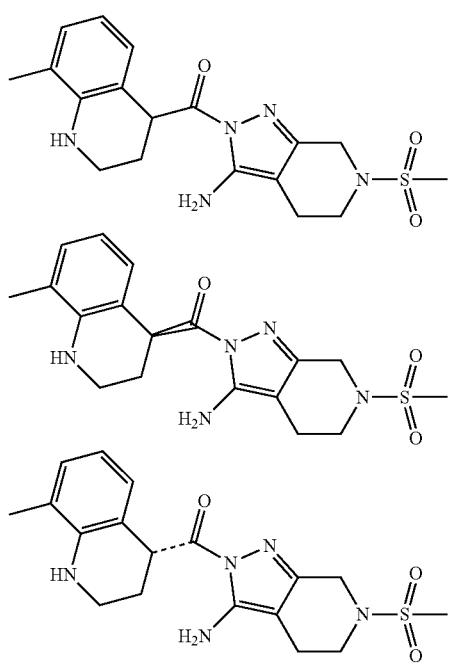

Step 1. 4-bromo-8-methylquinoline

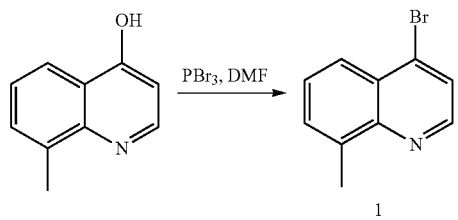

Into a 100-mL round-bottom flask, was placed 8-methylquinolin-4-ol (500 mg, 3.14 mmol, 1.00 equiv), N,N-dimethylformamide (20 mL). This was followed by the addition of tribromophosphine (851 mg, 3.14 mmol, 1.20 equiv) dropwise with stirring at room temperature. The resulting solution was stirred for 15 h at room temperature. The reaction was then quenched by the addition of water/ice (100 mL). The pH value of the solution was adjusted to 10 with sodium hydroxide (2 mol/L). The solids were collected by filtration. This resulted in 660 mg (95%) of 4-bromo-8-methylquinoline as a light yellow solid. MS (ES, m/z) [M+H]+: 222.

Step 2. Methyl 8-methylquinoline-4-carboxylate

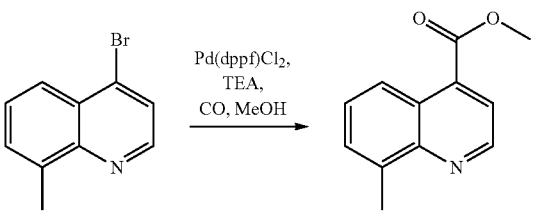

Into a 50-mL pressure tank reactor (CO, 60 atm), was placed 4-bromo-8-methylquinoline (600 mg, 2.70 mmol, 1.00 equiv), Pd(dppf)Cl$_2$CH$_2$Cl$_2$ (444 mg, 0.54 mmol, 0.20 equiv), TEA (1.4 g, 13.86 mmol, 5.00 equiv), methanol (15 mL). The resulting solution was stirred for 16 h at 80° C. After cooling to room temperature, the reaction mixture was concentrated and the residue was applied onto a silica gel column with ethyl acetate/hexane (0-30%). This resulted in 350 mg (64%) of methyl 8-methylquinoline-4-carboxylate as a white solid. MS (ES, m/z) [M+H]+: 202.

Step 3. 8-methylquinoline-4-carboxylic acid

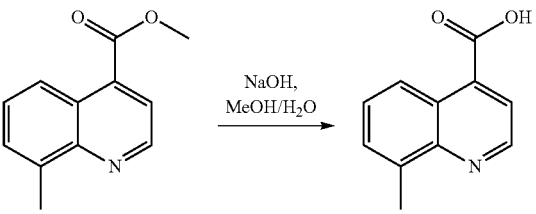

Into a 100-mL round-bottom flask, was placed methyl 8-methylquinoline-4-carboxylate (350 mg, 1.74 mmol, 1.00 equiv), sodium hydroxide (209 mg, 5.23 mmol, 3.00 equiv), water (20 mL), methanol (20 mL). The resulting solution was stirred for 14 h at room temperature. The resulting mixture was concentrated under vacuum. The resulting solution was extracted with ethyl acetate (20 mL×2) and the aqueous layers combined. The pH value of the solution was adjusted to 5-6 with hydrochloric acid (6 mol/L). The resulting solution was extracted with ethyl acetate (30 mL×3) and the organic layers combined. The resulting mixture was concentrated under vacuum. This resulted in 250 mg (77%) of 8-methylquinoline-4-carboxylic acid as a yellow solid. MS (ES, m/z) [M+H]+: 188.

Step 4.
8-methyl-1,2,3,4-tetrahydroquinoline-4-carboxylic acid

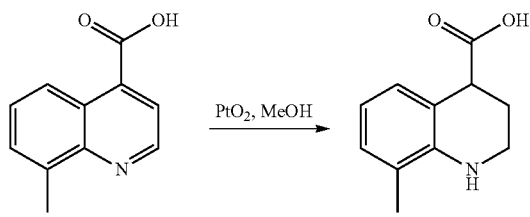

Into a 100-mL round-bottom flask, was placed 8-methylquinoline-4-carboxylic acid (250 mg, 1.34 mmol, 1.00 equiv), PtO2 (40 mg), methanol (20 mL). The flask was evacuated and flushed three times with nitrogen, followed by flushing with hydrogen. The mixture was stirred 1 h at room temperature under an atmosphere of hydrogen (balloon). The solids were filtered out. The resulting mixture was concentrated under vacuum. This resulted in 220 mg (86%) of 8-methyl-1,2,3,4-tetrahydroquinoline-4-carboxylic acid as a yellow solid. MS (ES, m/z) [M+H]+: 192.

Step 5. (3-amino-6-(methylsulfonyl)-4,5,6,7-tetrahydropyrazolo[3,4-c]pyridine-2-yl)(8-methyl-1,2,3,4-tetrahydroquinolin-4-yl)methanone

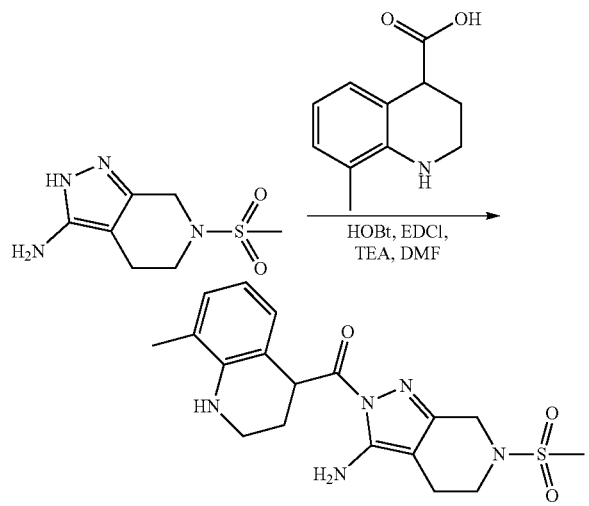

Into a 250-mL round-bottom flask, was placed 8-methyl-1,2,3,4-tetrahydroquinoline-4-carboxylic acid (1.8 g, 9.41 mmol, 1.00 equiv), 6-methanesulfonyl-4,5,6,7-tetrahydro- 2H-pyrazolo[3,4-c]pyridin-3-amine (2.2 g, 10.17 mmol, 1.10 equiv), EDCI (2.7 g, 14.08 mmol, 1.50 equiv), HOBt (1.9 g, 14.06 mmol, 1.50 equiv), TEA (4.7 g, 46.45 mmol, 5.00 equiv), N,N-dimethylformamide (30 mL). The resulting solution was stirred for 2 h at room temperature. The reaction was then quenched by the addition of water (200 mL). The resulting solution was extracted with ethyl acetate (300 mL×3) and the organic layers combined and concentrated under vacuum. The crude product was purified by Prep-HPLC with the following conditions: Column, XBridge Prep OBD C18 Column, 150 mm 5 um; mobile phase, water (0.1% FA) and ACN (15.0% ACN up to 45.0% in 9 min); Detector, uv 220 nm. The collected fraction was lyophilized to give 150 mg (5%) of (3-amino-6-(methylsulfonyl)-4,5,6,7-tetrahydropyrazolo[3,4-c]pyridine-2-yl) (8-methyl-1,2,3,4-tetrahydroquinolin-4-yl)methanone as a light yellow solid. Rt: 6.50 min. MS (ES, m/z) [M+H]+: 390. (DMSO-d6, 300 MHz, ppm): δ 6.83-6.81 (m, 1H), 6.66-6.62 (m, 3H), 6.37-6.32 (m, 1H), 5.23 (s, 1H), 5.05-5.01 (m, 1H), 4.20 (s, 2H), 3.43-3.39 (m, 2H), 3.32-3.30 (m, 1H), 3.27-3.26 (m, 1H), 2.9 (s, 3H), 2.49-2.45 (m, 2H), 2.11-1.98 (m, 5H).

Step 6. (S*)-(3-amino-6-(methylsulfonyl)-4,5,6,7-tetrahydropyrazolo[3,4-c]pyridine-2-yl)(8-methyl-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(8-methyl-1,2,3,4-tetrahydroquinolin-4-yl)methanone

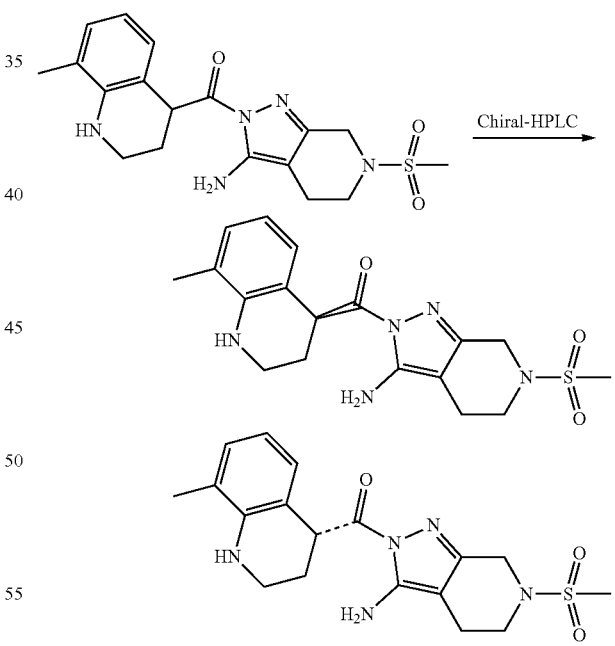

6-methanesulfonyl-2-[(8-methyl-1,2,3,4-tetrahydroquinolin-4-yl)carbonyl]-4,5,6,7-tetrahydro-2H-pyrazolo[3,4-c]pyridin-3-amine (150 mg) was separated by Prep-chiral-HPLC with the following conditions: Column: CHIRALPAK IG, 20 250 mm, 5 um; Mobile Phase A: Hex-HPLC, Mobile Phase B: EtOH-HPLC; Flow rate: 18 mL/min; Gradient: 50 B to 50 B in 26 min; 254/220 nm;

Enantiomer A. Example 35: This resulted in 55.9 mg (37%) of (S*)-(3-amino-6-(methylsulfonyl)-4,5,6,7-tetrahydropyrazolo[3,4-c]pyridine-2-yl)(8-methyl-1,2,3,4-tetrahydroquinolin-4-yl)methanone as a light yellow solid. Rt1: 16.47 min. MS (ES, m/z) [M+H]+: 390. (DMSO-d6, 300 MHz, ppm): δ 6.83-6.81 (m, 1H), 6.66-6.62 (m, 3H), 6.37-6.32 (m, 1H), 5.23 (s, 1H), 5.05-5.01 (m, 1H), 4.20 (s, 2H), 3.43-3.39 (m, 2H), 3.32-3.30 (m, 1H), 3.27-3.26 (m, 1H), 2.97 (s, 3H), 2.49-2.45 (m, 2H), 2.07-1.98 (m, 5H).

Enantiomer B. Example 36: This resulted in 43.8 mg (29%) of (R*)-(3-amino-6-(methylsulfonyl)-4,5,6,7-tetrahydropyrazolo[3,4-c]pyridin-2-yl)(8-methyl-1,2,3,4-tetrahydroquinolin-4-yl)methanone as a light yellow solid. Rt2: 20.84 min. MS (ES, m/z) [M+H]+: 390. (DMSO-d6, 300 MHz, ppm): δ 6.83-6.81 (m, 1H), 6.66-6.62 (m, 3H), 6.37-6.32 (m, 1H), 5.23 (s, 1H), 5.05-5.01 (m, 1H), 4.20 (s, 2H), 3.43-3.39 (m, 2H), 3.32-3.30 (m, 1H), 3.27-3.26 (m, 1H), 2.96 (s, 3H), 2.49-2.45 (m, 2H), 2.07- 1.96 (m, 5H).

Example 37 & 38: (3-amino-6-(methylsulfonyl)-4,5,6,7-tetrahydropyrazolo[3,4-c]pyridin-2-yl)(8-fluoro-1,2,3,4-tetrahydroquinolin-4-yl)methanone and (3-amino-6-(methylsulfonyl)-4,5,6,7-tetrahydropyrazolo[3,4-c]pyridin-1-yl)(8-fluoro-1,2,3,4-tetrahydroquinolin-4-yl)methanone

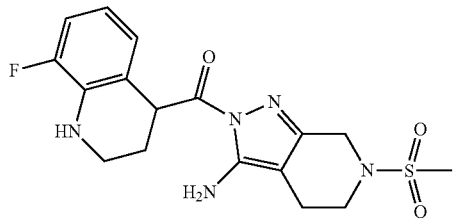

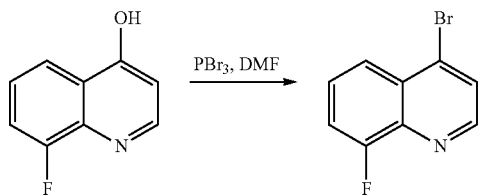 [SMILES: Oc1ccnc2c(F)cccc12 ; Fc1cccc2c(Br)ccnc12]

Step 1. 4-bromo-8-fluoroquinoline

Into a 100-mL round-bottom flask, was placed 8-fluoroquinolin-4-ol (1 g, 6.13 mmol, 1.00 equiv), N,N-dimethylformamide (20 mL). This was followed by the addition of PBr3 (1.8 g, 6.65 mmol, 1.10 equiv) dropwise with stirring at room temperature. The resulting solution was stirred for 1 h at room temperature. The reaction was then quenched by the addition of water (50 mL). The pH value of the solution was adjusted to 8 with potassium hydroxide a.q. The solids were collected by filtration. This resulted in 1.1 g of 4-bromo-8-fluoroquinoline as a yellow solid. MS (ES, m/z) [M+H]+: 226.

Step 2. Methyl 8-fluoroquinoline-4-carboxylate

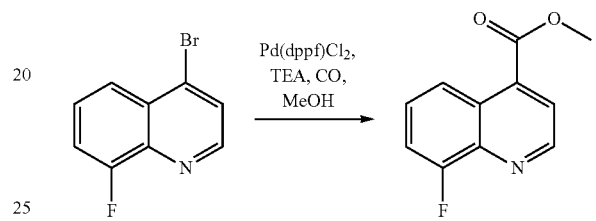

Into a 50-mL sealed tube (60 atm), was placed 4-bromo-8-fluoroquinoline (1.1 g, 4.87 mmol, 1.00 equiv), Pd(dppf)Cl$_2$CH$_2$Cl$_2$ (800 mg, 0.98 mmol, 0.20 equiv), TEA (2 g, 19.80 mmol, 4.00 equiv), methanol (15 mL). To the above CO was introduced in. The resulting solution was stirred overnight at 75° C. After cooled to room temperature, the solids were filtered out. The filtrate was concentrated under vacuum. The residue was applied onto a silica gel column with ethyl acetate/petroleum ether (0-50%). This resulted in 890 mg (89%) of methyl 8-fluoroquinoline-4-carboxylate as a white solid. MS (ES, m/z) [M+H]+: 206

Step 3. 8-fluoroquinoline-4-carboxylic acid

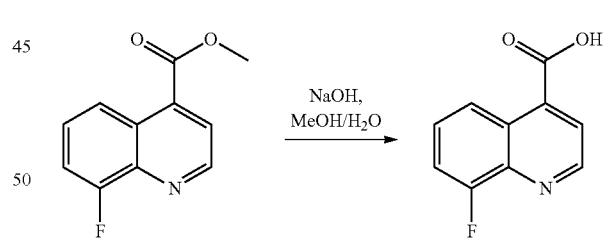

Into a 50-mL round-bottom flask, was placed methyl 8-fluoroquinoline-4-carboxylate (890 mg, 4.34 mmol, 1.00 equiv), methanol (15 mL), a solution of sodium hydroxide (520 mg, 13.00 mmol, 3.00 equiv) in water (8 mL). The resulting solution was stirred overnight at room temperature. The resulting mixture was concentrated under vacuum. The resulting solution was diluted with water (20 mL). The resulting solution was washed with ethyl acetate (30 mL×2). The pH value of the solution was adjusted to 5-6 with hydrochloric acid (1 mol/L). The solids were collected by filtration. This resulted in 710 mg (86%) of 8-fluoroquinoline-4-carboxylic acid as a white solid. MS (ES, m/z) [M+H]+: 192.

Step 4.
8-fluoro-1,2,3,4-tetrahydroquinoline-4-carboxylic acid

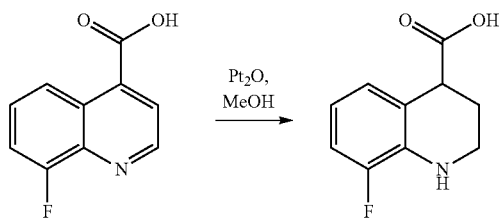 [SMILES: O=C(O)c1ccnc2c(F)cccc12 ; O=C(O)C1CCNc2c(F)cccc21]

Into a 50-mL round-bottom flask, was placed 8-fluoroquinoline-4-carboxylic acid (150 mg, 0.78 mmol, 1.00 equiv), methanol (8 mL), Pt2O (30 mg). To the above H2 was introduced in. The resulting solution was stirred for 50 min at room temperature. The solids were filtered out. The resulting mixture was concentrated under vacuum. This resulted in 140 mg (91%) of 8-fluoro-1,2,3,4-tetrahydroquinoline-4-carboxylic acid as a yellow solid. MS (ES, m/z) [M+H]+: 196.

Step 5. (3-amino-6-(methylsulfonyl)-4,5,6,7-tetrahydropyrazolo[3,4-c]pyridin-2-yl)(8-fluoro-1,2,3,4-tetrahydroquinolin-4-yl)methanone and (3-amino-6-(methylsulfonyl)-4,5,6,7-tetrahydropyrazolo[3,4-c]pyridin-1-yl)(8-fluoro-1,2,3,4-tetrahydroquinolin-4-yl)methanone

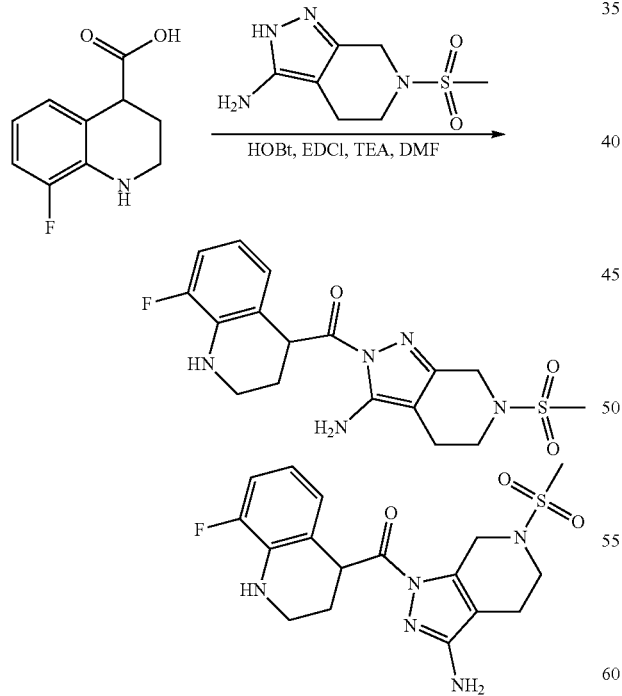

Into a 50-mL round-bottom flask, was placed 6-methanesulfonyl-4,5,6,7-tetrahydro-2H-pyrazolo[3,4-c]pyridin-3-amine (95 mg, 0.44 mmol, 1.20 equiv), 8-fluoroquinoline-4-carboxylic acid (70 mg, 0.37 mmol, 1.00 equiv), HOBT (75 mg, 0.56 mmol, 1.50 equiv), EDCI (105 mg, 0.55 mmol, 1.50 equiv), TEA (110 mg, 1.09 mmol, 3.00 equiv), N,N-dimethylformamide (5 mL). The resulting solution was stirred for 2 h at room temperature. The reaction was then quenched by the addition of water (30 mL). The resulting solution was extracted with ethyl acetate (30 mL×3) and the organic layers combined. The resulting mixture was concentrated under vacuum. The crude product was purified by Prep-HPLC with the following conditions: Column: XSelect CSH Prep C18 OBD Column, 5 um, 19×150 mm; Mobile Phase A: water (0.1% FA), Mobile Phase B: ACN; Flow rate: 20 mL/min; Gradient: 25% B to 60% B in 7 min; 254 nm.

Fraction A. Example 37: The collected fraction was lyophilized to give 1.8 mg (1%) of (3-amino-6-(methylsulfonyl)-4,5,6,7-tetrahydropyrazolo[3,4-c]pyridin-2-yl)(8-fluoro-1,2,3,4-tetrahydroquinolin-4-yl)methanone as a white solid. Rt2: 6.63 min. MS (ES, m/z) [M+H]+: 394. (DMSO-d6, 400 MHz, ppm): δ 6.91-6.86 (m, 1H), 6.74-6.64 (m, 3H), 6.42-6.38 (m, 1H), 5.79 (s, 1H), 5.08-5.05 (m, 1H), 4.24-4.20 (m, 2H), 3.45-3.42 (m, 2H), 3.29-3.26 (m, 2H), 2.97 (s, 3H), 2.48-2.45 (m, 2H), 2.10-2.02 (m, 2H).

Fraction B. Example 38: The collected fraction was lyophilized to give 4.3 mg (3%) of (3-amino-6-(methylsulfonyl)-4,5,6,7-tetrahydropyrazolo[3,4-c]pyridin-1-yl)(8-fluoro-1,2,3,4-tetrahydroquinolin-4-yl)methanone as a white solid. Rt1: 5.95 min. MS (ES, m/z) [M+H]+: 394. (DMSO-d6, 400 MHz, ppm): δ 6.90-6.85 (m, 1H), 6.69-6.67 (m, 1H), 6.41-6.36 (m, 1H), 5.81 (s, 2H), 5.76 (s, 1H), 4.97-4.94 (m, 1H), 4.57-4.47 (m, 2H), 3.46-3.40 (m, 2H), 3.29-3.24 (m, 2H), 2.96 (s, 3H), 2.47-2.44 (m, 2H), 2.11-1.99 (m, 2H).

Example 39 & 40: (3-amino-6-(methylsulfonyl)-4,5,6,7-tetrahydropyrazolo[3,4-c]pyridin-2-yl)(2,2-dimethyl-1,2,3,4-tetrahydroquinolin-4-yl)methanone and (3-amino-6-(methylsulfonyl)-4,5,6,7-tetrahydropyrazolo[3,4-c]pyridin-1-yl)(2,2-dimethyl-1,2,3,4-tetrahydroquinolin-4-yl)methanone

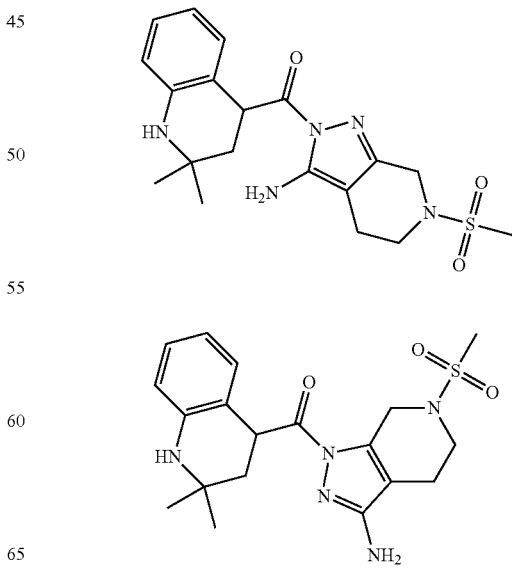

Step 1. 4-(2-aminophenyl)-2-methylbut-3-yn-2-ol

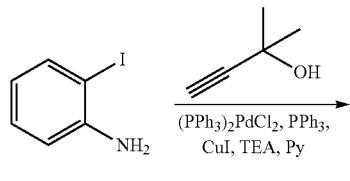

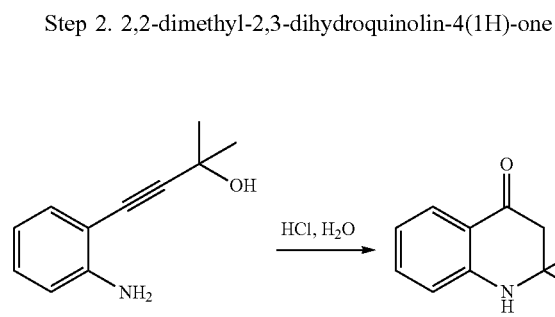

Into a 250-mL round-bottom flask purged and maintained with an inert atmosphere of nitrogen, was placed 2-iodoaniline (5 g, 22.83 mmol, 1.00 equiv), 2-methylbut-3-yn-2-ol (2.87 g, 34.12 mmol, 1.50 equiv), Pd(PPh3)$_2$Cl$_2$ (798 mg, 1.14 mmol, 0.05 equiv), PPh3 (3 g, 11.54 mmol, 0.50 equiv), CuI (216.6 mg, 1.14 mmol, 0.05 equiv), TEA (50 mL), pyridine (50 mL). The resulting solution was stirred for 15 h at 100° C. After cooling to room temperature, the resulting solution was diluted with water (100 mLl). The resulting solution was extracted with ethyl acetate (150 mL×3) and the organic layers combined and concentrated under vacuum. The residue was applied onto a silica gel column with ethyl acetate/PE (1:3). This resulted in 3.1 g (77%) of 4-(2-aminophenyl)-2-methylbut-3-yn-2-ol as a yellow liquid. MS (ES, m/z) [M+H]+: 176.

Step 2. 2,2-dimethyl-2,3-dihydroquinolin-4(1H)-one

Into a 250-mL round-bottom flask, was placed 4-(2-aminophenyl)-2-methylbut-3-yn-2-ol (3.1 g, 17.69 mmol, 1.00 equiv), hydrochloric acid (90 mL), water (90 mL). The resulting solution was stirred for 1.5 h at 120° C. After cooling to room temperature, the pH value of the solution was adjusted to 7 with saturated aqueous NaHCO$_3$. The resulting solution was extracted with ethyl acetate (200 mL×3) and the organic layers combined and concentrated under vacuum. The residue was applied onto a silica gel column with ethyl acetate/PE (3/1). This resulted in 2.91 g (94%) of 2,2-dimethyl-2,3-dihydroquinolin-4(1H)-one as a brown solid. MS (ES, m/z) [M+H]+: 176.

Step 3. 2,2-dimethyl-4-(trimethylsilyloxy)-1,2,3,4-tetrahydroquinoline-4-carbonitrile

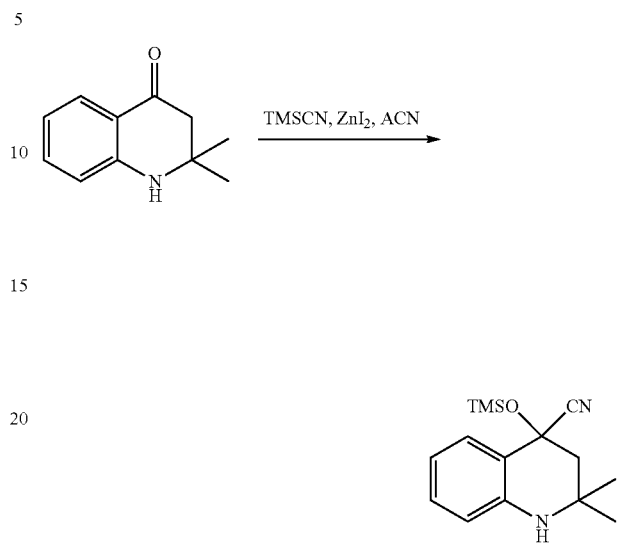

Into a 100-mL round-bottom flask, was placed 2,2-dimethyl-1,2,3,4-tetrahydroquinolin-4-one (1.5 g, 8.56 mmol, 1.00 equiv), acetonitrile (30 mL), TMSCN (16.8 g, 170.12 mmol, 20.00 equiv), ZnI$_2$ (5.5 g, 17.23 mmol, 2.00 equiv). The resulting solution was stirred for 15 h at room temperature. The reaction was then quenched by the addition of water (100 mL). The resulting solution was extracted with ethyl acetate (100 mL×3) and the organic layers combined concentrated under vacuum. This resulted in 2 g (85%) of 2,2-dimethyl-4-(trimethylsilyloxy)-1,2,3,4-tetrahydroquinoline-4-carbonitrile as brown oil. MS (ES, m/z) [M+H]+: 275.

Step 4. 2,2-dimethyl-1,2,3,4-tetrahydroquinoline-4-carboxylic acid

Into a 250-mL round-bottom flask, was placed 2,2-dimethyl-4-[(trimethylsilyl)oxy]-1,2,3,4-tetrahydroquinoline-4-carbonitrile (1.9 g, 6.92 mmol, 1.00 equiv), AcOH (10 mL), hydrochloric acid (12 mol/L, 10 mL), dichloro-2-stannane hydrate (1.88 g, 9.05 mmol, 1.20 equiv). The resulting solution was stirred for 15 h at room temperature. The crude product was purified by reversed phase column with the following conditions: Column, C18 silica gel, 120 g, 20-45 um, 100 A; mobile phase, water with 0.05% TFA and ACN (5% up to 65% ACN in 30 min); Detector, UV 220/254 nm. This resulted in 280 mg (20%) of 2,2-dimethyl-1,2,3,4-tetrahydroquinoline-4-carboxylic acid as a purple solid. MS (ES, m/z) [M+H]+: 206.

Step 4. (3-amino-6-(methylsulfonyl)-4,5,6,7-tetrahydropyrazolo[3,4-c]pyridin-2-yl)(2,2-dimethyl-1,2,3,4-tetrahydroquinolin-4-yl)methanone and (3-amino-6-(methylsulfonyl)-4,5,6,7-tetrahydropyrazolo[3,4-c]pyridin-1-yl)(2,2-dimethyl-1,2,3,4-tetrahydroquinolin-4-yl)methanone Example 41 & 42: (3-amino-6-(methylsulfonyl)-4,5,6,7-tetrahydropyrazolo[3,4-c]pyridin-2-yl)(1,2,3,4-tetrahydro-1,8-naphthyridin-4-yl)methanone and (3-amino-6-(methylsulfonyl)-4,5,6,7-tetrahydropyrazolo[3,4-c]pyridin-1-yl)(1,2,3,4-tetrahydro-1,8-naphthyridin-4-yl)methanone

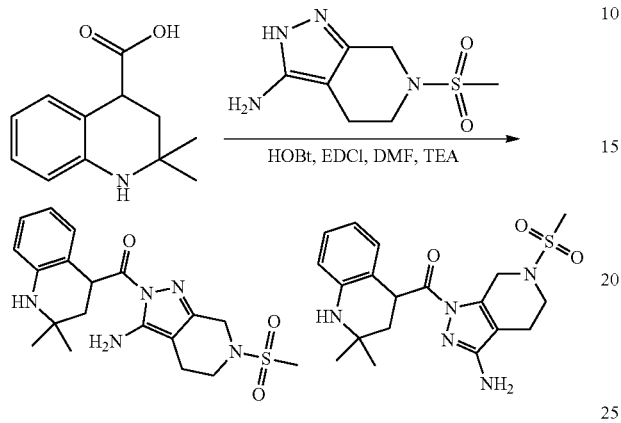

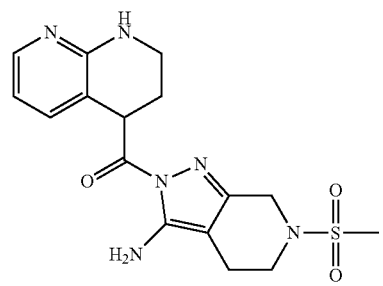

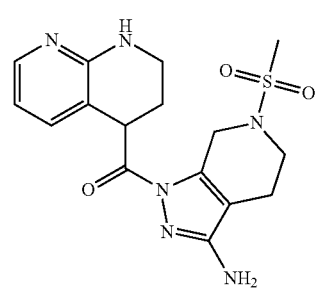

Into a 100-mL round-bottom flask, was placed 2,2-dimethyl-1,2,3,4-tetrahydroquinoline-4-carboxylic acid (150 mg, 0.73 mmol, 1.00 equiv), 6-methanesulfonyl-4,5,6,7-tetrahydro-2H-pyrazolo[3,4-c]pyridin-3-amine (159 mg, 0.74 mmol, 1.00 equiv), HOBt (150 mg, 1.11 mmol, 1.50 equiv), EDCI (210 mg, 1.10 mmol, 1.50 equiv), N,N-dimethylformamide (10 mL), TEA (375 mg, 3.71 mmol, 5.00 equiv). The resulting solution was stirred for 2 h at room temperature. The reaction was then quenched by the addition of water (50 mL). The resulting solution was extracted with ethyl acetate (60 mL×3) and the organic layers combined and concentrated under vacuum. The crude product was purified by Prep-HPLC with the following conditions: Column: XBridge C18 OBD Prep Column 100, 10 μm, 19 mm×250 mm; Mobile Phase A: water (0.1% FA), Mobile Phase B: ACN; Flow rate: 20 mL/min; Gradient: 20% B to 45% B in 7 min; 254/220 nm.

Fraction A. Example 39: The collected fraction was lyophilized to give 10.4 mg (3.5%) of (3-amino-6-(methylsulfonyl)-4,5,6,7-tetrahydropyrazolo[3,4-c]pyridin-2-yl)(2,2-dimethyl-1,2,3,4-tetrahydroquinolin-4-yl)methanone as a white solid. Rt2: 6.25 min. MS (ES, m/z) [M+H]+: 404. (DMSO-d6, 300 MHz, ppm): δ 6.93-6.88 (m, 1H), 6.68-6.60 (m, 3H), 6.52-6.50 (m, 1H), 6.42-6.37 (m, 1H), 5.69 (s, 1H), 5.14-5.08 (m, 1H), 4.23 (s, 2H), 3.44-3.41 (m, 2H), 2.97 (s, 3H), 2.47-2.44 (m, 2H), 1.94-1.84 (m, 2H), 1.22 (s, 3H), 1.11 (s, 3H).

Fraction B. Example 40: The collected fraction was lyophilized to give 14.7 mg (5%) of (3-amino-6-(methylsulfonyl)-4,5,6,7-tetrahydropyrazolo[3,4-c]pyridin-1-yl)(2,2-dimethyl-1,2,3,4-tetrahydroquinolin-4-yl)methanone as a white solid. Rt1: 5.77 min. MS (ES, m/z) [M+H]+: 404. (DMSO-d6, 300 MHz, ppm): δ 6.91-6.86 (m, 1H), 6.64-6.66 (m, 1H), 6.51-6.48 (m, 1H), 6.41-6.36 (m, 1H), 5.79 (s, 2H), 5.66 (s, 1H), 5.05-4.99 (m, 1H), 4.57 (s, 2H), 3.44-3.42 (m, 2H), 2.98 (s, 3H), 2.47-2.44 (m, 2H), 1.91-1.85 (m, 2H), 1.23 (s, 3H), 1.12 (s, 3H).

Step 1. 3-(pyridin-2-ylamino)propanoic acid

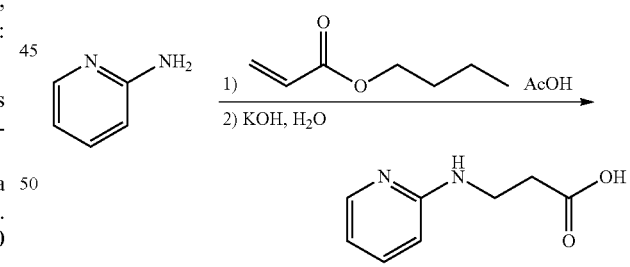

Into a 250-mL round-bottom flask, was placed pyridin-2-amine (4 g, 42.50 mmol, 1.00 equiv), AcOH (752 mg, 12.52 mmol, 0.52 equiv), butyl prop-2-enoate (3.7 g, 28.87 mmol, 1.20 equiv). The resulting solution was stirred overnight at 70° C. Potassium hydroxide (3.37 g, 60.06 mmol, 2.50 equiv), water (10 mL) was added. The resulting solution was stirred overnight at 25° C. The resulting mixture was concentrated under vacuum. The resulting mixture was washed with DCM (200 mL×6). The solids were filtered out. The filtrate was concentrated to give 4 g (57%) of 3-(pyridin-2-ylamino)propanoic acid as brown oil. MS (ES, m/z) [M+H]+: 167.

Step 2. 2,3-dihydro-1,8-naphthyridin-4(1H)-one

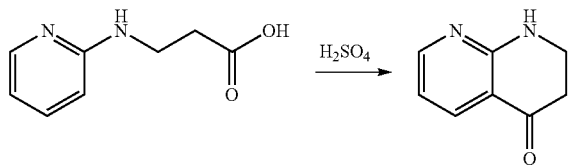

Into a 250-mL round-bottom flask, was placed 3-[(pyridin-2-yl)amino]propanoic acid (4 g, 24.07 mmol, 1.00 equiv), sulfuric acid (70 mL). The resulting solution was stirred overnight at 80° C. The mixture was cooled to 30° C. The pH value of the solution was adjusted to 12 with sodium hydroxide (100%). The resulting solution was extracted with ethyl acetate (400 mL×4) and concentrated. The residue was applied onto a silica gel column with ethyl acetate/petroleum ether (1/1). The collected fractions were combined and concentrated under vacuum. This resulted in 400 mg (11%) of 2,3-dihydro-1,8-naphthyridin-4(1H)-one as a yellow solid. MS (ES, m/z) [M+H]+: 149.

Step 3. 4-(trimethylsilyloxy)-1,2,3,4-tetrahydro-1,8-naphthyridine-4-carbonitrile

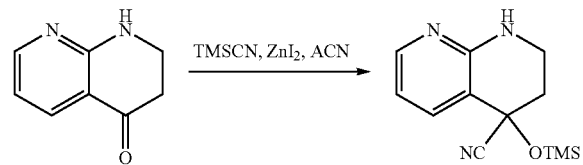

Into a 250-mL round-bottom flask, was placed 1,2,3,4-tetrahydro-1,8-naphthyridin-4-one (680 mg, 4.59 mmol, 1.00 equiv), ACN (20 mL), ZnI2 (380 mg, 5.51 mmol, 1.20 equiv), TMSCN (4.5 g, 46.10 mmol, 10.00 equiv). The resulting solution was stirred overnight at 25° C. The reaction was then quenched by the addition of water (50 mL). The resulting solution was extracted with dichloromethane (50 mL×3) and the organic layers combined and concentrated under vacuum. This resulted in 880 mg (78%) of 4-(trimethylsilyloxy)-1,2,3,4-tetrahydro-1,8-naphthyridine-4-carbonitrile as a yellow solid. MS (ES, m/z) [M+H]+: 248.

Step 4. 1,2,3,4-tetrahydro-1,8-naphthyridine-4-carboxylic acid

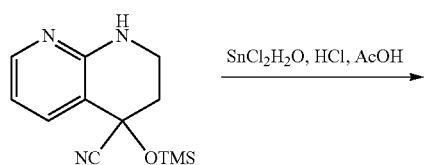

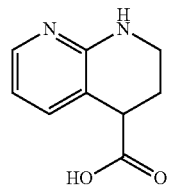

Into a 250-mL round-bottom flask, was placed 4-[trimethylsilyl)oxy]-1,2,3,4-tetrahydro-1,8-naphthyridine-4-carbonitrile (880 mg, 3.56 mmol, 1.00 equiv), SnCl2H2O (3.22 g, 14.25 mmol, 4.00 equiv), AcOH (10 mL), hydrochloric acid (12 mol/L, 10 mL). The resulting solution was stirred overnight at 115° C. The mixture was cooled to 30° C. The reaction was then quenched by the addition of water (100 mL). The resulting solution was extracted with dichloromethane (150 mL×6) and the organic layers combined and concentrated under vacuum. This resulted in 1.26 g (crude) of 1,2,3,4-tetrahydro-1,8-naphthyridine-4-carboxylic acid as a yellow solid. MS (ES, m/z) [M+H]+: 179.

Step 5. (3-amino-6-(methylsulfonyl)-4,5,6,7-tetrahydropyrazolo[3,4-c]pyridin-2-yl)(1,2,3,4-tetrahydro-1,8-naphthyridin-4-yl)methanone and (3-amino-6-(methylsulfonyl)-4,5,6,7-tetrahydropyrazolo[3,4-c]pyridin-1-yl)(1,2,3,4-tetrahydro-1,8-naphthyridin-4-yl)methanone

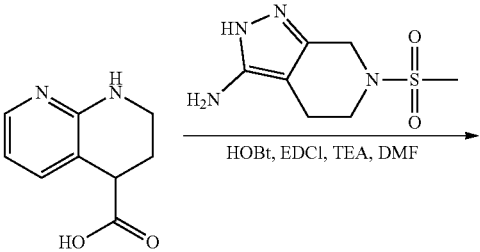

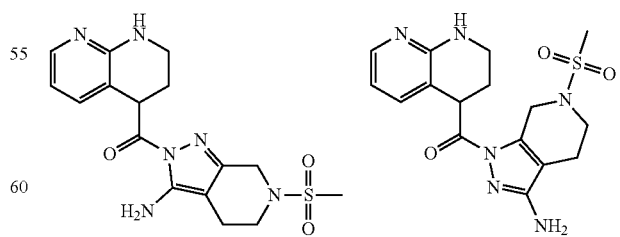

Into a 25-mL round-bottom flask, was placed 1,2,3,4-tetrahydro-1,8-naphthyridine-4-carboxylic acid (66 mg, 0.37 mmol, 1.00 equiv), 6-methanesulfonyl-4,5,6,7-tetrahydro-2H-pyrazolo[3,4-c]pyridin-3-amine (96 mg, 0.44 mmol, 1.20 equiv), HOBt (76 mg, 0.56 mmol, 1.50 equiv), EDCI (107 mg, 0.56 mmol, 1.50 equiv), N,N-dimethylformamide (10 mL), TEA (187 mg, 1.85 mmol, 5.00 equiv). The resulting solution was stirred for 4 h at 25° C. The reaction mixture was diluted with DCM (80 mL), washed with H2O (50 mL×3) and brine (50 mL×3) and dried with Na2SO4. After filtration, the filtrate was concentrated under reduced pressure. The crude product was purified by Prep-HPLC with the following conditions (Analyse HPLC-SHI-MADZU): Column: XBridge Prep OBD C18 Column 150 mm 5 um; Mobile Phase A: water (10 mM NH$_4$HCO$_3$), Mobile Phase B: ACN; Flow rate: 60 mL/min; Gradient: 5% B to 35% B in 8 min; 220 nm.

Fraction A. Example 41: The collected fraction was lyophilized to give 5 mg (4%) of (3-amino-6-(methylsulfonyl)-4,5,6,7-tetrahydropyrazolo[3,4-c]pyridin-2-yl)(1,2,3,4-tetrahydro-1,8-naphthyridin-4-yl)methanone as a white solid. Rt2: 7.27 min. MS (ES, m/z) [M+H]+: 377. (400 MHz, DMSO-d6, ppm): δ 7.83-7.82 (m, 1H), 7.14-7.13 (m, 1H), 6.65 (s, 2H), 6.59 (s, 1H), 6.43-6.40 (m, 1H), 5.00-4.96 (m, 1H), 4.23 (s, 2H), 3.43-3.35 (m, 2H), 3.32-3.30 (m, 2H), 2.90 (s, 3H), 2.49-2.46 (m, 2H), 2.33-2.00 (m, 2H).

Fraction B. Example 42: The collected fraction was lyophilized to give 15 mg (11%) of (3-amino-6-(methylsulfonyl)-4,5,6,7-tetrahydropyrazolo[3,4-c]pyridin-1-yl)(1,2,3,4-tetrahydro-1,8-naphthyridin-4-yl)methanone as a white solid. Rt1: 6.57 min. MS (ES, m/z) [M+H]+: 377. (400 MHz, DMSO-d6, ppm): δ 7.82-7.80 (m, 1H), 7.14-7.12 (m, 1H), 6.60 (s, 1H), 6.42-6.40 (m, 1H), 5.82 (s, 2H), 4.90-4.87 (m, 1H), 4.48 (s, 2H), 3.47-3.41 (m, 3H), 3.28-3.27 (m, 1H), 2.90 (s, 3H), 2.49-2.47 (m, 2H), 2.10-1.98 (m, 2H).

Example 43 & 44: 4-(3-amino-6-(methylsulfonyl)-4,5,6,7-tetrahydro-2H-pyrazolo[3,4-c]pyridine-2-carbonyl)-6-fluoro-3,4-dihydroquinolin-2(1H)-one and 4-(3-amino-6-(methylsulfonyl)-4,5,6,7-tetrahydro-1H-pyrazolo[3,4-c]pyridine-1-carbonyl)-6-fluoro-3,4-dihydroquinolin-2(1H)-one Into a 50-mL round-bottom flask, was placed 6-fluoro-2-oxo-1,2,3,4-tetrahydroquinoline-4-carboxylic acid (commercially available, Chembridge, 200 mg, 0.96 mmol, 1.00 equiv), 6-methanesulfonyl-4,5,6,7-tetrahydro-2H-pyrazolo[3,4-c]pyridin-3-amine (210 mg, 0.97 mmol, 1.10 equiv), HOBT (195 mg, 1.44 mmol, 1.50 equiv), EDCI (175 mg, 0.91 mmol, 1.50 equiv), TEA (290 mg, 2.87 mmol, 3.00 equiv), N,N-dimethylformamide (5 mL). The resulting solution was stirred for 2 h at room temperature. The reaction was then quenched by the addition of water (30 mL). The resulting solution was extracted with ethyl acetate (30 mL×3) and the organic layers combined and concentrated under vacuum. The crude product was purified by Prep-HPLC with the following conditions: Column: XBridge Shield RP18 OBD Column, 5 um, 19×150 mm; Mobile Phase A: water (0.1% FA), Mobile Phase B: ACN; Flow rate: 20 mL/min; Gradient: 20% B to 40% B in 11 min; 254/220 nm;

Fraction A. Example 43: The collected fraction was lyophilized to give 7.7 mg (2%) of 4-(3-amino-6-(methylsulfonyl)-4,5,6,7-tetrahydro-2H-pyrazolo[3,4-c]pyridine-2-carbonyl)-6-fluoro-3,4-dihydroquinolin-2(1H)-one as an off-white solid. Rt2: 9.48 min. MS (ES, m/z) [M+H]+: 408; (DMSO-d6, 300 MHz, ppm): δ 10.11 (s, 1H), 7.23-7.19 (m, 1H), 7.06-6.99 (m, 1H), 6.88-6.82 (m, 1H), 6.59 (s, 2H), 5.13-5.10 (m, 1H), 4.23 (s, 2H), 3.39-3.35 (m, 2H), 2.94 (s, 3H), 2.87-2.79 (m, 1H), 2.68-2.62 (m, 1H), 2.48-2.39 (m, 2H).

Fraction B. Example 44: The collected fraction was lyophilized to give 11.7 mg (3%) of 4-(3-amino-6-(methylsulfonyl)-4,5,6,7-tetrahydro-1H-pyrazolo[3,4-c]pyridine-1-carbonyl)-6-fluoro-3,4-dihydroquinolin-2(1H)-one as a white solid. Rt1: 8.33 min. MS (ES, m/z) [M+H]+: 408; (DMSO-d6, 300 MHz, ppm): δ 10.10 (s, 1H), 7.31-7.28 (m, 1H), 7.07-7.02 (m, 1H), 6.89-6.86 (m, 1H), 5.88 (s, 2H), 5.04-5.02 (m, 1H), 4.55-4.41 (m, 1H), 3.48-3.42 (m, 1H), 3.37-3.32 (m, 1H), 2.94 (s, 3H), 2.85-2.79 (m, 1H), 2.69-2.64 (m, 1H), 2.49-2.45 (m, 2H).

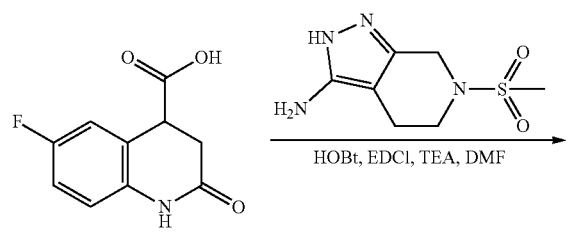

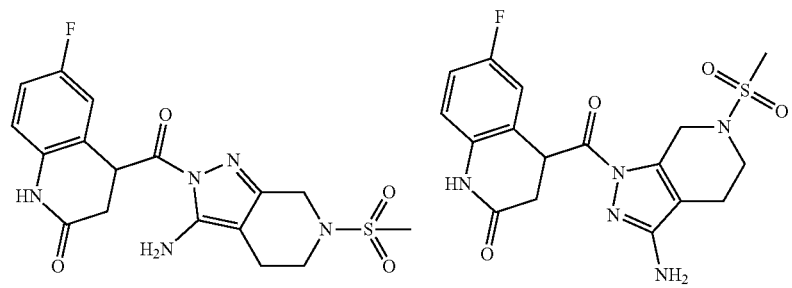

Example 45 & 46: (3-amino-6-(methylsulfonyl)-4,5,6,7-tetrahydropyrazolo[3,4-c]pyridin-2-yl)(6-isopropyl-1,2,3,4-tetrahydroquinolin-4-yl)methanone and (3-amino-6-(methylsulfonyl)-4,5,6,7-tetrahydropyrazolo[3,4-c]pyridin-1-yl)(6-isopropyl-1,2,3,4-tetrahydroquinolin-4-yl)methanone

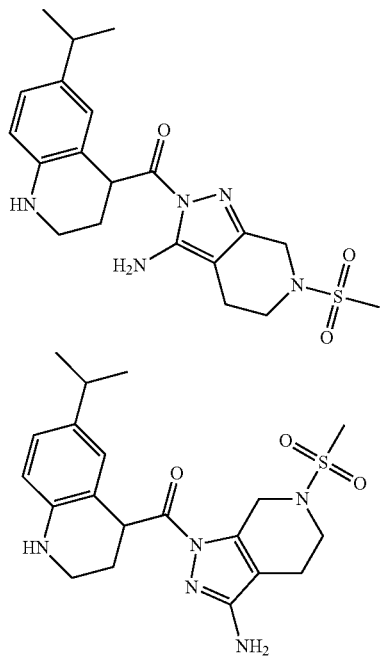

Step 1. 6-(prop-1-en-2-yl)quinoline-4-carboxylic acid

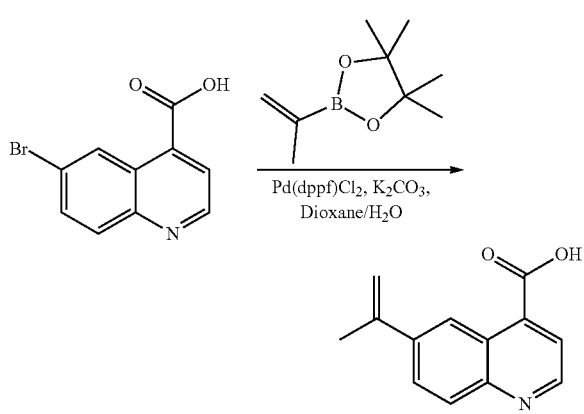

Into a 250-mL round-bottom flask, was placed 6-bromoquinoline-4-carboxylic acid (1.0 g, 3.97 mmol, 1.00 equiv), potassium carbonate (1.65 g, 11.94 mmol, 3.00 equiv), Pd(dppf)Cl$_2$CH$_2$Cl$_2$ (294 mg, 0.40 mmol, 0.10 equiv), 4,4,5,5-tetramethyl-2-(prop-1-en-2-yl)-1,3,2-dioxaborolane (1.08 g, 6.43 mmol, 1.50 equiv), Dioxane (50 mL), water (5.0 mL). The resulting solution was stirred overnight at 85° C. in an oil bath. After cooled to room temperature, the solids were filtered out. The resulting solution was diluted with water (50 mL) and extracted with ethyl acetate (50 mL×2) and the aqueous layers combined. The pH value of the solution was adjusted to 5-6 with hydrochloric acid (1 mol/L). The solids were collected by filtration. This resulted in 700 mg (83%) of 6-(prop-1-en-2-yl)quinoline-4-carboxylic acid as a off-white solid. MS (ES, m/z) [M+H]+: 214.

Step 2. 6-isopropylquinoline-4-carboxylic acid

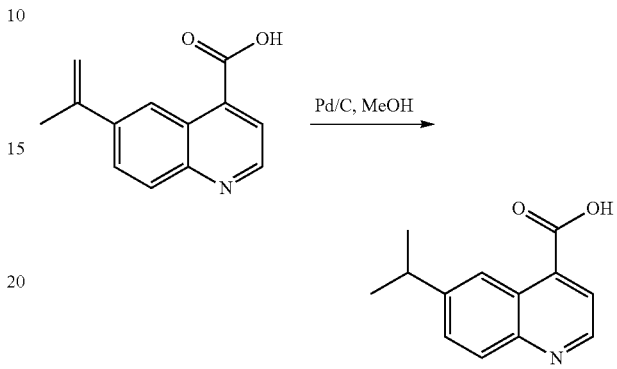

Into a 500-mL round-bottom flask, was placed 6-(prop-1-en-2-yl)quinoline-4-carboxylic acid (700 mg, 3.28 mmol, 1.00 equiv), methanol (200 mL), Palladium carbon (10%, 700 mg). The flask was evacuated and flushed three times with nitrogen, followed by flushing with hydrogen. The mixture was stirred 2 h at room temperature under an atmosphere of hydrogen (balloon). The solids were filtered out. The resulting mixture was concentrated under vacuum. This resulted in 300 mg (42%) of 6-(propan-2-yl)-1,2,3,4-tetrahydroquinoline-4-carboxylic acid as a white solid. MS (ES, m/z) [M+H]+: 216.

Step 3. 6-isopropyl-1,2,3,4-tetrahydroquinoline-4-carboxylic acid

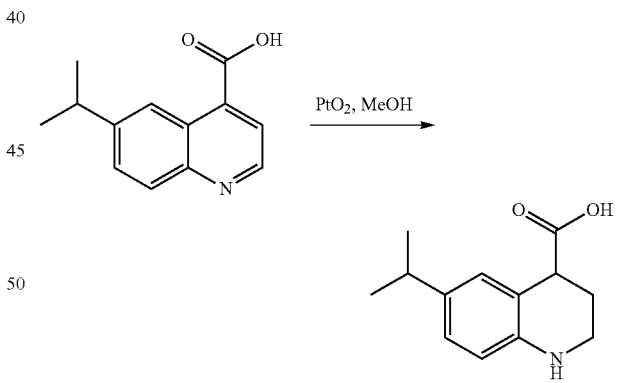

Into a 100-mL round-bottom flask, was placed 6-(propan-2-yl)quinoline-4-carboxylic acid (90 mg, 0.42 mmol, 1.00 equiv), methanol (15.0 mL), dioxoplatinum (90 mg, 0.40 mmol, 0.95 equiv). The flask was evacuated and flushed three times with nitrogen, followed by flushing with hydrogen. The mixture was stirred 2 h at room temperature (20° C.) under an atmosphere of hydrogen (balloon). The resulting mixture was concentrated under vacuum. The residue was dissolved in 10.0 mL of methanol. The residue was applied onto a silica gel column with MeCN/H$_2$O (0-40%). This resulted in 50 mg (55%) of 6-(propan-2-yl)-1,2,3,4-tetrahydroquinoline-4-carboxylic acid as a white solid. MS (ES, m/z) [M+H]+: 220.

Step 4. (3-amino-6-(methylsulfonyl)-4,5,6,7-tetrahydropyrazolo[3,4-c]pyridin-2-yl)(6-isopropyl-1,2,3,4-tetrahydroquinolin-4-yl)methanone and (3-amino-6-(methylsulfonyl)-4,5,6,7-tetrahydropyrazolo[3,4-c]pyridin-1-yl)(6-isopropyl-1,2,3,4-tetrahydroquinolin-4-yl)methanone

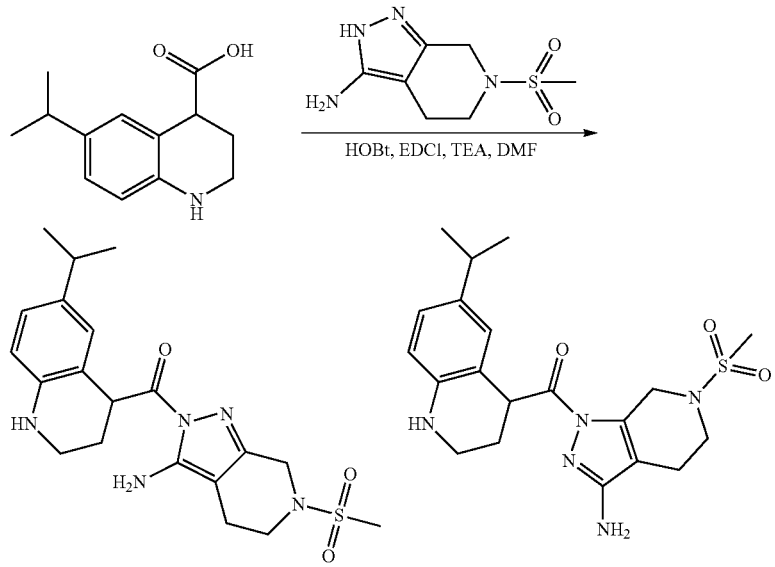

Into a 100-mL round-bottom flask, was placed 6-(propan-2-yl)-1,2,3,4-tetrahydroquinoline-4-carboxylic acid (219 mg, 1.00 mmol, 1.00 equiv), 6-methanesulfonyl-4,5,6,7-tetrahydro-2H-pyrazolo[3,4-c]pyridin-3-amine (216 mg, 1.00 mmol, 1.00 equiv), 1H-1,2,3-benzotriazol-1-ol (202 mg, 1.49 mmol, 1.50 equiv), EDCI (287 mg, 1.50 mmol, 1.50 equiv), TEA (505 mg, 4.99 mmol, 5.00 equiv), N,N-dimethylformamide (15 mL). The resulting solution was stirred for 2 h at 20° C. The reaction was then quenched by the addition of water (20 mL). The resulting solution was extracted with ethyl acetate (30 mL×3) and the organic layers combined and dried over anhydrous sodium sulfate. The solids were filtered out. The resulting mixture was concentrated under vacuum. The crude product was purified by Prep-HPLC with the following conditions: Column, XBridge C18 OBD Prep Column, 10 μm, 19 mm×250 mm; mobile phase, water (0.1% FA) and ACN (20.0% ACN up to 40.0% in 9 min); Detector, UV 254 nm.

Fraction A: The collected fraction was lyophilized to give 11.1 mg (3%) of (3-amino-6-(methylsulfonyl)-4,5,6,7-tetrahydropyrazolo[3,4-c]pyridin-2-yl)(6-isopropyl-1,2,3,4-tetrahydroquinolin-4-yl)methanone as an off-white solid. Rt2: 7.03 min. MS (ES, m/z) [M+H]+: 418. (DMSO-d6, 400 MHz, ppm): δ 6.81 (d, J=8.4 Hz, 1H), 6.65-6.63 (m, 3H), 6.45 (d, J=8.4 Hz, 1H), 5.85 (s, 1H), 4.99-4.97 (m, 1H), 4.23 (s, 2H), 3.46-3.39 (m, 2H), 3.26-3.21 (m, 1H), 3.16-3.13 (m, 1H), 2.97 (s, 3H), 2.67-2.59 (m, 1H), 2.47-2.41 (m, 2H), 2.07-1.99 (m, 2H), 1.06-1.05 (m, 6H).

Fraction B: The collected fraction was lyophilized to give 13.2 mg (3%) of (3-amino-6-(methylsulfonyl)-4,5,6,7-tetrahydropyrazolo[3,4-c]pyridin-1-yl)(6-isopropyl-1,2,3,4-tetrahydroquinolin-4-yl)methanone as a white solid. Rt1: 6.52 min. MS (ES, m/z) [M+H]+: 418. (DMSO-d6, 400 MHz, ppm): δ 6.81 (d, J=8.4 Hz, 1H), 6.66-6.65 (m, 1H), 6.45 (d, J=8.4 Hz, 1H), 5.78 (s, 3H), 4.91-4.88 (m, 1H), 4.52 (s, 2H), 3.45-3.38 (m, 2H), 3.27-3.24 (m, 1H), 3.16-3.11 (m, 1H), 2.97 (s, 3H), 2.67-2.59 (m, 1H), 2.47-2.45 (m, 2H), 2.07-1.99 (m, 2H), 1.07-1.05 (m, 6H).

Example 47 & 48: N-(4-(3-amino-6-(methylsulfonyl)-4,5,6,7-tetrahydro-2H-pyrazolo[3,4-c]pyridine-2-carbonyl)-1,2,3,4-tetrahydroquinolin-6-yl)acetamide and N-(4-(3-amino-6-(methylsulfonyl)-4,5,6,7-tetrahydro-1H-pyrazolo[3,4-c]pyridine-1-carbonyl)-1,2,3,4-tetrahydroquinolin-6-yl)acetamide

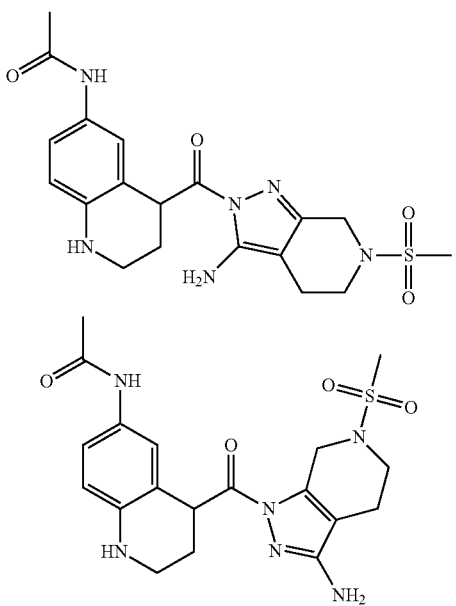

Step 1. Methyl 6-aminoquinoline-4-carboxylate

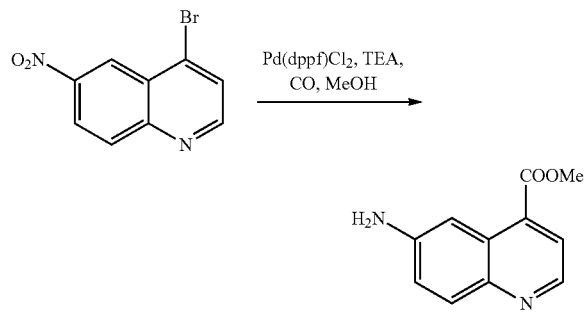

Into a 50-mL pressure tank reactor (50 atm) purged and maintained with an inert atmosphere of CO, was placed a solution of 4-bromo-6-nitroquinoline (2.0 g, 7.90 mmol, 1.00 equiv) in methanol (20 mL), TEA (4.0 g, 39.60 mmol, 5.00 equiv), Pd(dppf)Cl$_2$CH$_2$Cl$_2$ (1.29 g, 1.58 mmol, 0.20 equiv). The resulting solution was stirred for 24 h at 70° C. The reaction mixture was cooled to 20 degree C. with a water bath. The resulting mixture was concentrated under vacuum. The crude product was purified by reversed phase column with the following conditions: Column, C18 silica gel, 120 g, 20-45 um, 100 A; mobile phase, water with 0.05% FA and ACN (5% up to 40% ACN in 15 min); Detector, UV 220/254 nm. This resulted in 322 mg (20%) of methyl 6-aminoquinoline-4-carboxylate as a yellow solid. MS (ES, m/z) [M+H]+: 203.

Step 2. Methyl 6-acetamidoquinoline-4-carboxylate

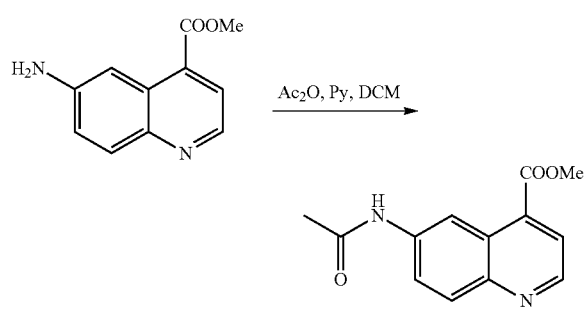

Into a 100-mL round-bottom flask, was placed a solution of methyl 6-aminoquinoline-4-carboxylate (350 mg, 1.73 mmol, 1.00 equiv) in dichloromethane (15 mL), acetyl acetate (195 mg, 1.91 mmol, 1.10 equiv), Pyridine (273 mg, 3.46 mmol, 2.00 equiv). The resulting solution was stirred for 4.0 h at 20° C. The resulting mixture was concentrated under vacuum. The crude product was purified by reversed phase column with the following conditions: Column, C18 silica gel, 80 g, 20-45 um, 100 A; mobile phase, water with 0.05% FA and ACN (2% up to 40% ACN in 20 min); Detector, UV 220/254 nm. This resulted in 417 mg (99%) of methyl 6-acetamidoquinoline-4-carboxylate as a yellow solid. MS (ES, m/z) [M+H]+: 245.

Step 3. Methyl 6-acetamido-1,2,3,4-tetrahydroquinoline-4-carboxylate

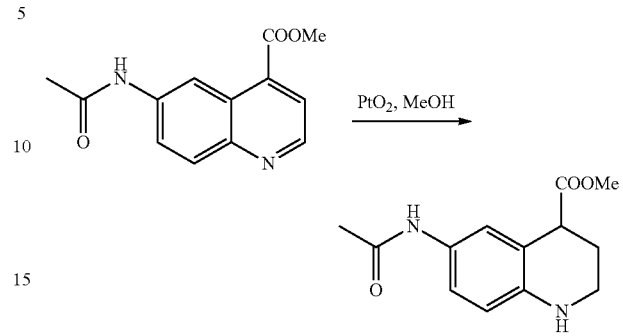

Into a 50-mL round-bottom flask, was placed a solution of methyl 6-acetamidoquinoline-4-carboxylate (392 mg, 1.60 mmol, 1.00 equiv) in methanol (15 mL), PtO$_2$ (196 mg). The flask was evacuated and flushed three times with nitrogen, followed by flushing with hydrogen. The mixture was stirred 1.0 h at 20° C. under an atmosphere of hydrogen (balloon). Then PtO$_2$ (200 mg) was added. The resulting solution was allowed to react, with stirring, for an additional 1.0 h at 20° C. The solids were filtered out. The filtrate was concentrated under vacuum. This resulted in 338 mg (85%) of methyl 6-acetamido-1,2,3,4-tetrahydroquinoline-4-carboxylate as yellow oil. MS (ES, m/z) [M+H]+: 249.

Step 4. 6-acetamido-1,2,3,4-tetrahydroquinoline-4-carboxylic acid

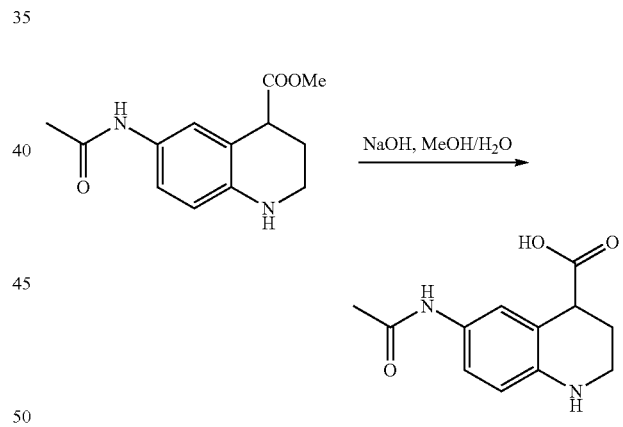

Into a 50-mL round-bottom flask purged and maintained with an inert atmosphere of nitrogen, was placed a solution of methyl 6-acetamido-1,2,3,4-tetrahydroquinoline-4-carboxylate (338 mg, 1.36 mmol, 1.00 equiv) in methanol (6 mL), water (6.0 mL), sodium hydroxide (272 mg, 6.80 mmol, 5.0 equiv). The resulting solution was stirred for 2.0 h at 20° C. The pH value of the solution was adjusted to 5-6 with hydrochloric acid (1.0 mol/L). The resulting mixture was concentrated under vacuum. The crude product was purified by reversed phase column with the following conditions: Column, C18 silica gel, 80 g, 20-45 um, 100 A; mobile phase, water with 0.05% FA and ACN (2% up to 20% ACN in 20 min); Detector, UV 220/254 nm. This resulted in 254 mg (80%) of 6-acetamido-1,2,3,4-tetrahydroquinoline-4-carboxylic acid as a brown solid. MS (ES, m/z) [M+H]+: 249.

Step 5. N-(4-(3-amino-6-(methylsulfonyl)-4,5,6,7-tetrahydro-2H-pyrazolo[3,4-c]pyridine-2-carbonyl)-1,2,3,4-tetrahydroquinolin-6-yl)acetamide and N-(4-(3-amino-6-(methylsulfonyl)-4,5,6,7-tetrahydro-1H-pyrazolo[3,4-c]pyridine-1-carbonyl)-1,2,3,4-tetrahydroquinolin-6-yl)acetamide

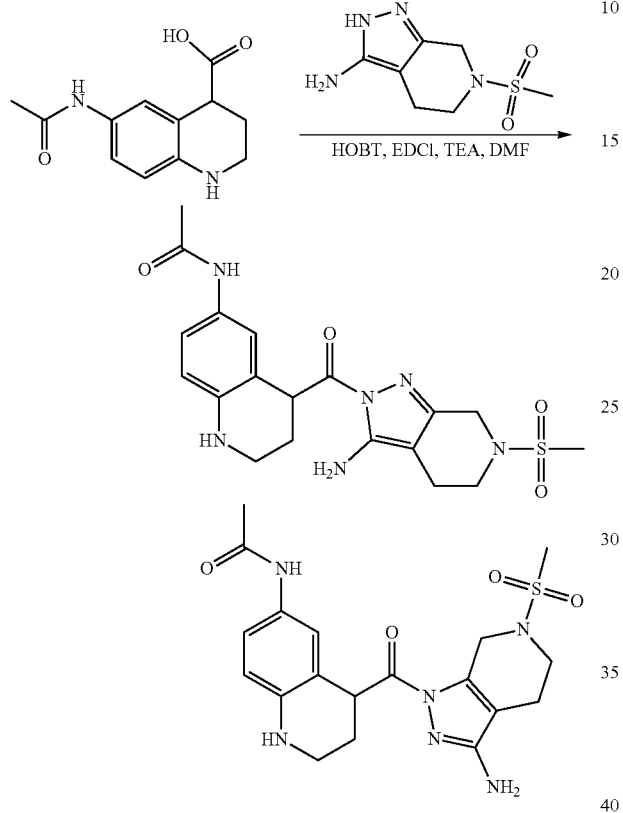

Into a 50-mL round-bottom flask, was placed 6-acetamido-1,2,3,4-tetrahydroquinoline-4-carboxylic acid (16 mg, 0.07 mmol, 1.50 equiv), 6-methanesulfonyl-4,5,6,7-tetrahydro-2H-pyrazolo[3,4-c]pyridin-3-amine (10 mg, 0.05 mmol, 1.00 equiv), HOBt (9.3 mg, 0.07 mmol, 1.50 equiv), EDCI (13 mg, 0.07 mmol, 1.50 equiv), TEA (14 mg, 0.14 mmol, 3.00 equiv), N,N-dimethylformamide (10 ml). The resulting solution was stirred for 2 h at room temperature. The reaction was then quenched by the addition of water (20 mL). The resulting solution was extracted with dichloromethane (20 mL×3) and the organic layers combined and concentrated under vacuum. The crude product was purified by Prep-HPLC with the following conditions: Column, XBridge Prep OBD C18 Column, 19×250 mm, 5 um; mobile phase, water (10 mM NH$_4$HCO$_3$) and ACN (25.0% ACN up to 50.0% in 7 min); Detector, UV 254 nm.

Fraction A: The collected fraction was lyophilized to give 4.2 mg (21%) of N-(4-(3-amino-6-(methylsulfonyl)-4,5,6,7-tetrahydro-2H-pyrazolo[3,4-c]pyridine-2-carbonyl)-1,2,3,4-tetrahydroquinolin-6-yl)acetamide as a pink solid. Rt2: 6.48 min. MS (ES, m/z) [M+H]+: 433; (DMSO, 400 MHz, ppm): δ 9.42 (s, 1H), 7.42-7.13 (m, 1H), 6.98 (s, 1H), 6.64 (s, 1H), 6.46-6.440 (m, 1H), 5.67 (s, 1H), 5.01 (m, 1H), 4.25-4.24 (m, 2H), 3.43-3.41 (m, 2H), 3.31-3.28 (m, 2H), 2.97 (s, 3H), 2.50-2.46 (m, 2H), 2.02-2.01 (m, 2H), 1.90 (s, 3H).

Fraction B: The collected fraction was lyophilized to give 2.3 mg (11.5%) of N-(4-(3-amino-6-(methylsulfonyl)-4,5,6,7-tetrahydro-1H-pyrazolo[3,4-c]pyridine-1-carbonyl)-1,2,3,4-tetrahydroquinolin-6-yl)acetamide as a pink solid. Rt1: 6.01 min. MS (ES, m/z) [M+H]+: 433; (DMSO, 400 MHz, ppm): δ 9.43 (s, 1H), 7.42-7.13 (m, 1H), 6.92-6.92 (s, 1H), 6.45-6.43 (s, 1H), 5.81 (s, 1H), 5.67 (s, 1H), 4.93-4.90 (m, 1H), 4.53 (s, 2H), 3.43-3.40 (m, 2H), 3.33-3.26 (m, 1H), 3.25 (m, 1H), 2.97 (s, 3H), 2.54-2.34 (m, 2H), 2.02-1.99 (m, 2H), 1.90 (s, 3H).

Example 49 & 50: (3-amino-6-(methylsulfonyl)-4,5,6,7-tetrahydropyrazolo[3,4-c]pyridin-2-yl)(6-phenyl-1,2,3,4-tetrahydroquinolin-4-yl)methanone and (3-amino-6-(methylsulfonyl)-4,5,6,7-tetrahydropyrazolo[3,4-c]pyridin-1-yl)(6-phenyl-1,2,3,4-tetrahydroquinolin-4-yl)methanone

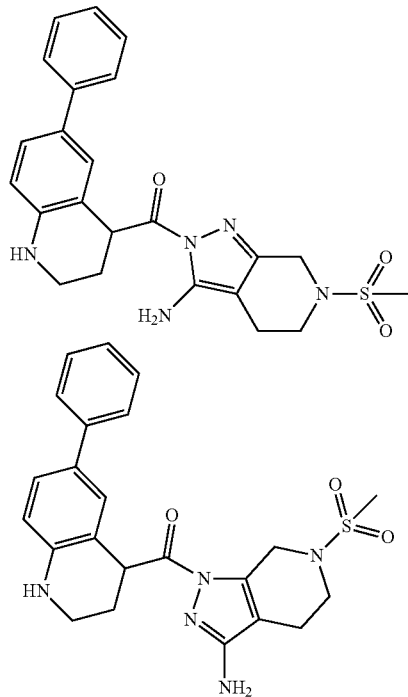

Step 1. 6-phenylquinoline-4-carboxylic acid

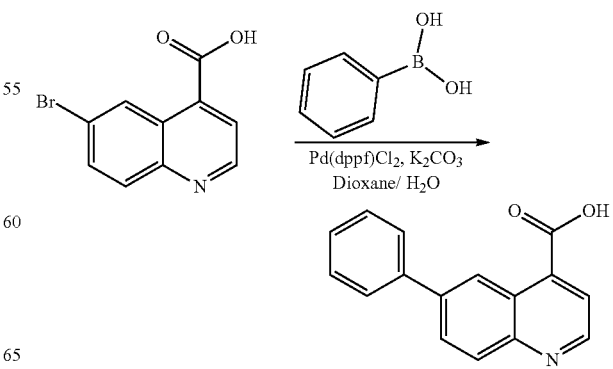

Into a 100-mL round-bottom flask, was placed 6-bromoquinoline-4-carboxylic acid (500 mg, 1.98 mmol, 1.00 equiv), Potassium carbonate (828 mg, 5.99 mmol, 3.00 equiv), Pd(dppf)Cl$_2$CH$_2$Cl$_2$ (147 mg, 0.20 mmol, 0.10 equiv), phenylboronic acid (366 mg, 3.00 mmol, 1.50 equiv), dioxane (30 mL), water (3 mL). To the above N$_2$ was introduced in. The resulting solution was stirred overnight at 85° C. in an oil bath. After cooling to room temperature, the solids were filtered out. The resulting mixture was concentrated under vacuum. The residue was dissolved in H$_2$O (50 mL). The resulting solution was extracted with ethyl acetate (30 mL×2) and the aqueous layers combined. The pH value of the solution was adjusted to 6 with hydrochloric acid (1 mol/L). The isolated solid was collected. This resulted in 180 mg (36%) of 6-phenylquinoline-4-carboxylic acid as a white solid. MS (ES, m/z) [M+H]+: 250.

Step 2.
6-phenyl-1,2,3,4-tetrahydroquinoline-4-carboxylic acid

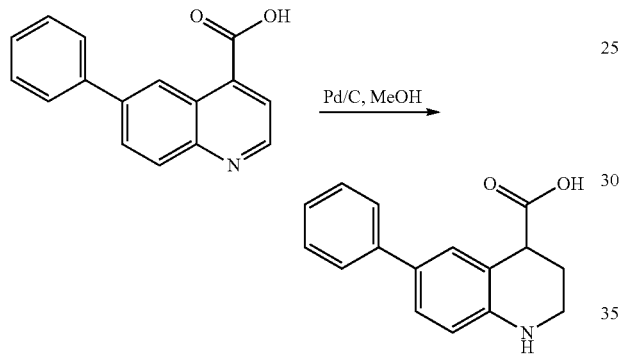

Into a 250-mL round-bottom flask, was placed 6-phenylquinoline-4-carboxylic acid (500 mg, 2.01 mmol, 1.00 equiv), methanol (90 mL), AceticAcid (20 mL), Palladium carbon (10%, 500 mg), The flask was evacuated and flushed three times with nitrogen, followed by flushing with hydrogen. The mixture was stirred overnight at 20° C. under an atmosphere of hydrogen (balloon). The resulting mixture was filtered and the filtrate was concentrated under vacuum. This resulted in 100 mg (20%) of 6-phenyl-1,2,3,4-tetrahydroquinoline-4-carboxylic acid as a yellow solid. MS (ES, m/z) [M+H]+: 254.

Step 3. (3-amino-6-(methylsulfonyl)-4,5,6,7-tetrahydropyrazolo[3,4-c]pyridin-2-yl)(6-phenyl-1,2,3,4-tetrahydroquinolin-4-yl)methanone and (3-amino-6-(methylsulfonyl)-4,5,6,7-tetrahydropyrazolo[3,4-c]pyridin-1-yl)(6-phenyl-1,2,3,4-tetrahydroquinolin-4-yl)methanone

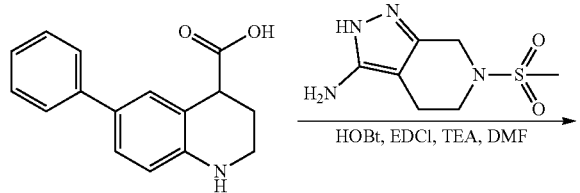

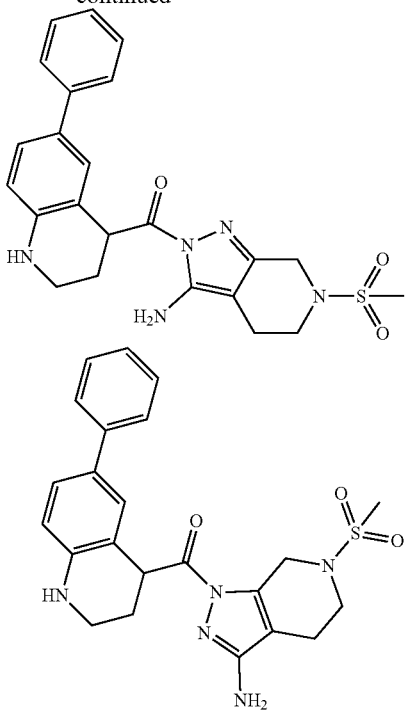

Into a 40-mL vial, was placed 6-phenyl-1,2,3,4-tetrahydroquinoline-4-carboxylic acid (120 mg, 0.47 mmol, 1.00 equiv), 1H-1,2,3-benzotriazol-1-ol (96 mg, 0.71 mmol, 1.50 equiv), EDCI (138 mg, 0.72 mmol, 1.50 equiv), TEA (144 mg, 1.42 mmol, 3.00 equiv), N,N-dimethylformamide (10.0 mL), 6-methanesulfonyl-4,5,6,7-tetrahydro-2H-pyrazolo[3,4-c]pyridin-3-amine (102 mg, 0.47 mmol, 1.00 equiv). The resulting solution was stirred for 6.0 h at 20° C. The reaction was then quenched by the addition of water (20 mL). The resulting solution was extracted with ethyl acetate (30 mL×3) and the organic layers combined and dried over anhydrous sodium sulfate. The solids were filtered out. The resulting mixture was concentrated under vacuum. The crude product was purified by Prep-HPLC with the following conditions: Column, XSelect CSH Prep C18 OBD Column, 5 um, 19×150 mm; mobile phase, water (0.1% FA) and ACN (35.0% ACN up to 70.0% in 7 min); Detector, uv 254 nm.

Fraction A: The collected fraction was lyophilized to give 13.6 mg (6%) of (3-amino-6-(methylsulfonyl)-4,5,6,7-tetrahydropyrazolo[3,4-c]pyridin-2-yl)(6-phenyl-1,2,3,4-tetrahydroquinolin-4-yl)methanone as an off-white solid. Rt2: 6.12 min. MS (ES, m/z) [M+H]+: 452. (DMSO, 400 MHz, ppm): δ 7.45-7.43 (m, 2H), 7.35-7.28 (m, 3H), 7.19-7.17 (m, 2H), 6.63-6.60 (m, 3H), 6.10 (s, 1H), 5.07-5.05 (m, 1H), 4.26 (s, 2H), 3.44-3.42 (m, 2H), 3.29-3.23 (m, 2H), 2.97 (s, 3H), 2.44-2.40 (m, 2H), 2.14-2.08 (m, 2H).

Fraction B: The collected fraction was lyophilized to give 32.5 mg (15%) of (3-amino-6-(methylsulfonyl)-4,5,6,7-tetrahydropyrazolo[3,4-c]pyridin-1-yl)(6-phenyl-1,2,3,4-tetrahydroquinolin-4-yl)methanone as an off-white solid. Rt1: 5.50 min. MS (ES, m/z) [M+H]+: 452. (DMSO, 400 MHz, ppm): δ 7.46-7.44 (m, 2H), 7.34-7.31 (m, 2H), 7.28-7.25 (m, 1H), 7.19-7.16 (m, 2H), 6.61-6.59 (m, 1H), 6.07 (s, 1H), 5.82 (s, 2H), 4.99-4.97 (m, 1H), 4.53 (s, 2H), 3.46-3.42 (m, 1H), 3.39-3.35 (m, 2H), 3.22-3.20 (m, 1H), 2.98 (s, 3H), 2.44-2.41 (m, 2H), 2.11-2.03 (m, 2H).

Example 51 & 52 & 53 & 54: (3-amino-6-(methyl-sulfonyl)-4,5,6,7-tetrahydropyrazolo[3,4-c]pyridin-2-yl)(6-fluoro-8-methyl-1,2,3,4-tetrahydroquinolin-4-yl)methanone and (3-amino-6-(methylsulfonyl)-4,5,6,7-tetrahydropyrazolo[3,4-c]pyridin-1-yl)(6-fluoro-8-methyl-1,2,3,4-tetrahydroquinolin-4-yl)methanone and (S*)-(3-amino-6-(methylsulfonyl)-4,5,6,7-tetrahydropyrazolo[3,4-c]pyridin-2-yl)(6-fluoro-8-methyl-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(6-fluoro-8-methyl-1,2,3,4-tetrahydroquinolin-4-yl)methanone

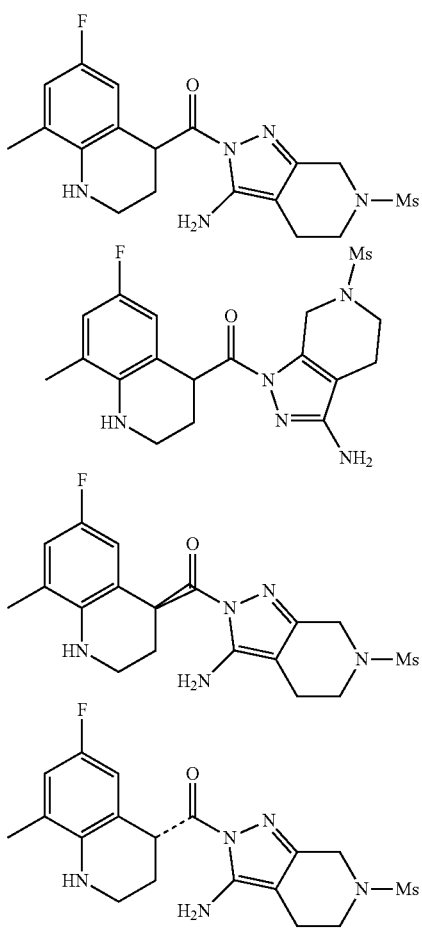

Step 1. Diethyl 2-((4-fluoro-2-methylphenylamino)methylene)malonate

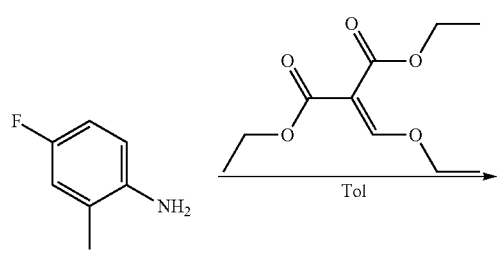

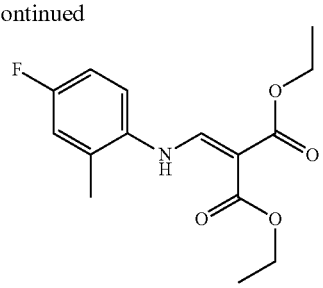

Into a 500-mL round-bottom flask, was placed 4-fluoro-2-methylbenzenamine (25 g, 200 mmol, 1.00 equiv), Toluene (30 mL), 1,3-diethyl 2-(ethoxymethylidene)propanedioate (65 g, 300 mmol, 1.50 equiv). The resulting solution was stirred overnight at 110° C. The mixture was cooled to 35° C. The resulting mixture was concentrated under vacuum. The residue was applied onto a silica gel column with ethyl acetate/petroleum ether (1/10). This resulted in 50 g (85%) of diethyl 2-((4-fluoro-2-methylphenylamino)methylene)malonate as pink solid. MS (ES, m/z) [M+H]+: 295.

Step 2. Ethyl 6-fluoro-8-methyl-4-oxo-1,4-dihydro-quinoline-3-carboxylate

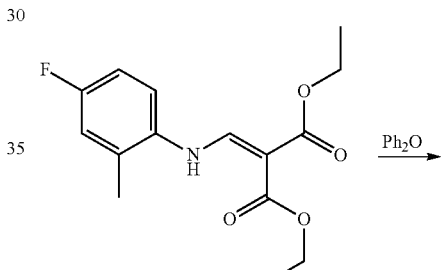

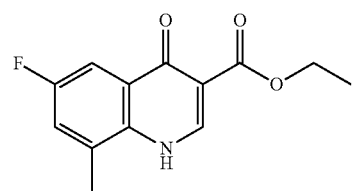

Into a 1000-mL 3-necked round-bottom flask, was placed 1,3-diethyl 2-[[(4-fluoro-2-methylphenyl)amino]methyl-idene]propanedioate (30 g, 101.59 mmol, 1.00 equiv). This was followed by the addition of phenoxybenzene (500 mL). The resulting solution was stirred for 1 h at 240° C. After cooling to room temperature, the product was precipitated by the addition of n-hexane. The solids were collected by filtration. This resulted in 21 g (83%) of ethyl 6-fluoro-8-methyl-4-oxo-1,4-dihydroquinoline-3-carboxylate as a gray solid. MS (ES, m/z) [M+H]+: 250.

Step 3. 6-fluoro-8-methylquinolin-4(1H)-one

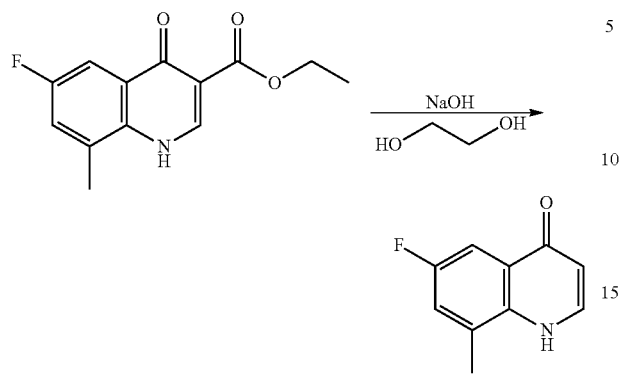

Into a 500-mL 3-necked round-bottom flask, was placed ethyl 6-fluoro-8-methyl-4-oxo-1,4-dihydroquinoline-3-carboxylate (21 g, 84.26 mmol, 1.00 equiv), ethane-1,2-diol (200 mL), sodium hydroxide (17 g, 425.00 mmol, 5.00 equiv), water (5 mL). The resulting solution was stirred for 2 h at 190° C. After cooled to room temperature, the resulting solution was diluted with $H_2O$ (300 mL). Hydrochloric acid (3 mol/L) was employed to adjust the pH to 5-6. The solids were collected by filtration. This resulted in 14.5 g (97%) of 6-fluoro-8-methylquinolin-4(1H)-one as a white solid. MS (ES, m/z) [M+H]+: 178.

Step 4. 4-bromo-6-fluoro-8-methylquinoline

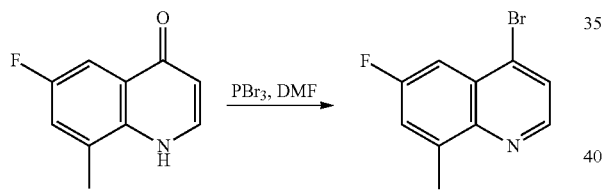

Into a 500-mL round-bottom flask, was placed 6-fluoro-8-methyl-1,4-dihydroquinolin-4-one (14.5 g, 81.84 mmol, 1.00 equiv), N,N-dimethylformamide (150 mL). This was followed by the addition of PBr3 (24 g, 88.66 mmol, 1.10 equiv) dropwise with stirring at 0° C. The resulting solution was stirred for 3 h at room temperature. The reaction was then quenched by the addition of water/ice (300 mL). Sodium hydroxide (20%) was employed to adjust the pH to 8-9. The solids were collected by filtration. This resulted in 16 g (81%) of 4-bromo-6-fluoro-8-methylquinoline as a white solid. MS (ES, m/z) [M+H]+: 240.

Step 5. Methyl 6-fluoro-8-methylquinoline-4-carboxylate

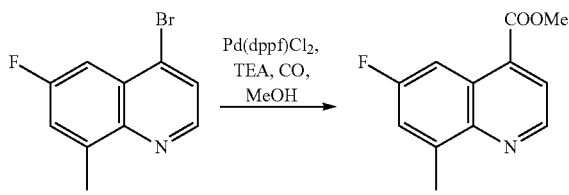 [SMILES: Cc1cc(F)cc2c(Br)ccnc12 ; "Pd(dppf)Cl2,TEA, CO,MeOH" ; COC(=O)c1ccnc2c(C)cc(F)cc12]

Into a 300-mL pressure tank reactor (50 atm) purged and maintained with an inert atmosphere of carbon monoxide, was placed 4-bromo-6-fluoro-8-methylquinoline (16 g, 66.65 mmol, 1.00 equiv), methanol (100 mL), Pd(dppf) $Cl_2CH_2Cl_2$ (8 g, 9.79 mmol, 0.15 equiv), TEA (20 g, 197.65 mmol, 3.00 equiv). The resulting solution was stirred overnight at 70° C. After cooling to room temperature, the resulting mixture was concentrated under vacuum. The residue was applied onto a silica gel column with ethyl acetate/petroleum ether (0-30%). This resulted in 10 g (68%) of methyl 6-fluoro-8-methylquinoline-4-carboxylate as a white solid. MS (ES, m/z) [M+H]+: 220.

Step 6. Methyl 6-fluoro-8-methyl-1,2,3,4-tetrahydroquinoline-4-carboxylate

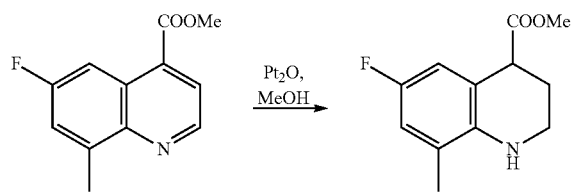

Into a 250-mL round-bottom flask, was placed methyl 6-fluoro-8-methylquinoline-4-carboxylate (2 g, 9.75 mmol, 1.00 equiv), methanol (50 mL), $PtO_2$ (1 g). To the above hydrogen was introduced in. The resulting solution was stirred for 1 h at room temperature. The solids were filtered out. The resulting mixture was concentrated under vacuum. This resulted in 1.5 g (74%) of methyl 6-fluoro-8-methyl-1,2,3,4-tetrahydroquinoline-4-carboxylate as yellow oil. MS (ES, m/z) [M+H]+: 222.

Step 7. 6-fluoro-8-methyl-1,2,3,4-tetrahydroquinoline-4-carboxylic acid

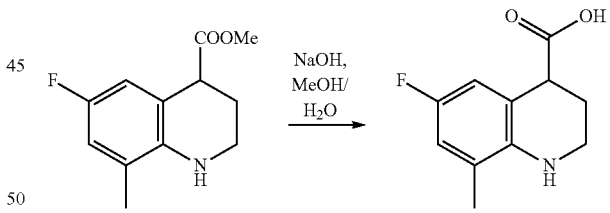

Into a 250-mL round-bottom flask, was placed methyl 6-fluoro-8-methyl-1,2,3,4-tetrahydroquinoline-4-carboxylate (1.5 g, 6.72 mmol, 1.00 equiv), methanol (80 mL), a solution of sodium hydroxide (800 mg, 20.00 mmol, 3.00 equiv) in water (40 mL). The resulting solution was stirred overnight at room temperature. The resulting mixture was concentrated under vacuum. The resulting solution was extracted with ethyl acetate (40 mL×2) and the aqueous layers combined. Hydrochloric acid (3 mol/L) was employed to adjust the pH to 5-6. The resulting solution was extracted with ethyl acetate (50 mL×3) and the organic layers combined. The resulting mixture was concentrated under vacuum. This resulted in 1.3 g (92%) of 6-fluoro-8-methyl-1,2,3,4-tetrahydroquinoline-4-carboxylic acid as a yellow solid. MS (ES, m/z) [M+H]+: 208.

Step 8. (3-amino-6-(methylsulfonyl)-4,5,6,7-tetrahydropyrazolo[3,4-c]pyridin-2-yl)(6-fluoro-8-methyl-1,2,3,4-tetrahydroquinolin-4-yl)methanone and (3-amino-6-(methylsulfonyl)-4,5,6,7-tetrahydropyrazolo[3,4-c]pyridin-1-yl)(6-fluoro-8-methyl-1,2,3,4-tetrahydroquinolin-4-yl)methanone

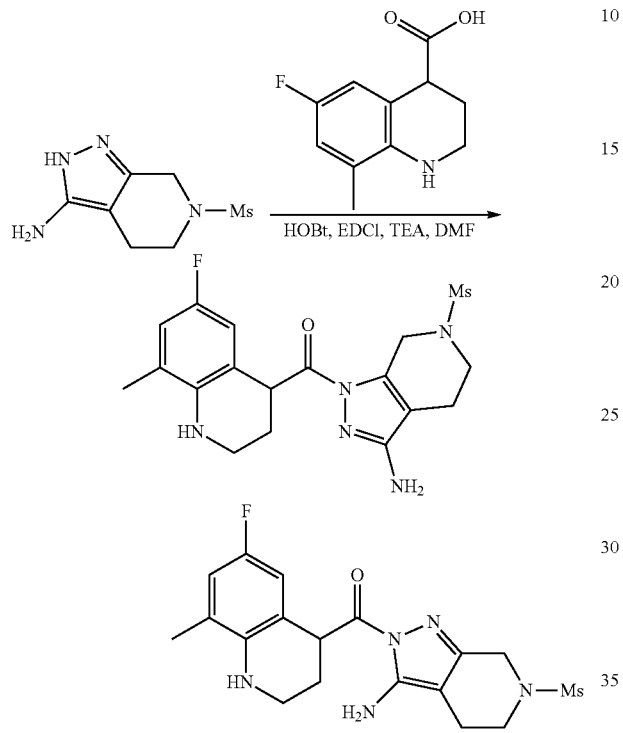

Into a 50-mL round-bottom flask, was placed 6-methanesulfonyl-4,5,6,7-tetrahydro-2H-pyrazolo[3,4-c]pyridin-3-amine (115 mg, 0.53 mmol, 1.10 equiv), 6-fluoro-8-methyl-1,2,3,4-tetrahydroquinoline-4-carboxylic acid (100 mg, 0.48 mmol, 1.00 equiv), HOBt (100 mg, 0.74 mmol, 1.50 equiv), EDCI (140 mg, 0.73 mmol, 1.50 equiv), TEA (145 mg, 1.43 mmol, 3.00 equiv), N,N-dimethylformamide (5 mL). The resulting solution was stirred for 2 h at room temperature. The reaction was then quenched by the addition of water (30 mL). The resulting solution was extracted with ethyl acetate (30 mL×3) and the organic layers combined and concentrated under vacuum. The crude product was purified by Prep-HPLC with the following conditions: Column: XSelect CSH Prep C18 OBD Column, 5 um, 19×150 mm; Mobile Phase A: water (0.1% FA), Mobile Phase B: ACN; Flow rate: 20 mL/min; Gradient: 25% B to 54.6% B in 8 min; 254 nm;

Fraction A. Example 51: The collected fraction was lyophilized to give 4.1 mg (2%) of (3-amino-6-(methylsulfonyl)-4,5,6,7-tetrahydropyrazolo[3,4-c]pyridin-2-yl)(6-fluoro-8-methyl-1,2,3,4-tetrahydroquinolin-4-yl)methanone as an off-white solid. Rt2: 7.23 min. MS (ES, m/z) [M+H]+: 408; (DMSO-d6, 400 MHz, ppm): δ 6.78-6.73 (m, 1H), 6.65 (s, 2H), 6.56-6.53 (m, 1H), 5.15 (s, 1H), 5.01-4.98 (m, 1H), 4.24 (s, 2H), 3.45-3.40 (m, 2H), 3.28-3.21 (m, 2H), 2.96 (s, 3H), 2.49-2.46 (m, 2H), 2.11-1.98 (m, 5H).

Fraction B. Example 52: The collected fraction was lyophilized to give 14.6 mg (7%) of (3-amino-6-(methylsulfonyl)-4,5,6,7-tetrahydropyrazolo[3,4-c]pyridin-1-yl)(6-fluoro-8-methyl-1,2,3,4-tetrahydroquinolin-4-yl)methanone as an off-white solid. Rt1: 6.27 min. MS (ES, m/z) [M+H]+: 408; (DMSO-d6, 300 MHz, ppm): δ 6.75-6.71 (m, 1H), 6.58-6.54 (m, 1H), 5.80 (s, 2H), 5.11 (s, 1H), 4.93-4.89 (m, 1H), 4.53 (s, 2H), 3.49-3.36 (m, 2H), 3.23-3.19 (m, 2H), 2.96 (s, 3H), 2.49-2.45 (m, 2H), 2.07-1.96 (m, 5H).

Step 9. (S*)-(3-amino-6-(methylsulfonyl)-4,5,6,7-tetrahydropyrazolo[3,4-c]pyridin-2-yl)(6-fluoro-8-methyl-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(6-fluoro-8-methyl-1,2,3,4-tetrahydroquinolin-4-yl)methanone

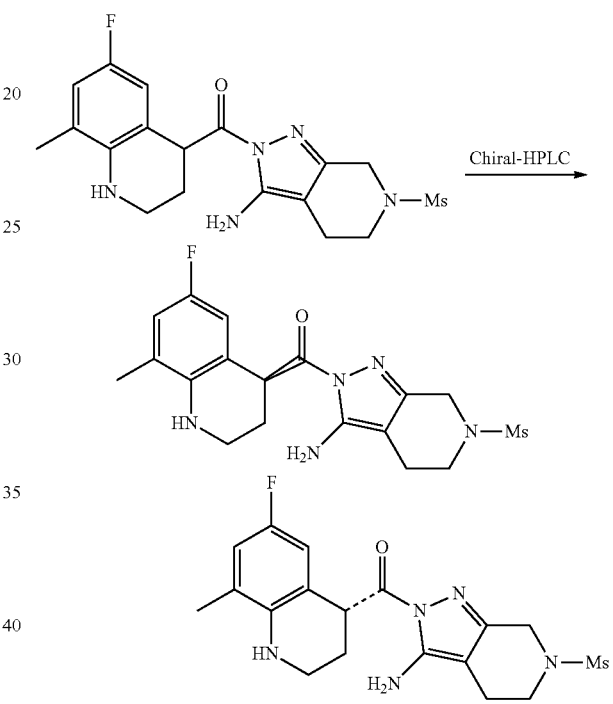

(3-amino-6-(methylsulfonyl)-4,5,6,7-tetrahydropyrazolo[3,4-c]pyridin-2-yl)(6-fluoro-8-methyl-1,2,3,4-tetrahydroquinolin-4-yl)methanone (130 mg, 0.32 mmol, 1.00 equiv) was separated by Chiral-Prep-HPLC with the following conditions: Column: CHIRAL ART Cellulose-SB S-5 um, 2×25 cm, 5 um; Mobile Phase A: Hex-HPLC, Mobile Phase B: EtOH-HPLC; Flow rate: 20 mL/min; Gradient: 50 B to 50 B in 13 min; 220/254 nm.

Enantiomer A. Example 53: This resulted in 49.6 mg (38%) of (S*)-(3-amino-6-(methylsulfonyl)-4,5,6,7-tetrahydropyrazolo[3,4-c]pyridin-2-yl)(6-fluoro-8-methyl-1,2,3,4-tetrahydroquinolin-4-yl)methanone as a white solid. Rt2: 11.39 min. MS (ES, m/z) [M+H]+: 408; (DMSO-d6, 400 MHz, ppm): δ 6.76-6.73 (m, 1H), 6.65 (s, 2H), 6.56-6.53 (m, 1H), 5.15 (s, 1H), 5.01-4.98 (m, 1H), 4.24 (s, 2H), 3.47-3.41 (m, 2H), 3.29-3.22 (m, 2H), 2.97 (s, 3H), 2.49-2.46 (m, 2H), 2.12-1.90 (m, 5H).

Enantiomer B. Example 54: This resulted in 43.6 mg (34%) of (R*)-(3-amino-6-(methylsulfonyl)-4,5,6,7-tetrahydropyrazolo[3,4-c]pyridin-2-yl)(6-fluoro-8-methyl-1,2,3,4-tetrahydroquinolin-4-yl)methanone as a white solid. Rt1: 9.81 min; MS (ES, m/z) [M+H]+: 408; (DMSO-d6, 400 MHz, ppm): δ 6.76-6.73 (m, 1H), 6.64 (s, 2H), 6.56-6.53 (m, 1H), 5.15 (s, 1H), 5.01-4.98 (m, 1H), 4.24 (s, 2H), 3.47-3.41 (m, 2H), 3.29-3.21 (m, 2H), 2.97 (s, 3H), 2.49-2.46 (m, 2H), 2.11-1.95 (m, 5H).

Example 55 & 56: (3-amino-6-(methylsulfonyl)-4,5,6,7-tetrahydropyrazolo[3,4-c]pyridin-2-yl)(6-ethyl-8-methyl-1,2,3,4-tetrahydroquinolin-4-yl)methanone and (3-amino-6-(methylsulfonyl)-4,5,6,7-tetrahydropyrazolo[3,4-c]pyridin-1-yl)(6-ethyl-8-methyl-1,2,3,4-tetrahydroquinolin-4-yl)methanone

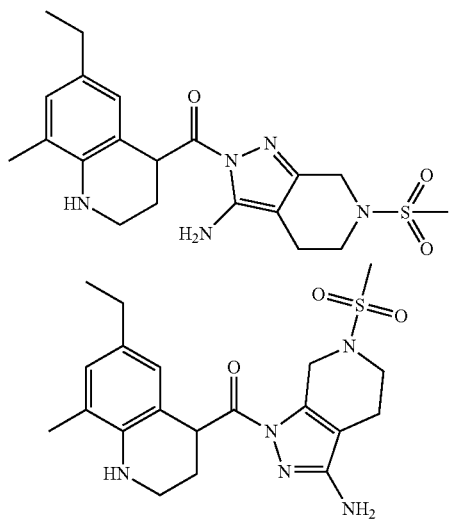

Step 1. 8-methyl-6-vinylquinolin-4(1H)-one

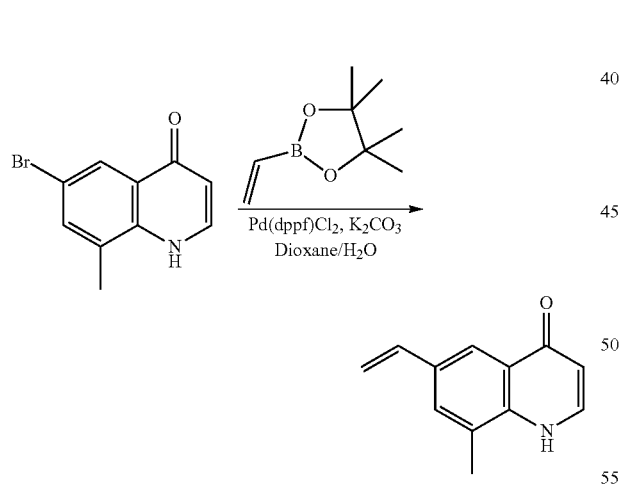

Into a 1-L round-bottom flask, was placed 6-bromo-8-methyl-1,4-dihydroquinolin-4-one (11.8 g, 49.56 mmol, 1.00 equiv), 2-ethenyl-4,4,5,5-tetramethyl-1,3,2-dioxaborolane (15.4 g, 99.99 mmol, 2.00 equiv), Pd(dppf)Cl2 (4.1 g, 5.60 mmol, 0.10 equiv), potassium carbonate (20.7 g, 3.00 equiv), dioxone (600 mL), water (60 mL). The resulting solution was stirred for 15 h at 80° C. After cooled to room temperature, the residue was applied onto a silica gel column with dichloromethane/methanol (10:1). This resulted in 5.3 g (58%) of 8-methyl-6-vinylquinolin-4(1H)-one as a brown solid. MS (ES, m/z) [M+H]+: 186.

Step 2. 4-bromo-8-methyl-6-vinylquinoline

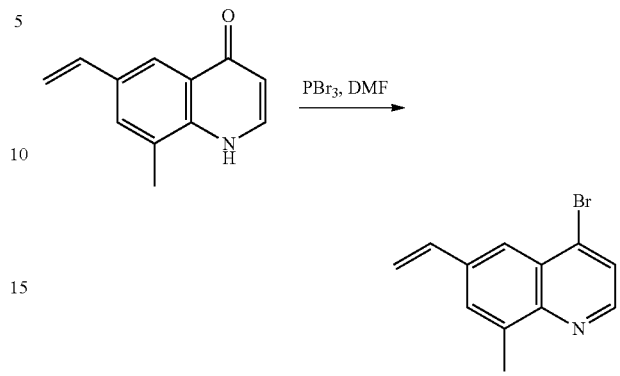

Into a 250-mL round-bottom flask, was placed 8-methyl-6-vinylquinolin-4(1H)-one (3.2 g, 17.28 mmol, 1.00 equiv), N,N-dimethylformamide (50 mL), tribromophosphane (5.6 g, 20.69 mmol, 1.20 equiv). The resulting solution was stirred for 15 h at room temperature. The reaction was then quenched by the addition of water/ice (100 mL). The pH value of the solution was adjusted to 9 with sodium hydroxide (6 mol/L). The solids were collected by filtration. This resulted in 3.5 g (87%) of 4-bromo-8-methyl-6-vinylquinoline as a white solid. MS (ES, m/z) [M+H]+: 248.

Step 3. Methyl 8-methyl-6-vinylquinoline-4-carboxylate

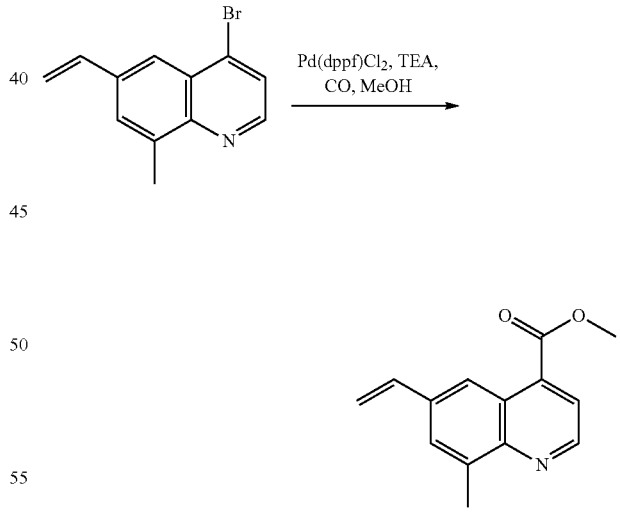

Into a 50-mL pressure tank reactor (CO, 60 atm), was placed 4-bromo-8-methyl-6-vinylquinoline (1 g, 4.27 mmol, 1.00 equiv), Pd(dppf)Cl2CH2Cl2 (0.66 g, 0.20 equiv), TEA (2.02 g, 5.00 equiv), methanol (20 mL). The resulting solution was stirred for 15 h at room temperature. The residue was applied onto a silica gel column with ethyl acetate/hexane (1:3). This resulted in 600 mg (62%) of methyl 8-methyl-6-vinylquinoline-4-carboxylate as a yellow solid. MS (ES, m/z) [M+H]+: 228.

Step 4. Methyl 6-ethyl-8-methyl-1,2,3,4-tetrahydroquinoline-4-carboxylate

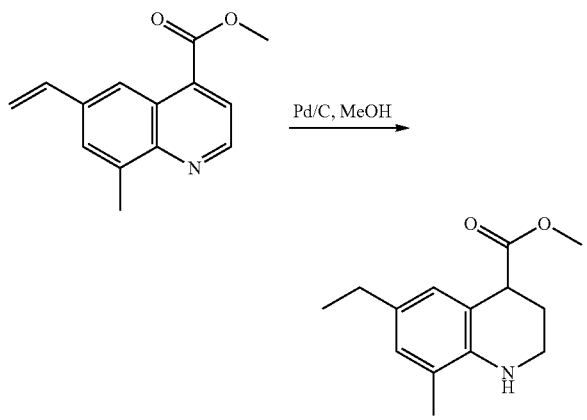

Into a 100-mL round-bottom flask, was placed methyl 6-ethenyl-8-methylquinoline-4-carboxylate (700 mg, 3.08 mmol, 1.00 equiv), methanol (30 mL), Palladium carbon (10%, 350 mg). The resulting solution was stirred for 15 h at room temperature. The flask was evacuated and flushed three times with nitrogen, followed by flushing with hydrogen. The mixture was stirred 2 h at room temperature under an atmosphere of hydrogen (balloon). The solid was filtered out. The filtrate was concentrated under vacuum. This resulted in 500 mg (70%) of methyl 6-ethyl-8-methyl-1,2,3,4-tetrahydroquinoline-4-carboxylate as yellow oil. MS (ES, m/z) [M+H]+: 234.

Step 5. Sodium 6-ethyl-8-methyl-1,2,3,4-tetrahydroquinoline-4-carboxylate

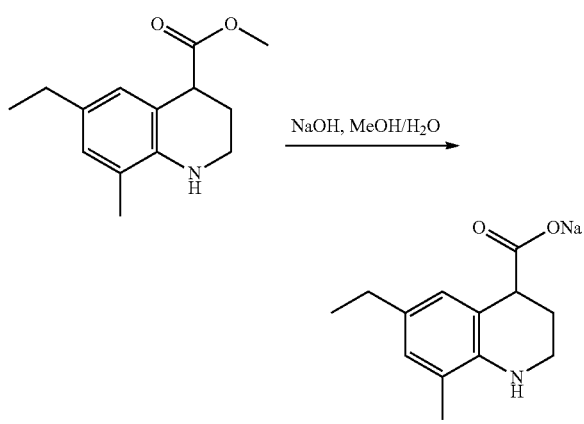

Into a 100-mL round-bottom flask, was placed methyl 6-ethyl-8-methyl-1,2,3,4-tetrahydroquinoline-4-carboxylate (360 mg, 1.54 mmol, 1.00 equiv), methanol (30 mL), water (15 mL), NaOH (185 mg, 4.64 mmol, 3.00 equiv). The resulting solution was stirred for 15 h at room temperature. The reaction liquid was removed by distillation under vacuum. This resulted in 200 mg (54%) of sodium 6-ethyl-8-methyl-1,2,3,4-tetrahydroquinoline-4-carboxylate as a yellow solid. MS (ES, m/z) [M+H]+: 242.

Step 6. (3-amino-6-(methylsulfonyl)-4,5,6,7-tetrahydropyrazolo[3,4-c]pyridin-2-yl)(6-ethyl-8-methyl-1,2,3,4-tetrahydroquinolin-4-yl)methanone and (3-amino-6-(methylsulfonyl)-4,5,6,7-tetrahydropyrazolo[3,4-c]pyridin-1-yl)(6-ethyl-8-methyl-1,2,3,4-tetrahydroquinolin-4-yl)methanone

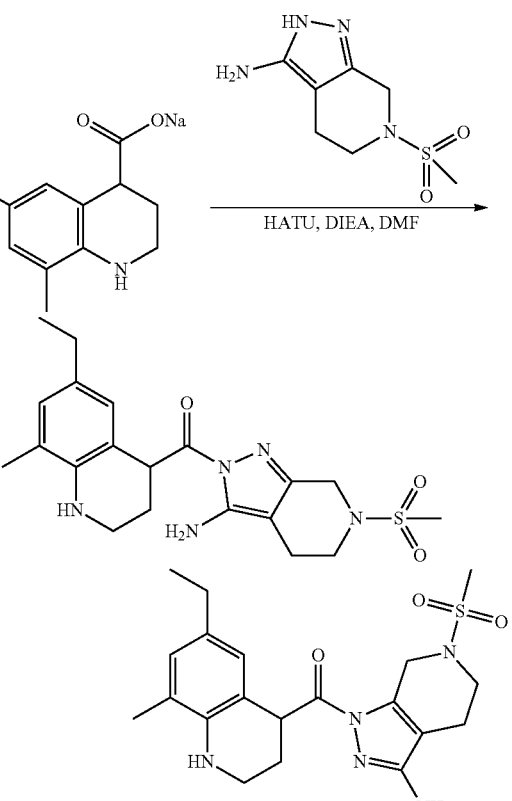

Into a 100-mL round-bottom flask, was placed sodium 6-ethyl-8-methyl-1,2,3,4-tetrahydroquinoline-4-carboxylate (150 mg, 0.62 mmol, 1.00 equiv), 6-methanesulfonyl-4,5,6,7-tetrahydro-2H-pyrazolo[3,4-c]pyridin-3-amine (148 mg, 0.68 mmol, 1.10 equiv), HATU (353 mg, 0.93 mmol, 1.50 equiv), DIEA (340 mg, 2.63 mmol, 129.00 equiv), N,N-dimethylformamide (10 mL). The resulting solution was stirred for 2 h at room temperature. The reaction was then quenched by the addition of water (50 mL). The resulting solution was extracted with ethyl acetate (50 mL×3) and the organic layers combined and concentrated under vacuum. The crude product was purified by reversed phase column with the following conditions: Column: XBridge Shield RP18 OBD Column 30×150 mm, 5 um; Mobile Phase A: water (0.1% FA), Mobile Phase B: ACN; Flow rate: 60 mL/min; Gradient: 10% B to 50% B in 9 min; 254.220 nm.

Fraction A: The collected fraction was lyophilized to give 5 mg (2%) of (3-amino-6-(methylsulfonyl)-4,5,6,7 tetrahydropyrazolo[3,4-c]pyridin-2-yl)(6-ethyl-8-methyl-1,2,3,4-tetrahydroquinolin-4-yl)methanone as a white solid. Rt2: 8.45 min. MS (ES, m/z) [M+H]+: 418. (DMSO-d6, 300 MHz, ppm): δ 6.70 (s, 1H), 6.63 (s, 2H), 6.49 (s, 1H), 5.04-5.00 (m, 2H), 4.24 (s, 2H), 3.44-3.40 (m, 2H), 3.25-3.23 (m, 2H), 2.97 (s, 3H), 2.47-2.45 (m, 2H), 2.38-2.30 (m, 2H), 2.09-1.98 (m, 5H), 1.07- 1.02 (m, 3H).

Fraction B: The collected fraction was lyophilized to give 10.3 mg (4%) of (3-amino-6-(methylsulfonyl)-4,5,6,7-tetrahydropyrazolo[3,4-c]pyridin-1-yl)(6-ethyl-8-methyl-1,2,3,4-tetrahydroquinolin-4-yl)methanone as a white solid. Rt1: 6.67 min. MS (ES, m/z) [M+H]+: 418. (DMSO-d6, 300 MHz, ppm): δ 6.73 (s, 1H), 6.54 (s, 1H), 5.80 (s, 3H), 4.95-4.92 (m, 1H), 4.52 (s, 2H), 3.44-3.41 (m, 2H), 3.32-3.31 (m, 1H), 3.25-3.22 (m, 1H), 2.96 (s, 3H), 2.47-2.45 (m, 2H), 2.39-2.34 (m, 2H), 2.05- 1.97 (m, 5H), 1.08-1.03 (m, 3H).

Example 57 & 58 & 59 & 60: (3-amino-6-(methylsulfonyl)-4,5,6,7-tetrahydropyrazolo[3,4-c]pyridin-2-yl)(8-chloro-1,2,3,4-tetrahydroquinolin-4-yl)methanone and (3-amino-6-(methylsulfonyl)-4,5,6,7-tetrahydropyrazolo[3,4-c]pyridin-1-yl)(8-chloro-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(8-chloro-1,2,3,4-tetrahydroquinolin-4-yl)methanone and (S*)-(3-amino-6-(methylsulfonyl)-4,5,6,7-tetrahydropyrazolo[3,4-c]pyridin-2-yl)(8-chloro-1,2,3,4-tetrahydroquinolin-4-yl)methanone

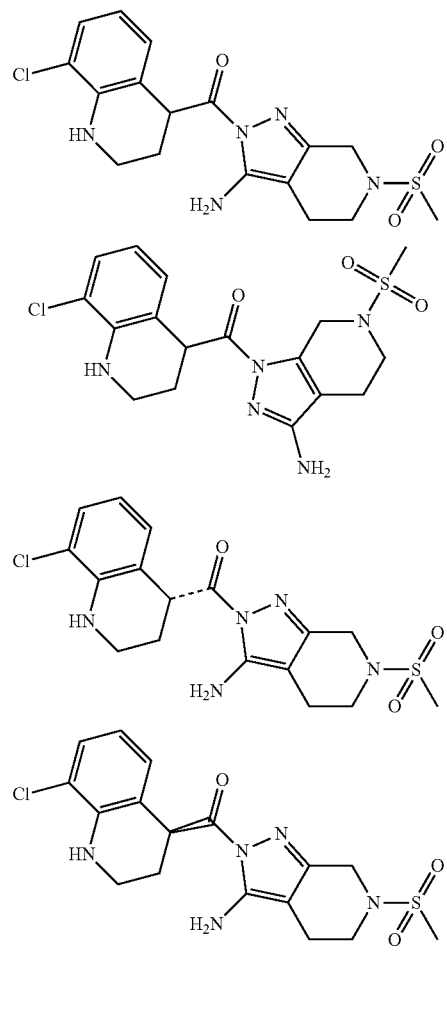

Step 1. Methyl 8-chloroquinoline-4-carboxylate

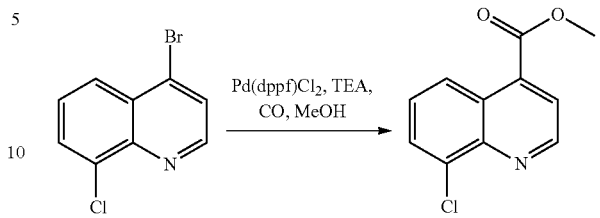

Into a 250-mL pressure tank reactor (50 atm) purged and maintained with an inert atmosphere of CO, was placed 4-bromo-8-chloroquinoline (4 g, 16.49 mmol, 1.00 equiv), Pd(dppf)Cl$_2$CH$_2$Cl$_2$ (2 g, 2.45 mmol, 0.15 equiv), methanol (70 mL), TEA (5 g, 49.50 mmol, 3.00 equiv). The resulting solution was stirred for 38 h at 70 degree C. The reaction was cooled to room temperature. The resulting mixture was concentrated under vacuum. The residue was applied onto a silica gel column with ethyl acetate/petroleum ether (0-30%, 30 min). This resulted in 3.5 g (96%) of methyl 8-chloroquinoline-4-carboxylate as a yellow solid. MS (ES, m/z) [M+H]+: 222.

Step 2. Methyl 8-chloro-1,2,3,4-tetrahydroquinoline-4-carboxylate

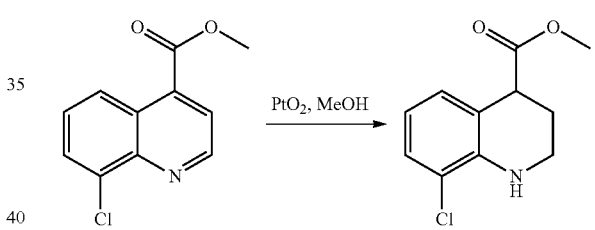

Into a 100-mL round-bottom flask, was placed methyl 8-chloroquinoline-4-carboxylate (400 mg, 1.80 mmol, 1.00 equiv), methanol (20 mL), PtO$_2$ (200 mg). To the above hydrogen was introduced in. The resulting solution was stirred for 1 h at room temperature. The solids were filtered out. The resulting mixture was concentrated under vacuum. This resulted in 320 mg (79%) of methyl 8-chloro-1,2,3,4-tetrahydroquinoline-4-carboxylate as a white solid. MS (ES, m/z) [M+H]+: 226.

Step 3. 8-chloro-1,2,3,4-tetrahydroquinoline-4-carboxylic acid

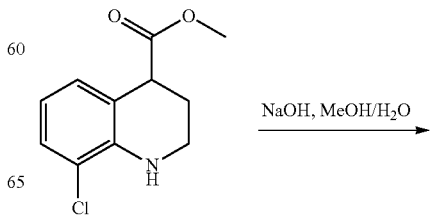

-continued

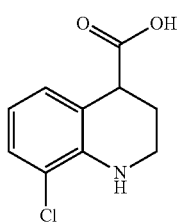

Into a 100-mL round-bottom flask, was placed methyl 8-chloro-1,2,3,4-tetrahydroquinoline-4-carboxylate (320 mg, 1.42 mmol, 1.00 equiv), methanol (15 mL), a solution of sodium hydroxide (175 mg, 4.38 mmol, 3.00 equiv) in water (10 mL). The resulting solution was stirred overnight at room temperature. The resulting mixture was concentrated under vacuum. The resulting solution was diluted with $H_2O$ (20 mL). The resulting solution was extracted with ethyl acetate (30 mL×2) and the aqueous layers combined. The pH value of the solution was adjusted to 5-6 with hydrochloric acid (6 mol/L). The resulting solution was extracted with ethyl acetate (40 mL×3) and the organic layers combined. The resulting mixture was concentrated under vacuum. This resulted in 220 mg (73%) of 8-chloro-1,2,3,4-tetrahydroquinoline-4-carboxylic acid as a yellow solid. MS (ES, m/z) [M+H]+: 212.

Step 4. (3-amino-6-(methylsulfonyl)-4,5,6,7-tetrahydropyrazolo[3,4-c]pyridin-2-yl)(8-chloro-1,2,3,4-tetrahydroquinolin-4-yl)methanone and (3-amino-6-(methylsulfonyl)-4,5,6,7-tetrahydropyrazolo[3,4-c]pyridin-1-yl)(8-chloro-1,2,3,4-tetrahydroquinolin-4-yl)methanone

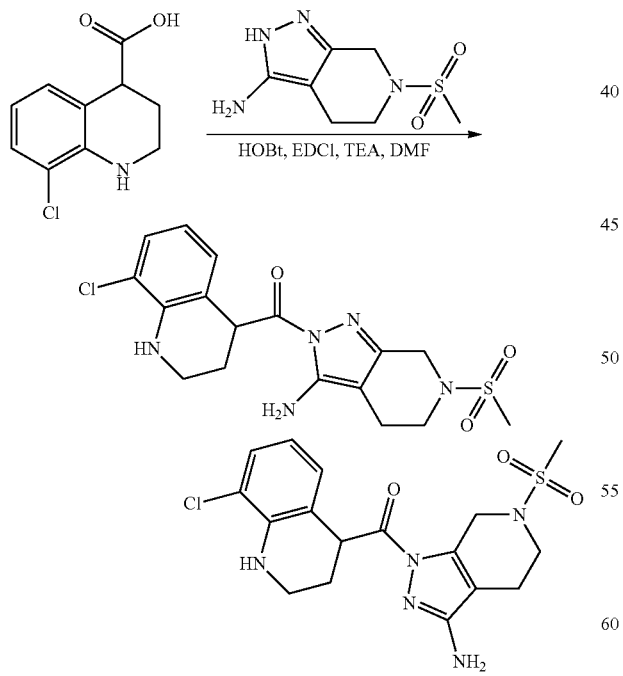

Into a 50-mL round-bottom flask, was placed 8-chloro-1,2,3,4-tetrahydroquinoline-4-carboxylic acid (100 mg, 0.47 mmol, 1.00 equiv), 6-methanesulfonyl-4,5,6,7-tetrahydro-2H-pyrazolo[3,4-c]pyridin-3-amine (150 mg, 0.69 mmol, 1.50 equiv), HOBt (95 mg, 0.70 mmol, 1.50 equiv), EDCI (135 mg, 0.70 mmol, 1.50 equiv), TEA (145 mg, 1.43 mmol, 3.00 equiv), N,N-dimethylformamide (5 mL). The resulting solution was stirred for 2 h at room temperature. The reaction was then quenched by the addition of water (30 mL). The resulting solution was extracted with ethyl acetate (30 mL×3) and the organic layers combined. The resulting mixture was washed with brine (100 mL×2). The mixture was dried over anhydrous sodium sulfate. The solids were filtered out. The resulting mixture was concentrated under vacuum. The crude product was purified by Prep-HPLC with the following conditions: Column: XBridge C18 OBD Prep Column, 19 mm×250 mm; Mobile Phase A: water (10 mM $NH_4HCO_3$), Mobile Phase B: ACN; Flow rate: 20 mL/min; Gradient: 30% B to 50% B in 7 min; 254 nm.

Fraction A: The collected fraction was lyophilized to give 10.5 mg (5%) of (3-amino-6-(methylsulfonyl)-4,5,6,7-tetrahydropyrazolo[3,4-c]pyridin-2-yl)(8-chloro-1,2,3,4-tetrahydroquinolin-4-yl)methanone as an off-white solid. Rt2: 6.48 min. MS (ES, m/z) [M+H]+: 410. (DMSO-d6, 400 MHz, ppm): δ 7.12 (d, J=9.2 Hz, 1H), 6.82 (d, J=7.2 Hz, 1H), 6.64 (s, 2H), 6.45-6.41 (m, 1H), 5.77 (s, 1H), 5.07-5.04 (m, 1H), 4.28-4.20 (m, 2H), 3.43-3.40 (m, 2H), 3.36-3.34 (m, 1H), 3.29-3.27 (m, 1H), 2.97 (s, 3H), 2.49-2.45 (m, 2H), 2.14-2.11 (m, 1H), 2.07-1.98 (m, 1H).

Fraction B: The collected fraction was lyophilized to give 15.4 mg (8%) of (3-amino-6-(methylsulfonyl)-4,5,6,7-tetrahydropyrazolo[3,4-c]pyridin-1-yl)(8-chloro-1,2,3,4-tetrahydroquinolin-4-yl)methanone as an off-white solid. Rt1: 5.61 min. MS (ES, m/z) [M+H]+: 410. (DMSO-d6, 400 MHz, ppm): δ 7.10 (d, J=9.2 Hz, 1H), 6.82 (d, J=7.6 Hz, 1H), 6.45-6.41 (m, 1H), 5.81 (s, 2H), 5.74 (s, 1H), 4.97-4.94 (m, 1H), 4.57-4.51 (m, 2H), 3.47-3.37 (m, 3H), 3.31-3.28 (m, 1H), 2.96 (s, 3H), 2.49-2.47 (m, 2H), 2.12-2.07 (m, 1H), 2.03-1.98 (m, 1H).

Step 5. (R*)-(3-amino-6-(methylsulfonyl)-4,5,6,7-tetrahydropyrazolo[3,4-c]pyridin-2-yl)(8-chloro-1,2,3,4-tetrahydroquinolin-4-yl)methanone and (S*)-(3-amino-6-(methylsulfonyl)-4,5,6,7-tetrahydropyrazolo[3,4-c]pyridin-2-yl)(8-chloro-1,2,3,4-tetrahydroquinolin-4-yl)methanone

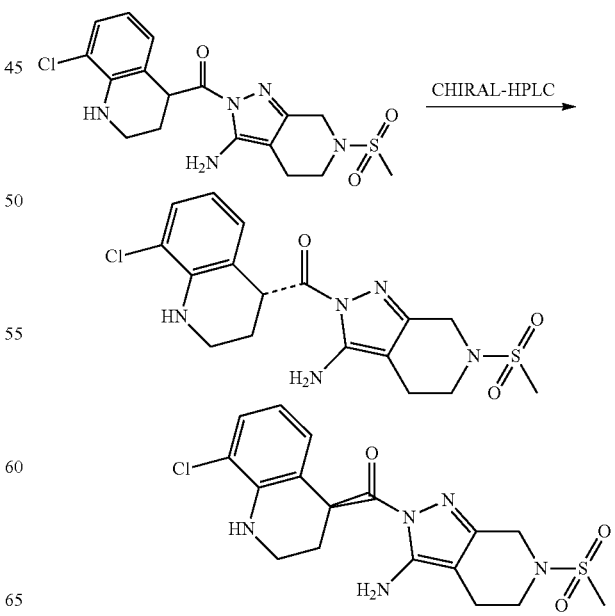

(3-amino-6-(methylsulfonyl)-4,5,6,7-tetrahydropyrazolo[3,4-c]pyridin-2-yl)(8-chloro-1,2,3,4-tetrahydroquinolin-4-yl)methanone (7 mg, 0.02 mmol, 1.00 equiv) was separated by Prep-chiral-HPLC with the following conditions: Column: CHIRALPAK IG, 20×250 mm, 5 um; Mobile Phase A: Hex-HPLC, Mobile Phase B: EtOH-HPLC; Flow rate: 20 mL/min; Gradient: 50 B to 50 B in 23 min; 254/220 nm;

Enantiomer A. Example 59: This resulted in 2.9 mg (41%) of (R*)-(3-amino-6-(methylsulfonyl)-4,5,6,7-tetrahydropyrazolo[3,4-c]pyridin-2-yl)(8-chloro-1,2,3,4-tetrahydroquinolin-4-yl)methanone as a white solid. RT2: 18.74 min. MS (ES, m/z) [M+H]+: 410. (DMSO-d6, 400 MHz, ppm): δ 7.13-7.11 (m, 1H), 6.83-6.81 (m, 1H), 6.65 (s, 2H), 6.45-6.41 (m, 1H), 5.79 (s, 1H), 5.08-5.04 (m, 1H), 4.24 (s, 2H), 3.43-3.37 (m, 2H), 3.28-3.26 (m, 2H), 2.97 (s, 3H), 2.48-2.42 (m, 2H), 2.14-2.04 (m, 2H).

Enantiomer B. Example 60: This resulted in 2.5 mg (36%) of (S*)-(3-amino-6-(methylsulfonyl)-4,5,6,7-tetrahydropyrazolo[3,4-c]pyridin-2-yl)(8-chloro-1,2,3,4-tetrahydroquinolin-4-yl)methanone as a white solid. RT1: 14.75 min. MS (ES, m/z) [M+H]+: 410. (DMSO-d6, 400 MHz, ppm): δ 7.13-7.11 (m, 1H), 6.83-6.82 (m, 1H), 6.65 (s, 2H), 6.45-6.41 (m, 1H), 5.79 (s, 1H), 5.08-5.04 (m, 1H), 4.24 (s, 2H), 3.43-3.40 (m, 2H), 3.28-3.26 (m, 2H), 2.97 (s, 3H), 2.48-2.45 (m, 2H), 2.14-1.96 (m, 2H).

Example 61 & 62 & 63 & 64: (3-amino-6-(methylsulfonyl)-4,5,6,7-tetrahydropyrazolo[3,4-c]pyridin-2-yl)(8-methoxy-1,2,3,4-tetrahydroquinolin-4-yl)methanone and (3-amino-6-(methylsulfonyl)-4,5,6,7-tetrahydropyrazolo[3,4-c]pyridin-1-yl)(8-methoxy-1,2,3,4-tetrahydroquinolin-4-yl)methanone and (S*)-(3-amino-6-(methylsulfonyl)-4,5,6,7-tetrahydropyrazolo[3,4-c]pyridin-2-yl)(8-methoxy-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(8-methoxy-1,2,3,4-tetrahydroquinolin-4-yl)methanone

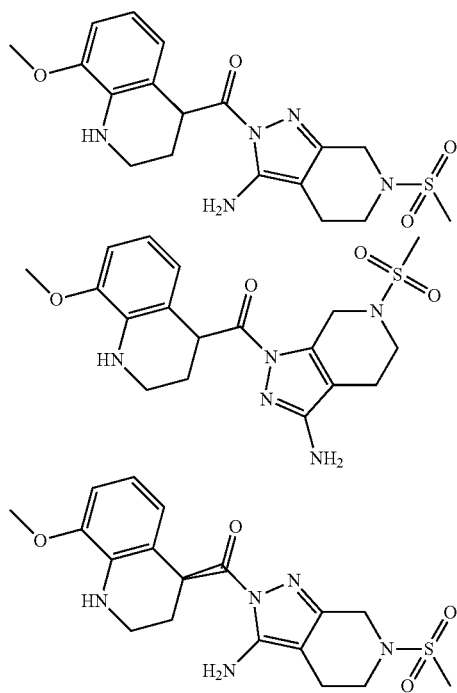

-continued

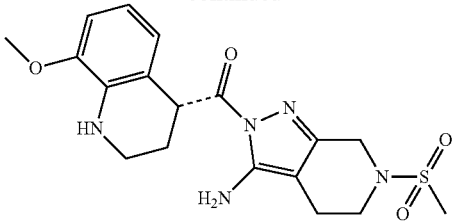

Step 1. 4-bromo-8-methoxyquinoline

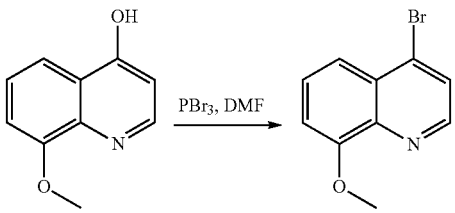

Into a 100-mL round-bottom flask, was placed 8-methoxyquinolin-4-ol (2 g, 11.42 mmol, 1.00 equiv), N,N-dimethylformamide (20 mL). This was followed by the addition of PBr₃ (3.4 g, 12.56 mmol, 1.10 equiv) dropwise with stirring at room temperature. The resulting solution was stirred for 1 h at room temperature. The reaction was then quenched by the addition of water (70 mL). The pH value of the solution was adjusted to 7-8 with potassium hydroxide. The resulting solution was extracted with ethyl acetate (80 mL×3) and the organic layers combined and concentrated under vacuum. This resulted in 2 g (74%) of 4-bromo-8-methoxyquinoline as a gray solid. MS (ES, m/z) [M+H]+: 238.

Step 2. Methyl 8-methoxyquinoline-4-carboxylate

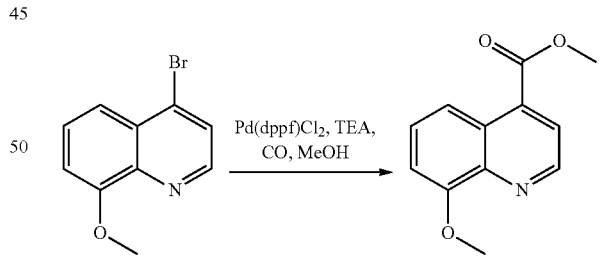

Into a 50-mL pressure tank reactor (50 atm) purged and maintained with an inert atmosphere of CO, was placed 4-bromo-8-methoxyquinoline (1 g, 4.20 mmol, 1.00 equiv), Pd(dppf)Cl₂CH₂Cl₂ (0.5 g, 0.15 equiv), TEA (1.3 g, 12.6 mmol, 3.00 equiv), methanol (15 mL). The resulting solution was stirred for 36 h at 70° C. After cooled to room temperature, the resulting mixture was concentrated under vacuum. The residue was applied onto a silica gel column with ethyl acetate/petroleum ether (0-40%). This resulted in 800 mg (88%) of methyl 8-methoxyquinoline-4-carboxylate as a red solid. MS (ES, m/z) [M+H]+: 218.

Step 3. Methyl 8-methoxy-1,2,3,4-tetrahydroquinoline-4-carboxylate

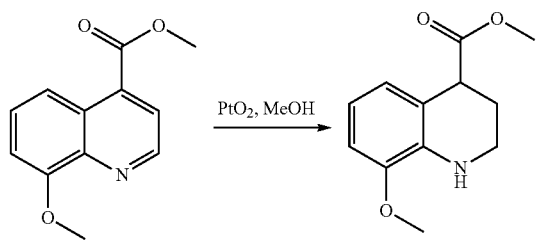 [SMILES: COC(=O)c1ccnc2c(OC)cccc12 ; COC(=O)C1CCNc2c(OC)cccc21]

Into a 50-mL round-bottom flask, was placed methyl 8-methoxyquinoline-4-carboxylate (400 mg, 1.84 mmol, 1.00 equiv), methanol (20 mL), PtO₂ (200 mg). To the above hydrogen was introduced in. The resulting solution was stirred for 2 h at room temperature. The solids were filtered out. The resulting mixture was concentrated under vacuum. This resulted in 360 mg (88%) of methyl 8-methoxy-1,2,3,4-tetrahydroquinoline-4-carboxylate as a red solid. MS (ES, m/z) [M+H]+: 222.

Step 4. 8-methoxy-1,2,3,4-tetrahydroquinoline-4-carboxylic acid

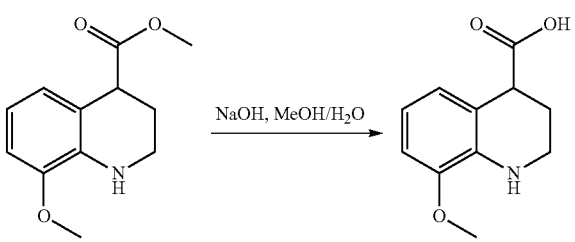 [SMILES: COC(=O)C1CCNc2c(OC)cccc21 ; COc1cccc2c1NCCC2C(=O)O]

Into a 50-mL round-bottom flask, was placed methyl 8-methoxy-1,2,3,4-tetrahydroquinoline-4-carboxylate (360 mg, 1.63 mmol, 1.00 equiv), methanol (10 mL), a solution of sodium hydroxide (200 mg, 5.00 mmol, 3.00 equiv) in water (10 mL). The resulting solution was stirred overnight at room temperature. The resulting mixture was concentrated under vacuum. The resulting solution was extracted with ethyl acetate (10 mL×2) and the aqueous layers combined. The pH value of the solution was adjusted to 5-6 with hydrochloric acid (6 mol/L). The resulting solution was extracted with ethyl acetate (20 mL×3) and the organic layers combined. The resulting mixture was concentrated under vacuum. This resulted in 200 mg (59%) of 8-methoxy-1,2,3,4-tetrahydroquinoline-4-carboxylic acid as a white solid. MS (ES, m/z) [M+H]+: 208.

Step 5. (3-amino-6-(methylsulfonyl)-4,5,6,7-tetrahydropyrazolo[3,4-c]pyridin-2-yl)(8-methoxy-1,2,3,4-tetrahydroquinolin-4-yl)methanone and (3-amino-6-(methylsulfonyl)-4,5,6,7-tetrahydropyrazolo[3,4-c]pyridin-1-yl)(8-methoxy-1,2,3,4-tetrahydroquinolin-4-yl)methanone

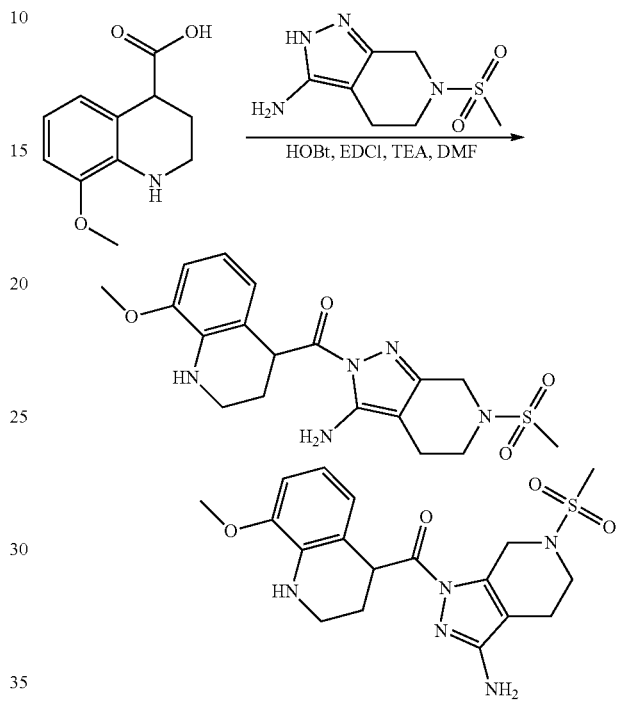

Into a 50-mL round-bottom flask, was placed 8-methoxy-1,2,3,4-tetrahydroquinoline-4-carboxylic acid (100 mg, 0.48 mmol, 1.00 equiv), 6-methanesulfonyl-4,5,6,7-tetrahydro-2H-pyrazolo[3,4-c]pyridin-3-amine (160 mg, 0.74 mmol, 1.50 equiv), HOBt (97 mg, 0.72 mmol, 1.50 equiv), EDCI (140 mg, 0.73 mmol, 1.50 equiv), TEA (150 mg, 1.48 mmol, 3.00 equiv), N,N-dimethylformamide (5 mL). The resulting solution was stirred for 2 h at room temperature. The reaction was then quenched by the addition of water (30 mL). The resulting solution was extracted with ethyl acetate (30 mL×3) and the organic layers combined. The resulting mixture was washed with Brine (100 mL×2). The mixture was dried over anhydrous sodium sulfate. The solids were filtered out. The resulting mixture was concentrated under vacuum. The crude product was purified by Prep-HPLC with the following conditions: Column: XSelect CSH Prep C18 OBD Column, 5 um, 19×150 mm; Mobile Phase A: water (0.1% FA), Mobile Phase B: ACN; Flow rate: 20 mL/min; Gradient: 15% B to 55% B in 7 min; 254 nm.

Fraction A: The collected fraction was lyophilized to give 11.1 mg (6%) of (3-amino-6-(methylsulfonyl)-4,5,6,7-tetrahydropyrazolo[3,4-c]pyridin-2-yl)(8-methoxy-1,2,3,4-tetrahydroquinolin-4-yl)methanone as a yellow solid. Rt2: 6.9 min. MS (ES, m/z) [M+H]+: 406. (DMSO-d6, 400 MHz, ppm): δ 6.69-6.62 (m, 3H), 6.46-6.37 (m, 2H), 5.21 (s, 1H), 5.06-5.03 (m, 1H), 4.28-4.20 (m, 2H), 3.76 (s, 3H), 3.43-3.40 (m, 2H), 3.28-3.22 (m, 2H), 2.97 (s, 3H), 2.49-2.45 (m, 2H), 2.09-2.01 (m, 2H).

Fraction B: The collected fraction was lyophilized to give 20 mg (10%) of (3-amino-6-(methylsulfonyl)-4,5,6,7-tetrahydropyrazolo[3,4-c]pyridin-1-yl)(8-methoxy-1,2,3,4-tetrahydroquinolin-4-yl)methanone as a yellow solid. Rt1: 6.12 min. MS (ES, m/z) [M+H]+: 406. (DMSO-d6, 400 MHz, ppm): δ 6.74-6.71 (m, 1H), 6.55-6.51 (m, 2H), 6.00-6.50 (m, 3H), 4.98-4.95 (m, 1H), 4.57-4.85 (m, 2H), 3.78 (s, 3H), 3.45-3.36 (m, 3H), 3.29-3.21 (m, 1H), 2.97 (s, 3H), 2.49-2.47 (m, 2H), 2.10-1.98 (m, 2H).

Step 6. (S*)-(3-amino-6-(methylsulfonyl)-4,5,6,7-tetrahydropyrazolo[3,4-c]pyridin-2-yl)(8-methoxy-1,2,3,4-tetrahydroquinolin-4-yl)methanone and (R*)-(3-amino-6-(methylsulfonyl)-4,5,6,7-tetrahydropyrazolo[3,4-c]pyridin-2-yl)(8-methoxy-1,2,3,4-tetrahydroquinolin-4-yl)methanone

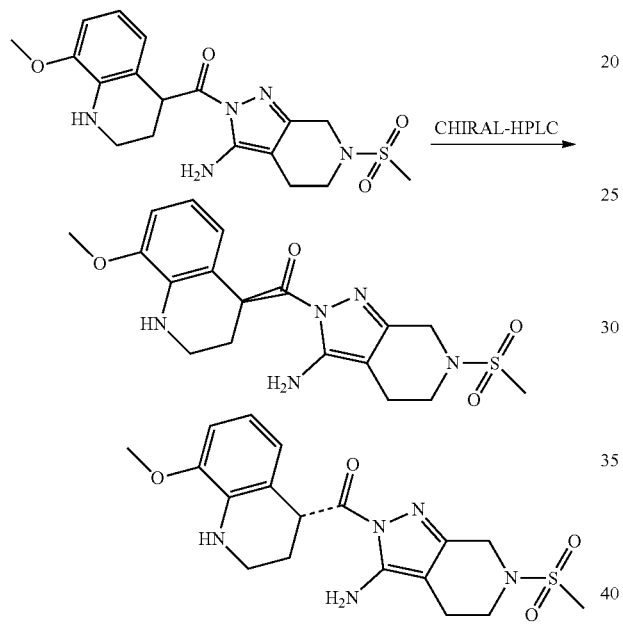

(3-amino-6-(methylsulfonyl)-4,5,6,7-tetrahydropyrazolo[3,4-c]pyridin-2-yl) (8-methoxy-1,2,3,4-tetrahydroquinolin-4-yl)methanone (10 mg, 0.02 mmol, 1.00 equiv) was separated by Prep-chiral-HPLC with the following conditions: Column: CHIRAL ART Cellulose-SB S-5 um, 2×25 cm, 5 um; Mobile Phase A: Hex-HPLC, Mobile Phase B: EtOH-HPLC; Flow rate: 20 mL/min; Gradient: 50 B to 50 B in 25 min; 220/254 nm.

Enantiomer A. Example 63: This resulted in 3.4 mg (34%) of (S*)-(3-amino-6-(methylsulfonyl)-4,5,6,7-tetrahydropyrazolo[3,4-c]pyridin-2-yl)(8-methoxy-1,2,3,4-tetrahydroquinolin-4-yl)methanone as a white solid. Rt2:22.96 min. MS (ES, m/z) [M+H]+: 406. (DMSO-d6, 400 MHz, ppm): δ 6.68-6.66 (m, 1H), 6.63 (s, 2H), 6.48-6.37 (m, 2H), 5.21 (s, 1H), 5.06-5.03 (m, 1H), 4.24 (s, 2H), 3.76 (s, 3H), 3.43-3.40 (m, 2H), 3.31-3.28 (m, 2H), 2.97 (s, 3H), 2.47-2.45 (m, 2H), 2.09-1.97 (m, 2H).

Enantiomer B. Example 64: This resulted in 3.5 mg (35%) of (R*)-(3-amino-6-(methylsulfonyl)-4,5,6,7-tetrahydropyrazolo[3,4-c]pyridin-2-yl)(8-methoxy-1,2,3,4-tetrahydroquinolin-4-yl)methanone as a white solid. Rt1:17.57 min. MS (ES, m/z) [M+H]+: 406. (DMSO-d6, 400 MHz, ppm): δ 6.68-6.67 (m, 1H), 6.63 (s, 2H), 6.46-6.37 (m, 2H), 5.21 (s, 1H), 5.06-5.03 (m, 1H), 4.24 (s, 2H), 3.76 (s, 3H), 3.43-3.40 (m, 2H), 3.30-3.28 (m, 2H), 2.97 (s, 3H), 2.47-2.45 (m, 2H), 2.09-1.97 (m, 2H).

Example 65 & 66: (3-amino-6-(methylsulfonyl)-4,5,6,7-tetrahydropyrazolo[3,4-c]pyridin-2-yl)(8-ethyl-1,2,3,4-tetrahydroquinolin-4-yl)methanone and (3-amino-6-(methylsulfonyl)-4,5,6,7-tetrahydropyrazolo[3,4-c]pyridin-1-yl)(8-ethyl-1,2,3,4-tetrahydroquinolin-4-yl)methanone

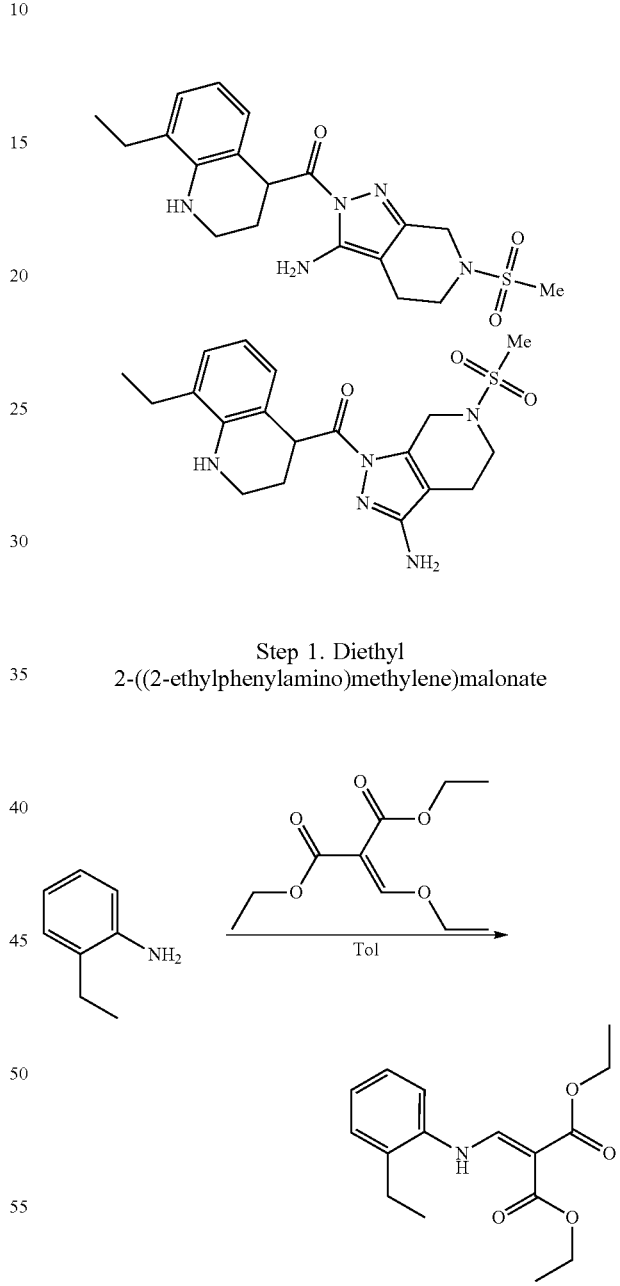

Step 1. Diethyl 2-((2-ethylphenylamino)methylene)malonate

Into a 500-mL round-bottom flask, was placed 2-ethylbenzenamine (25 g, 200 mmol, 1.00 equiv), toluene (30 mL), 1,3-diethyl 2-(ethoxymethylidene)propanedioate (65 g, 300 mmol, 1.50 equiv). The resulting solution was stirred overnight at 110° C. The mixture was cooled to 25° C. The resulting mixture was concentrated under vacuum. The residue was applied onto a silica gel column with ethyl acetate/petroleum ether (1/10). This resulted in 50 g (85%)

of diethyl 2-((2-ethylphenylamino)methylene)malonate as a yellow solid. MS (ES, m/z) [M+H]+: 292.

Step 2. Ethyl 8-ethyl-4-oxo-1,4-dihydroquinoline-3-carboxylate

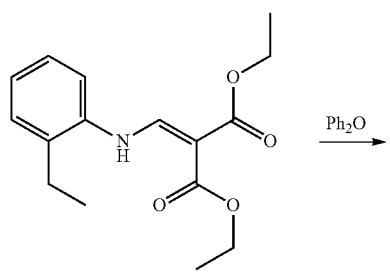

Into a 1000-mL 3-necked round-bottom flask, was placed Ph2O (500 g). This was followed by the addition of 1,3-diethyl 2[[(2-ethylphenyl)amino]methylidene]propanedioate (25 g, 85.81 mmol, 1.00 equiv), in portions at 250 degree C. The resulting solution was stirred for 4 h at 250 degree C. The reaction mixture was cooled to 20 degree C. with a water bath. This resulted in 16 g (76%) of ethyl 8-ethyl-4-oxo-1,4-dihydroquinoline-3-carboxylate as a brown solid. MS (ES, m/z) [M+H]+: 246.

Step 3. 8-ethylquinolin-4(1H)-one

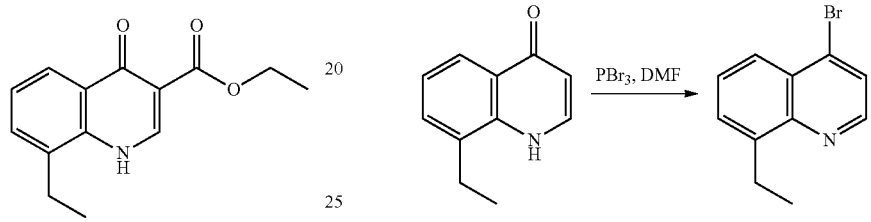

Into a 500-mL 3-necked round-bottom flask, was placed ethyl 8-ethyl-4-oxo-1,4-dihydroquinoline-3-carboxylate (16 g, 65.23 mmol, 1.00 equiv), sodium hydroxide (13.06 g, 326.50 mmol, 5.00 equiv), water (5 mL), HOCH$_2$CH$_2$OH (240 mL). The resulting solution was stirred for 4 h at 160 degree C. The reaction mixture was cooled to 25 degree C. with a water bath. The resulting solution was diluted with H$_2$O (100 mL). The residue was applied onto a silica gel column with dichloromethane/methanol (20/1). This resulted in 10 g (89%) of 8-ethylquinolin-4(1H)-one as yellow oil. MS (ES, m/z) [M+H]+: 174.

Step 4. 4-bromo-8-ethylquinoline

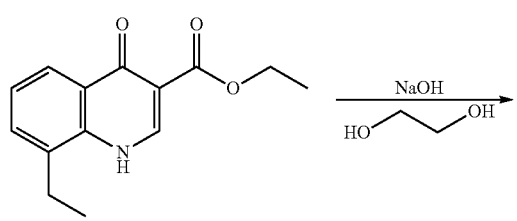

Into a 250-mL round-bottom flask, was placed 8-ethyl-1,4-dihydroquinolin-4-one (10 g, 57.73 mmol, 1.00 equiv), N,N-dimethylformamide (150 mL), PBr$_3$ (47 g, 173.63 mmol, 3.00 equiv). The resulting solution was stirred overnight at 25 degree C. The reaction was then quenched by the addition of water (200 mL). The pH value of the solution was adjusted to 8 with potassium hydroxide. The resulting solution was extracted with dichloromethane (400 mL×4) and the organic layers combined. The resulting mixture was washed with sodium chloride (100 mL×8). The resulting mixture was concentrated under vacuum. This resulted in 9 g (66%) of 4-bromo-8-ethylquinoline as brown oil. MS (ES, m/z) [M+H]+: 236.

Step 5. Methyl 8-ethylquinoline-4-carboxylate

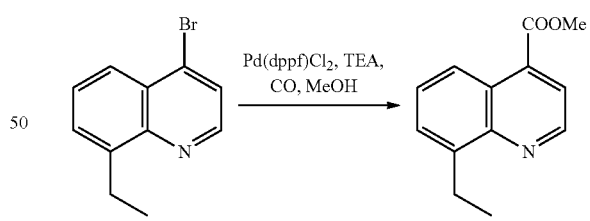

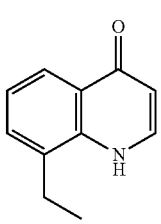

Into a 50-mL pressure tank reactor (60 atm) purged and maintained with an inert atmosphere of CO, was placed 4-bromo-8-ethylquinoline (2 g, 8.47 mmol, 1.00 equiv), TEA (2.58 g, 25.50 mmol, 3.00 equiv), methanol (30 mL), Pd(dppf)Cl$_2$CH$_2$Cl$_2$ (1.04 g, 1.27 mmol, 0.15 equiv). The resulting solution was stirred overnight at 120 degree C. The mixture was cooled to 25 degree C. The resulting mixture was concentrated under vacuum. The residue was applied onto a silica gel column with ethyl acetate/petroleum ether (1/10). This resulted in 1.3 g (71%) of methyl 8-ethylquinoline-4-carboxylate as yellow oil. MS (ES, m/z) [M+H]+: 216.

Step 6. Methyl 8-ethyl-1,2,3,4-tetrahydroquinoline-4-carboxylate

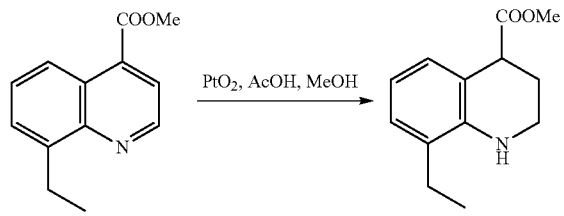 [SMILES: CCc1cccc2c(C(=O)OC)ccnc12 ; CCc1cccc2c1NCCC2C(=O)OC]

Into a 100-mL round-bottom flask, was placed methyl 8-ethylquinoline-4-carboxylate (1.3 g, 6.04 mmol, 1.00 equiv), methanol (20 mL), AcOH (2.5 mL), PtO₂ (1.3 g). The flask was evacuated and flushed three times with nitrogen, followed by flushing with hydrogen. The mixture was stirred 2 h at room temperature under an atmosphere of hydrogen (balloon). The solids were filtered out. The resulting mixture was concentrated under vacuum. This resulted in 1.3 g (98%) of methyl 8-ethyl-1,2,3,4-tetrahydroquinoline-4-carboxylate as yellow oil. MS (ES, m/z) [M+H]+: 220.

Step 7. 8-ethyl-1,2,3,4-tetrahydroquinoline-4-carboxylic acid

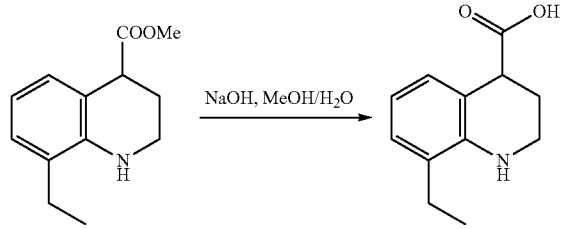 [SMILES: CCc1cccc2c1NCCC2C(=O)OC ; CCc1cccc2c1NCCC2C(=O)O]

Into a 250-mL round-bottom flask, was placed methyl 8-ethyl-1,2,3,4-tetrahydroquinoline-4-carboxylate (1.57 g, 7.16 mmol, 1.00 equiv), water (5 mL), methanol (40 mL), sodium hydroxide (1.43 g, 35.75 mmol, 5.00 equiv). The resulting solution was stirred overnight at 25 degree C. The resulting solution was diluted with H2O (40 mL). The resulting mixture was washed with DCM (100 mL×3). The pH value of the solution was adjusted to 3-4 with hydrochloric acid (1 mol/L). The resulting solution was extracted with dichloromethane (150 mL×4) and the organic layers combined and concentrated under vacuum. This resulted in 1.1 g (75%) of 8-ethyl-1,2,3,4-tetrahydroquinoline-4-carboxylic acid as a yellow solid. MS (ES, m/z) [M+H]+: 206.

Step 8. (3-amino-6-(methylsulfonyl)-4,5,6,7-tetrahydropyrazolo[3,4-c]pyridin-2-yl)(8-ethyl-1,2,3,4-tetrahydroquinolin-4-yl)methanone and (3-amino-6-(methylsulfonyl)-4,5,6,7-tetrahydropyrazolo[3,4-c]pyridin-1-yl)(8-ethyl-1,2,3,4-tetrahydroquinolin-4-yl)methanone

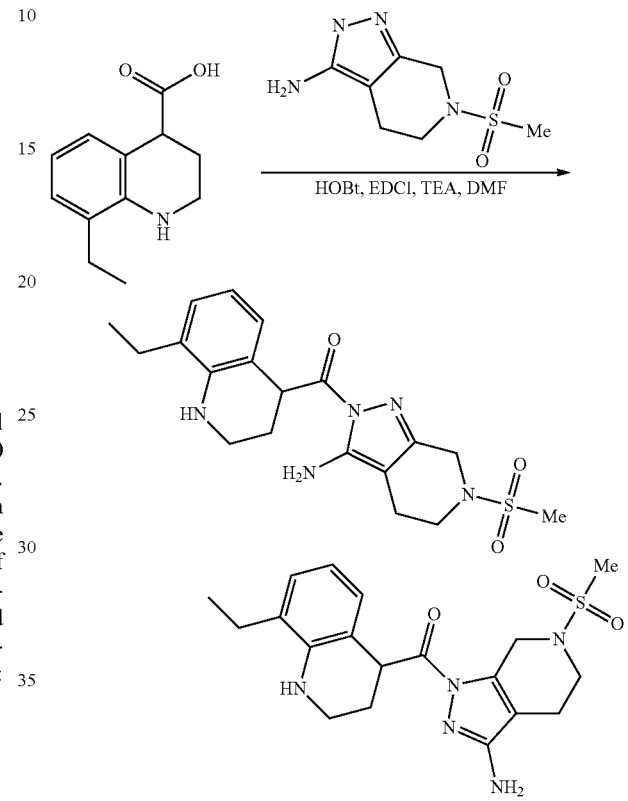

Into a 100-mL round-bottom flask, was placed 8-ethylquinoline-4-carboxylic acid (150 mg, 0.75 mmol, 1.00 equiv), 6-methanesulfonyl-4,5,6,7-tetrahydro-2H-pyrazolo[3,4-c]pyridin-3-amine (238 mg, 1.10 mmol, 1.50 equiv), HOBt (149 mg, 1.10 mmol, 1.50 equiv), EDCI (210 mg, 1.10 mmol, 1.50 equiv), N,N-dimethylformamide (8 mL), TEA (220 mg, 2.17 mmol, 3.00 equiv). The resulting solution was stirred for 3 h at 25 degree C. The reaction mixture was diluted with DCM (80 mL), washed with H2O (50 mL×3) and brine (50 mL×3) and dried with Na₂SO₄. After filtration, the filtrate was concentrated under reduced pressure. The crude product was purified by Prep-HPLC with the following conditions (Analyse HPLC-SHIMADZU): Column: XSelect CSH Prep C18 OBD Column, 5 um, 19×150 mm; Mobile Phase A: water (0.1% FA), Mobile Phase B: ACN; Flow rate: 20 mL/min; Gradient: 35% B to 65% B in 7 min; 254 nm;

Fraction A: The collected fraction was lyophilized to give 26.7 mg (5%) of (3-amino-6-(methylsulfonyl)-4,5,6,7-tetrahydropyrazolo[3,4-c]pyridin-2-yl)(8-ethyl-1,2,3,4-tetrahydroquinolin-4-yl)methanone as a white solid. Rt2: 5.93 min. MS (ES, m/z) [M+H]+: 404. (300 MHz, DMSO-d6, ppm): δ 6.83 (d, J=6.9 Hz, 1H), 6.67-6.62 (m, 3H), 6.42-6.37 (m, 1H), 5.29 (s, 1H), 5.06-5.03 (m, 1H), 4.24 (s, 2H), 3.44-3.10 (m, 4H), 3.20 (s, 3H), 2.50-2.37 (m, 4H), 2.10-1.99 (m, 2H), 1.16-1.11 (m, 3H).

Fraction B: The collected fraction was lyophilized to give 41 mg (14%) of (3-amino-6-(methylsulfonyl)-4,5,6,7-tetrahydropyrazolo[3,4-c]pyridin-1-yl)(8-ethyl-1,2,3,4-tetrahydroquinolin-4-yl)methanone as a white solid. Rt1: 5.28 min. MS (ES, m/z) [M+H]+: 404. (300 MHz, DMSO-d6, ppm): δ 6.82 (d, J=6.9 Hz, 1H), 6.68-6.66 (m, 1H), 6.41-6.36 (m, 1H), 5.77 (m, 2H), 5.26 (s, 1H), 4.97-4.93 (m, 1H), 4.52 (s, 2H), 3.47-3.10 (m, 4H), 2.95 (s, 3H), 2.50-2.37 (m, 4H), 2.07-1.99 (m, 2H), 1.15-1.10 (m, 3H).

Example 67 & 68: (3-amino-6-(methylsulfonyl)-4,5,6,7-tetrahydropyrazolo[3,4-c]pyridin-2-yl)(8-(trifluoromethyl)-1,2,3,4-tetrahydroquinolin-4-yl)methanone and (3-amino-6-(methylsulfonyl)-4,5,6,7-tetrahydropyrazolo[3,4-c]pyridin-1-yl)(8-(trifluoromethyl)-1,2,3,4-tetrahydroquinolin-4-yl)methanone

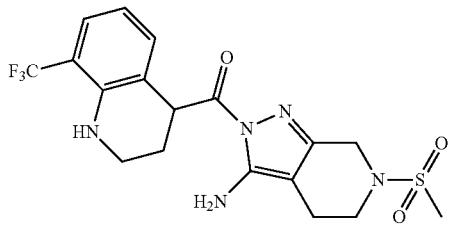

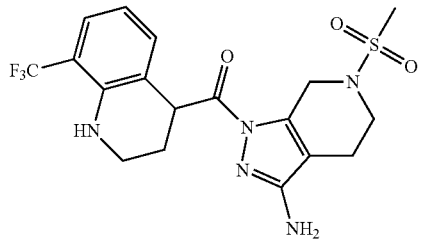

Step 1. 4-bromo-8-(trifluoromethyl)quinoline

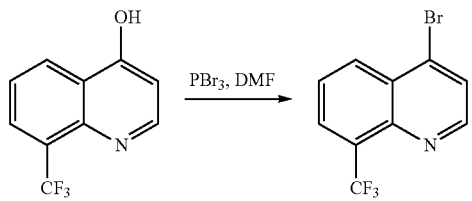 [SMILES: Oc1ccnc2c(C(F)(F)F)cccc12 ; FC(F)(F)c1cccc2c(Br)ccnc12]

Into a 250-mL round-bottom flask, was placed 8-(trifluoromethyl)quinolin-4-ol (2 g, 9.38 mmol, 1.00 equiv), N,N-dimethylformamide (30 mL), PBr3 (2.8 g, 10.34 mmol, 1.10 equiv). The resulting solution was stirred for 1 h at room temperature. The reaction was then quenched by the addition of water (200 mL). The pH value of the solution was adjusted to 8 with saturated aqueous potassium hydroxide. The solids were collected by filtration. This resulted in 2.1 g (81%) of 4-bromo-8-(trifluoromethyl)quinoline as an off-white solid. MS (ES, m/z) [M+H]+: 276.

Step 2. Methyl 8-(trifluoromethyl)quinoline-4-carboxylate

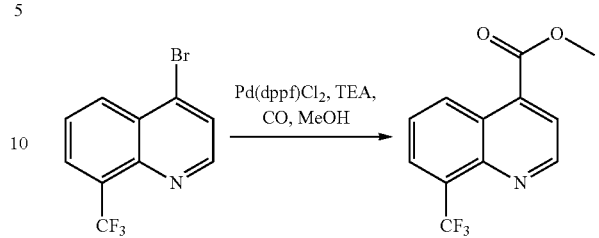

Into a 50-mL pressure tank reactor (60 atm) purged and maintained with an inert atmosphere of CO, was placed 4-bromo-8-(trifluoromethyl)quinoline (1 g, 3.62 mmol, 1.00 equiv), Pd(dppf)Cl2CH2Cl2 (445 mg, 0.54 mmol, 0.15 equiv), TEA (1.1 g, 10.89 mmol, 3.00 equiv), methanol (15 mL). The resulting solution was stirred overnight at room temperature. The resulting mixture was concentrated under vacuum. The residue was applied onto a silica gel column with ethyl acetate/petroleum ether (0-30%, 40 min). This resulted in 820 mg (89%) of methyl 8-(trifluoromethyl)quinoline-4-carboxylate as a white solid. MS (ES, m/z) [M+H]+: 256.

Step 3. Methyl 8-(trifluoromethyl)-1,2,3,4-tetrahydroquinoline-4-carboxylate

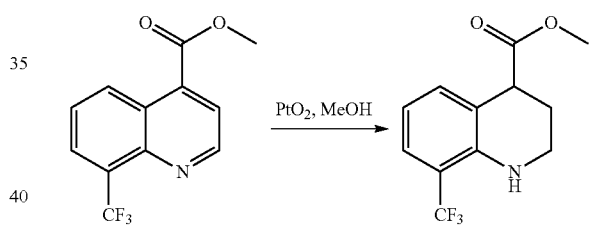

Into a 50-mL round-bottom flask, was placed methyl 8-(trifluoromethyl)quinoline-4-carboxylate (350 mg, 1.37 mmol, 1.00 equiv), methanol (15 mL), dioxoplatinum (200 mg, 0.88 mmol, 0.64 equiv). The resulting solution was stirred for 1 h at room temperature. The solids were filtered out. The resulting mixture was concentrated under vacuum. This resulted in 300 mg (84%) of methyl 8-(trifluoromethyl)-1,2,3,4-tetrahydroquinoline-4-carboxylate as a yellow solid. MS (ES, m/z) [M+H]+: 260.

Step 4. 8-(trifluoromethyl)-1,2,3,4-tetrahydroquinoline-4-carboxylic acid

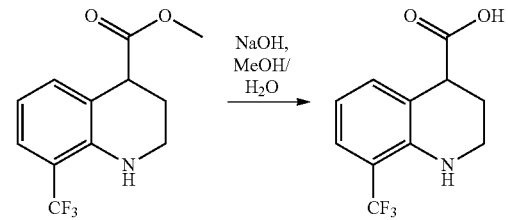 [SMILES: COC(=O)C1CCNc2c1cccc2C(F)(F)F ; O=C(O)C1CCNc2c1cccc2C(F)(F)F]

Into a 100-mL round-bottom flask, was placed methyl 8-(trifluoromethyl)-1,2,3,4-tetrahydroquinoline-4-carboxylate (300 mg, 1.16 mmol, 1.00 equiv), methanol (20 mL), a solution of sodium hydroxide (140 mg, 3.50 mmol, 3.00 equiv) in water (10 mL). The resulting solution was stirred overnight at room temperature. The resulting mixture was concentrated under vacuum. The resulting solution was extracted with ethyl acetate (10 mL×2) and the aqueous layers combined. Hydrochloric acid (3 mol/L) was employed to adjust the pH to 5-6. The resulting solution was extracted with ethyl acetate (20 mL×3) and the organic layers combined. The resulting mixture was concentrated under vacuum. This resulted in 280 mg (99%) of 8-(trifluoromethyl)-1,2,3,4-tetrahydroquinoline-4-carboxylic acid as a yellow solid. MS (ES, m/z) [M+H]+: 246.

Step 5. (3-amino-6-(methylsulfonyl)-4,5,6,7-tetrahydropyrazolo[3,4-c]pyridin-2-yl) (8-(trifluoromethyl)-1,2,3,4-tetrahydroquinolin-4-yl)methanone and (3-amino-6-(methylsulfonyl)-4,5,6,7-tetrahydropyrazolo[3,4-c]pyridin-1-yl)(8-(trifluoromethyl)-1,2,3,4-tetrahydroquinolin-4-yl)methanone of water (30 mL). The resulting solution was extracted with ethyl acetate (30 mL×3) and the organic layers combined. The resulting mixture was washed with Brine (100 mL×2). The mixture was dried over anhydrous sodium sulfate. The solids were filtered out. The resulting mixture was concentrated under vacuum. The crude product was purified by Prep-HPLC with the following conditions: Column: XSelect CSH Prep C18 OBD Column, 5 um, 19×150 mm; Mobile Phase A: water (0.1% FA), Mobile Phase B: ACN; Flow rate: 20 mL/min; Gradient: 40% B to 75% B in 7 min; 254 nm;

Fraction A: The collected fraction was lyophilized to give 16.7 mg (9%) of (3-amino-6-(methylsulfonyl)-4,5,6,7-tetrahydropyrazolo[3,4-c]pyridin-2-yl)(8-(trifluoromethyl)-1,2,3,4-tetrahydroquinolin-4-yl)methanone as a white solid. Rt2: 5.60 min. MS (ES, m/z) [M+H]+: 444. (DMSO-d6, 400 MHz, ppm): δ 7.28 (d, J=7.2 Hz, 1H), 7.09 (d, J=7.6 Hz, 1H), 6.66 (s, 2H), 6.58-6.51 (m, 1H), 5.90 (s, 1H), 5.07-5.04 (m, 1H), 4.24 (s, 2H), 3.43-3.40 (m, 2H), 3.37-3.36 (m, 1H), 3.29-3.24 (m, 1H), 2.98 (s, 3H), 2.48-2.45 (m, 2H), 2.15-2.02 (m, 2H).

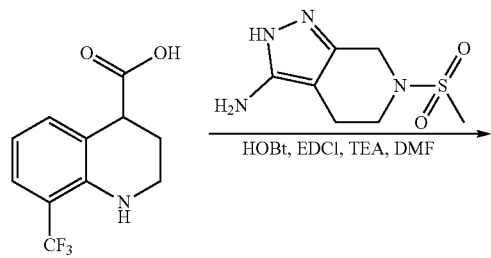

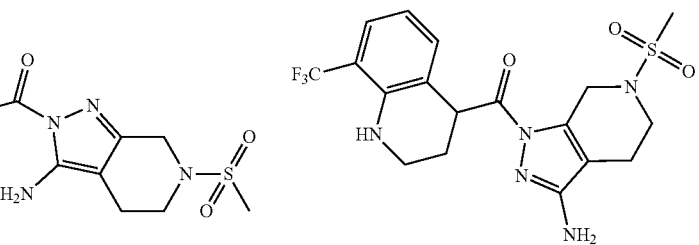

Into a 50-mL round-bottom flask, was placed 8-(trifluoromethyl)-1,2,3,4-tetrahydroquinoline-4-carboxylic acid (100 mg, 0.41 mmol, 1.00 equiv), 6-methanesulfonyl-4,5,6,7-tetrahydro-2H-pyrazolo[3,4-c]pyridin-3-amine (135 mg, 0.62 mmol, 1.50 equiv), HOBt (85 mg, 0.63 mmol, 1.50 equiv), EDCI (120 mg, 0.63 mmol, 1.50 equiv), TEA (125 mg, 1.24 mmol, 3.00 equiv), N,N-dimethylformamide (3 mL). The resulting solution was stirred for 2 h at room temperature. The reaction was then quenched by the addition Fraction B: The collected fraction was lyophilized to give 61.8 mg (34%) of (3-amino-6-(methylsulfonyl)-4,5,6,7-tetrahydropyrazolo[3,4-c]pyridin-1-yl)(8-(trifluoromethyl)-1,2,3,4-tetrahydroquinolin-4-yl)methanone as a white solid. Rt1: 5.08 min. MS (ES, m/z) [M+H]+: 444. (DMSO-d6, 400 MHz, ppm): δ 7.27 (d, J=6.8 Hz, 1H), 7.09 (d, J=7.6 Hz, 1H), 6.54-6.51 (m, 1H), 5.89 (s, 1H), 5.84 (s, 2H), 4.97-4.94 (m, 1H), 4.52 (s, 2H), 3.47-3.37 (m, 2H), 3.32-3.28 (m, 2H), 2.97 (s, 3H), 2.48-2.46 (m, 2H), 2.14-2.00 (m, 2H).

Example 69 & 70: (3-amino-6-(methylsulfonyl)-4,5,6,7-tetrahydropyrazolo[3,4-c]pyridin-2-yl)((S*)-6-ethyl-8-methyl-1,2,3,4-tetrahydroquinolin-4-yl)methanone and (3-amino-6-(methylsulfonyl)-4,5,6,7-tetrahydropyrazolo[3,4-c]pyridin-2-yl)((R*)-6-ethyl-8-methyl-1,2,3,4-tetrahydroquinolin-4-yl)methanone

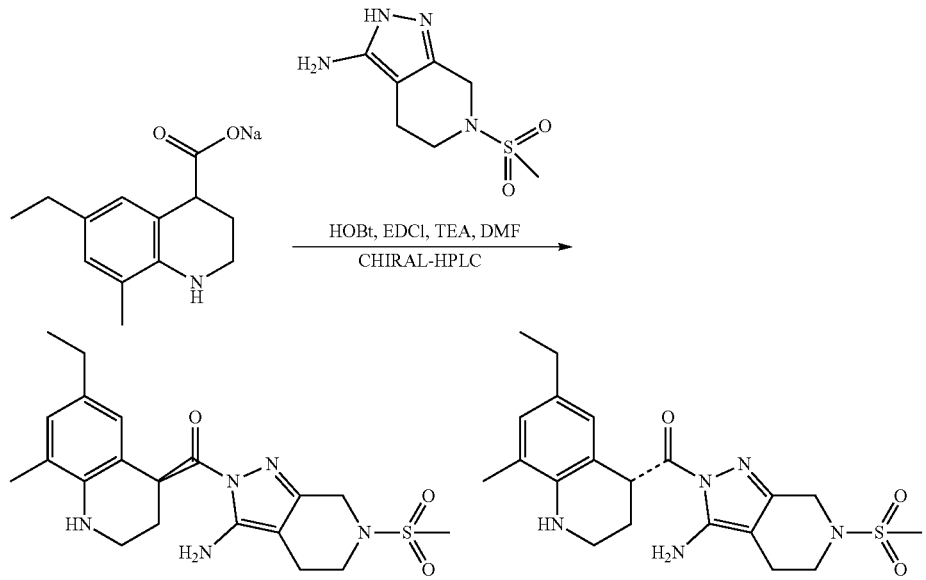

Into a 100-mL round-bottom flask, was placed 6-ethyl-8-methyl-1,2,3,4-tetrahydroquinoline-4-carboxylic acid (300 mg, 1.37 mmol, 1.00 equiv), 6-methanesulfonyl-4,5,6,7-tetrahydro-2H-pyrazolo[3,4-c]pyridin-3-amine (326 mg, 1.51 mmol, 1.10 equiv), EDCI (403 mg, 2.10 mmol, 1.50 equiv), HOBt (284 mg, 2.10 mmol, 1.50 equiv), N,N-dimethylformamide (10 mL), TEA (692 mg, 6.84 mmol, 5.00 equiv). The resulting solution was stirred for 2 h at room temperature. The reaction was then quenched by the addition of water (30 mL). The resulting solution was extracted with ethyl acetate (50 mL×2) and the organic layers combined and concentrated under vacuum. The crude product was purified by Prep-HPLC with the following conditions: Column: XSelect CSH Prep C18 OBD Column, 5 um, 19×150 mm; Mobile Phase A: water (0.05% TFA), Mobile Phase B: ACN; Flow rate: 20 mL/min; Gradient: 10% B to 40% B in 10 min; 254 nm; The collected fraction was lyophilized and separated by Prep-chiral-HPLC with the following conditions: Column: Chiralpak IA, 2×25 cm, 5 um; Mobile Phase A: Hex-HPLC, Mobile Phase B: EtOH-HPLC; Flow rate: 20 mL/min; Gradient: 30 B to 30 B in 23 min; 254/220 nm.

Enantiomer A: This resulted in 8.9 mg (2%) of (3-amino-6-(methylsulfonyl)-4,5,6,7-tetrahydropyrazolo[3,4-c]pyridin-2-yl)((S*)-6-ethyl-8-methyl-1,2,3,4-tetrahydroquinolin-4-yl)methanone as a white solid. Rt2:17.86 min. MS (ES, m/z) [M+H]+: 418. (DMSO-d6, 300 MHz, ppm): δ 6.70 (s, 1H), 6.61 (s, 2H), 6.49 (s, 1H), 5.03-4.99 (m, 2H), 4.24 (s, 2H), 3.44-3.40 (m, 2H), 3.25-3.20 (m, 2H), 2.97 (s, 3H), 2.45-2.40 (m, 2H), 2.38-2.30 (m, 2H), 2.05-1.98 (m, 5H), 1.07-1.02 (m, 3H).

Enantiomer B: This resulted in 9.8 mg (2%) of (3-amino-6-(methylsulfonyl)-4,5,6,7-tetrahydropyrazolo[3,4-c]pyridin-2-yl)((R*)-6-ethyl-8-methyl-1,2,3,4-tetrahydroquinolin-4-yl)methanone as a white solid. Rt1:12.89 min. MS (ES, m/z) [M+H]+: 418. (DMSO-d6, 300 MHz, ppm): δ 6.70 (s, 1H), 6.61 (s, 2H), 6.48 (s, 1H), 5.03-4.99 (m, 2H), 4.24 (s, 2H), 3.44-3.40 (m, 2H), 3.24-3.20 (m, 2H), 2.96 (s, 3H), 2.43-2.38 (m, 2H), 2.38-2.28 (m, 2H), 2.07-1.98 (m, 5H), 1.07-1.02 (m, 3H).

Example 71 & 72 & 73: (3-amino-4,5,6,7-tetrahydropyrazolo[3,4-c]pyridin-1-yl)(8-chloro-1,2,3,4-tetrahydroquinolin-4-yl)methanone and (S*)-(3-amino-4,5,6,7-tetrahydropyrazolo[3,4-c]pyridin-2-yl)(8-chloro-1,2,3,4-tetrahydroquinolin-4-yl)methanone and (R*)-(3-amino-4,5,6,7-tetrahydropyrazolo[3,4-c]pyridin-2-yl)(8-chloro-1,2,3,4-tetrahydroquinolin-4-yl)methanone

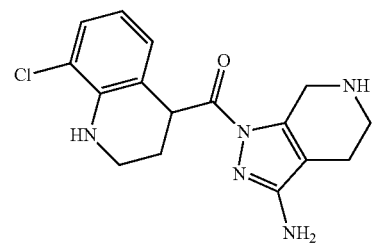

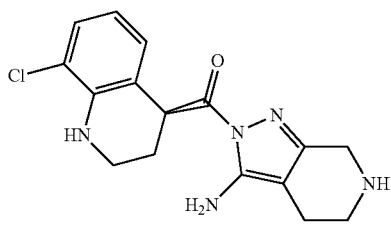

-continued

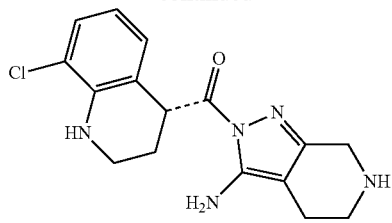

Step 1. (3-amino-6-benzyl-4,5,6,7-tetrahydropyrazolo[3,4-c]pyridin-2-yl)(8-chloro-1,2,3,4-tetrahydroquinolin-4-yl)methanone and (3-amino-6-benzyl-4,5,6,7-tetrahydropyrazolo[3,4-c]pyridin-1-yl)(8-chloro-1,2,3,4-tetrahydroquinolin-4-yl)methanone

Step 2. (3-amino-4,5,6,7-tetrahydropyrazolo[3,4-c]pyridin-2-yl)(8-chloro-1,2,3,4-tetrahydroquinolin-4-yl)methanone

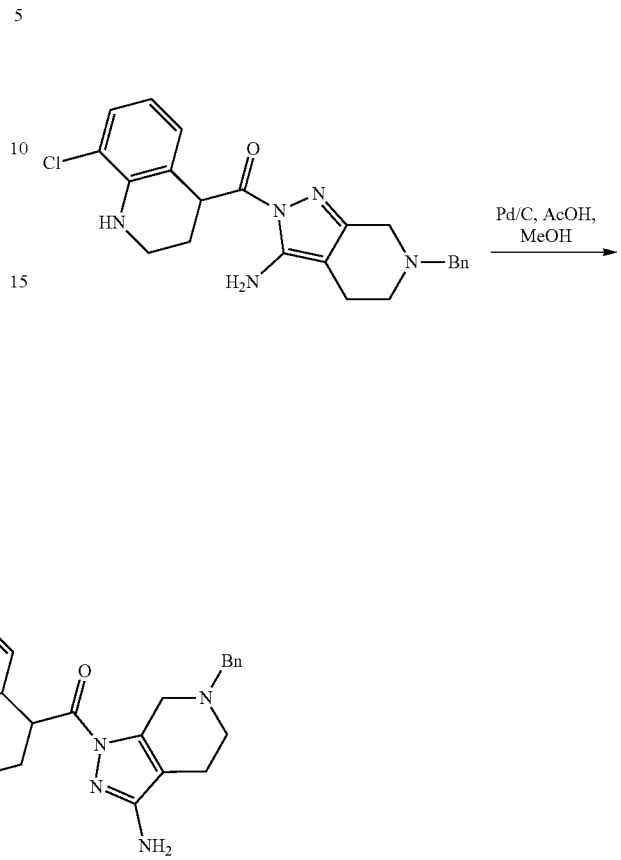

Into a 50-mL round-bottom flask, was placed 6-benzyl-4,5,6,7-tetrahydro-2H-pyrazolo[3,4-c]pyridin-3-amine (190 mg, 0.83 mmol, 1.10 equiv), 8-chloro-1,2,3,4-tetrahydroquinoline-4-carboxylic acid (160 mg, 0.76 mmol, 1.00 equiv), HOBT (150 mg, 1.11 mmol, 1.50 equiv), EDCI (220 mg, 1.15 mmol, 1.50 equiv), TEA (230 mg, 2.27 mmol, 3.00 equiv), N,N-dimethylformamide (3 mL). The resulting solution was stirred for 4 h at room temperature. The reaction was then quenched by the addition of water (40 mL). The resulting solution was extracted with ethyl acetate (40 mL×3) and the organic layers combined. The resulting mixture was washed with Brine (2×100 mL×2). The mixture was dried over anhydrous sodium sulfate. The solids were filtered out. The resulting mixture was concentrated under vacuum. The crude product was purified by Prep-HPLC with the following conditions: Column: XSelect CSH Prep C18 OBD Column, 5 um, 19×150 mm; Mobile Phase A: water (0.1% FA), Mobile Phase B: ACN; Flow rate: 20 mL/min; Gradient: 2% B to 30% B in 16 min; 254 nm; Rt1: 13.8 min. Rt2: 14.88 min. The collected fraction was lyophilized to give 150 mg (47%) of (3-amino-6-benzyl-4,5,6,7-tetrahydropyrazolo[3,4-c]pyridin-2-yl)(8-chloro-1,2,3,4-tetrahydroquinolin-4-yl)methanone as a white solid. MS (ES, m/z) [M+H]+: 422. And 120 mg (38%) of (3-amino-6-benzyl-4,5,6,7-tetrahydropyrazolo[3,4-c]pyridin-1-yl)(8-chloro-1,2,3,4-tetrahydroquinolin-4-yl)methanone as a white solid. MS (ES, m/z) [M+H]+: 422.

-continued

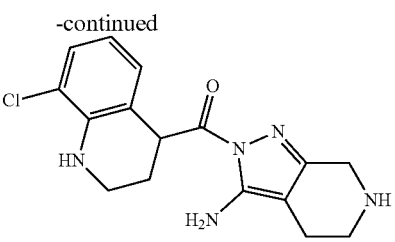

Into a 100-mL round-bottom flask, was placed (3-amino-6-benzyl-4,5,6,7-tetrahydropyrazolo[3,4-c]pyridin-2-yl)(8-chloro-1,2,3,4-tetrahydroquinolin-4-yl)methanone (250 mg, 0.59 mmol, 1.00 equiv), methanol (10 mL), Palladium carbon (10%, 200 mg), AcOH (0.4 mL). To the above hydrogen was introduced in. The resulting solution was stirred for 1.5 h at room temperature. The solids were filtered out. The resulting mixture was concentrated under vacuum. The crude product was purified by Prep-HPLC with the following conditions: Column: XBridge Shield RP18 OBD Column, 5 um, 19×150 mm; Mobile Phase A: water (10 mM NH4HCO3), Mobile Phase B: ACN; Flow rate: 20 mL/min; Gradient: 5% B to 30% B in 3 min; 254 nm; Rt: 7.63 min. The collected fraction was lyophilized to give 30 mg (15%) of (3-amino-4,5,6,7-tetrahydropyrazolo[3,4-c]pyridin-2-yl)(8-chloro-1,2,3,4-tetrahydroquinolin-4-yl)methanone as a white solid. MS (ES, m/z) [M+H]+: 332.

Step 3. (3-amino-4,5,6,7-tetrahydropyrazolo[3,4-c]pyridin-1-yl)(8-chloro-1,2,3,4-tetrahydroquinolin-4-yl)methanone

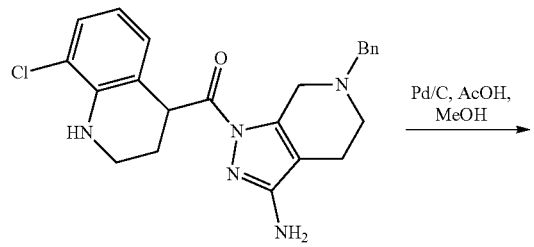

Pd/C, AcOH, MeOH →

Into a 100-mL round-bottom flask, was placed (3-amino-6-benzyl-4,5,6,7-tetrahydropyrazolo[3,4-c]pyridin-1-yl)(8-chloro-1,2,3,4-tetrahydroquinolin-4-yl)methanone (120 mg, 0.28 mmol, 1.00 equiv), methanol (20 mL), Palladium carbon (10%, 120 mg), AcOH (0.2 mL). To the above hydrogen was introduced in. The resulting solution was stirred for 40 min at room temperature. The solids were filtered out. The resulting mixture was concentrated under vacuum. The crude product was further purified by Prep-HPLC with the following conditions: Column: XBridge Prep C18 OBD Column 19×150 mm 5 um; Mobile Phase A: water (10 MMOL/L NH4HCO3), Mobile Phase B: ACN; Flow rate: 20 mL/min; Gradient: 30% B to 43.5% B in 5 min; 254/220 nm; Rt: 4.35 min. The collected fraction was lyophilized to give 6.8 mg (7%) of (3-amino-4,5,6,7-tetrahydropyrazolo[3,4-c]pyridin-1-yl)(8-chloro-1,2,3,4-tetrahydroquinolin-4-yl)methanone as a white solid. MS (ES, m/z) [M+H]+: 332. (DMSO-d6, 300 MHz, ppm): δ 7.09 (d, J=7.5 Hz, 1H), 6.79 (d, J=7.2 Hz, 1H), 6.52-6.39 (m, 1H), 5.71 (s, 1H), 5.63 (m, 2H), 4.98-4.94 (m, 1H), 3.88 (s, 2H), 3.45-3.38 (m, 2H), 2.82-2.79 (m, 2H), 2.25-2.22 (m, 2H), 2.10-1.93 (m, 2H).

Step 4. (S*)-(3-amino-4,5,6,7-tetrahydropyrazolo[3,4-c]pyridin-2-yl)(8-chloro-1,2,3,4-tetrahydroquinolin-4-yl)methanone and (R*)-(3-amino-4,5,6,7-tetrahydropyrazolo[3,4-c]pyridin-2-yl)(8-chloro-1,2,3,4-tetrahydroquinolin-4-yl)methanone

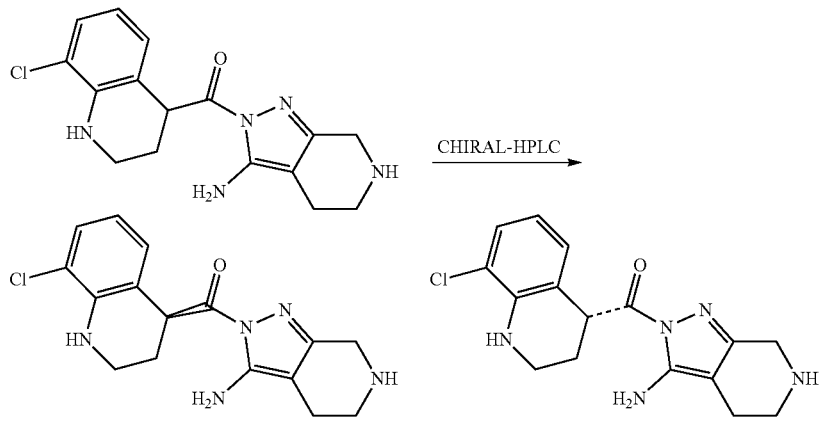

CHIRAL-HPLC →

-continued

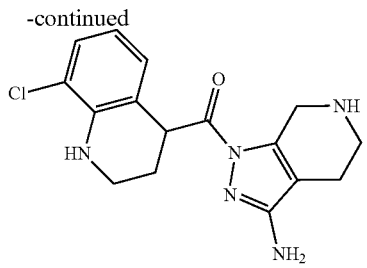

(3-amino-4,5,6,7-tetrahydropyrazolo[3,4-c]pyridin-2-yl)(8-chloro-1,2,3,4-tetrahydroquinolin-4-yl)methanone (30 mg, 0.09 mmol, 1.00 equiv) was separated by Prep-CHIRAL-HPLC with the following conditions: Column: CHIRALPAK AD-H, 2.0 cm I.D.×25 cm L; Mobile Phase A: Hex (% DEA)-HPLC, Mobile Phase B: IPA-HPLC; Flow rate: 20 mL/min; Gradient: 30 B to 30 B in 20 min; 220/254 nm.

Enantiomer A. Example 72: This resulted in 14.9 mg (50%) of (S*)-(3-amino-4,5,6,7-tetrahydropyrazolo[3,4-c]pyridin-2-yl)(8-chloro-1,2,3,4-tetrahydroquinolin-4-yl)methanone as a white solid. Rt2:16.51 min. MS (ES, m/z) [M+H]+: 332. (DMSO-d6, 300 MHz, ppm): δ 7.09 (d, J=6.9 Hz, 1H), 6.78 (d, J=7.2 Hz, 1H), 6.45 (s, 2H), 6.43-6.39 (m, 1H), 5.74 (s, 1H), 5.05-5.02 (m, 1H), 3.71 (s, 2H), 3.60-3.45 (m, 2H), 2.89-2.87 (m, 2H), 2.31-2.27 (m, 2H), 2.18-1.91 (m, 2H).

Enantiomer B. Example 73: This resulted in 11.6 mg (39%) of (R*)-(3-amino-4,5,6,7-tetrahydropyrazolo[3,4-c]pyridin-2-yl)(8-chloro-1,2,3,4-tetrahydroquinolin-4-yl)methanone as a white solid. Rt1:12.86 min. MS (ES, m/z) [M+H]+: 332. (DMSO-d6, 300 MHz, ppm): δ 7.09 (d, J=7.8 Hz, 1H), 6.78 (d, J=7.5 Hz, 1H), 6.43 (s, 2H), 6.41-6.38 (m, 1H), 5.73 (s, 1H), 5.05-5.02 (m, 1H), 3.87 (s, 2H), 3.68-3.63 (m, 2H), 2.87-2.84 (m, 2H), 2.29-2.28 (m, 2H), 2.18-1.95 (m, 2H).

Example 74 & 75: (3-amino-6,7-dihydropyrano[4,3-c]pyrazol-2(4H)-yl)(6-fluoro-1,2,3,4-tetrahydroquinolin-4-yl)methanone and (3-amino-6,7-dihydropyrano[4,3-c]pyrazol-1(4H)-yl)(6-fluoro-1,2,3,4-tetrahydroquinolin-4-yl)methanone

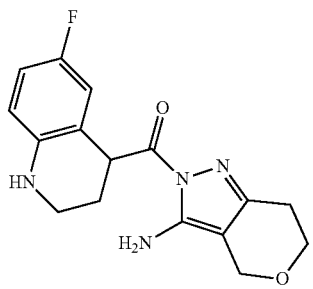

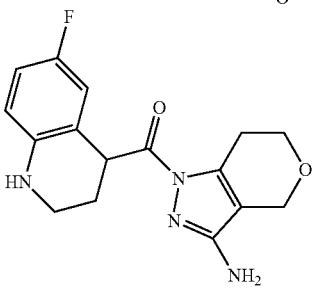

Step 1. 4-oxooxane-3-carbonitrile

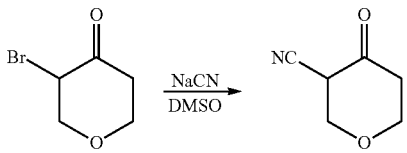

Into a 100-mL round-bottom flask, was placed 3-bromooxan-4-one (1.5 g, 8.38 mmol, 1.00 equiv), DMSO (40 mL), NaCN (616 g, 12.57 mmol, 1.50 equiv). The resulting solution was stirred overnight at 25 degree C. The reaction was then quenched by the addition of FeSO4 (aq) (150 mL). The resulting solution was extracted with dichloromethane (200 mL×6) and the organic layers combined and concentrated under vacuum. This resulted in 1.5 g (crude) of 4-oxooxane-3-carbonitrile as yellow oil. MS (ES, m/z) [M+H]+: 126.

Step 2. 2H,4H,6H,7H-pyrano[4,3-c]pyrazol-3-amine

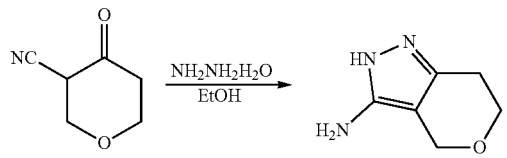

Into a 250-mL round-bottom flask, was placed 4-oxooxane-3-carbonitrile (1.5 g, 11.99 mmol, 1.00 equiv), ethanol (20 mL), NH2NH2H2O (10 mL). The resulting solution was stirred overnight at 25 degree C. The resulting mixture was concentrated under vacuum. The residue was applied onto a silica gel column with dichloromethane/methanol (10/1). This resulted in 150 mg of 2H,4H,6H,7H-pyrano[4,3-c]pyrazol-3-amine as yellow oil. MS (ES, m/z) [M+H]+: 140.

Step 3. (3-amino-6,7-dihydropyrano[4,3-c]pyrazol-2(4H)-yl)(6-fluoro-1,2,3,4-tetrahydroquinolin-4-yl)methanone and (3-amino-6,7-dihydropyrano[4,3-c]pyrazol-1(4H)-yl)(6-fluoro-1,2,3,4-tetrahydroquinolin-4-yl)methanone

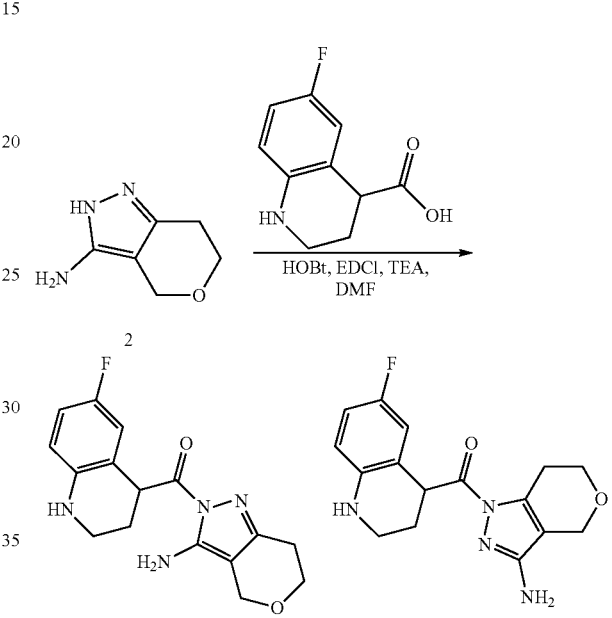

Into a 100-mL round-bottom flask, was placed 6-fluoro-1,2,3,4-tetrahydroquinoline-4-carboxylic acid (168 mg, 0.86 mmol, 1.20 equiv), 2H,4H,6H,7H-pyrano[4,3-c]pyrazol-3-amine (100 mg, 0.72 mmol, 1.00 equiv), HOBt (146 mg, 1.08 mmol, 1.50 equiv), EDCI (207 mg, 1.08 mmol, 1.50 equiv), N,N-dimethylformamide (8 mL), TEA (218 mg, 2.15 mmol, 3.00 equiv). The resulting solution was stirred for 1 h at 25 degree C. The reaction mixture was diluted with DCM (80 mL), washed with H2O (50 mL×3) and brine (50 mL×3) and dried with Na2SO4. After filtration, the filtrate was concentrated under reduced pressure. The crude product was purified by Prep-HPLC with the following conditions (Analyse HPLC-SHIMADZU): Column: XBridge Shield RP18 OBD Column, 5 um, 19×150 mm; Mobile Phase A: water (0.1% FA), Mobile Phase B: ACN; Flow rate: 20 mL/min; Gradient: 15% B to 40% B in 8 min; 254 nm.

Fraction A: The collected fraction was lyophilized to give 28 mg (12%) (3-amino-6,7-dihydropyrano[4,3-c]pyrazol-2(4H)-yl)(6-fluoro-1,2,3,4-tetrahydroquinolin-4-yl)methanone as a white solid. Rt2: 7.25 min. MS (ES, m/z) [M+H]+: 317. (400 MHz, DMSO-d6, ppm): δ 6.81-6.77 (m, 1H), 6.68-6.65 (m, 1H), 6.58 (s, 2H), 6.52-6.49 (m, 1H), 5.80 (s, 1H), 5.00-4.98 (m, 1H), 4.42 (s, 2H), 3.84-3.79 (m, 2H), 3.25-3.15 (m, 2H), 2.62-2.59 (m, 2H), 2.10-1.98 (m, 2H).

Fraction B: The collected fraction was lyophilized to give 28 mg (12%) (3-amino-6,7-dihydropyrano[4,3-c]pyrazol-1(4H)-yl)(6-fluoro-1,2,3,4-tetrahydroquinolin-4-yl)methanone as a white solid. Rt1: 6.19 min. MS (ES, m/z) [M+H]+:

317. (400 MHz, DMSO-d6, ppm): δ 6.80-6.77 (m, 1H), 6.77-6.75 (m, 1H), 6.69-6.66 (m, 1H), 5.78 (s, 1H), 5.71 (s, 2H), 4.91-4.88 (m, 1H), 4.41 (s, 2H), 3.77-3.75 (m, 2H), 3.33-3.12 (m, 2H), 2.90-2.88 (m, 2H), 2.08-1.92 (m, 2H).

Example 76 & 77: (S*)-(3-amino-4,5-dihydropyrano[3,4-c]pyrazol-2(7H)-yl)(6-fluoro-8-methyl-1,2,3,4-tetrahydroquinolin-4-yl)methanone and (R*)-(3-amino-4,5-dihydropyrano[3,4-c]pyrazol-2(7H)-yl)(6-fluoro-8-methyl-1,2,3,4-tetrahydroquinolin-4-yl)methanone

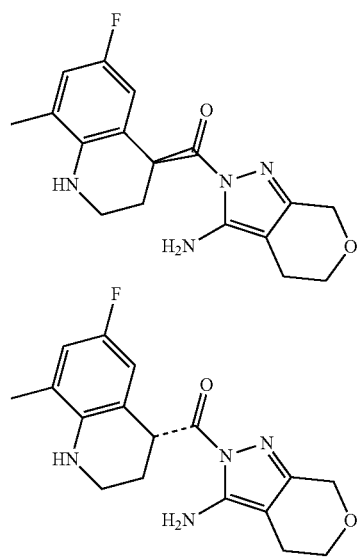

Step 1. ethyl 2-(3-(benzyloxy)propoxy)acetate

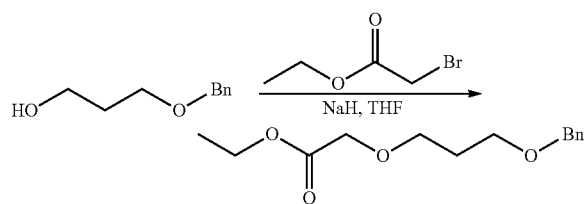

Into a 250-mL 3-necked round-bottom flask purged and maintained with an inert atmosphere of nitrogen, was placed ethyl 2-bromoacetate (3.5 g, 20.96 mmol, 1.00 equiv), tetrahydrofuran (40 mL). This was followed by the addition of sodium hydride (1.01 g, 25.25 mmol, 1.20 equiv, 60%), in portions at 0° C. The mixture was stirred for 40 min at 0° C. To this was added 3-(benzyloxy)propan-1-ol (10.50 g, 63.17 mmol, 3.00 equiv) at 0° C. The resulting solution was stirred overnight at 25° C. The reaction was then quenched by the addition of water (100 mL). The resulting solution was extracted with ethyl acetate (100 mL×3) and the organic layers combined. The solvent was removed under vacuum and the residue was applied onto a silica gel column with ethyl acetate/hexane (1/10). The collected fractions were combined and concentrated under vacuum. This resulted in 3 g (57%) of ethyl 2-(3-(benzyloxy)propoxy)acetate as white oil. MS (ES, m/z) [M+H]: 253.

Step 2. ethyl 2-(3-hydroxypropoxy)acetate

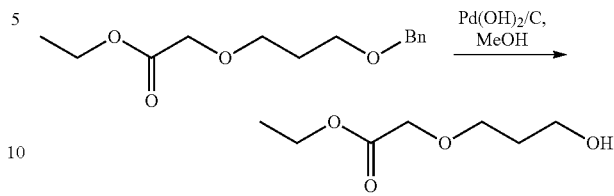

Into a 250-mL round-bottom flask, was placed ethyl 2-[3-(benzyloxy)propoxy]acetate (2.8 g, 11.10 mmol, 1.00 equiv), Pd(OH)$_2$ (2.8 g, 19.94 mmol, 1.80 equiv), methanol (15 mL). The resulting solution was stirred overnight at 25° C. The solids were collected by filtration. The resulting mixture was concentrated under vacuum. This resulted in 1.2 g (67%) of ethyl 2-(3-hydroxypropoxy)acetate as white oil. MS (ES, m/z) [M+H]: 163.

Step 3. Ethyl 2-(3-bromopropoxy)acetate

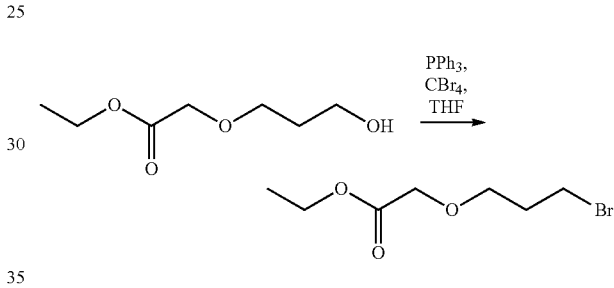

Into a 100-mL round-bottom flask purged and maintained with an inert atmosphere of nitrogen, was placed ethyl 2-(3-hydroxypropoxy)acetate (1.23 g, 7.58 mmol, 1.00 equiv), CBr$_4$ (3.78 g, 1.50 equiv), PPh$_3$ (2.39 g, 9.11 mmol, 1.20 equiv), tetrahydrofuran (30 mL). The resulting solution was stirred overnight at 25° C. The reaction was then quenched by the addition of water (30 mL). The resulting solution was extracted with dichloromethane (80 mL×2) and the organic layers combined. The residue was applied onto a silica gel column with ethyl acetate/petroleum ether (1/10). This resulted in 1.4 g (82%) of ethyl 2-(3-bromopropoxy)acetate as yellow oil. MS (ES, m/z) [M+H]: 225.

Step 4. ethyl 2-(3-cyanopropoxy)acetate

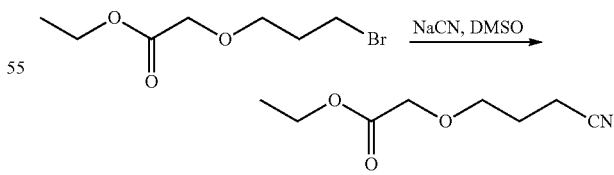

Into a 250-mL round-bottom flask, was placed ethyl 2-(3-bromopropoxy)acetate (1.4 g, 6.22 mmol, 1.00 equiv), DMSO (10 mL), NaCN (460 mg, 9.33 mmol, 1.50 equiv). The resulting solution was stirred overnight at 20° C. The reaction was then quenched by the addition of FeSO4 (aq) (100 mL). The resulting solution was extracted with dichloromethane (50 mL×3) and the organic layers combined. The resulting mixture was washed with sodium chloride (100 mL×4). The resulting mixture was concentrated under vacuum. This resulted in 1 g (94%) of ethyl 2-(3-cyanopropoxy)acetate as yellow oil. MS (ES, m/z) [M+H]: 172.

Step 5. 3-oxooxane-4-carbonitrile

Into a 100-mL 3-necked round-bottom flask purged and maintained with an inert atmosphere of nitrogen, was placed ethyl 2-(3-cyanopropoxy)acetate (1.2 g, 7.01 mmol, 1.00 equiv), tetrahydrofuran (30 mL). This was followed by the addition of t-BuOK (1.18 g, 10.52 mmol, 1.50 equiv), in portions at 0° C. The resulting solution was stirred overnight at 25° C. The reaction was then quenched by the addition of water/ice (25 mL). The pH value of the solution was adjusted to 4-5 with hydrochloric acid (1 mol/L). The resulting solution was extracted with dichloromethane (100 mL×5) and the organic layers combined and concentrated under vacuum. This resulted in 800 mg (91%) of 3-oxooxane-4-carbonitrile as red oil. MS (ES, m/z) [M+H]: 126.

Step 6. 2,4,5,7-tetrahydropyrano[3,4-c]pyrazol-3-amine

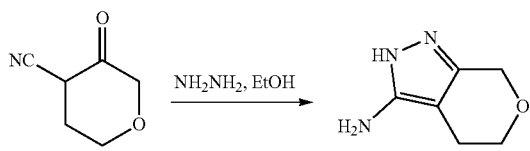

Into a 100-mL round-bottom flask, was placed 3-oxooxane-4-carbonitrile (750 mg, 5.99 mmol, 1.00 equiv), ethanol (25 mL), NH₂NH₂H₂O (10 mL). The resulting solution was stirred overnight at 25° C. The resulting mixture was concentrated under vacuum. The residue was applied onto a silica gel column with dichloromethane/methanol (10/1). This resulted in 240 mg (29%) of 2,4,5,7-tetrahydropyrano[3,4-c]pyrazol-3-amine as a yellow solid. MS (ES, m/z) [M+H]: 140.

Step 7: (S*)-(3-amino-4,5-dihydropyrano[3,4-c]pyrazol-2(7H)-yl)(6-fluoro-8-methyl-1,2,3,4-tetrahydroquinolin-4-yl)methanone and (R*)-(3-amino-4,5-dihydropyrano[3,4-c]pyrazol-2(7H)-yl)(6-fluoro-8-methyl-1,2,3,4-tetrahydroquinolin-4-yl)methanone

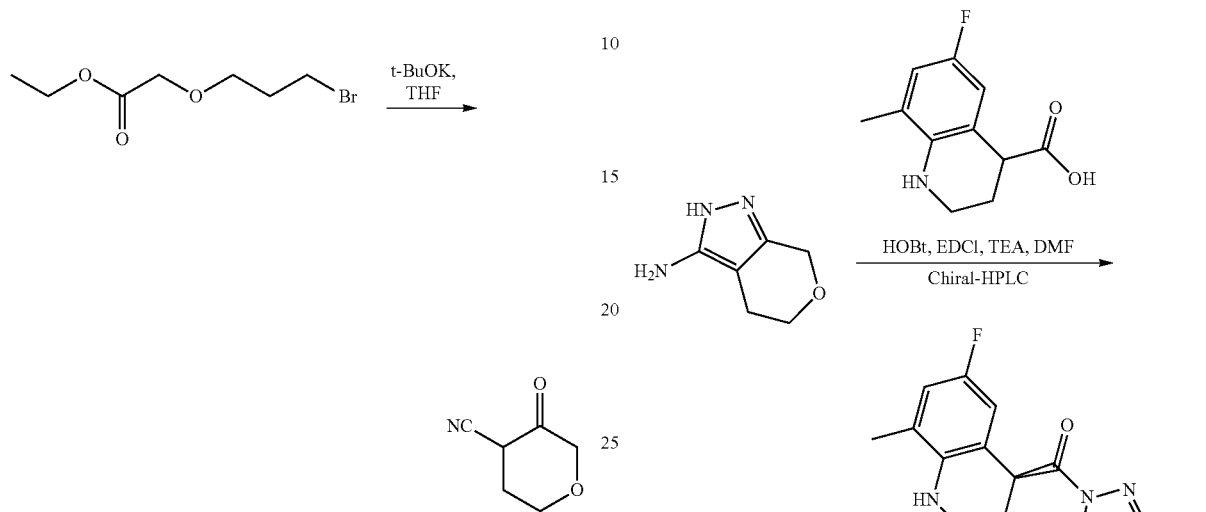

Into a 50-mL round-bottom flask, was placed 6-fluoro-8-methyl-1,2,3,4-tetrahydroquinoline-4-carboxylic acid (207 mg, 0.99 mmol, 1.20 equiv), 2H,4H,5H,7H-pyrano[3,4-c]pyrazol-3-amine (150 mg, 1.08 mmol, 1.00 equiv), HOBT (219 mg, 1.62 mmol, 1.50 equiv), EDCI (311 mg, 1.62 mmol, 1.50 equiv), N,N-dimethylformamide (6 mL), TEA (327 mg, 3.23 mmol, 3.00 equiv). The resulting solution was stirred for 3 h at 25 degree C. The reaction mixture was diluted with DCM (80 mL), washed with H2O (50 mL×3) and brine (50 mL×3) and dried with Na₂SO₄. After filtration, the filtrate was concentrated under reduced pressure. The crude product was purified by Prep-HPLC with the following conditions (Analyse HPLC-SHIMADZU): Column: XSelect CSH Prep C18 OBD Column, 5 um, 19×150 mm; Mobile Phase A: water (0.1% FA), Mobile Phase B: ACN; Flow rate: 20 mL/min; Gradient: 25% B to 65% B in 7 min; 220 nm; Rt: 5.38, 6.18 min. The product was separated by Prep-chiral-HPLC with the following conditions: Column, CHIRALPAK IF, 2×25 cm, 5 um; mobile phase, Hex- and ethanol- (hold 20.0% ethanol- in 20 min); Detector, UV 254/220 nm.

Enantiomer A: This resulted in 16 mg (4%) of (S*)-(3-amino-4,5-dihydropyrano[3,4-c]pyrazol-2(7H)-yl)(6- fluoro-8-methyl-1,2,3,4-tetrahydroquinolin-4-yl)methanone as a white solid. Rt2:6.18 min. MS (ES, m/z) [M+H]+: 331. (400 MHz, DMSO-d6, ppm): δ 6.75 (d, J=2.8 Hz, 1H), 6.73-6.52 (m, 3H), 5.13 (s, 1H), 5.00-4.97 (m, 1H), 4.59-4.51 (m, 2H), 3.80-3.75 (m, 2H), 3.32-3.21 (m, 2H), 2.50-2.41 (m, 2H), 2.11-2.07 (m, 5H).

Enantiomer B: This resulted in 15.7 mg (4%) of (R*)-(3-amino-4,5-dihydropyrano[3,4-c]pyrazol-2(7H)-yl)(6-fluoro-8-methyl-1,2,3,4-tetrahydroquinolin-4-yl)methanone as a white solid. Rt1:5.37 min. MS (ES, m/z) [M+H]+: 331. (400 MHz, DMSO-d6, ppm): δ 6.75 (d, J=2.8 Hz, 1H), 6.73-6.52 (m, 3H), 5.13 (s, 1H), 5.00-4.97 (m, 1H), 4.59-4.51 (m, 2H), 3.80-3.77 (m, 2H), 3.32-3.21 (m, 2H), 2.50-2.41 (m, 2H), 2.10-2.02 (m, 5H).

Example 78 & 79 & 80 & 81: (3-amino-7-methyl-6-(methylsulfonyl)-4,5,6,7-tetrahydropyrazolo[3,4-c]pyridin-2-yl)(8-methyl-1,2,3,4-tetrahydroquinolin-4-yl)methanone diastereomer A and (3-amino-7-methyl-6-(methylsulfonyl)-4,5,6,7-tetrahydropyrazolo[3,4-c]pyridin-2-yl)(8-methyl-1,2,3,4-tetrahydroquinolin-4-yl)methanone diastereomer B and (3-amino-7-methyl-6-(methylsulfonyl)-4,5,6,7-tetrahydropyrazolo[3,4-c]pyridin-1-yl)-8-methyl-1,2,3,4-tetrahydroquinolin-4-yl)methanone (diastereomer A) and (3-amino-7-methyl-6-(methylsulfonyl)-4,5,6,7-tetrahydropyrazolo[3,4-c]pyridin-1-yl)-8-methyl-1,2,3,4-tetrahydroquinolin-4-yl)methanone (diastereomer B)

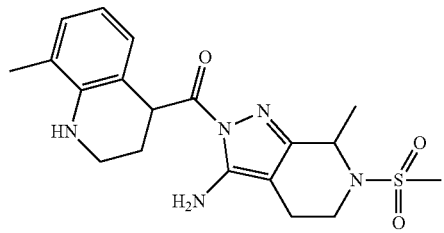

2-acyl diastereomer A

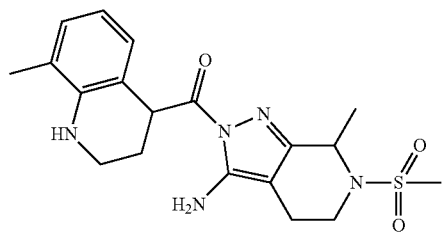

2-acyl diastereomer B

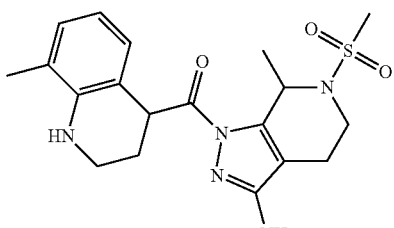

1-acyl diastereomer A

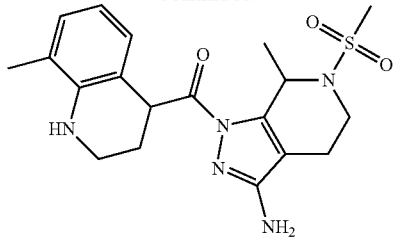

1-acyl diastereomer B

Step 1. Ethyl 2-(3-cyanopropylamino)propanoate

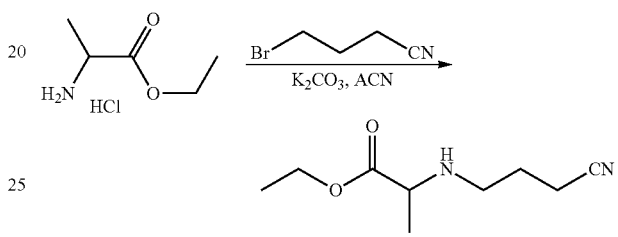

Into a 500-mL round-bottom flask, was placed 4-bromobutanenitrile (10 g, 67.57 mmol, 1.00 equiv), ethyl 2-aminopropanoate hydrochloride (11.5 g, 74.87 mmol, 1.20 equiv), potassium potassium methaneperoxoate (36 g, 258.60 mmol, 4.00 equiv), ACN (150 mL). The resulting solution was stirred overnight at 70° C. After cooled to room temperature, the solids were filtered out. The resulting mixture was concentrated under vacuum. The residue was applied onto a silica gel column with ethyl acetate/petroleum ether (0-100%, 50 min). This resulted in 6 g (48%) of ethyl 2-[(3-cyanopropyl)amino]propanoate as yellow oil. MS (ES, m/z) [M+H]+: 185.

Step 2. Ethyl 2-(benzyl(3-cyanopropyl)amino)propanoate

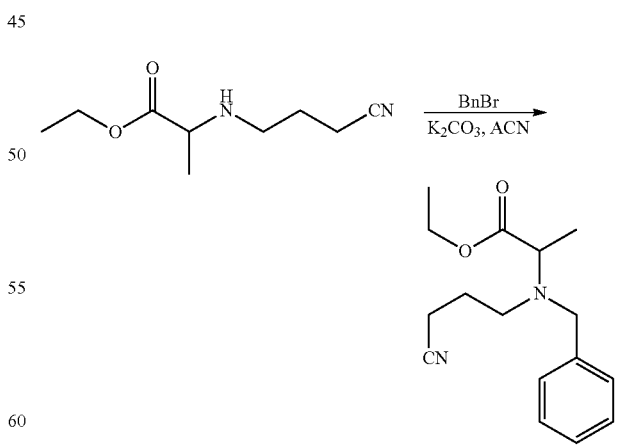

Into a 500-mL round-bottom flask, was placed ethyl 2-[(3-cyanopropyl)amino]propanoate (6 g, 32.57 mmol, 1.00 equiv), ACN (200 mL), (bromomethyl)benzene (8.3 g, 48.53 mmol, 1.50 equiv), potassium potassium methaneperoxoate (13.5 g, 96.97 mmol, 3.00 equiv). The resulting solution was stirred overnight at 90° C. After cooling to room temperature, the solids were filtered out. The resulting mixture was concentrated under vacuum. The residue was applied onto a silica gel column with ethyl acetate/petroleum ether (0-50%, 40 min). This resulted in 8.5 g (95%) of ethyl 2-[benzyl(3-cyanopropyl)amino]propanoate as yellow oil. MS (ES, m/z) [M+H]+: 275.

Step 3.
1-benzyl-2-methyl-3-oxopiperidine-4-carbonitrile

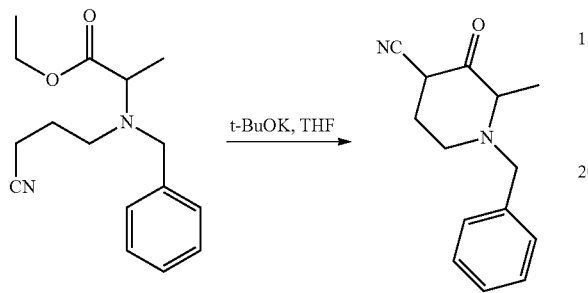

Into a 500-mL 3-necked round-bottom flask purged and maintained with an inert atmosphere of nitrogen, was placed ethyl 2-[benzyl(3-cyanopropyl)amino]propanoate (8.5 g, 30.98 mmol, 1.00 equiv), tetrahydrofuran (200 mL). This was followed by the addition of t-BuOK (10 g, 89.12 mmol, 3.00 equiv) in several batches at 0° C. The resulting solution was stirred for 3 h at room temperature. The reaction was then quenched by the addition of NH4Cl a.q (300 mL). The pH value of the solution was adjusted to 7-8 with hydrochloric acid (3 mol/L). The resulting solution was extracted with dichloromethane (10% of MeOH) (400 mL×3) and the organic layers combined and concentrated under vacuum. This resulted in 6.7 g (crude) of 1-benzyl-2-methyl-3-oxopiperidine-4-carbonitrile as a yellow solid. MS (ES, m/z) [M+H]+: 229.

Step 4. 6-benzyl-7-methyl-4,5,6,7-tetrahydro-2H-pyrazolo[3,4-c]pyridin-3-amine

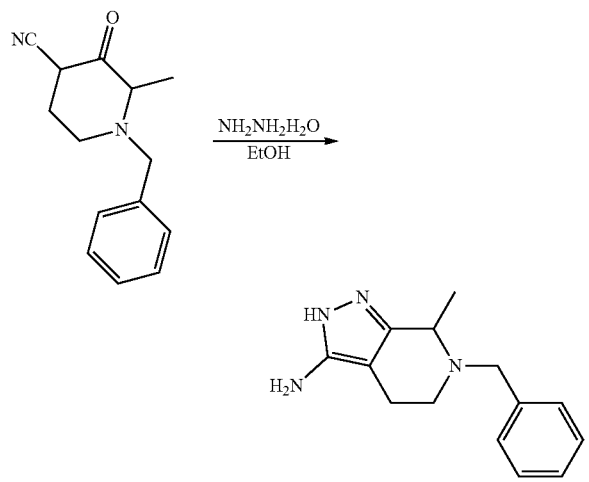

Into a 250-mL round-bottom flask, was placed 1-benzyl-2-methyl-3-oxopiperidine-4-carbonitrile (2.5 g, 10.95 mmol, 1.00 equiv), NH2NH2H2O (2.5 mL), ethanol (60 mL). The resulting solution was stirred overnight at room temperature. The resulting mixture was concentrated under vacuum. The residue was applied onto a silica gel column with methanol/dichloromethane (0-10%, 30 min). This resulted in 1.4 g (53%) of 6-benzyl-7-methyl-4,5,6,7-tetrahydro-2H-pyrazolo[3,4-c]pyridin-3-amine as a yellow solid. MS (ES, m/z) [M+H]+: 243.

Step 5. 7-methyl-4,5,6,7-tetrahydro-2H-pyrazolo[3,4-c]pyridin-3-amine

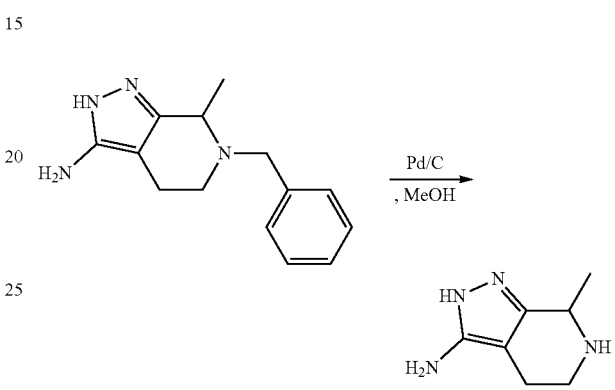

Into a 250-mL round-bottom flask, was placed 6-benzyl-7-methyl-4,5,6,7-tetrahydro-2H-pyrazolo[3,4-c]pyridin-3-amine (1.4 g, 5.78 mmol, 1.00 equiv), methanol (50 mL), Palladium carbon (10%, 700 mg). To the above hydrogen was introduced in. The resulting solution was stirred for 6 h at room temperature. The solids were collected by filtration. The resulting mixture was concentrated under vacuum. This resulted in 670 mg (76%) of 7-methyl-4,5,6,7-tetrahydro-2H-pyrazolo[3,4-c]pyridin-3-amine as a light yellow solid. MS (ES, m/z) [M+H]+: 153.

Step 6. 7-methyl-6-(methylsulfonyl)-4,5,6,7-tetrahydro-2H-pyrazolo[3,4-c] pyridine-3-amine

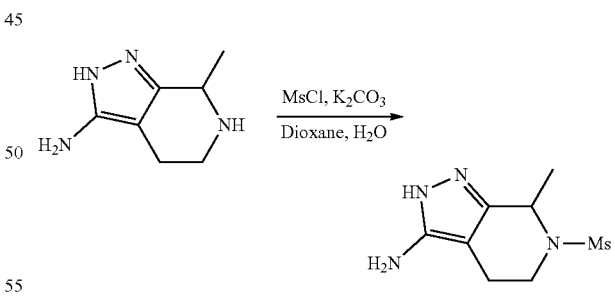

Into a 100-mL 3-necked round-bottom flask, was placed 7-methyl-4,5,6,7-tetrahydro-2H-pyrazolo[3,4-c]pyridin-3-amine (500 mg, 3.29 mmol, 1.00 equiv), dioxane (30 mL), a solution of potassium carbonate (900 mg, 6.51 mmol, 2.00 equiv) in water (10 mL). This was followed by the addition of a solution of methanesulfonyl chloride (370 mg, 3.23 mmol, 1.00 equiv) in dioxane (5 mL) dropwise with stirring at 0° C. The resulting solution was stirred overnight at room temperature. The solids were filtered out. The resulting mixture was concentrated under vacuum. The residue was applied onto a silica gel column with methanol/dichloromethane (0-10%, 30 min). This resulted in 300 mg (40%) of 6-methanesulfonyl-7-methyl-4,5,6,7-tetrahydro-2H-pyrazolo[3,4-c] pyridine-3-amine as a off-white solid. MS (ES, m/z) [M+H]+: 231.

Step 7: (3-amino-7-methyl-6-(methylsulfonyl)-4,5,6,7-tetrahydropyrazolo[3,4-c]pyridin-2-yl)(8-methyl-1,2,3,4-tetrahydroquinolin-4-yl)methanone diastereomer A and (3-amino-7-methyl-6-(methylsulfonyl)-4,5,6,7-tetrahydropyrazolo[3,4-c]pyridin-2-yl)(8-methyl-1,2,3,4-tetrahydroquinolin-4-yl)methanone diastereomer B and (3-amino-7-methyl-6-(methylsulfonyl)-4,5,6,7-tetrahydropyrazolo[3,4-c]pyridin-1-yl)-8-methyl-1,2,3,4-tetrahydroquinolin-4-yl)methanone (diastereomer A) and (3-amino-7-methyl-6-(methylsulfonyl)-4,5,6,7-tetrahydropyrazolo[3,4-c]pyridin-1-yl)-8-methyl-1,2,3,4-tetrahydroquinolin-4-yl)methanone (diastereomer B)

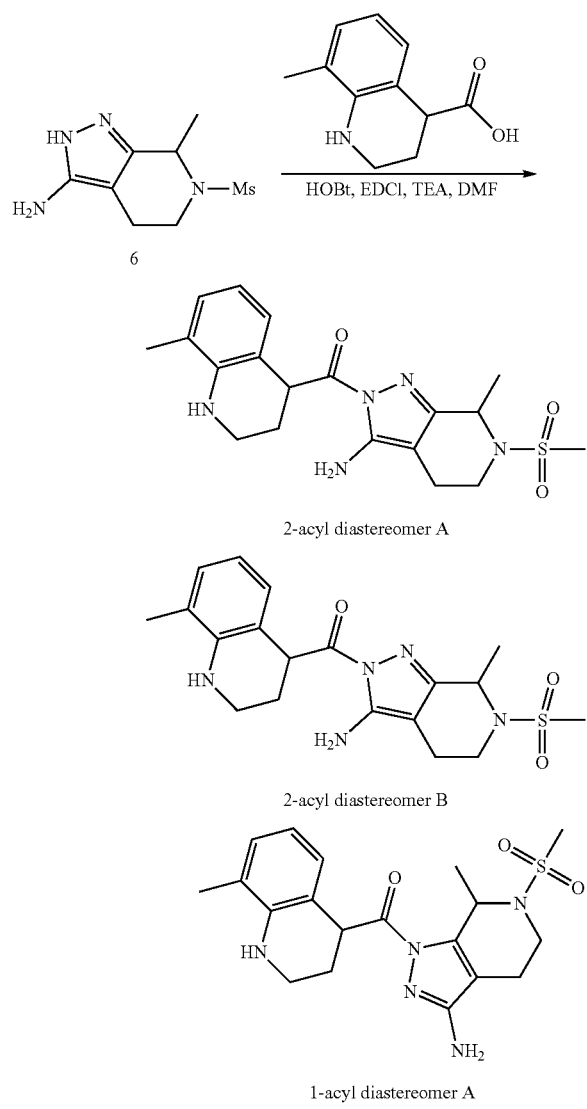

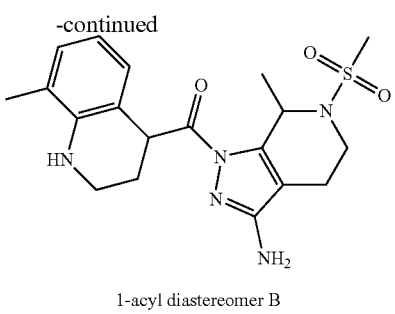

1-acyl diastereomer B

Into a 100-mL round-bottom flask, was placed 6-methanesulfonyl-7-methyl-4,5,6,7-tetrahydro-2H-pyrazolo[3,4-c]pyridin-3-amine (240 mg, 1.04 mmol, 1.00 equiv), 8-methyl-1,2,3,4-tetrahydroquinoline-4-carboxylic acid (200 mg, 1.05 mmol, 1.00 equiv), HOBt (210 mg, 1.55 mmol, 1.50 equiv), EDCI (300 mg, 1.56 mmol, 1.50 equiv), N,N-dimethylformamide (10 mL). The resulting solution was stirred for 2 h at room temperature. The reaction was then quenched by the addition of water (70 mL). The resulting solution was extracted with ethyl acetate (70 mL×3) and the organic layers combined. The resulting mixture was washed with Brine (200 mL×3). The mixture was dried over anhydrous sodium sulfate. The solids were filtered out. The resulting mixture was concentrated under vacuum. The residue was purified by preparative TLC (EA:PE=2:1). The crude product was purified by Prep-HPLC with the following conditions: Column: XSelect CSH Prep C18 OBD Column, 5 um, 19 150 mm; Mobile Phase A: water (0.1% FA), Mobile Phase B: ACN; Flow rate: 20 mL/min; Gradient: 25% B to 30% B in 15 min; 254 nm;

Fraction A: The collected fraction was lyophilized to give 45.3 mg (11%) of (3-amino-7-methyl-6-(methylsulfonyl)-4,5,6,7-tetrahydropyrazolo[3,4-c]pyridin-2-yl)(8-methyl-1,2,3,4-tetrahydroquinolin-4-yl)methanone diastereomer A as a yellow solid. Rt4: 16.55 min. MS (ES, m/z) [M+H]+: 404. (DMSO-d6, 400 MHz, ppm): δ 6.82 (d, J=7.2 Hz, 1H), 6.67 (d, J=7.2 Hz, 1H), 6.59 (s, 2H), 6.36-6.32 (m, 1H), 5.24 (s, 1H), 5.07-5.04 (m, 1H), 4.88-4.83 (m, 1H), 3.86-3.82 (m, 1H), 3.41-3.38 (m, 1H), 3.26-3.21 (m, 2H), 2.96 (s, 3H), 2.41-2.39 (m, 2H), 2.11-2.00 (m, 5H), 1.44 (s, 3H).

Fraction B: The collected fraction was lyophilized to give 37.6 mg (9%) of (3-amino-7-methyl-6-(methylsulfonyl)-4,5,6,7-tetrahydropyrazolo[3,4-c]pyridin-2-yl)(8-methyl-1,2,3,4-tetrahydroquinolin-4-yl)methanone diastereomer B as a yellow solid. Rt3: 15.39 min. MS (ES, m/z) [M+H]+: 404. (DMSO-d6, 400 MHz, ppm): δ 6.82 (d, J=7.2 Hz, 1H), 6.67 (d, J=7.6 Hz, 1H), 6.59 (s, 2H), 6.37-6.33 (m, 1H), 5.23 (s, 1H), 5.02-4.99 (m, 1H), 4.89-4.84 (m, 1H), 3.86-3.82 (m, 1H), 3.26-3.21 (m, 3H), 2.97 (s, 3H), 2.43- 2.39 (m, 2H), 2.11-2.03 (m, 5H), 1.44 (s, 3H).

Fraction C: The collected fraction was lyophilized to give 50.7 mg (12%) of (3-amino-7-methyl-6-(methylsulfonyl)-4,5,6,7-tetrahydropyrazolo[3,4-c]pyridin-1-yl)-8-methyl-1,2,3,4-tetrahydroquinolin-4-yl)methanone (diastereomer A) as a yellow solid. Rt2: 11.87 min. MS (ES, m/z) [M+H]+: 404. (DMSO-d6, 400 MHz, ppm): δ 6.81 (d, J=7.2 Hz, 1H), 6.62 (d, J=7.2 Hz, 1H), 6.36-6.33 (m, 1H), 5.77 (s, 2H), 5.31-5.26 (m, 1H), 5.22 (s, 1H), 5.01-4.98 (m, 1H), 3.88-3.83 (m, 1H), 3.42-3.38 (m, 1H), 3.26-3.22 (m, 2H), 2.92 (s, 3H), 2.46-2.41 (m, 2H), 2.08-1.95 (m, 5H), 1.35 (s, 3H).

Fraction D: The collected fraction was lyophilized to give 37.6 mg (9%) of (3-amino-7-methyl-6-(methylsulfonyl)-4,5,6,7-tetrahydropyrazolo[3,4-c]pyridin-1-yl)-8-methyl-1,2, 3,4-tetrahydroquinolin-4-yl)methanone (diastereomer B) as a yellow solid. Rt1: 10.32 min. MS (ES, m/z) [M+H]+: 404. (DMSO-d6, 400 MHz, ppm): δ 6.82 (d, J=6.8 Hz, 1H), 6.64 (d, J=7.6 Hz, 1H), 6.37-6.33 (m, 1H), 5.77 (s, 2H), 5.28-5.23 (m, 1H), 5.20 (s, 1H), 4.94-4.91 (m, 1H), 3.88-3.83 (m, 1H), 3.28-3.26 (m, 3H), 2.90 (s, 3H), 2.44-2.40 (m, 2H), 2.09-1.99 (m, 5H), 1.38 (s, 3H).

Example 82 & 83 & 84: (S*)-(3-amino-4,5,6,7-tetrahydropyrazolo[4,3-c]pyridin-2-yl)(6-fluoro-8-methyl-1,2,3,4-tetrahydroquinolin-4-yl)methanone and (R*)-(3-amino-4,5,6,7-tetrahydropyrazolo[4,3-c]pyridin-2-yl)(6-fluoro-8-methyl-1,2,3,4-tetrahydroquinolin-4-yl)methanone and (3-amino-4,5,6,7-tetrahydropyrazolo[4,3-c]pyridin-1-yl)(6-fluoro-8-methyl-1,2,3,4-tetrahydroquinolin-4-yl)methanone

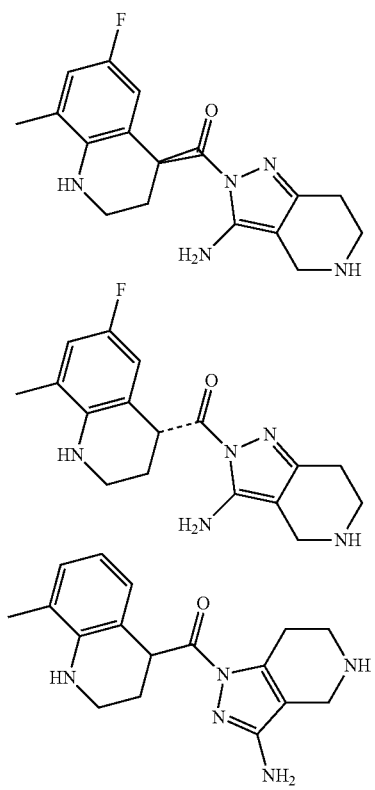

Step 1. tert-butyl 3-amino-4,5,6,7-tetrahydro-2H-pyrazolo[4,3-c]pyridin-5-carboxylate

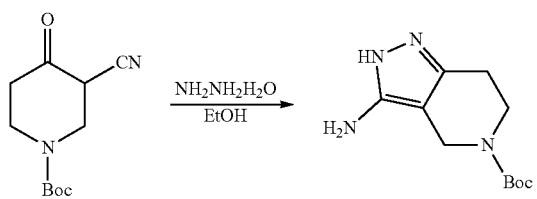

Into a 250-mL round-bottom flask (1 atm), was placed tert-butyl 3-cyano-4-oxopiperidine-1-carboxylate (5 g, 22.30 mmol, 1.00 equiv), NH₂NH₂H₂O (11.1 g, 223 mmol, 10.00 equiv), EtOH (100 mL). The resulting solution was stirred overnight at 25° C. The residue was applied onto a silica gel column with chloroform/methanol (95/5). This resulted in 4.9 g (93%) of tert-butyl 3-amino-4,5,6,7-tetrahydro-2H-pyrazolo[4,3-c]pyridine-5-carboxylate as a white solid. MS (ES, m/z) [M+H]+: 239.

Step 2. Tert-butyl (3-amino-4,5,6,7-tetrahydro-2H-pyrazolo[4,3-c]pyridin-2-yl)(6-fluoro-8-methyl-1,2,3,4-tetrahydroquinolin-4-yl)methanone and tert-butyl (3-amino-4,5,6,7-tetrahydro-2H-pyrazolo[4,3-c]pyridin-1-yl)(6-fluoro-8-methyl-1,2,3,4-tetrahydroquinolin-4-yl)methanone

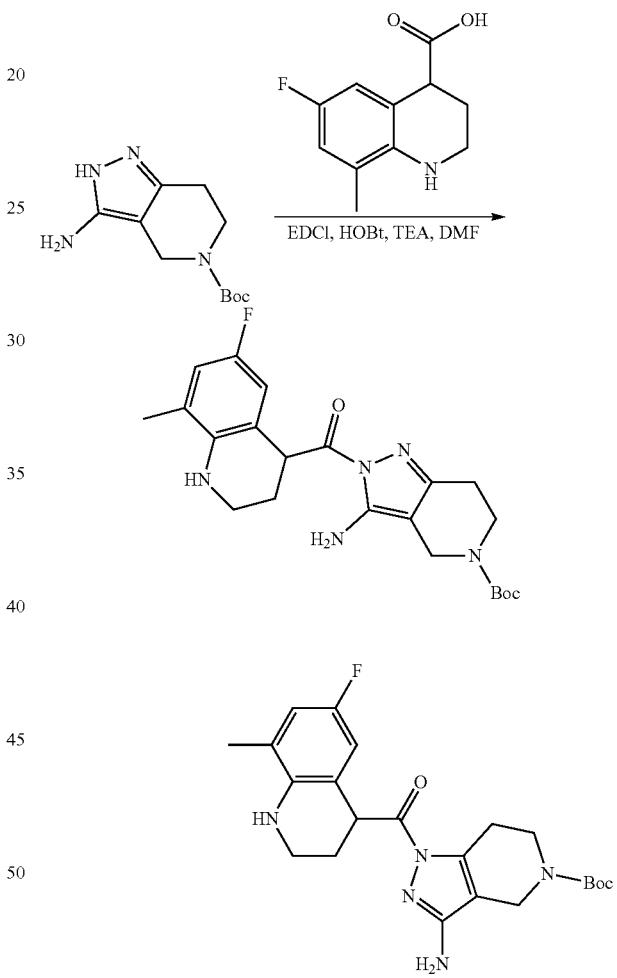

Into a 50-mL round-bottom flask, was placed tert-butyl 3-amino-4,5,6,7-tetrahydro-2H-pyrazolo[4,3-c]pyridine-5-carboxylate (227.8 mg, 0.96 mmol, 1.00 equiv), EDCI (275.6 mg, 1.44 mmol, 1.00 equiv), HOBt (193.8 mg, 1.43 mmol, 1.50 equiv), 6-fluoro-8-methyl-1,2,3,4-tetrahydroquinoline-4-carboxylic acid (200 mg, 0.96 mmol, 1.50 equiv), TEA (289.9 mg, 2.87 mmol, 3.00 equiv), DMF (10 mL). The resulting solution was stirred overnight at 25° C. The reaction was then quenched by the addition of water (40 mL). The resulting solution was extracted with ethyl acetate (50 mL×3) and the organic layers combined and concentrated under vacuum. The residue was purified by preparative TLC (DCM:MeOH=10:1). This resulted in 170 mg (41%) of tert-butyl (3-amino-4,5,6,7-tetrahydro-2H-pyrazolo[4,3-c]pyridin-2-yl)(6-fluoro-8-methyl-1,2,3,4-tetrahydroquinolin-4-yl)methanone as yellow oil. MS (ES, m/z) [M+H]+: 430. And 184 mg (45%) of and (3-amino-4,5,6,7-tetrahydro-2H-pyrazolo[4,3-c]pyridin-1-yl)(6-fluoro-8-methyl-1,2,3,4-tetrahydroquinolin-4-yl)methanone as yellow oil. MS (ES, m/z) [M+H]+: 430.

Step 3. Tert-butyl (S*)-(3-amino-4,5,6,7-tetrahydro-2H-pyrazolo[4,3-c]pyridin-2-yl)(6-fluoro-8-methyl-1,2,3,4-tetrahydroquinolin-4-yl)methanone and tert-butyl (R*)-(3-amino-4,5,6,7-tetrahydro-2H-pyrazolo[4,3-c]pyridin-2-yl)(6-fluoro-8-methyl-1,2,3,4-tetrahydroquinolin-4-yl)methanone

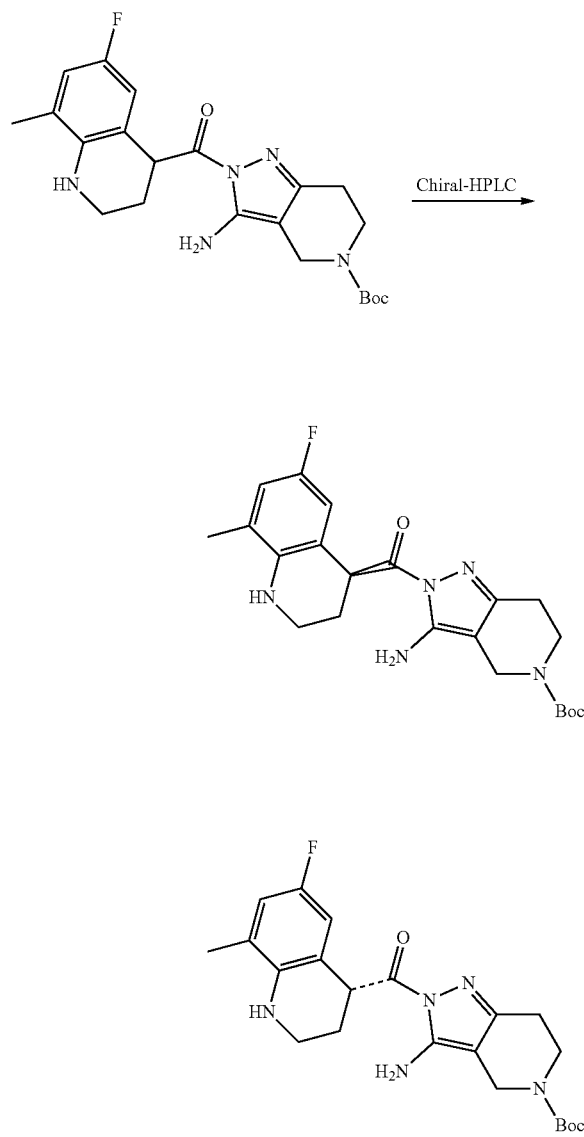

Tert-butyl-(3-amino-4,5,6,7-tetrahydro-2H-pyrazolo[4,3-c]pyridin-2-yl)(6-fluoro-8-methyl-1,2,3,4-tetrahydroquinolin-4-yl)methanone (170 mg, 0.40 mmol, 1.00 equiv) was separated by Prep-chiral-HPLC with the following conditions: Column: CHIRAL ART Cellulose-SB S-5 um, 2×25 cm, 5 um; Mobile Phase A: Hex-HPLC, Mobile Phase B: EtOH-HPLC; Flow rate: 20 mL/min; Gradient: 20 B to 20 B in 15 min; 254/220 nm; Rt1:8.38 min; Rt2:10.99 min. This resulted in 76.5 mg (45%) of tert-butyl (S*)-(3-amino-4,5,6,7-tetrahydro-2H-pyrazolo[4,3-c]pyridin-2-yl)(6-fluoro-8-methyl-1,2,3,4-tetrahydroquinolin-4-yl)methanone as yellow oil. MS (ES, m/z) [M+H]+: 430. And 77.2 mg (45%) of tert-butyl (R*)-(3-amino-4,5,6,7-tetrahydro-2H-pyrazolo[4,3-c]pyridin-2-yl)(6-fluoro-8-methyl-1,2,3,4-tetrahydroquinolin-4-yl)methanone as white oil. MS (ES, m/z) [M+H]+: 430.

Step 4. (S*)-(3-amino-4,5,6,7-tetrahydro-2H-pyrazolo[4,3-c]pyridin-2-yl)(6-fluoro-8-methyl-1,2,3,4-tetrahydroquinolin-4-yl)methanone

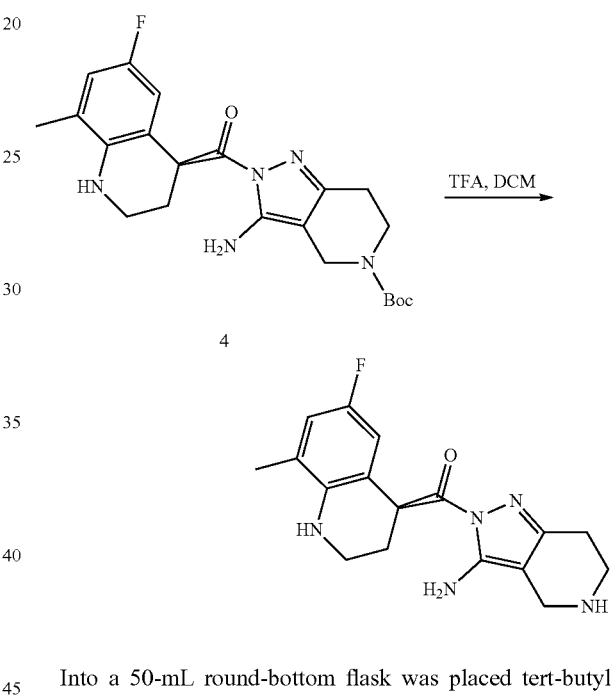

Into a 50-mL round-bottom flask was placed tert-butyl (S*)-(3-amino-4,5,6,7-tetrahydro-2H-pyrazolo[4,3-c]pyridin-2-yl)(6-fluoro-8-methyl-1,2,3,4-tetrahydroquinolin-4-yl)methanone (76.5 mg, 0.18 mmol, 1.00 equiv), dichloromethane (10 mL). This was followed by the addition of trifluoroacetic acid (1 mL) dropwise with stirring at room temperature. The resulting solution was stirred for 30 min at 25° C. The resulting mixture was concentrated under vacuum. The crude product was purified by Prep-HPLC with the following conditions: Column: XBridge Prep C18 OBD Column 19×150 mm 5 um; Mobile Phase A: water (10 mM NH4HCO3), Mobile Phase B: ACN; Flow rate: 20 mL/min; Gradient: 10% B to 40% B in 10 min; 254/220 nm; Rt: 9.53 min. The collected fraction was lyophilized to give 13.8 mg (24%) of (S*)-(3-amino-4,5,6,7-tetrahydro-2H-pyrazolo[4,3-c]pyridin-2-yl)(6-fluoro-8-methyl-1,2,3,4-tetrahydro-quinolin-4-yl)methanone as a white solid. MS (ES, m/z) [M+H]+: 330; (DMSO-d6, 400 MHz, ppm): δ 6.76-6.72 (m, 1H), 6.55-6.51 (m, 1H), 6.42 (s, 2H), 5.12 (s, 1H), 5.04-5.00 (m, 1H), 3.51 (s, 2H), 3.25-3.20 (m, 2H), 2.85-2.86 (m, 2H), 2.46-2.42 (m, 2H), 2.12-1.98 (m, 5H).

Step 5. (R*)-(3-amino-4,5,6,7-tetrahydro-2H-pyrazolo[4,3-c]pyridin-2-yl)(6-fluoro-8-methyl-1,2,3,4-tetrahydroquinolin-4-yl)methanone

Step 6. 3-amino-4,5,6,7-tetrahydro-1H-pyrazolo[4,3-c]pyridin-1-yl)(6-fluoro-8-methyl-1,2,3,4-tetrahydroquinolin-4-yl)methanone

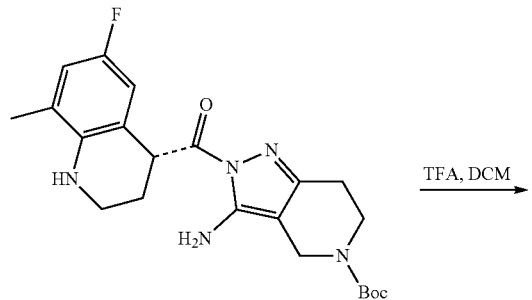

TFA, DCM →

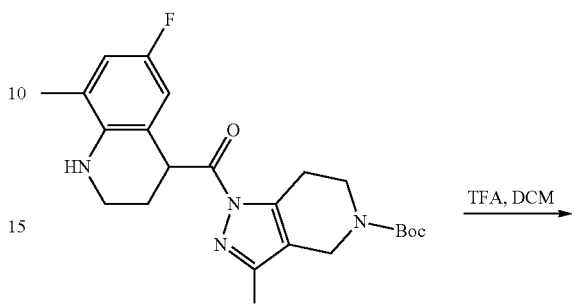

TFA, DCM →

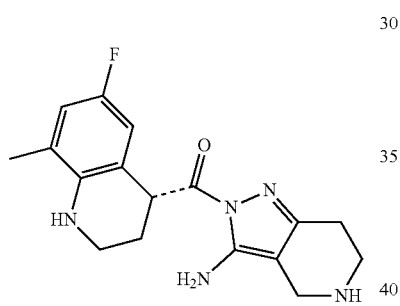

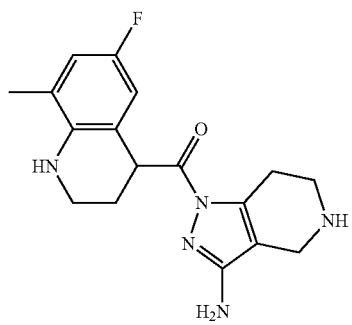

Into a 50-mL round-bottom flask was placed tert-butyl (R*)-(3-amino-4,5,6,7-tetrahydro-2H-pyrazolo[4,3-c]pyridin-2-yl)(6-fluoro-8-methyl-1,2,3,4-tetrahydroquinolin-4-yl)methanone (77.2 mg, 0.18 mmol, 1.00 equiv), dichloromethane (10 mL). This was followed by the addition of trifluoroacetic acid (1 mL) dropwise with stirring at room temperature. The resulting solution was stirred for 30 min at 25° C. The resulting mixture was concentrated under vacuum. The crude product was purified by Prep-HPLC with the following conditions: Column: XBridge Shield RP18 OBD Column, 5 um, 19×150 mm; Mobile Phase A: water (10 mM NH$_4$HCO$_3$), Mobile Phase B: ACN; Flow rate: 20 mL/min; Gradient: 5% B to 50% B in 9 min; 254 nm; Rt: 8.85 min. The collected fraction was lyophilized to give 4.8 mg (8%) of (R*)-(3-amino-4,5,6,7-tetrahydro-2H-pyrazolo[4,3-c]pyridin-2-yl)(6-fluoro-8-methyl-1,2,3,4-tetrahydroquinolin-4-yl)methanone as a white solid. MS (ES, m/z) [M+H]+: 330; (DMSO-d6, 400 MHz, ppm): δ 6.75-6.72 (m, 1H), 6.55-6.52 (m, 1H), 6.44 (s, 2H), 5.13 (s, 1H), 5.03-5.00 (m, 1H), 3.52 (s, 2H), 3.26-3.21 (m, 2H), 2.96-2.90 (m, 2H), 2.46-2.41 (m, 2H), 2.10-1.90 (m, 5H).

Into a 50-mL round-bottom flask, was placed tert-butyl (3-amino-4,5,6,7-tetrahydro-2H-pyrazolo[4,3-c]pyridin-1-yl)(6-fluoro-8-methyl-1,2,3,4-tetrahydroquinolin-4-yl) methanone (150 mg, 0.35 mmol, 1.00 equiv), dichloromethane (10 mL). This was followed by the addition of trifluoroacetic acid (1 mL) dropwise with stirring at room temperature. The resulting solution was stirred for 30 min at room temperature. The resulting mixture was concentrated under vacuum. The crude product was purified by Prep-HPLC with the following conditions: Column: XBridge Prep C18 OBD Column 19×150 mm 5 um; Mobile Phase A: water (10 mM NH$_4$HCO$_3$), Mobile Phase B: ACN; Flow rate: 20 mL/min; Gradient: 25% B to 55% B in 7 min; 254/220 nm; Rt: 6.03 min. The collected fraction was lyophilized to give 19.2 mg (17%) of 3-amino-4,5,6,7-tetrahydro-1H-pyrazolo[4,3-c]pyridin-1-yl)(6-fluoro-8-methyl-1,2,3,4-tetrahydroquinolin-4-yl)methanone as a white solid. MS (ES, m/z) [M+H]+: 330. (DMSO-d6, 300 MHz, ppm): δ 6.74-6.70 (m, 1H), 6.55-6.51 (m, 1H), 5.61 (s, 2H), 5.09 (s, 1H), 4.96-4.93 (m, 1H), 3.47 (s, 2H), 3.39-3.36 (m, 1H), 3.24-3.18 (m, 1H), 2.83-2.75 (m, 7H), 2.09-1.92 (m, 5H).

The following examples were prepared using methods similar to those shown above:

TABLE 1

List of the examples

| Example | Structure | Name | ¹HNMR | (ES, m/z) [M + H]⁺ |
|---|---|---|---|---|
| Example 85 | 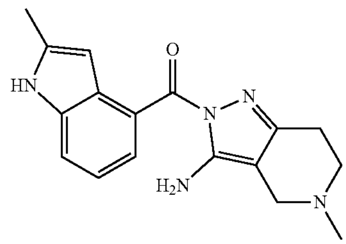 | (3-amino-5-methyl-4,5,6,7-tetrahydro-pyrazolo[4,3-c]pyridin-2-yl)(2-methyl-1H-indol-4-yl)methanone | (300 MHz, DMSO-d₆, ppm): δ 11.21(s, 1H), 7.55(d, J = 6.9 Hz, 1H), 7.46(d, J = 8.1 Hz, 1H), 7.08-7.03(m, 1H), 6.46(s, 2H), 6.27(s, 1H), 3.21(m, 2H), 2.55-2.54(m, 4H), 2.40(s, 3H), 2.35(s, 3H). | 310 |
| Example 86 | 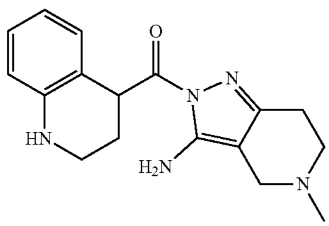 [SMILES: CN1CCc2nn(C(=O)C3CCNc4ccccc43)c(N)c2C1] | (3-amino-5-methyl-4,5,6,7-tetrahydro-pyrazolo[4,3-c]pyridin-2-yl)(1,2,3,4-tetrahydro-quinolin-4-yl)methanone | (300 MHz, DMSO-d₆, ppm): δ 6.92-6.87(m, 1H), 6.77-6.75(m, 1H), 6.54-6.36(m, 4H), 5.83(s, 1H), 5.03-5.00(m, 1H), 3.29-3.16(s, 4H), 2.59(s, 4H), 2.34(s, 3H), 2.50-1.95(m, 2H). | 312 |
| Example 87 | 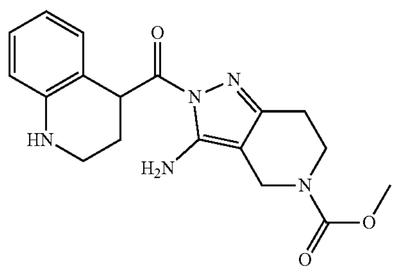 [SMILES: COC(=O)N1CCc2nn(C(=O)C3CCNc4ccccc43)c(N)c2C1] | methyl 3-amino-2-(1,2,3,4-tetrahydro-quinoline-4-carbonyl)-6,7-dihydro-2H-pyrazolo[4,3-c]pyridine-5(4H)-carboxylate | (DMSO-d₆, 400 MHz, ppm): δ 6.91-6.87(m, 1H), 6.76-6.75(d, J = 7.6 Hz, 1H), 6.64(s, 2H), 6.51-6.49(d, J = 7.6 Hz, 1H), 6.39-6.36(m, 1H), 5.84(s, 1H),5.02-4.99(m, 1H), 4.26(s, 2H), 3.64-3.61(m, 5H), 3.27-3.25(m, 1H), 3.18-3.15(m, 1H), 2.67-2.57(m, 2H), 2.08-1.99(m, 2H). | 356 |
| Example 88 | 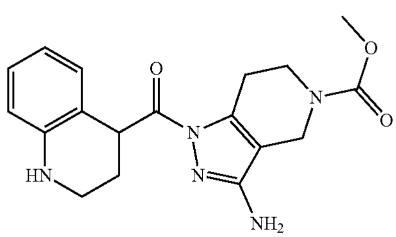 [SMILES: COC(=O)N1CCc2c(c(N)nn2C(=O)C2CCNc3ccccc32)C1] | methyl 3-amino-1-(1,2,3,4-tetrahydro-quinoline-4-carbonyl)-6,7-dihydro-1H-pyrazolo[4,3-c]pyridine-5(4H)-carboxylate | (DMSO-d₆, 400 MHz, ppm): δ 6.92-6.87 (m, 1H), 6.76-6.75(d, J = 7.6 Hz, 1H), 6.49-6.47(m, 1H), 6.32-6.38(m, 1H), 5.80-5.76(m, 3H), 4.92(s, 1H), 4.24(s, 2H), 3.63(s, 3H), 3.59-3.57(m, 2H), 3.31-3.29(m, 1H), 3.19-3.11(m, 1H), 2.91-2.89(m, 2H), 2.10-1.90(m, 2H). | 356 |
| Example 89 | 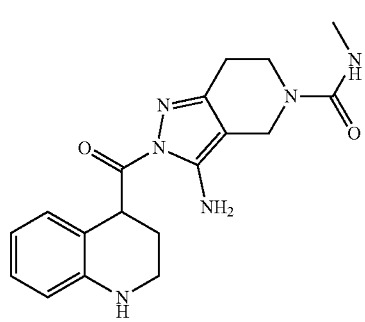 [SMILES: CNC(=O)N1CCc2nn(C(=O)C3CCNc4ccccc43)c(N)c2C1] | 3-amino-N-methyl-2-(1,2,3,4-tetrahydro-quinoline-4-carbonyl)-6,7-dihydro-2H-pyrazolo[4,3-c]pyridine-5(4H)-carboxamide | (300 MHz, DMSO-d₆, ppm): δ 6.93-6.88(m, 1H), 6.78-6.75(m, 1H), 6.55-6.50(m, 4H), 6.41-6.36(m, 1H), 5.86(s, 1H), 5.04-5.00(m, 1H), 4.20(s, 2H), 3.56-3.53(m, 2H), 3.28-3.15(m, 2H), 2.61-2.51(m, 5H), 2.05-1.98(m, 2H). | 355 |

TABLE 1-continued

List of the examples

| Example | Structure | Name | ¹HNMR | (ES, m/z) [M + H]⁺ |
|---|---|---|---|---|
| Example 90 | 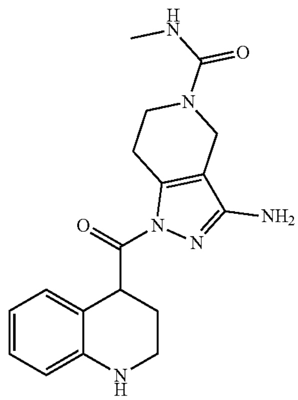 [SMILES: CNC(=O)N1CCc2c(c(N)nn2C(=O)C2CCNc3ccccc32)C1] | 3-amino-N-methyl-1-(1,2,3,4-tetrahydroquinoline-4-carbonyl)-6,7-dihydro-1H-pyrazolo[4,3-c]pyridine-5(4H)-carboxamide | (300 MHz, DMSO-d₆, ppm): δ 6.89-6.85(m, 1H),6.76-6.73(m, 1H), 6.53-6.46(m, 2H), 6.36-6.34(m, 1H), 5.78(s, 1H), 5.65(s, 2H), 4.93-4.90(m, 1H), 3.50-3.46(m, 2H), 3.30-3.15(m, 2H), 2.85(s, 2H), 2.49(s, 3H), 2.00-1.96(m, 2H). | 355 |
| Example 91 | 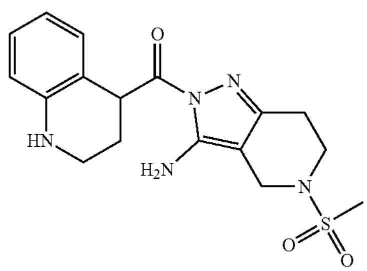 [SMILES: CS(=O)(=O)N1CCc2nn(C(=O)C3CCNc4ccccc43)c(N)c2C1] | (3-amino-5-(methylsulfonyl)-4,5,6,7-tetrahydropyrazolo[4,3-c]pyridin-2-yl)(1,2,3,4-tetrahydroquinolin-4-yl)methanone | (300 MHz, DMSO-d₆, ppm): δ 6.89-6.87(m, 1H), 6.77(d, J = 7.5 Hz, 1H), 6.66(s, 2H), 6.51-6.48(m, 1H), 6.40-6.35(m, 1H), 5.83(s, 1H), 5.03-5.00(m, 1H), 4.09(s, 2H), 3.47-3.43(m, 2H), 3.19-3.11(m, 2H), 2.93(s, 3H), 2.72-2.68(m, 2H), 2.04-2.03(m, 2H). | 376 |
| Example 92 | 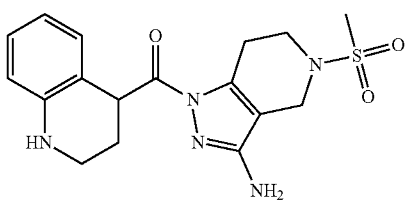 [SMILES: CS(=O)(=O)N1CCc2c(c(N)nn2C(=O)C2CCNc3ccccc32)C1] | (3-amino-5-(methylsulfonyl)-4,5,6,7-tetrahydropyrazolo[4,3-c]pyridin-1-yl)(1,2,3,4-tetrahydroquinolin-4-yl)methanone | (300 MHz, DMSO-d₆, ppm): δ 6.90-6.82(m, 1H), 6.76(d, J = 7.2 Hz, 1H), 6.50-6.47(m, 1H), 6.39-6.34(m, 1H), 5.88(s, 1H), 5.79(s, 2H), 4.95-4.91(m, 1H), 4.08(s, 2H), 3.48-3.40(m, 2H), 3.29-3.01(m, 2H), 2.93(s, 2H), 2.93(s, 3H), 2.04-1.94(m, 2H). | 376 |
| Example 93 | 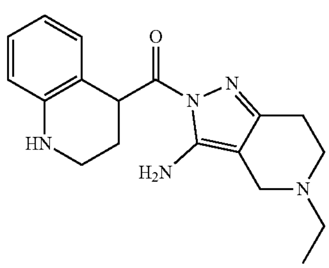 [SMILES: CCN1CCc2nn(C(=O)C3CCNc4ccccc43)c(N)c2C1] | (3-amino-5-ethyl-4,5,6,7-tetrahydropyrazolo[4,3-c]pyridin-2-yl)(1,2,3,4-tetrahydroquinolin-4-yl)methanone | (300 MHz, DMSO-d₆, ppm): δ 6.93-6.88(m, 1H), 6.77-6.75(m, 1H), 6.51-6.46(m, 3H), 6.41-6.36(m, 1H), 5.84(s, 1H), 5.04-5.00(m, 1H), 3.32-3.19(m, 5H), 2.73-2.59(m, 5H), 2.04-1.99(m,2H), 1.10-1.06(m, 3H). | 326 |
| Example 94 | 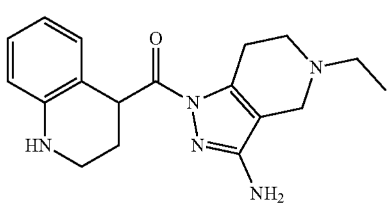 [SMILES: CCN1CCc2c(c(N)nn2C(=O)C2CCNc3ccccc32)C1] | (3-amino-5-ethyl-4,5,6,7-tetrahydropyrazolo[4,3-c]pyridin-1-yl)(1,2,3,4-tetrahydroquinolin-4-yl)methanone | (300 MHz, DMSO-d₆, ppm): δ 6.88-6.86(m, 1H), 6.77-6.75(m, 1H), 6.50-6.47(m, 1H), 6.40-6.38(m, 1H), 5.80(s, 1H), 5.63(s, 2H), 4.99-4.02(m, 1H), 3.32-3.19(m, 5H), 2.73-2.59(m, 5H), 2.04-1.92(m, 2H), 1.11-1.07(m, 3H). | 326 |

TABLE 1-continued

List of the examples

| Example | Structure | Name | ¹HNMR | (ES, m/z) [M + H]⁺ |
|---|---|---|---|---|
| Example 95 | 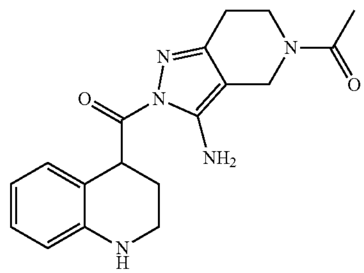 [SMILES: CC(=O)N1CCc2nn(C(=O)C3CCNc4ccccc43)c(N)c2C1] | 1-(3-amino-2-(1,2,3,4-tetrahydro-quinoline-4-carbonyl)-6,7-dihydro-2H-pyrazolo[4,3-c]pyridin-5(4H)-yl)ethanone | (300 MHz, DMSO-d₆, ppm): δ 6.95-6.90(m, 1H), 6.82-6.75(m, 1H), 6.64(s, 2H), 6.50-6.41(m, 1H), 6.40-6.31(m, 1H), 5.80(s, 1H), 5.09-5.01(m, 1H), 4.31(d, J = 3.3 Hz, 2H), 6.80-6.65(m, 2H), 3.30-3.11(m, 3H), 2.70-2.65(m, 1H), 2.11-1.98(m, 5H). | 340 |
| Example 96 | 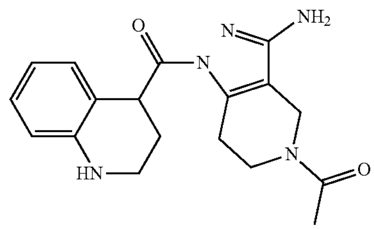 [SMILES: CC(=O)N1CCC(NC(=O)C2CCNc3ccccc32)=C(C(=N)N)C1] | 1-(3-amino-1-(1,2,3,4-tetrahydro-quinoline-4-carbonyl)-6,7-dihydro-1H-pyrazolo[4,3-c]pyridin-5(4H)-yl)ethanone | (300 MHz, DMSO-d₆, ppm): δ 6.95-6.89(m, 1H), 6.77-6.75(m, 1H), 6.50-6.48(m, 1H), 6.40-6.35(m, 1H), 5.90-5.75(m, 3H), 4.93-4.98(m, 1H), 4.30(s, 2H), 3.70-3.62(m, 2H), 3.33-3.31(m, 2H), 2.97-2.80(m, 2H), 2.08-1.99(m, 5H). | 340 |
| Example 97 | 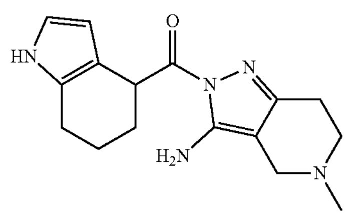 [SMILES: CN1CCc2nn(C(=O)C3CCCc4[nH]ccc43)c(N)c2C1] | (3-amino-5-methyl-4,5,6,7-tetrahydro-pyrazolo[4,3-c]pyridin-2-yl)(4,5,6,7-tetrahydro-1H-indol-4-yl)methanone | (DMSO-d₆, 400 MHz, ppm): δ 10.36(s, 1H), 6.46-6.45(m, 1H), 6.39(s, 2H), 5.58-5.57(m, 1H), 4.78-4.75(m, 1H), 3.16(s, 2H), 2.58-2.51(m, 4H), 2.34(s, 3H), 1.98-1.82(m, 4H), 1.71-1.68(m, 2H). | 300 |
| Example 98 | 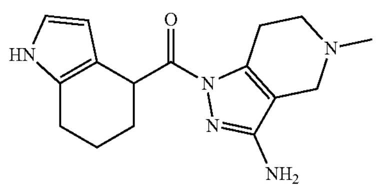 [SMILES: CN1CCc2c(c(N)nn2C(=O)C2CCCc3[nH]ccc32)C1] | (3-amino-5-methyl-4,5,6,7-tetrahydro-pyrazolo[4,3-c]pyridin-1-yl)(4,5,6,7-tetrahydro-1H-indol-4-yl)methanone | (DMSO-d₆, 400 MHz, ppm): δ 10.31(s, 1H), 6.45-6.44(m, 1H), 5.60-5.59(m, 1H), 5.48(s, 2H), 4.69-4.66(m, 1H), 3.13(s, 2H), 2.87-2.85(m, 2H), 2.67-2.51(m, 4H), 2.34(s, 3H), 2.02-1.82(m, 3H), 1.68-1.64(m, 1H). | 300 |
| Example 99 | 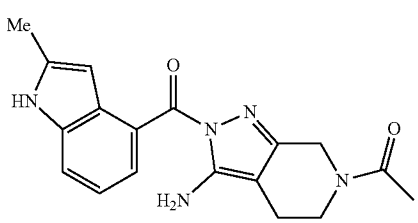 [SMILES: CC(=O)N1CCc2c(nn(C(=O)c3cccc4[nH]c(C)cc34)c2N)C1] | 1-(3-amino-2-(2-methyl-1H-indole-4-carbonyl)-4,5-dihydro-2H-pyrazolo[3,4-c]pyridin-6(7H)-yl)ethanone | (DMSO-d₆, 400 MHz, ppm): δ 11.23(s, 1H), 7.60-7.54( m, 1H), 7.48(d, J = 8.0 Hz, 1H), 7.20-7.06(m, 1H), 6.58 (s, 2H), 6.27(s, 1H), 4.39(d, J = 10.8 Hz, 2H), 3.67-3.62(m, 2H), 2.51-2.49(m, 5H), 2.09(s, 3H). | 338 |
| Example 100 | 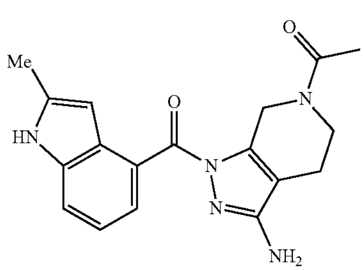 [SMILES: CC(=O)N1CCc2c(N)nn(C(=O)c3cccc4[nH]c(C)cc34)c2C1] | 1-(3-amino-1-(2-methyl-1H-indole-4-carbonyl)-4,5-dihydro-1H-pyrazolo[3,4-c]pyridin-6(7H)-yl)ethanone | (DMSO-d₆, 400 MHz, ppm): δ 11.16(s, 1H), 7.61-7.55(m, 1H), 7.44(d, J = 8.0 Hz, 1H), 7.08-7.02(m, 1H), 6.31-6.26(m, 1H), 5.54(s, 2H), 4.89(s, 2H), 3.73-3.66(m, 2H), 2.51-2.49(m, 2H), 2.45-2.39(m, 3H), 2.13-2.12(m, 3H). | 338 |

TABLE 1-continued

List of the examples

| Example | Structure | Name | ¹HNMR | (ES, m/z) [M + H]⁺ |
|---|---|---|---|---|
| Example 101 | 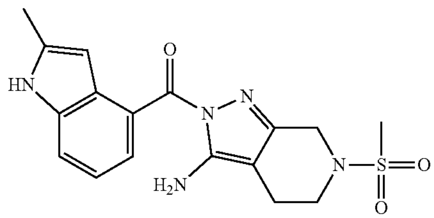 [SMILES: Cc1cc2c(C(=O)n3nc4c(c3N)CCN(S(C)(=O)=O)C4)cccc2[nH]1] | (3-amino-6-(methylsulfonyl)-4,5,6,7-tetrahydro-pyrazolo[3,4-c]pyridin-2-yl)(2-methyl-1H-indol-4-yl)methanone | (DMSO-d₆, 400 MHz, ppm): δ 11.24(s, 1H), 7.57(d, J = 7.6 Hz, 1H), 7.48(d, J = 8 Hz, 1H), 7.08-7.04(m, 1H), 6.62(s, 1H), 6.28 (s, 1H), 4.13(s, 2H), 3.43-3.33(m, 2H), 2.94(s, 3H), 2.50(s, 2H), 2.41(s, 3H). | 374 |
| Example 102 | 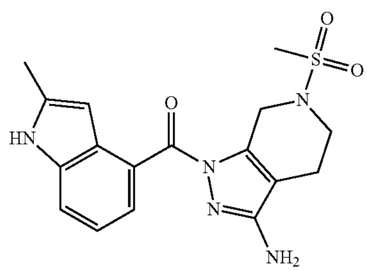 [SMILES: Cc1cc2c(C(=O)n3nc(N)c4c3CN(S(C)(=O)=O)CC4)cccc2[nH]1] | (3-amino-6-(methylsulfonyl)-4,5,6,7-tetrahydro-pyrazolo[3,4-c]pyridin-1-yl)(2-methyl-1H-indol-4-yl)methanone | (DMSO-d₆, 400 MHz, ppm): δ 11.17(s, 1H), 7.60(d, J = 6.8 Hz, 1H), 7.44(d, J = 8.0 Hz, 1H), 7.07-7.03(m, 1H), 6.28(s, 1H), 5.59(s, 2H), 4.70(s, 2H), 3.49-3.46(m, 2H), 3.02(s, 3H), 2.51-2.49(m, 2H), 2.39(s, 3H). | 374 |
| Example 103 | 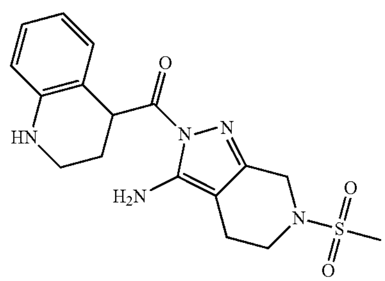 [SMILES: CS(=O)(=O)N1CCc2c(nn(C(=O)C3CCNc4ccccc43)c2N)C1] | (3-amino-6-(methylsulfonyl)-4,5,6,7-tetrahydro-pyrazolo[3,4-c]pyridin-2-yl)(1,2,3,4-tetrahydro-quinolin-4-yl)methanone | (DMSO-d₆, 400 MHz, ppm): δ 6.93-6.88(m, 1H), 6.77(d, J = 7.6, 1H), 6.64(s, 1H), 6.50(d, J = 8.4, 1H), 6.41-6.37(m, 1H), 5.87(s, 1H), 5.03-5.00(m, 1H), 4.28-4.14(m, 2H), 3.43-3.30(m, 2H), 3.32-3.28(m, 1H), 3.19-3.18(m, 1H), 2.97(s, 3H), 2.51-2.41(m, 2H), 2.09-2.05(m, 2H). | 376 |
| Example 104 | 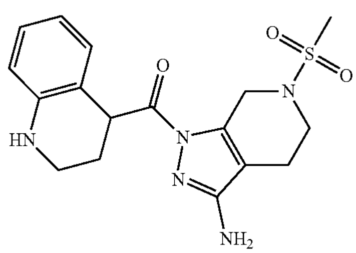 [SMILES: CS(=O)(=O)N1CCc2c(N)nn(C(=O)C3CCNc4ccccc43)c2C1] | (3-amino-6-(methylsulfonyl)-4,5,6,7-tetrahydro-pyrazolo[3,4-c]pyridin-1-yl)(1,2,3,4-tetrahydro-quinolin-4-yl)methanone | (DMSO-d₆, 400 MHz, ppm): δ 6.91-6.87(m, 1H), 6.78(d, J = 7.6, 1H), 6.49(d, J = 8.0, 1H), 6.40-6.36(m, 1H), 5.84(s, 1H), 5.79(s, 2H), 4.93-4.90(m, 1H), 4.58-4.48(m, 2H), 3.46-3.36(m, 2H), 3.29-3.28(m, 1H), 3.17-3.13(m, 1H), 2.96(s, 3H), 2.49-2.47(m, 2H), 2.05-1.94(m, 2H). | 376 |
| Example 105 | 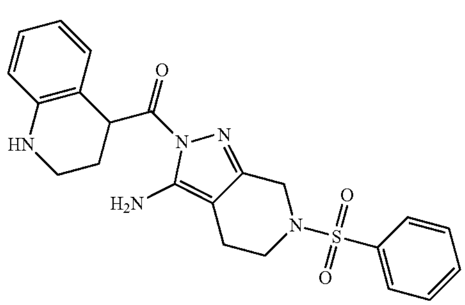 [SMILES: Nc1c2c(nn1C(=O)C1CCNc3ccccc31)CN(S(=O)(=O)c1ccccc1)CC2] | (3-amino-6-(phenylsulfonyl)-4,5,6,7-tetrahydro-pyrazolo[3,4-c]pyridin-2-yl)(1,2,3,4-tetrahydro-quinolin-4-yl)methanone | (DMSO-d₆, 400 MHz, ppm): δ 7.85-7.83(m, 2H), 7.73-7.71(m, 1H), 7.70-7.62(m, 2H), 6.92-6.88(m, 1H), 6.75(d, J = 7.2 Hz, 1H), 6.56(s, 2H), 6.51-6.49(m, 1H), 6.40-6.37(m, 1H), 5.85(s, 1H), 4.99-4.96(m, 1H), 4.13-4.08(m, 2H), 3.32(s, 2H), 3.31-3.18(m, 2H), 2.39-2.33(m, 2H), 2.06-1.96(m, 2H). | 438 |

TABLE 1-continued

List of the examples

| Example | Structure | Name | ¹HNMR | (ES, m/z) [M + H]⁺ |
|---|---|---|---|---|
| Example 106 | 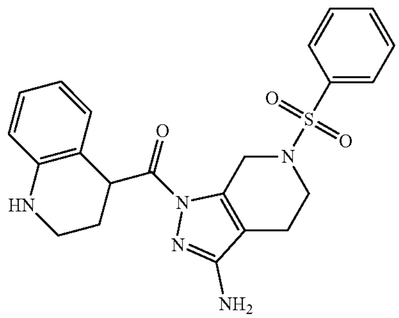 [SMILES: Nc1nn(C(=O)C2CCNc3ccccc32)c2c1CCN(S(=O)(=O)c1ccccc1)C2] | (3-amino-6-(phenylsulfonyl)-4,5,6,7-tetrahydro-pyrazolo[3,4-c]pyridin-1-yl)(1,2,3,4-tetrahydro-quinolin-4-yl)methanone | (DMSO-d₆, 400 MHz, ppm): δ 7.77(d, J = 7.2 Hz, 2H), 7.76-7.67(m, 1H), 7.63-7.60(m, 2H), 6.89-6.87(m, 1H), 6.74(d, J = 7.2 Hz, 1H), 6.49(d, J = 8.0 Hz, 1H), 6.40-6.36(m, 1H), 5.83(s, 1H), 5.72(s, 2H), 4.87-4.86(m, 1H), 4.42-4.38(m, 2H), 3.39-3.28(m, 3H), 3.16(s, 1H), 2.38(s, 2H), 2.10-1.93(m, 2H). | 438 |
| Example 107 | 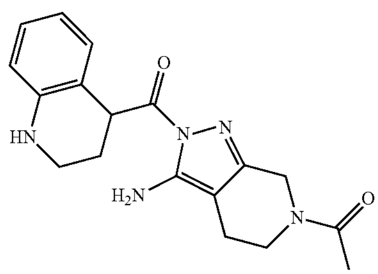 [SMILES: CC(=O)N1CCc2c(nn(C(=O)C3CCNc4ccccc43)c2N)C1] | 1-(3-amino-2-(1,2,3,4-tetrahydro-quinoline-4-carbonyl)-4,5-dihydro-2H-pyrazolo[3,4-c]pyridin-6(7H)-yl)ethanone | (DMSO-d₆, 400 MHz, ppm): δ 6.92-6.88(m, 1H), 6.78-6.75(m, 1H), 6.59(s, 2H), 6.53-6.50(m, 1H), 6.40-6.37(m, 1H), 5.85(s, 1H), 5.03-5.00(m, 1H), 4.53-4.44(m, 2H), 3.67-3.63(m, 2H), 3.32-3.25(m, 1H), 3.19(s, 1H), 2.51-2.50(m, 1H), 2.10-2.07(m, 1H), 2.06-1.93(m, 5H). | 340 |
| Example 108 | 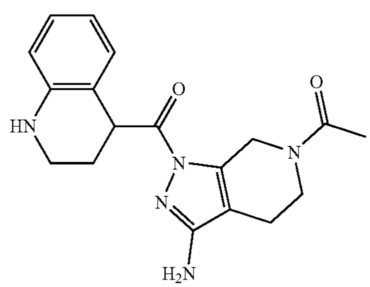 [SMILES: CC(=O)N1CCc2c(N)nn(C(=O)C3CCNc4ccccc43)c2C1] | 1-(3-amino-1-(1,2,3,4-tetrahydro-quinoline-4-carbonyl)-4,5-dihydro-1H-pyrazolo[3,4-c]pyridin-6(7H)-yl)ethanone | (DMSO-d₆, 400 MHz, ppm): δ 6.91-6.88(m, 1H), 6.87-6.79(m, 1H), 6.49(d, J = 8.4 Hz, 1H), 6.40-6.36(m, 1H), 5.83(s, 1H), 5.76(s, 2H), 4.93-4.91(m, 1H), 4.78-4.64(m, 2H), 3.70-3.61(m, 2H), 3.32(s, 1H), 3.17(s, 1H), 2.51-2.50(m, 1H), 2.49(s, 1H), 2.09-2.04(m, 5H). | 340 |
| Example 109 | 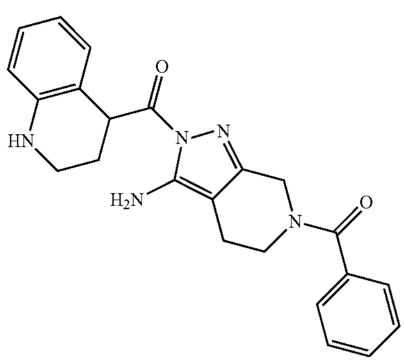 [SMILES: Nc1c2c(nn1C(=O)C1CCNc3ccccc31)CN(C(=O)c1ccccc1)CC2] | (3-amino-2-(1,2,3,4-tetrahydro-quinoline-4-carbonyl)-4,5-dihydro-2H-pyrazolo[3,4-c]pyridin-6(7H)-yl)(phenyl)-methanone | (DMSO-d₆, 400 MHz, ppm): δ 7.50-7.43(m, 5H), 6.92-6.89(m, 1H), 6.77(s, 1H), 6.61(s, 2H), 6.50(d, J = 7.6 Hz, 1H), 6.39(s, 1H), 5.85(s, 1H), 5.03-4.90(s, 1H), 4.65(s, 1H), 4.43(s, 1H), 3.87(s, 1H), 3.85(s, 1H), 3.32(s, 1H), 3.28-3 20(m; 1H), 2.50-2.49(m, 2H), 2.04(s, 2H). | 402 |
| Example 110 | 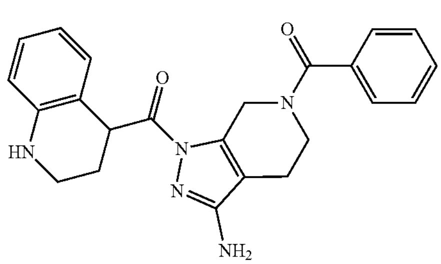 [SMILES: Nc1nn(C(=O)C2CCNc3ccccc32)c2c1CCN(C(=O)c1ccccc1)C2] | (3-amino-1-(1,2,3,4-tetrahydro-quinoline-4-carbonyl)-4,5-dihydro-1H-pyrazolo[3,4-c]pyridin-6(7H)-yl)(phenyl)-methanone | (DMSO-d₆, 400 MHz, ppm): δ 7.47-7.44 (m, 5H), 6.90-6.70(m, 2H), 6.52-6.39(m, 2H), 5.84-5.77(m, 3H), 4.95-4.69(m, 3H), 3.84-3.49(m, 2H), 3.16(s, 2H), 2.49-2.32(m, 2H), 2.09-1.90(m, 2H). | 402 |

TABLE 1-continued

List of the examples

| Example | Structure | Name | ¹HNMR | (ES, m/z) [M + H]⁺ |
|---|---|---|---|---|
| Example 111 | 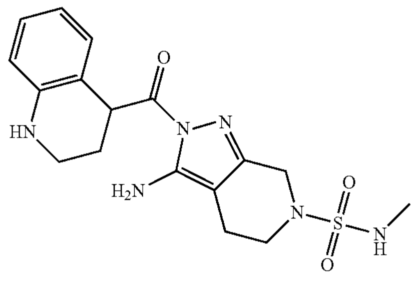 [SMILES: CNS(=O)(=O)N1CCc2c(nn(C(=O)C3CCNc4ccccc43)c2N)C1] | 3-amino-N-methyl-2-(1,2,3,4-tetrahydro-quinoline-4-carbonyl)-4,5-dihydro-2H-pyrazolo[3,4-c]pyridine-6(7H)-sulfonamide | (DMSO-d₆, 400 MHz, ppm): δ 7.28-7.24(m, 1H), 6.92-6.88(m, 1H), 6.76(d, J = 7.2, 1H), 6.60(s, 2H), 6.50(d, J = 8.0, 1H), 6.40-6.37(m, 1H), 5.86(s, 1H), 5.02-4.99(m, 1H), 4.16(s, 2H), 3.41-3.37(m, 2H), 3.32-3.28(m, 1H), 3.19-3.16(m, 1H), 2.49(s, 3H), 2.47-2.42(m, 2H), 2.09-2.01(m, 2H). | 391 |
| Example 112 | 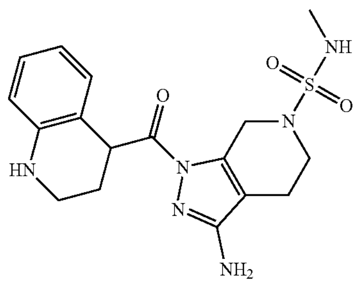 [SMILES: CNS(=O)(=O)N1CCc2c(N)nn(C(=O)C3CCNc4ccccc43)c2C1] | 3-amino-N-methyl-1-(1,2,3,4-tetrahydro-quinoline-4-carbonyl)-4,5-dihydro-1H-pyrazolo[3,4-c]pyridine-6(7H)-sulfonamide | (DMSO-d₆, 400 MHz, ppm): δ 7.28-7.25(m, 1H), 6.91-6.87(m, 1H), 6.78(d, J = 7.2, 1H), 6.49(d, J = 8.0, 1H), 6.40-6.36(m, 1H), 5.83(s, 1H), 5.77(s, 2H), 4.93-4.90(m, 1H), 4.45(s, 2H), 3.41-3.38(m, 2H), 3.32-3.29(m, 1H), 3.18-3.14(m, 1H), 2.51(s, 3H), 2.49-2.43(m, 2H), 2.08-1.96(m, 2H) | 391 |
| Example 113 | 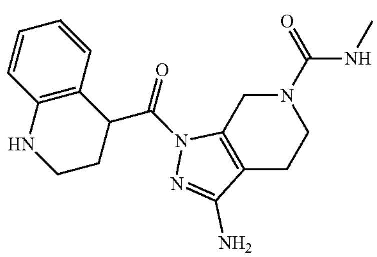 [SMILES: CNC(=O)N1CCc2c(N)nn(C(=O)C3CCNc4ccccc43)c2C1] | 3-amino-N-methyl-1-(1,2,3,4-tetrahydro-quinoline-4-carbonyl)-4,5-dihydro-1H-pyrazolo[3,4-c]pyridine-6(7H)-carboxamide | (300 MHz, DMSO-d₆, ppm): δ 6.92-6.89(m, 1H), 6.87-6.76(m, 1H), 6.61-6.36(m, 3H), 5.85-5.69(m, 3H), 4.94-4.91(m, 1H), 4.60(s, 2H), 3.52-3.15(m, 4H), 2.57(s, 3H), 2.35-2.25(m, 2H), 2.03-1.95(m, 2H). | 355 |
| Example 114 | 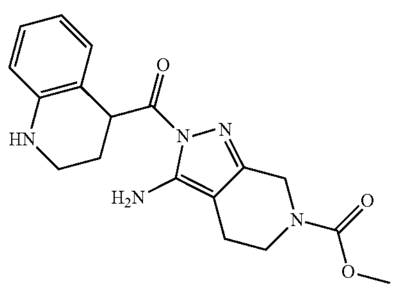 [SMILES: COC(=O)N1CCc2c(nn(C(=O)C3CCNc4ccccc43)c2N)C1] | methyl 3-amino-2-(1,2,3,4-tetrahydro-quinoline-4-carbonyl)-4,5-dihydro-2H-pyrazolo[3,4-c]pyridine-6(7H)-carboxylate | (DMSO-d₆, 400 MHz, ppm): δ 6.97-6.93(m, 1H), 6.77(d, J = 7.2 Hz, 1H), 6.52(d, J = 8.0 Hz, 3H), 6.43-6.39(m, 1H), 6.28-5.2(m, 1H), 5.00-4.98(m, 1H), 4.43(s, 2H), 3.64(s, 3H), 3.58(s, 2H), 3.52-3.12(m, 2H), 2.38-2.32(m, 2H), 2.06(s, 2H). | 356 |
| Example 115 | 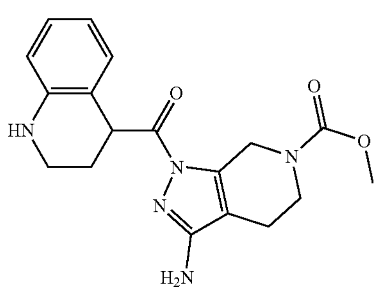 [SMILES: COC(=O)N1CCc2c(N)nn(C(=O)C3CCNc4ccccc43)c2C1] | methyl 3-amino-1-(1,2,3,4-tetrahydro-quinoline-4-carbonyl)-4,5-dihydro-1H-pyrazolo[3,4-c]pyridine-6(7H)-carboxylate | (DMSO-d₆, 400 MHz, ppm): δ 6.92(m, 1H), 6.88(d, J = 1.2 Hz, 1H), 6.49(d, J = 3.2 Hz, 1H), 6.49-6.41 (m, 1H), 5.82-5.74(m, 3H), 4.93-4.91(m, 1H), 4.72(s, 2H), 3.63-3.60(m, 5H), 3.30(s, 1H), 3.27(s, 1H), 2.38(s, 2H), 2.07-1.90(m, 2H). | 356 |

TABLE 1-continued

List of the examples

| Example | Structure | Name | ¹HNMR | (ES, m/z) [M + H]⁺ |
|---|---|---|---|---|
| Example 116 | 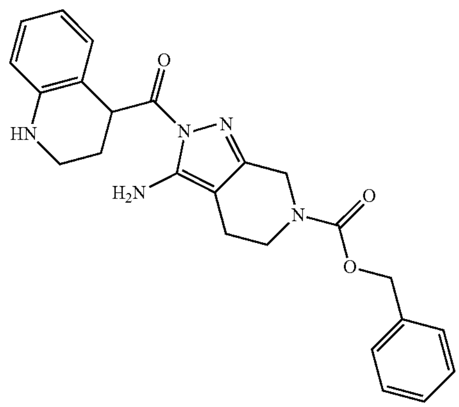 [SMILES: Nc1c2c(nn1C(=O)C1CCNc3ccccc31)CN(C(=O)OCc1ccccc1)CC2] | benzyl 3-amino-2-(1,2,3,4-tetrahydro-quinoline-4-carbonyl)-4,5-dihydro-2H-pyrazolo[3,4-c]pyridine-6(7H)-carboxylate | (DMSO-d$_6$, 400 MHz, ppm): δ 7.39-7.33(m, 5H), 6.90-6.89(m, 1H), 6.75(d, J = 7.6 Hz, 1H), 6.59(s, 2H), 6.5(d, J = 1.2 Hz, 1H), 6.40-6.38(m, 1H), 5.85(s, 1H), 5.12(s, 2H), 5.00(s, 1H), 4.46(s, 2H), 3.63(s, 2H), 3.32-3.30(m, 2H), 2.39-2.37(m, 2H), 2.01(s, 2H). | 432 |
| Example 117 | 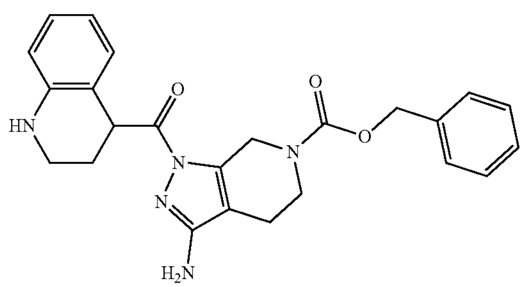 [SMILES: Nc1nn(C(=O)C2CCNc3ccccc32)c2c1CCN(C(=O)OCc1ccccc1)C2] | benzyl 3-amino-1-(1,2,3,4-tetrahydro-quinoline-4-carbonyl)-4,5-dihydro-1H-pyrazolo[3,4-c]pyridine-6(7H)-carboxylate | (DMSO-d$_6$, 400 MHz, ppm): δ 7.37(s, 5H), 6.92-6.90(m, 1H), 6.76(d, J = 3.2, 1H), 6.49(d, J = 3.6 Hz, 1H), 6.39-3.36(m, 1H), 5.82-5.75(m, 3H), 5.12(s, 2H), 4.90(s, 1H), 4.71(s, 2H), 3.62(s, 2H), 3.33(s, 1H), 3.27(s, 1H), 2.51-2.33(m, 2H), 2.08-1.98(m, 2H). | 432 |
| Example 118 | 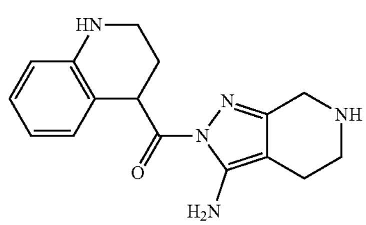 [SMILES: Nc1c2c(nn1C(=O)C1CCNc3ccccc31)CNCC2] | (3-amino-4,5,6,7-tetrahydro-pyrazolo[3,4-c]pyridin-2-yl)(1,2,3,4-tetrahydro-quinolin-4-yl)methanone | (DMSO-d$_6$, 400 MHz, ppm): δ 6.95-6.88(m, 1H), 6.76-6.75(m, 1H), 6.52-6.50(m, 3H), 6.46-6.37(m, 1H), 5.85(s, 2H), 5.03-5.00(m, 1H), 3.83(s, 2H), 3.29-3.25(m, 1H), 3.20-3.11(m, 1H), 2.99-2.93(m, 2H), 2.36-2.33(m, 2H), 2.07-1.96(m, 2H). | 298 |
| Example 119 | 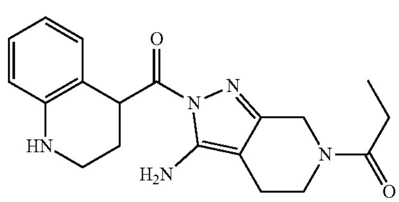 [SMILES: CCC(=O)N1CCc2c(nn(C(=O)C3CCNc4ccccc43)c2N)C1] | 1-(3-amino-2-(1,2,3,4-tetrahydro-quinoline-4-carbonyl)-4,5-dihydro-2H-pyrazolo[3,4-c]pyridin-6(7H)-yl)propan-1-one | (DMSO-d$_6$, 400 MHz, ppm): δ 6.92-6.89(m, 1H), 6.8-6.7(m, 1H), 6.58-6.37(m, 3H), 6.36-3.30(m, 1H), 5.86(s, 1H), 5.00(s, 1H), 3.68(s, 2H), 3.39-3.20(m, 2H), 2.50-2.41(m, 4H), 2.00(s, 2H), 1.04-0.97(m, 3H). | 354 |
| Example 120 | 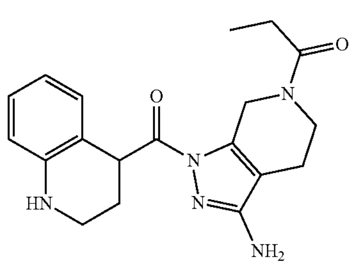 [SMILES: CCC(=O)N1CCc2c(N)nn(C(=O)C3CCNc4ccccc43)c2C1] | 1-(3-amino-1-(1,2,3,4-tetrahydro-quinoline-4-carbonyl)-4,5-dihydro-1H-pyrazolo[3,4-c]pyridin-6(7H)-yl)propan-1-one | (DMSO-d$_6$, 400 MHz, ppm): δ 6.91-6.87(m, 1H), 6.81-6.77(m, 1H), 6.51-6.40(m, 1H), 6.40-6.36(m, 1H), 5.83-5.74(m, 3H), 4.93(s, 1H), 4.92-4.66(m, 2H), 3.70-3.61(m, 2H), 3.30(s, 1H), 3.17-3.14(m, 1H), 2.51-3.49(m, 4H), 2.02(d, J = 3.6 Hz, 2H), 1.02-0.98(m, 3H). | 354 |

TABLE 1-continued

List of the examples

| Example | Structure | Name | ¹HNMR | (ES, m/z) [M + H]⁺ |
|---|---|---|---|---|
| Example 121 | 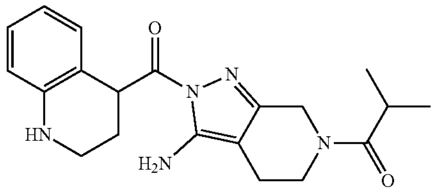 [SMILES: CC(C)C(=O)N1CCc2c(nn(C(=O)C3CCNc4ccccc43)c2N)C1] | 1-(3-amino-2-(1,2,3,4-tetrahydro-quinoline-4-carbonyl)-4,5-dihydro-2H-pyrazolo[3,4-c]pyridin-6(7H)-yl)-2-methylpropan-1-one | (DMSO-d₆, 400 MHz, ppm): δ 6.92-6.88(m, 1H), 6.77(d, J = 7.2 Hz, 1H), 6.59(s, 2H), 6.54-6.49(m, 1H), 6.40-6.37(m, 1H), 5.85(s, 1H), 5.03-5.00(m, 1H), 4.58-4.51(m, 2H), 3.71-3.68(m, 2H), 3.31-3.18(m, 2H), 3.01-3.00(m, 1H), 2.50(s, 1H), 2.33(s, 1H), 2.08-1.96(m, 2H), 1.04-0.98 (m, 6H). | 368 |
| Example 122 | 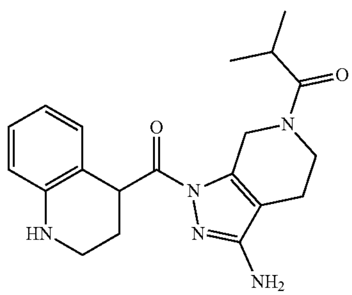 [SMILES: CC(C)C(=O)N1CCc2c(N)nn(C(=O)C3CCNc4ccccc43)c2C1] | 1-(3-amino-1-(1,2,3,4-tetrahydro-quinoline-4-carbonyl)-4,5-dihydro-1H-pyrazolo[3,4-c]pyridin-6(7H)-yl)-2-methylpropan-1-one | (DMSO-d₆, 400 MHz, ppm): δ 6.91-6.87(m, 1H), 6.78 (d, J = 13.6 Hz, 1H), 6.50(d, J = 8.0 Hz, 1H), 6.49-6.36(m, 1H), 5.83(s, 1H), 5.75(s, 2H), 4.93-4.90(m, 1H), 4.80-4.64(m, 2H), 3.71-3.68(m, 2H), 3.36-3.27(m, 1H), 3.16(d, J = 12.4 Hz, 1H), 3.00-2.83(m, 1H), 2.42(s, 1H), 2.32(s, 1H), 2.08-1.95(m, 2H), 1.02 (d, J = 6.4 Hz, 4H), 0.99-0.96(m, 2H). | 368 |
| Example 123 | 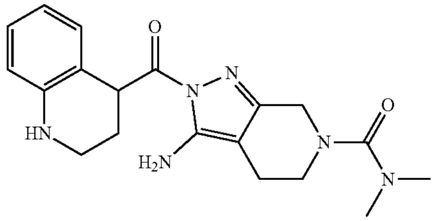 [SMILES: CN(C)C(=O)N1CCc2c(nn(C(=O)C3CCNc4ccccc43)c2N)C1] | 3-amino-N,N-dimethyl-2-(1,2,3,4-tetrahydro-quinoline-4-carbonyl)-4,5-dihydro-2H-pyrazolo[3,4-c]pyridine-6(7H)-carboxamide | (DMSO-d₆, 400 MHz, ppm): δ 6.92-6.88(m, 1H), 6.76(d, J = 7.2, 1H), 6.53-6.49(m, 3H), 6.40-6.37(m, 1H), 5.84(s, 1H), 5.02-4.99(m, 1H), 4.15(s, 2H), 3.36-3.34(m, 2H), 3.29-3.25(m, 1H), 3.19-3.16(m, 1H), 2.78(s, 6H), 2.42-2.39(m, 2H), 2.08-2.00(m, 2H). | 369 |
| Example 124 | 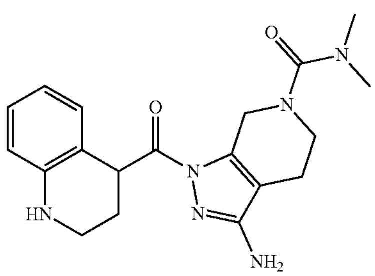 [SMILES: CN(C)C(=O)N1CCc2c(N)nn(C(=O)C3CCNc4ccccc43)c2C1] | 3-amino-N,N-dimethyl-1-(1,2,3,4-tetrahydro-quinoline-4-carbonyl)-4,5-dihydro-1H-pyrazolo[3,4-c]pyridine-6(7H)-carboxamide | (DMSO-d₆, 400 MHz, ppm): δ 6.91-6.87(m, 1H), 6.76(d, J = 7.6, 1H), 6.49(d, J = 8.0. 1H), 6.39-6.36(m, 1H), 5.83(s, 1H), 5.71(s, 2H), 4.93-4.90(m, 1H), 4.43(s, 2H), 3.34-3.33(m, 2H), 3.28-3.27(m, 1H), 3.16-3.13(m, 1H), 2.74(s, 6H), 2.40-2.38(m, 2H), 2.07-1.94(m, 2H). | 369 |
| Example 125 | 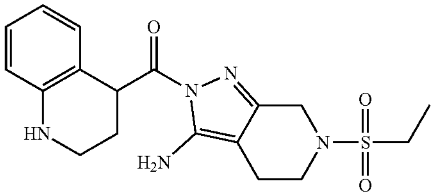 | (3-amino-6-(ethylsulfonyl)-4,5,6,7-tetrahydro-pyrazolo[3,4-c]pyridin-2-yl)(1,2,3,4-tetrahydro-quinolin-4-yl)methanone | (DMSO-d₆, 400 MHz, ppm): δ 6.95-6.89(m,, 1H), 6.78-6.76(m, 1H), 6.62(s, 2H), 6.52-6.50(m, 1H), 6.39-6.36(m, 1H), 5.86(s, 1H), 5.01-4.98(m, 1H), 4.29(s, 2H), 3.50-3.47(m, 2H), 3.28-3.27(m, 1H), 3.16-3.12(m, 3H), 2.46-2.43(m, 2H), 2.08-2.01(m, 2H), 1.23-1.20(m, 3H). | 390 |
| Example 126 | 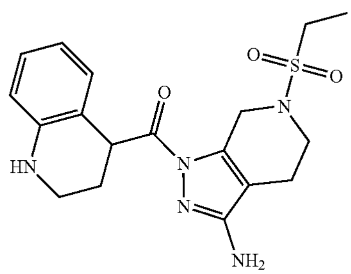 [SMILES: CCS(=O)(=O)N1CCc2c(N)nn(C(=O)C3CCNc4ccccc43)c2C1] | (3-amino-6-(ethylsulfonyl)-4,5,6,7-tetrahydro-pyrazolo[3,4-c]pyridin-1-yl)(1,2,3,4-tetrahydro-quinolin-4-yl)methanone | (DMSO-d₆, 400 MHz, ppm): δ 6.91-6.87(m, 1H), 6.79-6.77(m, 1H), 6.51-6.49(m, 1H), 6.40-6.36(m, 1H), 5.83(s, 1H), 5.78(s, 2H), 4.93-4.90(m, 1H), 4.57(s, 2H), 3.48-3.43(m, 2H), 3.18-3.10(m, 4H), 2.49-2.44(m, 2H), 2.02-1.98(m, 2H), 1.21-1.18(m, 3H). | 390 |

TABLE 1-continued

List of the examples

| Example | Structure | Name | ¹HNMR | (ES, m/z) [M + H]⁺ |
|---|---|---|---|---|
| Example 127 | 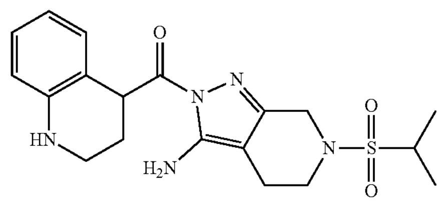 | (3-amino-6-(isopropyl-sulfonyl)-4,5,6,7-tetrahydro-pyrazolo[3,4-c]pyridin-2-yl)(1,2,3,4-tetrahydro-quinolin-4-yl)methanone | (DMSO-d₆, 400 MHz, ppm): δ 6.94-6.90(m, 1H), 6.77-6.76(m, 1H), 6.61(s, 2H), 6.52-6.50(m, 1H), 6.38-6.36(m, 1H), 5.85(s, 1H), 5.00-4.98(m, 1H), 4.33(s, 2H), 3.52-3.50(m, 2H), 3.28-3.27(m, 3H), 2.44-2.41 (m, 2H), 2.08-2.01(m, 2H), 1.25-1.23(m, 6H). | 404 |
| Example 128 | 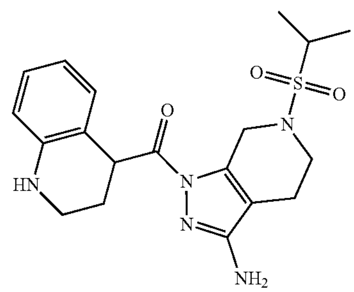 | (3-amino-6-(isopropyl-sulfonyl)-4,5,6,7-tetrahydro-pyrazolo[3,4-c]pyridin-1-yl)(1,2,3,4-tetrahydro-quinolin-4-yl)methanone | (DMSO-d₆, 400 MHz, ppm): δ 6.91-6.87(m, 1H), 6.78-6.76(m, 1H), 6.51-6.48(m, 1H), 6.40-6.36(m, 1H), 5.83(s, 1H), 5.78(s, 2H), 4.92-4.89(m, 1H), 4.61(s, 2H), 3.52-3.49(m, 2H), 3.47-3.38(m, 2H), 3.17-3.15(m, 1H), 2.44-2.42(m, 2H), 2.07-1.95(m, 2H), 1.22-1.20(m, 6H). | 404 |
| Example 129 | 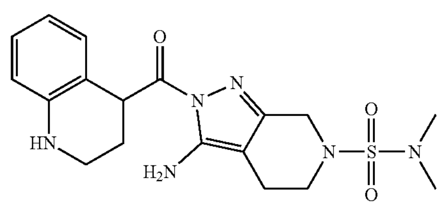 [SMILES: CC(C)S(=O)(=O)N1CCc2c(nn(C(=O)C3CCNc4ccccc43)c2N)C1] | 3-amino-N,N-dimethyl-2-(1,2,3,4-tetrahydro-quinoline-4-carbonyl)-4,5-dihydro-2H-pyrazolo[3,4-c]pyridine-6(7H)-sulfonamide | (DMSO-d₆, 400 MHz, ppm): δ 6.92-6.90(m, 1H), 6.88 (d, J = 1.2 Hz, 1H), 6.62(s, 2H), 6.50 (d, J = 8.4 Hz, 1H), 6.40-6.36(m, 1H), 5.86(s, 1H), 5.02-4.99(m, 1H), 4.25(s, 2H), 3.49-3.46(m, 2H), 3.30-3.20(m, 1H), 3.20-3.10(m, 1H), 2.77(s, 6H), 2.50-2.42(m, 2H), 2.07-2.03(m, 2H). | 404 |
| Example 130 | 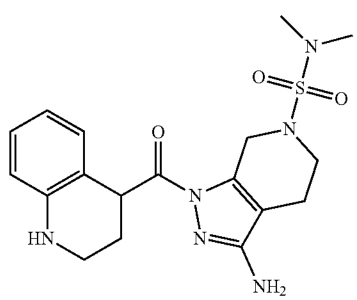 [SMILES: CN(C)S(=O)(=O)N1CCc2c(N)nn(C(=O)C3CCNc4ccccc43)c2C1] | 3-amino-N,N-dimethyl-1-(1,2,3,4-tetrahydro-quinoline-4-carbonyl)-4,5-dihydro-1H-pyrazolo[3,4-c]pyridine-6(7H)-sulfonamide | (DMSO-d₆, 400 MHz, ppm): δ 6.91-6.87(m, 1H), 6.78(d, J = 7.6 Hz, 1H), 6.49(d, J = 8.0 Hz, 1H), 6.40-6.36(m, 1H), 5.81(d, J = 17.6 Hz, 3H), 4.92-4.89(m, 1H), 4.52(s, 2H), 3.48-3.45(m, 2H), 3.27(s, 1H), 3.16 (d, J = 11.2 Hz, 1H), 2.73 (s, 6H), 2.42(s, 2H), 2.03-1.96(m, 2H). | 404 |
| Example 131 | 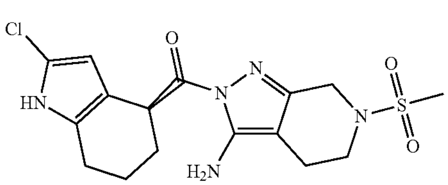 [SMILES: CS(=O)(=O)N1CCc2c(nn(C(=O)[C@H]3CCCc4[nH]c(Cl)cc43)c2N)C1] | (S*)-(3-amino-6-(methylsulfonyl)-4,5,6,7-tetrahydro-pyrazolo[3,4-c]pyridin-2-yl)(2-chloro-4,5,6,7-tetrahydro-1H-indol-4-yl)methanone | (DMSO-d₆, 400 MHz, ppm): δ 11.08(s, 1H), 6.57(s, 2H), 5.55(s, 1H), 4.70-4.68(m, 1H), 4.27(s, 2H), 3.43-3.36(m, 2H), 2.97(s, 3H), 2.47-2.43(m, 4H), 1.97-1.84(m, 3H), 1.72-1.66(m, 1H). | 398 |

TABLE 1-continued

List of the examples

| Example | Structure | Name | ¹HNMR | (ES, m/z) [M + H]⁺ |
|---|---|---|---|---|
| Example 132 | 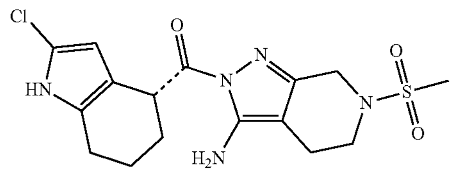 | (R*)-(3-amino-6-(methylsulfonyl)-4,5,6,7-tetrahydro-pyrazolo[3,4-c]pyridin-2-yl)(2-chloro-4,5,6,7-tetrahydro-1H-indol-4-yl)methanone | (DMSO-d₆, 400 MHz, ppm): δ 11.08(s, 1H), 6.58(s, 2H), 5.55(s, 1H), 4.71-4.68(m, 1H), 4.27(s, 2H), 3.44-3.41(m, 2H), 2.95(s, 3H), 2.47-2.41(m, 4H), 1.97-1.84(m, 3H), 1.72-1.66(m, 1H). | 398 |
| Example 133 | 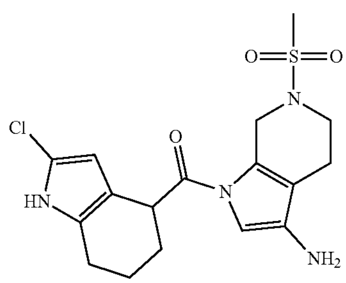 [SMILES: CS(=O)(=O)N1CCc2c(N)cn(C(=O)C3CCCc4[nH]c(Cl)cc43)c2C1] | (3-amino-6-(methylsulfonyl)-4,5,6,7-tetrahydro-pyrazolo[3,4-c]pyridin-1-yl)(2-chloro-4,5,6,7-tetrahydro-1H-indol-4-yl)methanone | (DMSO-d₆, 300 MHz, ppm): δ 11.03(s, 1H), 5.68(s, 1H), 5.57(s, 2H), 4.58-4.43(m, 3H), 3.41-3.39(m, 2H), 2.94(s, 3H), 2.48-2.45(m, 4H), 1.96-1.65(m, 4H). | 398 |
| Example 134 | 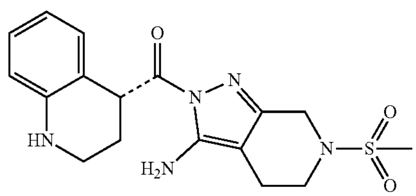 [SMILES: CS(=O)(=O)N1CCc2c(nn(C(=O)[C@@H]3CCNc4ccccc43)c2N)C1] | (R*)-(3-amino-6-(methylsulfonyl)-4,5,6,7-tetrahydro-pyrazolo[3,4-c]pyridin-2-yl)(1,2,3,4-tetrahydro-quinolin-4-yl)methanone | (DMSO-d₆, 400 MHz, ppm): δ 6.93-6.89(m, 1H), 6.77(d, J = 7.2, 1H), 6.64(s, 2H), 6.51(d, J = 8.0, 1H), 6.41-6.39(m, 1H), 5.87(s, 1H), 5.02-4.99(m, 1H), 4.24(s, 2H), 3.42-3.40(m, 2H), 3.33-3.25(m, 1H), 3.20-3.16(m, 1H), 2.97(s, 3H), 2.49-2.45(m, 2H), 2.09-1.99(m, 2H). | 372 |
| Example 135 | 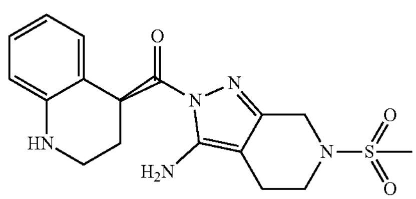 [SMILES: CS(=O)(=O)N1CCc2c(nn(C(=O)[C@H]3CCNc4ccccc43)c2N)C1] | (S*)-(3-amino-6-(methylsulfonyl)-4,5,6,7-tetrahydro-pyrazolo[3,4-c]pyridin-2-yl)(1,2,3,4-tetrahydro-quinolin-4-yl)methanone | (DMSO-d₆, 400 MHz, ppm): δ 6.92-6.88(m, 1H), 6.77(d, J = 7.2, 1H), 6.64(s, 2H), 6.51(d, J = 8.0, 1H), 6.41-6.38(m, 1H), 5.89(s, 1H), 5.03-4.99(m, 1H), 4.23(s, 2H), 3.43-3.40(m, 2H), 3.32-3.26(m, 1H), 3.21-3.15(m, 1H), 2.97(s, 3H), 2.48-2.45(m, 2H), 2.09-2.02(m, 2H). | 372 |
| Example 136 | 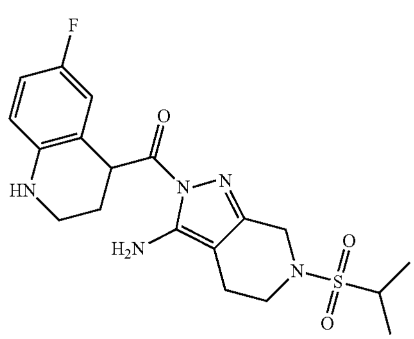 [SMILES: CC(C)S(=O)(=O)N1CCc2c(nn(C(=O)C3CCNc4ccc(F)cc43)c2N)C1] | (3-amino-6-(isopropyl-sulfonyl)-4,5,6,7-tetrahydro-pyrazolo[3,4-c]pyridin-2-yl)(6-fluoro-1,2,3,4-tetrahydro-quinolin-4-yl)methanone | (DMSO-d₆, 400 MHz, ppm): δ 6.82-6.75(m, 1H), 6.69-6.61(m, 3H), 6.53-6.49(m, 1H), 5.79(s, 1H), 4.99-4.95(m, 1H), 4.34(s, 2H), 3.55-3.51(m, 2H), 3.46-3.37(m, 1H), 3.23-3.18(m, 2H), 2.44-2.41(m, 2H), 2.11-1.99(m, 2H), 1.25(s, 3H), 1.22(s, 3H). | 422 |

TABLE 1-continued

List of the examples

| Example | Structure | Name | ¹HNMR | (ES, m/z) [M + H]⁺ |
|---|---|---|---|---|
| Example 137 | 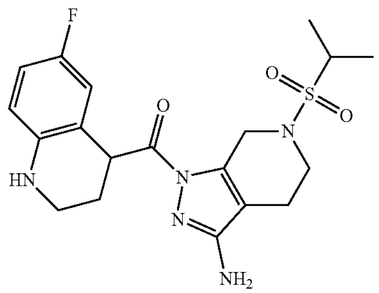 [SMILES: CC(C)S(=O)(=O)N1CCc2c(N)nn(C(=O)C3CCNc4ccc(F)cc43)c2C1] | (3-amino-6-(isopropyl-sulfonyl)-4,5,6,7-tetrahydro-pyrazolo[3,4-c]pyridin-1-yl)(6-fluoro-1,2,3,4-tetrahydro-quinolin-4-yl)methanone | (DMSO-d₆, 300 MHz, ppm): δ 6.81-6.74(m, 1H), 6.69-6.65(m, 1H), 652-6.47(m, 1H), 5.80(s, 2H), 5.77(s, 1H), 4.89-4.86(m, 1H), 4.61(s, 2H), 3.51-3.44(m, 2H), 3.41-3.35(m, 1H), 3.26-3.24(m, 1H), 3.16-3.12(m, 1H), 2.49-2.42(m, 2H), 2.04-1.95(m, 2H), 1.23(s, 3H), 1.21 (s, 3H). | 422 |
| Example 138 | 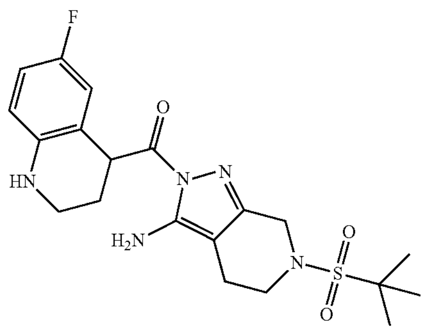 [SMILES: CC(C)(C)S(=O)(=O)N1CCc2c(nn(C(=O)C3CCNc4ccc(F)cc43)c2N)C1] | (3-amino-6-(tert-butylsulfonyl)-4,5,6,7-tetrahydro-pyrazolo[3,4-c]pyridin-2-yl)(6-fluoro-1,2,3,4-tetrahydro-quinolin-4-yl)methanone | (DMSO-d₆, 300 MHz, ppm): δ 6.81-6.75(m, 1H), 6.69-6.65(m, 1H), 6.61(s, 2H), 6.53-6.48(m, 1H), 5.79(s, 1H), 4.98-4.95(m, 1H), 4.39(s, 2H), 3.58-3.56(m, 2H), 3.23-3.15(m, 2H), 2.44-2.39(m, 2H), 2.06-1.99(m, 2H), 1.32(s, 9H). | 436 |
| Example 139 | 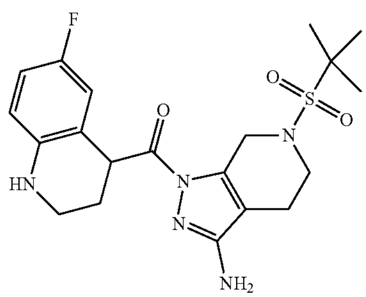 [SMILES: CC(C)(C)S(=O)(=O)N1CCc2c(N)nn(C(=O)C3CCNc4ccc(F)cc43)c2C1] | (3-amino-6-(tert-butylsulfonyl)-4,5,6,7-tetrahydro-pyrazolo[3,4-c]pyridin-1-yl)(6-fluoro-1,2,3,4-tetrahydro-quinolin-4-yl)methanone | (DMSO-d₆, 300 MHz, ppm): δ 6.81-6.74(m, 1H), 6.69-6.65(m, 1H), 6.52-6.47(m, 1H), 5.80(s, 2H), 5.78(s, 1H), 4.89-4.85(m, 1H), 4.66(s, 2H), 3.56-3.54(m, 2H), 3.25-3.22(m, 1H), 3.20-3.15(m, 1H), 2.41-2.38(m, 2H), 2.07-1.96(m, 2H), 1.30(s, 9H). | 436 |
| Example 140 | 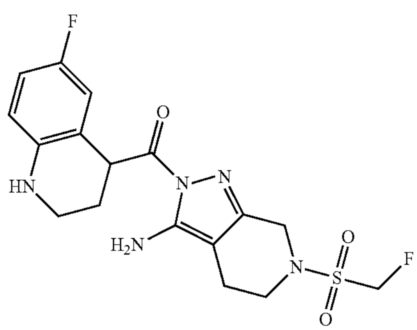 [SMILES: Nc1c2c(nn1C(=O)C1CCNc3ccc(F)cc31)CN(S(=O)(=O)CF)CC2] | (3-amino-6-(fluoromethyl-sulfonyl)-4,5,6,7-tetrahydro-pyrazolo[3,4-c]pyridin-2-yl)(6-fluoro-1,2,3,4-tetrahydro-quinolin-4-yl)methanone | (DMSO-d₆, 400 MHz, ppm): δ 6.81-6.76(m, 1H), 6.68-6.65(m, 3H), 6.53-6.49(m, 1H), 5.80(s, 1H), 5.64(s, 1H), 5.52(s, 1H), 4.98-4.96(m, 1H), 4.40(s, 2H), 3.60-3.57(m, 2H), 3.25-3.16(m, 2H), 2.49-2.44(m, 2H), 2.10-2.02(m, 2H). | 412 |
| Example 141 | 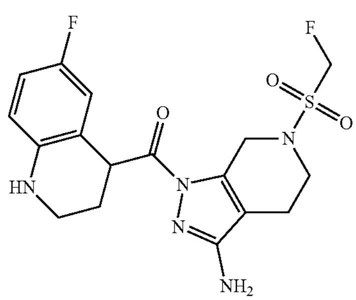 [SMILES: Nc1nn(C(=O)C2CCNc3ccc(F)cc32)c2c1CCN(S(=O)(=O)CF)C2] | (3-amino-6-(fluoromethyl-sulfonyl)-4,5,6,7-tetrahydro-pyrazolo(3,4-c]pyridin-1-yl)(6-fluoro-1,2,3,4-tetrahydro-quinolin-4-yl)methanone | (DMSO-d₆, 400 MHz, ppm): δ 6.80-6.75(m, 1H), 6.70-6.67(m, 1H), 6.52-6.48(m, 1H), 5.82-5.77(m, 3H), 5.62(s, 1H), 5.51(s, 1H), 4.89-4.86(m, 1H), 4.67(s, 2H), 3.58-3.56(m, 2H), 3.27-3.25(m, 1H), 3.15-3.13(m, 1H), 2.49-2.46(m, 2H), 2.06-1.96(m, 2H). | 412 |

TABLE 1-continued

List of the examples

| Example | Structure | Name | ¹HNMR | (ES, m/z) [M + H]⁺ |
|---------|-----------|------|-------|---------------------|
| Example 142 | 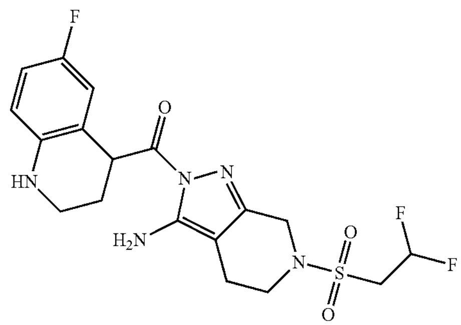 [SMILES: Nc1c2c(nn1C(=O)C1CCNc3ccc(F)cc31)CN(S(=O)(=O)CC(F)F)CC2] | (3-amino-6-(2,2-difluoroethyl-sulfonyl)-4,5,6,7-tetrahydro-pyrazolo[3,4-c]pyridin-2-yl)(6-fluoro-1,2,3,4-tetrahydro-quinolin-4-yl)methanone | (DMSO-$d_6$, 400 MHz, ppm): δ 6.81-6.75(m, 1H), 6.69-6.58(m, 3H), 6.53-6.39(m, 2H), 5.81(s, 1H), 4.99-4.95(m, 1H), 4.33 (s, 2H), 4.09-3.97(m, 2H), 3.52-3.48(m, 2H), 3.23-3.17(m, 2H), 2.46-2.44(m, 2H), 2.07-1.98(m, 2H). | 444 |
| Example 143 | 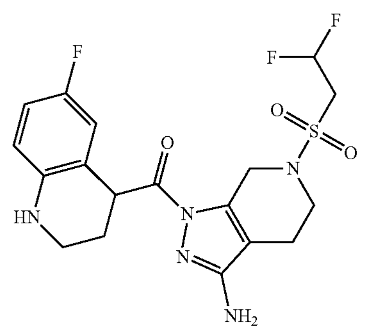 [SMILES: Nc1nn(C(=O)C2CCNc3ccc(F)cc32)c2c1CCN(S(=O)(=O)CC(F)F)C2] | (3-amino-6-(2,2-difluoroethyl-sulfonyl)-4,5,6,7-tetrahydro-pyrazolo[3,4-c]pyridin-1-yl)(6-fluoro-1,2,3,4-tetrahydro-quinolin-4-yl)methanone | (DMSO-$d_6$, 300 MHz, ppm): δ 6.81-6.74(m, 1H), 6.71-6.67(m, 1H), 6.55-6.54(m, 1H), 6.52-6.48(m, 1H), 5.83(s, 2H), 5.79(s, 1H), 4.90-4.86(m, 1H), 4.62(s, 2H), 4.07-3.96(m, 2H), 3.50-3.48(m, 2H), 3.27-3.22(m, 1H), 3.18-3.14(m, 1H), 2.46-2.43(m, 2H), 2.07-1.97(m, 2H). | 444 |
| Example 144 | 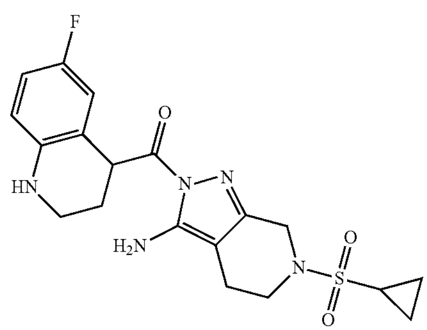 [SMILES: Nc1c2c(nn1C(=O)C1CCNc3ccc(F)cc31)CN(S(=O)(=O)C1CC1)CC2] | (3-amino-6-(cyclopropyl-sulfonyl)-4,5,6,7-tetrahydro-pyrazolo[3,4-c]pyridin-2-yl)(6-fluoro-1,2,3,4-tetrahydro-quinolin-4-yl)methanone | (DMSO-$d_6$, 300 MHz, ppm): δ 6.82-6.76(m, 1H), 6.69-6.66(m, 3H), 6.53-6.49(m, 1H), 5.81(s, 1H), 5.00-4.96(m, 1H), 4.30(s, 2H), 3.52-3.48(m, 2H), 3.24-3.17(m, 2H), 2.64-2.62(m, 1H), 2.54-2.52(m, 1H), 2.47-2.44(m, 1H), 2.08-2.00(m, 2H), 0.98-0.96(m, 4H). | 420 |
| Example 145 | 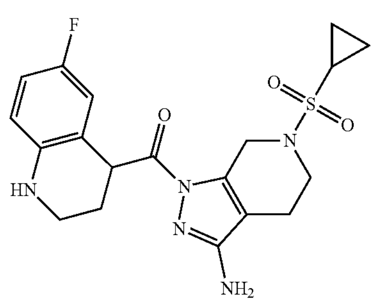 [SMILES: Nc1nn(C(=O)C2CCNc3ccc(F)cc32)c2c1CCN(S(=O)(=O)C1CC1)C2] | (3-amino-6-(cyclopropyl-sulfonyl)-4,5,6,7-tetrahydro-pyrazolo[3,4-c]pyridin-1-yl)(6-fluoro-1,2,3,4-tetrahydro-quinolin-4-yl)methanone | (DMSO-$d_6$, 300 MHz, ppm): δ 6.85-6.74(m, 1H), 6.70-6.66(m, 1H), 6.53-6.48(m, 1H), 5.82(s, 3H), 4.89-4.86(m, 1H), 4.59(s, 2H), 3.54-3.12(m, 5H), 2.67-2.63(m, 1H), 2.47-2.45(m, 1H), 2.07-1.97(m, 2H), 0.99-0.95(m, 4H). | 420 |

TABLE 1-continued

List of the examples

| Example | Name | ¹HNMR | (ES, m/z) [M + H]⁺ |
|---|---|---|---|
| Example 146 | (S*)-(3-amino-4,5,6,7-tetrahydro-pyrazolo[3,4-c]pyridin-2-yl)(6-fluoro-1,2,3,4-tetrahydro-quinolin-4-yl)methanone | (DMSO-d₆, 300 MHz, ppm): δ 6.81-6.74(m, 1H), 6.66-6.62(m, 1H), 6.53-6.48(m, 1H), 6.45(s, 2H), 5.79(s, 1H), 5.00-4.97(m, 1H), 3.88(s, 2H), 3.27-3.18(m, 2H), 2.92-2.83(m, 2H), 2.31-2.27(m, 2H), 2.09-1.91(m, 2H). | 316 |
| Example 147 | (R*)-(3-amino-4,5,6,7-tetrahydro-pyrazolo[3,4-c]pyridin-2-yl)(6-fluoro-1,2,3,4-tetrahydro-quinolin-4-yl)methanone | (DMSO-d₆, 300 MHz, ppm): δ 6.81-6.75(m, 1H), 6.66-6.62(m, 1H), 6.52-6.48(m, 1H), 6.43(s, 2H), 5.78(s, 1H), 5.00-4.97(m, 1H), 3.68(s, 2H), 3.24-3.14(m, 2H), 2.95-2.84(m, 2H), 2.30-2.26(m, 2H), 2.09-1.93(m, 2H). | 316 |
| Example 148 | (3-amino-4,5,6,7-tetrahydro-pyrazolo[3,4-c]pyridin-1-yl)(6-fluoro-1,2,3,4-tetrahydro-quinolin-4-yl)methanone | (DMSO-d₆, 300 MHz, ppm): δ 6.79-6.72(m, 1H), 6.66-6.62(m, 1H), 6.51-6.46(m, 1H), 5.75(s, 1H), 5.63(s, 2H), 4.91-4.87(m, 1H), 3.89(s, 2H), 3.29-3.26(m, 1H), 3.18-3.06(m, 1H), 2.88-2.79(m, 2H), 2.24-2.22(m, 2H), 2.06-1.92(m, 2H). | 316 |
| Example 149 | (3-amino-6-propyl-4,5,6,7-tetrahydro-pyrazolo[3,4-c]pyridin-2-yl)(6-fluoro-1,2,3,4-tetrahydro-quinolin-4-yl)methanone | (DMSO-d₆, 400 MHz, ppm): δ 6.82-6.77(m, 1H), 6.68-6.65(m, 1H), 6.53-6.47(m, 3H), 5.79(s, 1H), 5.00-4.97(m, 1H), 3.42-3.32(m, 2H), 3.27-3.22(m, 1H), 3.17-3.15(m, 1H), 2.63-2.60(m, 2H), 2.45-2.41(m, 2H), 2.37-2.34(m, 2H), 2.10-1.99(m, 2H), 1.55-1.48(m, 2H), 0.91-0.87(m, 3H). | 358 |
| Example 150 | (3-amino-6-propyl-4,5,6,7-tetrahydro-pyrazolo[3,4-c]pyridin-1-yl)(6-fluoro-1,2,3,4-tetrahydro-quinolin-4-yl)methanone | (DMSO-d₆, 400 MHz, ppm): δ 6.80-6.75(m, 1H), 6.68-6.65(m, 1H), 6.52-6.48(m, 1H), 5.76(s, 1H), 5.68(s, 2H), 4.90-4.88(m, 1H), 3.68-3.65(m, 2H), 3.27-3.25(m, 1H), 3.15-3.12(m, 1H), 2.65-2.62(m, 2H), 2.47-2.44(m, 2H), 2.34(s, 2H), 2.08-1.93(m, 2H), 1.53-1.44(m, 2H), 0.89-0.85(m, 3H). | 358 |

TABLE 1-continued

List of the examples

| Example | Name | ¹HNMR | (ES, m/z) [M + H]⁺ |
|---|---|---|---|
| Example 151 | Formic Acid salt of (3-amino-6-isopropyl-4,5,6,7-tetrahydro-pyrazolo[3,4-c]pyridin-2-yl)(6-fluoro-1,2,3,4-tetrahydro-quinolin-4-yl)methanone | (DMSO-d₆, 300 MHz, ppm): δ 6.82-6.75(m, 1H), 6.67-6.63(m, 1H), 6.53-6.45(m, 1H), 6.45(s, 2H), 5.78(s, 1H), 4.99-4.96(m, 1H), 3.55(s, 2H), 3.27-3.13(m, 2H), 2.98-2.90(m, 1H), 2.73-2.68(m, 2H), 2.35-2.32(m, 2H), 2.10-1.95(m, 2H), 1.06(s, 3H), 1.04(s, 3H). | 358 |
| Example 152 | Formic Acid salt of (3-amino-6-isopropyl-4,5,6,7-tetrahydro-pyrazolo[3,4-c]pyridin-1-yl)(6-fluoro-1,2,3,4-tetrahydro-quinolin-4-yl)methanone | (DMSO-d₆, 300 MHz, ppm): δ 6.80-6.73(m, 1H), 6.68-6.63(m, 1H), 6.52-6.47(m, 1H), 5.75(s, 1H), 5.68(s, 2H), 4.90-4.87(m, 1H), 3.80(s, 2H), 3.29-3.22(m, 1H), 3.15-3.11(m, 1H), 3.02-2.98(m, 1H), 2.75-2.71(m, 2H), 2.34-2.31(m, 2H), 2.07-1.91(m, 2H), 1.05(s, 3H), 1.03(s, 3H). | 328 |
| Example 153 | (3-amino-6-isobutyl-4,5,6,7-tetrahydro-pyrazolo[3,4-c]pyridin-2-yl)(6-fluoro-1,2,3,4-tetrahydro-quinolin-4-yl)methanone | (DMSO-d₆, 400 MHz, ppm): δ 6.82-6.77(m, 1H), 6.68-6.65(m, 1H), 6.53-6.47(m, 3H), 5.79(s, 1H), 4.99-4.87(m, 1H), 3.37-3.35(m, 2H), 3.28-3.24(m, 1H), 3.19-2.13(m, 1H), 2.61-2.57(m, 2H), 2.35-2.33(m, 2H), 2.24-2.22(m, 2H), 2.08-2.00(m, 2H), 1.88-1.82(m, 1H), 0.92(s, 3H), 0.89(s, 3H). | 372 |
| Example 154 | (3-amino-6-isobutyl-4,5,6,7-tetrahydro-pyrazolo[3,4-c]pyridin-1-yl)(6-fluoro-1,2,3,4-tetrahydro-quinolin-4-yl)methanone | (DMSO-d₆, 400 MHz, ppm): δ 6.78-6.77(m, 1H), 6.69-6.66(m, 1H), 6.52-6.48(m, 1H), 5.76(s, 1H), 5.68(s, 2H), 4.91-4.88(m, 1H), 3.66(s, 2H), 3.28-3.25(m, 1H), 3.15-3.10(m, 1H), 2.62-2.58(m, 2H), 2.34-3.33(m, 2H), 2.27-2.24(m, 2H), 2.08-1.92(m, 2H), 1.85-1.79(m, 1H), 0.88(s, 3H), 0.87(s, 3H). | 372 |
| Example 155 | (3-amino-6-(pyridin-4-ylsulfonyl)-4,5,6,7-tetrahydro-pyrazolo[3,4-c]pyridin-2-yl)(6-fluoro-1,2,3,4-tetrahydro-quinolin-4-yl)methanone | (300 MHz, DMSO-d₆, ppm): δ 8.88-8.86 (m, 2H), 7.81-7.79(m, 2H), 6.80-6.79(m, 1H), 6.68-6.64(m, 4H), 5.82(s, 1H), 4.92-4.94(m, 1H), 4.24(s, 2H), 3.45-3.43(m, 1H), 3.20-3.17(m, 3H), 2.50-2.41(m, 2H), 2.04-2.01(m, 2H). | 457 |

TABLE 1-continued

List of the examples

| Example | Structure | Name | ¹HNMR | (ES, m/z) [M + H]⁺ |
|---|---|---|---|---|
| Example 156 | 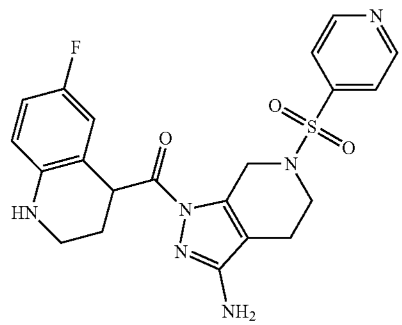 [SMILES: Nc1nn(C(=O)C2CCNc3ccc(F)cc32)c2c1CCN(S(=O)(=O)c1ccncc1)C2] | (3-amino-6-(pyridin-4-ylsulfonyl)-4,5,6,7-tetrahydro-pyrazolo[3,4-c]pyridin-1-yl)(6-fluoro-1,2,3,4-tetrahydro-quinolin-4-yl)methanone | (300 MHz, DMSO-d₆, ppm): δ 8.88-8.86(m, 2H), 7.76-7.74(m, 2H), 6.98-6.72(m, 3H), 4.88-4.86(m, 2H), 4.50-4.48(m, 4H), 3.39-3.52(m, 2H), 3.15-3.35(m, 2H), 2.41-2.38(m, 2H), 2.15-2.05(m, 2H). | 457 |
| Example 157 | 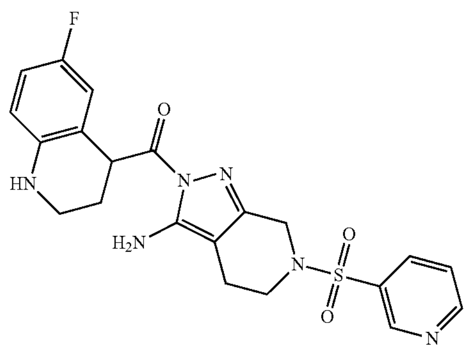 [SMILES: Nc1c2c(nn1C(=O)C1CCNc3ccc(F)cc31)CN(S(=O)(=O)c1cccnc1)CC2] | (3-amino-6-(pyridin-3-ylsulfonyl)-4,5,6,7-tetrahydro-pyrazolo[3,4-c]pyridin-2-yl)(6-fluoro-1,2,3,4-tetrahydro-quinolin-4-yl)methanone | (DMSO-d₆, 300 MHz, ppm): δ 9.01-8.99(m, 1H), 8.87-8.85(m, 1H), 8.27-8.24(m, 1H), 7.66-7.63(m, 1H), 6.81-6.76(m, 1H), 6.67-6.64(m, 1H), 6.59(s, 2H), 6.52-6.49(m, 1H), 5.81(s, 1H), 4.95-4.93(m, 1H), 4.23(s, 2H), 3.44-3.41(m, 2H), 3.21-3.16(m, 2H), 2.39-2.32(m, 2H), 2.06-2.00(m, 2H). | 457 |
| Example 158 | 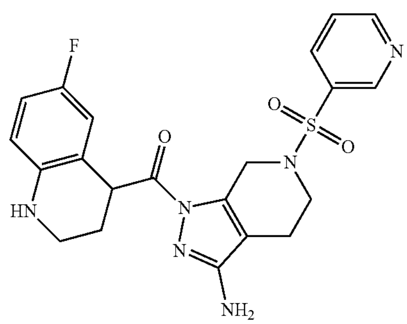 [SMILES: Nc1nn(C(=O)C2CCNc3ccc(F)cc32)c2c1CCN(S(=O)(=O)c1cccnc1)C2] | (3-amino-6-(pyridin-3-ylsulfonyl)-4,5,6,7-tetrahydro-pyrazolo[3,4-c]pyridin-1-yl)(6-fluoro-1,2,3,4-tetrahydro-quinolin-4-yl)methanone | (DMSO-d₆, 300 MHz, ppm): δ 8.94-8.93(m, 1H), 8.87-8.85(m, 1H), 8.21-8.17(m, 1H), 7.67-7.62(m, 1H), 6.81-6.74(m, 1H), 6.68-6.65(m, 1H), 6.52-6.47(m, 1H), 5.75(s, 3H), 4.85-4.81(m, 1H), 4.50(s, 2H), 3.52-3.41(m, 2H), 3.26-3.23(m, 1H), 3.15-3.14(m, 1H), 2.38-2.35(m, 2H), 2.07-1.95(m, 2H). | 457 |
| Example 159 | 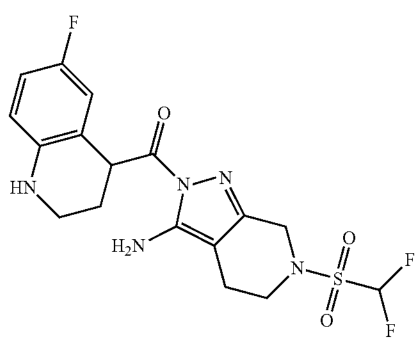 [SMILES: Nc1c2c(nn1C(=O)C1CCNc3ccc(F)cc31)CN(S(=O)(=O)C(F)F)CC2] | (3-amino-6-(difluoromethyl-sulfonyl)-4,5,6,7-tetrahydro-pyrazolo[3,4-c]pyridin-2-yl)(6-fluoro-1,2,3,4-tetrahydro-quinolin-4-yl)methanone | (300 MHz, DMSO-d₆, ppm): δ 8.29(m, 1H), 6.98-6.81(m, 1H), 6.80-6.68(m, 3H), 6.65-6.64(m, 1H), 5.80(s, 1H), 4.98-4.95(m, 1H), 4.54-4.43(m, 2H), 3.69-3.66(m, 2H), 3.31-3.18(m, 2H), 2.49-2.47(m, 2H), 2.07-1.95(m, 2H). | 430 |

TABLE 1-continued

List of the examples

| Example | Name | ¹HNMR | (ES, m/z) [M + H]⁺ |
|---|---|---|---|
| Example 160 | (3-amino-6-(difluoromethyl-sulfonyl)-4,5,6,7-tetrahydro-pyrazolo[3,4-c]pyridin-1-yl)(6-fluoro-1,2,3,4-tetrahydro-quinolin-4-yl)methanone | (300 MHz, DMSO-d₆, ppm): δ 7.38-7.33 (m, 1H), 6.98-6.81(m, 1H), 6.80-6.69(m, 1H), 6.52-6.51(m, 1H), 5.82-8.78(m, 3H), 4.88-4.85(m, 1H), 4.61(s, 2H), 3.68-3.64(m, 2H), 3.40-3.12(m, 2H), 2.49-2.47(m, 2H), 2.08-1.95(m, 2H). | 430 |
| Example 161 | (3-amino-6-ethyl-4,5,6,7-tetrahydro-pyrazolo[3,4-c]pyridin-2-yl)(6-chloro-1,2,3,4-tetrahydro-quinolin-4-yl)methanone | (DMSO-d₆, 300 MHz, ppm): δ 6.95-6.92(m, 1H), 6.83-6.82(m, 1H), 6.53-6.47(m, 3H), 6.09(s, 1H); 4.98-4.96(m, 1H), 3.37-3.35(m, 2H), 3.30-3.27(m, 2H), 3.25-3.20(m, 2H), 2.60-2.59(m, 2H), 2.36-2.34(m, 2H), 2.12-1.96(m, 2H), 1.09-1.05(m, 3H). | 360 |
| Example 162 | (3-amino-6-ethyl-4,5,6,7-tetrahydro-pyrazolo[3,4-c]pyridin-1-yl)(6-chloro-1,2,3,4-tetrahydro-quinolin-4-yl)methanone | (DMSO-d₆, 300 MHz, ppm): δ 6.95-6.91(m, 1H), 6.83-6.82(m, 1H), 6.53-6.50(m, 1H), 6.09(s, 1H); 5.82(s, 2H), 4.89-4.86(m, 1H), 3.41-3.35(m, 2H), 3.28-3.25(m, 2H), 3.19-3.16(m, 2H), 2.71-2.59(m, 2H), 2.43-2.35(m, 2H), 2.08-1.95(m, 2H), 1.12-1.08(m, 3H). | 360 |
| Example 163 | (3-amino-6-ethyl-4,5,6,7-tetrahydro-pyrazolo[3,4-c]pyridin-2-yl)(6-fluoro-1,2,3,4-tetrahydro-quinolin-4-yl)methanone | (DMSO-d₆, 400 MHz, ppm): δ 6.81-6.75(m, 1H), 6.67-6.64(m, 1H), 6.52-6.46(m, 3H), 5.78(s, 1H), 4.99-4.96(m, 1H), 3.41-3.37(m, 2H), 3.29-3.21(m, 1H), 3.16-3.15(m, 1H), 2.62-2.58(m, 2H), 2.54-2.51(m, 2H), 2.36-2.33(m, 2H), 2.09-1.93(m, 2H), 1.09-1.02(m, 3H). | 344 |
| Example 164 | (3-amino-6-ethyl-4,5,6,7-tetrahydro-pyrazolo[3,4-c]pyridin-1-yl)(6-fluoro-1,2,3,4-tetrahydro-quinolin-4-yl)methanone | (DMSO-d₆, 400 MHz, ppm): δ 6.79-6.74(m, 1H), 6.67-6.64(m, 1H), 6.51-6.47(m, 3H), 5.75(s, 1H), 5.67(s, 2H), 4.89-4.87(m, 1H), 3.67(s, 2H), 3.29-3.23(m, 1H), 3.14-3.11(m, 1H), 2.67-2.55(m, 2H), 2.53-2.51(m, 2H), 2.33(s, 2H), 2.07-1.98(m, 2H), 1.09-1.00(m, 3H). | 344 |

TABLE 1-continued

List of the examples

| Example | Name | ¹HNMR | (ES, m/z) [M + H]⁺ |
|---|---|---|---|
| Example 165 | (S*)-(3-amino-6-ethyl-4,5,6,7-tetrahydro-pyrazolo[3,4-c]pyridin-2-yl)(6-fluoro-1,2,3,4-tetrahydro-quinolin-4-yl)methanone | (DMSO-d₆, 300 MHz, ppm): δ 6.83-6.76(m, 1H), 6.68-6.64(m, 1H), 6.54-6.49(m, 1H), 6.47(s, 2H), 5.80(s, 1H), 5.00-4.96(m, 1H), 3.38(s, 2H), 3.25-3.17(m, 2H), 2.63-2.59(m, 2H), 2.56-2.54(m, 2H), 2.37-2.33(m, 2H), 2.08-2.01(m, 2H), 1.10-1.05(m, 3H). | 344 |
| Example 166 | (R*)-(3-amino-6-ethyl-4,5,6,7-tetrahydro-pyrazolo[3,4-c]pyridin-2-yl)(6-fluoro-1,2,3,4-tetrahydro-quinolin-4-yl)methanone | (DMSO-d₆, 300 MHz, ppm): δ 6.82-6.76(m, 1H), 6.68-6.64(m, 1H), 6.54-6.49(m, 1H), 6.47(s, 2H), 5.80(s, 1H), 5.00-4.96(m, 1H), 3.38(s, 2H), 3.25-3.17(m, 2H), 2.63-2.59(m, 2H), 2.56-2.52(m, 2H), 2.37-2.33(m, 2H), 2.11-1.99(m, 2H), 1.10-1.05(m, 3H). | 344 |
| Example 167 | (3-amino-6-(pyridin-2-yl)-4,5,6,7-tetrahydro-pyrazolo[3,4-c]pyridin-2-yl)(6-fluoro-1,2,3,4-tetrahydro-quinolin-4-yl)methanone | (DMSO-d₆, 300 MHz, ppm): δ 8.40-8.38(m, 1H), 7.94-7.88(m, 1H), 7.81-7.76(m, 1H), 7.23-7.19(m, 1H), 6.78(s, 1H), 6.75-6.71(m, 1H), 6.50-6.41(m, 2H), 5.69(s, 1H), 4.69-4.49(m, 2H), 4.28-4.24(m, 1H), 3.85-3.73(m, 2H), 3.18-3.14(m, 2H), 2.54-2.51(m, 1H), 2.42-2.41(m, 1H), 1.91-1.80(m, 2H). | 393 |
| Example 168 | (3-amino-6-(methylsulfonyl)-4,5,6,7-tetrahydro-pyrazolo[3,4-c]pyridin-2-yl)(6-(pyridin-4-yl)-1,2,3,4-tetrahydro-quinolin-4-yl)methanone | (DMSO-d₆, 400 MHz, ppm): δ 8.44-8.42(m, 2H), 7.49-7.40(m, 4H), 6.64-6.62(m, 3H), 6.39(s, 1H), 5.07-5.05(m, 1H), 4.31-4.23(m, 2H), 3.32(m, 4H), 2.98(s, 3H), 2.51-2.47(m, 4H). | 453 |

TABLE 1-continued

List of the examples

| Example | Structure | Name | ¹HNMR | (ES, m/z) [M + H]⁺ |
|---|---|---|---|---|
| Example 169 | 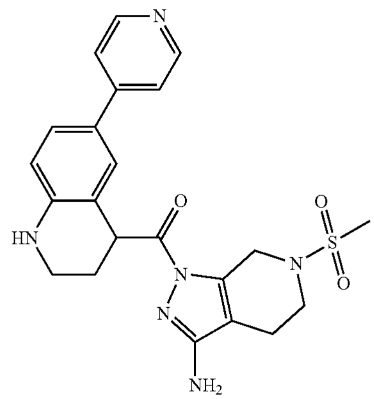 [SMILES: CS(=O)(=O)N1CCc2c(N)nn(C(=O)C3CCNc4ccc(-c5ccncc5)cc43)c2C1] | (3-amino-6-(methylsulfonyl)-4,5,6,7-tetrahydropyrazolo[3,4-c]pyridin-1-yl)(6-(pyridin-4-yl)-1,2,3,4-tetrahydroquinolin-4-yl)methanone | (DMSO-d₆, 400 MHz, ppm): δ 8.44-8.42(m, 2H), 7.49-7.39(m, 4H), 6.64-6.61(m, 1H), 6.38(s, 1H), 5.83(s, 2H), 4.97-4.95(m, 1H), 4.53(s, 2H), 3.46-3.29(m, 2H), 3.26-3.22(m, 2H), 2.95(s, 3H), 2.51-2.50(m, 2H), 2.14-1.99(m, 2H). | 453 |
| Example 170 | 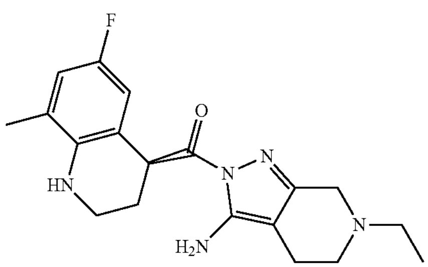 [SMILES: CCN1CCc2c(nn(C(=O)[C@H]3CCNc4c(C)cc(F)cc43)c2N)C1] | (S*)-(3-amino-6-ethyl-4,5,6,7-tetrahydropyrazolo[3,4-c]pyridin-2-yl)(6-fluoro-8-methyl-1,2,3,4-tetrahydroquinolin-4-yl)methanone | (DMSO-d₆, 400 MHz, ppm): δ 6.75-6.72(m, 1H), 6.55-6.52(m, 1H), 6.46(s, 2H), 5.13(s, 1H), 5.01-4.98(m, 1H), 3.37(s, 2H), 3.27-3.20(m, 2H), 2.63-3.61(m, 2H), 2.59-2.54(m, 2H), 2.36-2.33(m, 2H), 2.11-1.95(m, 5H), 1.11-1.08(m, 3H). | 358 |
| Example 171 | 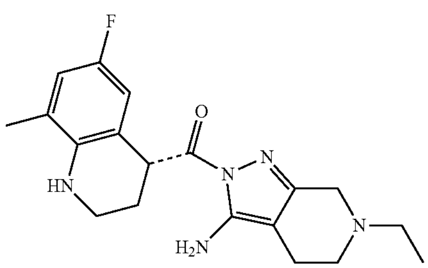 [SMILES: CCN1CCc2c(nn(C(=O)[C@@H]3CCNc4c(C)cc(F)cc43)c2N)C1] | (R*)-(3-amino-6-ethyl-4,5,6,7-tetrahydropyrazolo[3,4-c]pyridin-2-yl)(6-fluoro-8-methyl-1,2,3,4-tetrahydroquinolin-4-yl)methanone | (DMSO-d₆, 400 MHz, ppm): δ 6.75-6.72(m, 1H), 6.55-6.52(m, 1H), 6.46(s, 2H), 5.13(s, 1H), 5.01-4.98(m, 1H), 3.37(s, 2H), 3.27-3.21(m, 2H), 2.67-3.60(m, 2H), 2.58-2.54(m, 2H), 2.36-2.33(m, 2H), 2.10-1.99(m, 5H), 1.10-1.08(m, 3H). | 358 |
| Example 172 | 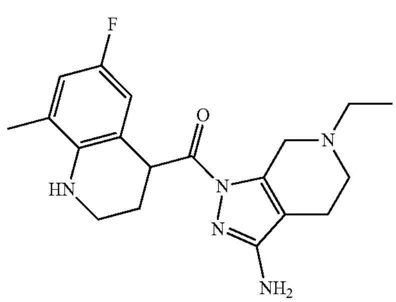 [SMILES: CCN1CCc2c(N)nn(C(=O)C3CCNc4c(C)cc(F)cc43)c2C1] | (3-amino-6-ethyl-4,5,6,7-tetrahydropyrazolo[3,4-c]pyridin-1-yl)(6-fluoro-8-methyl-1,2,3,4-tetrahydroquinolin-4-yl)methanone | (DMSO-d₆, 400 MHz, ppm): δ 6.73-6.71(m, 1H), 6.56-6.53(m, 1H), 5.67(s, 2H), 5.10(s, 1H), 4.93-4.90(m, 1H), 3.67(s, 2H), 3.35-3.30(m, 1H), 3.23-3.19(m, 1H), 2.64-2.62(m, 2H), 2.57-2.52(m, 2H), 2.34-2.31(m, 2H), 2.08-1.93(m, 5H), 1.06-1.03(m, 3H). | 358 |
| Example 173 | 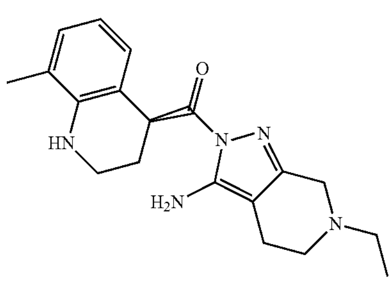 [SMILES: CCN1CCc2c(nn(C(=O)[C@H]3CCNc4c(C)cccc43)c2N)C1] | (S*)-(3-amino-6-ethyl-4,5,6,7-tetrahydropyrazolo[3,4-c]pyridin-2-yl)(8-methyl-1,2,3,4-tetrahydroquinolin-4-yl)methanone | (DMSO-d₆, 400 MHz, ppm): δ 6.82(d, J = 7.2 Hz, 1H), 6.65(d, J = 7.6 Hz, 1H), 6.45(s, 2H), 6.37-6.33(m, 1H), 5.22(s, 1H), 5.05-5.02(m, 1H), 3.42-3.37(m, 3H), 3.29-3.25(m, 1H), 2.67-2.51(m, 4H), 2.36-2.33(m, 2H), 2.09-1.97(m, 5H), 1.05-1.03(m, 3H). | 340 |

TABLE 1-continued

List of the examples

| Example | Structure | Name | ¹HNMR | (ES, m/z) [M + H]⁺ |
|---|---|---|---|---|
| Example 174 | 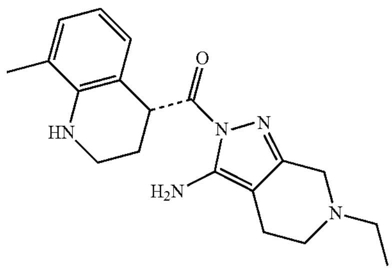 [SMILES: CCN1CCc2c(nn(C(=O)[C@@H]3CCNc4c(C)cccc43)c2N)C1] | (R*)-(3-amino-6-ethyl-4,5,6,7-tetrahydropyrazolo[3,4-c]pyridin-2-yl)(8-methyl-1,2,3,4-tetrahydroquinolin-4-yl)methanone | (DMSO-d₆, 400 MHz, ppm): δ 6.82(d, J = 7.2 Hz, 1H), 6.65(d, J = 12 Hz, 1H), 6.44(s, 2H), 6.37-6.33(m, 1H), 5.21(s, 1H), 5.05-5.02(m, 1H), 3.41-3.34(m, 3H), 3.29-3.21(m, 1H), 2.65-2.52(m, 4H), 2.35-2.33(m, 2H), 2.10-1.93(m, 5H), 1.08-1.04(m, 3H). | 340 |
| Example 175 | 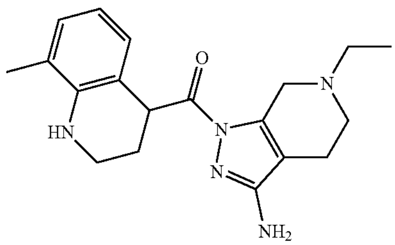 [SMILES: CCN1CCc2c(N)nn(C(=O)C3CCNc4c(C)cccc43)c2C1] | (3-amino-6-ethyl-4,5,6,7-tetrahydropyrazolo[3,4-c]pyridin-1-yl)(8-methyl-1,2,3,4-tetrahydroquinolin-4-yl)methanone | (DMSO-d₆, 300 MHz, ppm): δ 6.89-6.79(m, 1H), 6.66-6.64(m, 1H), 6.36-6.31(m, 1H), 5.61(s, 2H), 5.16(s, 1H), 4.96-4.93(m, 1H), 3.66(s, 2H), 3.39-3.35(m, 1H), 3.31-3.25(m, 1H), 2.64-2.51(m, 4H), 2.33-2.28(m, 2H), 2.07-1.87(m, 5H), 1.06-1.04(m, 3H). | 340 |
| Example 176 | 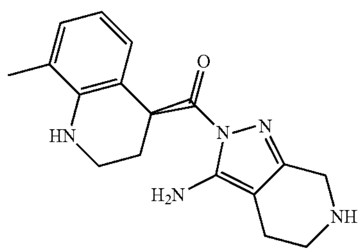 [SMILES: Cc1cccc2c1NCC[C@@H]2C(=O)n1nc2c(c1N)CCNC2] | (S*)-(3-amino-4,5,6,7-tetrahydropyrazolo[3,4-c]pyridin-2-yl)(8-methyl-1,2,3,4-tetrahydroquinolin-4-yl)methanone | (DMSO-d₆, 400 MHz, ppm): δ 6.82(d, J = 7.2 Hz, 1H), 6.64(d, J = 7.6 Hz, 1H), 6.48(s, 2H), 6.40-6.33(m, 1H), 5.21(s, 1H), 5.05-5.03(m, 1H), 3.68-3.60(m, 2H), 3.37-3.34(m, 1H), 3.27-3.25(m, 1H), 2.87-2.77(m, 2H), 2.29-2.24(m, 2H), 2.08-1.97(m, 5H). | 312 |
| Example 177 | 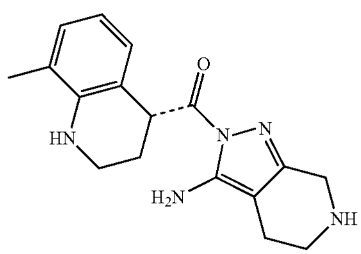 [SMILES: Cc1cccc2c1NCC[C@H]2C(=O)n1nc2c(c1N)CCNC2] | (R*)-(3-amino-4,5,6,7-tetrahydropyrazolo[3,4-c]pyridin-2-yl)(8-methyl-1,2,3,4-tetrahydroquinolin-4-yl)methanone | (DMSO-d₆, 400 MHz, ppm): δ 6.82(d, J = 7.2 Hz, 1H), 6.64(d, J = 7.6 Hz, 1H), 6.48(s, 2H), 6.40-6.33(m, 1H), 5.21(s, 1H), 5.05-5.03(m, 1H), 3.68-3.60(m, 2H), 3.37-3.34(m, 1H), 3.27-3.25(m, 1H), 2.83-2.77(m, 2H), 2.27-2.24(m, 2H), 2.08-1.99(m, 5H). | 312 |
| Example 178 | 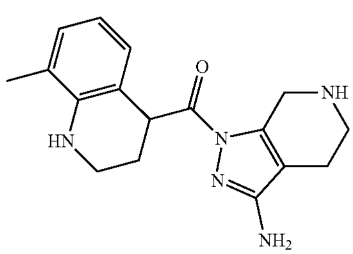 | (3-amino-4,5,6,7-tetrahydropyrazolo[3,4-c]pyridin-1-yl)(8-methyl-1,2,3,4-tetrahydroquinolin-4-yl)methanone | (DMSO-d₆, 400 MHz, ppm): δ 6.81(d, J = 7.2 Hz, 1H), 6.64(d, J = 1.2 Hz, 1H), 6.36-6.32(m, 1H), 5.59(s, 2H), 5.17(s, 1H), 4.96-4.94(m, 1H), 3.88-3.87(m, 2H), 3.37-3.35(m, 1H), 3.25-3.21(m, 1H), 2.81-2.79(m, 2H), 2.23-2.21(m, 2H), 2.05-1.91(m, 5H). | 312 |
| Example 179 | 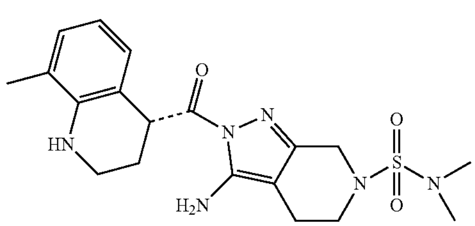 | (R*)-3-amino-N,N-dimethyl-2-(8-methyl-1,2,3,4-tetrahydroquinoline-4-carbonyl)-4,5-dihydro-2H-pyrazolo[3,4-c]pyridine-6(7H)-sulfonamide | (DMSO-d₆, 300 MHz, ppm): δ 6.84-6.81(m, 1H), 6.67-6.60(m, 3H), 6.38-6.33(m, 1H), 5.22(s, 1H), 5.05-5.01(m, 1H), 4.25(s, 2H), 3.49-3.42(m, 2H), 3.26-3.22(m, 2H), 2.72(s, 6H), 2.45-2.41(m, 2H), 2.09-1.99(m, 5H). | 419 |

TABLE 1-continued

List of the examples

| Example | Name | ¹HNMR | (ES, m/z) [M + H]⁺ |
|---|---|---|---|
| Example 180 | (S*)-3-amino-N,N-dimethyl-2-(8-methyl-1,2,3,4-tetrahydroquinoline-4-carbonyl)-4,5-dihydro-2H-pyrazolo[3,4-c]pyridine-6(7H)-sulfonamide | (DMSO-d₆, 300 MHz, ppm): δ 6.84-6.81(m, 1H), 6.66-6.60(m, 3H), 6.38-6.33(m, 1H), 5.22(s, 1H), 5.05-5.01(m, 1H), 4.25(s, 2H), 3.49-3.40(m, 2H), 3.25-3.22(m, 2H), 2.72(s, 6H), 2.45-2.41(m, 2H), 2.11-1.99(m, 5H). | 419 |
| Example 181 | 3-amino-N,N-dimethyl-1-(8-methyl-1,2,3,4-tetrahydroquinoline-4-carbonyl)-4,5-dihydro-1H-pyrazolo[3,4-c]pyridine-6(7H)-sulfonamide | (DMSO-d₆, 300 MHz, ppm): δ 6.82-6.81(m, 1H), 6.68-6.66(m, 1H), 6.36-6.33(m, 1H), 5.78(s, 2H), 5.20(s, 1H), 4.95-4.92(m, 1H), 4.52(s, 2H), 3.47-3.45(m, 2H), 3.38-3.36(m, 1H), 3.26-3.24(m, 1H), 2.72(s, 6H), 2.43-2.41(m, 2H), 2.05-1.97(m, 5H). | 419 |
| Example 182 | (S*)-(3-amino-6-(cyclobutylsulfonyl)-4,5,6,7-tetrahydropyrazolo[3,4-c]pyridin-2-yl)(8-methyl-1,2,3,4-tetrahydroquinolin-4-yl)methanone | (DMSO-d₆, 400 MHz, ppm): δ 6.82(d, J = 7.2 Hz, 1H), 6.64(d, J = 7.2 Hz, 1H), 6.60(s, 2H), 6.36-6.33(m, 1H), 5.22(s, 1H), 5.04-5.01(m, 1H), 4.26(s, 2H), 4.10-4.02(m, 1H), 3.47-3.44(m, 2H), 3.36-3.34(m, 1H), 3.27-3.26(m, 1H), 2.44-2.29(m, 4H), 2.24-2.16(m, 2H), 2.09-1.86(m, 7H). | 430 |
| Example 183 | (R*)-(3-amino-6-(cyclobutylsulfonyl)-4,5,6,7-tetrahydropyrazolo[3,4-c]pyridin-2-yl)(8-methyl-1,2,3,4-tetrahydroquinolin-4-yl)methanone | (DMSO-d₆, 400 MHz, ppm): δ 6.82(d, J = 7.2 Hz, 1H), 6.64(d, J = 7.6 Hz, 1H), 6.60(s, 2H), 6.36-6.33(m, 1H), 5.22(s, 1H), 5.04-5.01(m, 1H), 4.26(s, 2H), 4.08-4.04(m, 1H), 3.47-3.44(m, 2H), 3.34-3.33(m, 1H), 3.28-3.25(m, 1H), 2.44-2.29(m, 4H), 2.23-2.15(m, 2H), 2.09-1.86(m, 7H). | 430 |
| Example 184 | (3-amino-6-(cyclobutylsulfonyl)-4,5,6,7-tetrahydropyrazolo[3,4-c]pyridin-1-yl)(8-methyl-1,2,3,4-tetrahydroquinolin-4-yl)methanone | (DMSO-d₆, 300 MHz, ppm): δ 6.81-6.80(m, 1H), 6.67-6.65(m, 1H), 6.37-6.32(m, 1H), 5.77(s, 2H), 5.20(s, 1H), 4.95-4.92(m, 1H), 4.53(s, 2H), 4.06-3.98(m, 1H), 3.45-3.36(m, 3H), 3.26-3.21(m, 1H), 2.44-2.42(m, 2H), 2.35-2.12(m, 4H), 2.08-1.82(m, 7H). | 430 |

TABLE 1-continued

List of the examples

| Example | Structure | Name | $^1$HNMR | (ES, m/z) [M + H]$^+$ |
|---|---|---|---|---|
| Example 185 | 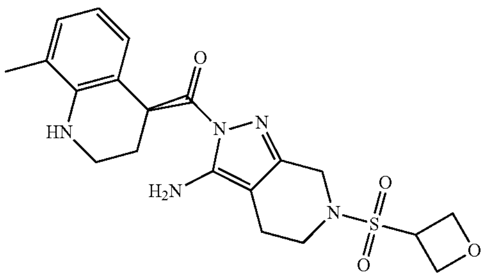 [SMILES: Cc1cccc2c1NCC[C@@H]2C(=O)n1nc2c(c1N)CCN(S(=O)(=O)C1COC1)C2] | (S*)-(3-amino-6-(oxetan-3-ylsulfonyl)-4,5,6,7-tetrahydropyrazolo[3,4-c]pyridin-2-yl)(8-methyl-1,2,3,4-tetrahydroquinolin-4-yl)methanone | (DMSO-d$_6$, 400 MHz, ppm): δ 6.82(d, J = 7.2 Hz, 1H), 6.64(d, J = 8.0 Hz, 1H), 6.62(s, 2H), 6.37-6.33(m, 1H), 5.23(s, 1H), 5.04-5.01(m, 1H), 4.86-4.71(m, 5H), 4.29(s, 2H), 3.50-3.47(m, 2H), 3.36-3.34(m, 1H), 3.27-3.26(m, 1H), 2.47-2.40(m, 2H), 2.09-1.96(m, 5H). | 432 |
| Example 186 | 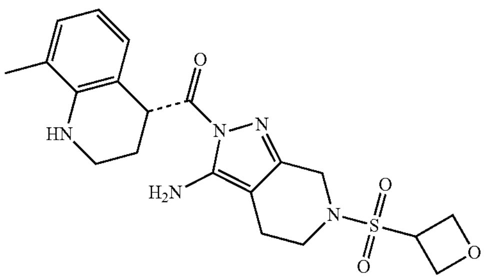 [SMILES: Cc1cccc2c1NCC[C@H]2C(=O)n1nc2c(c1N)CCN(S(=O)(=O)C1COC1)C2] | (R*)-(3-amino-6-(oxetan-3-ylsulfonyl)-4,5,6,7-tetrahydropyrazolo[3,4-c]pyridin-2-yl)(8-methyl-1,2,3,4-tetrahydroquinolin-4-yl)methanone | (DMSO-d$_6$, 400 MHz, ppm): δ 6.82(d, J = 7.2 Hz, 1H), 6.64(d, J = 7.6 Hz, 1H), 6.62(s, 2H), 6.37-6.33(m, 1H), 5.22(s, 1H), 5.04-5.01(m, 1H), 4.86-4.71(m, 5H), 4.29(s, 2H), 3.50-3.47(m, 2H), 3.36-3.34(m, 1H), 3.27-3.26(m, 1H), 2.44-2.41(m, 2H), 2.09-1.95(m, 5H). | 432 |
| Example 187 | 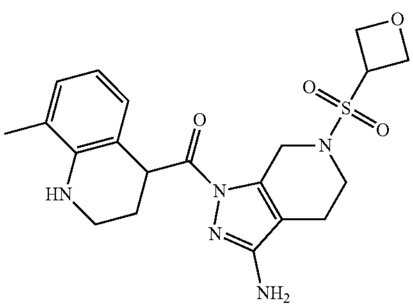 [SMILES: Cc1cccc2c1NCCC2C(=O)n1nc(N)c2c1CN(S(=O)(=O)C1COC1)CC2] | (3-amino-6-(oxetan-3-ylsulfonyl)-4,5,6,7-tetrahydropyrazolo[3,4-c]pyridin-1-yl)(8-methyl-1,2,3,4-tetrahydroquinolin-4-yl)methanone | (DMSO-d$_6$, 300 MHz, ppm): δ 6.81-6.80(m, 1H), 6.68-6.65(m, 1H), 6.37-6.32(m, 1H), 5.78(s, 2H), 5.20(s, 1H), 4.95-4.91(m, 1H), 4.89-4.62(m, 5H), 4.56-4.55(m, 2H), 3.54-3.36(m, 3H), 3.26-3.25(m, 1H), 2.44-2.41(m, 2H), 2.10-1.91(m, 5H). | 432 |
| Example 188 | 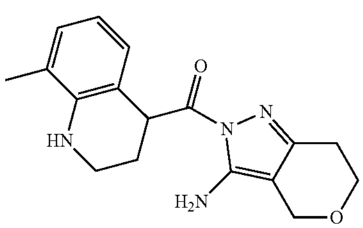 [SMILES: Cc1cccc2c1NCCC2C(=O)n1nc2c(c1N)COCC2] | (3-amino-6,7-dihydropyrano[4,3-c]pyrazol-2(4H)-yl)(8-methyl-1,2,3,4-tetrahydroquinolin-4-yl)methanone | (DMSO-d$_6$, 400 MHz, ppm): δ 6.82 (d, J = 7.2 Hz, 1H), 6.66 (d, J = 7.2 Hz, 1H), 6.55 (s, 2H), 6.37-6.34 (s, 1H), 5.23 (s, 1H), 5.06-5.04 (m, 1H), 4.42 (s, 2H), 3.83-3.80 (m,2H), 3.33-3.26 (m, 2H), 2.62-2.51 (m, 2H), 2.11-1.98 (m, 5H). | 313 |
| Example 189 | 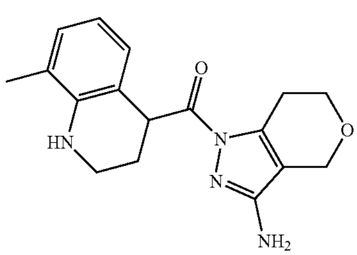 [SMILES: Cc1cccc2c1NCCC2C(=O)n1nc(N)c2c1CCOC2] | (3-amino-6,7-dihydropyrano[4,3-c]pyrazol-1(4H)-yl)(8-methyl-1,2,3,4-tetrahydroquinolin-4-yl)methanone | (400 MHz, DMSO-d$_6$, ppm): δ 6.81 (d, J = 7.2 Hz, 1H), 6.67(d, J = 7.2 Hz, 1H), 6.36-6.33 (m, 1H), 5.67 (s, 2H), 5.20 (s, 1H), 4.97-4.94 (m, 1H), 4.40 (s, 2H), 3.77-3.74 (m, 2H), 3.31-3.23 (m, 2H), 2.88-2.67 (m, 2H), 2.08-1.92 (m, 5H). | 313 |

TABLE 1-continued

List of the examples

| Example | Structure | Name | ¹HNMR | (ES, m/z) [M + H]⁺ |
|---|---|---|---|---|
| Example 190 | 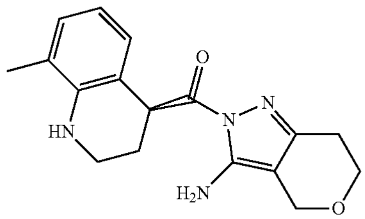 [SMILES: Cc1cccc2c1NCC[C@@H]2C(=O)n1nc2c(c1N)COCC2] | (S*)-(3-amino-6,7-dihydropyrano[4,3-c]pyrazol-2(4H)-yl)(8-methyl-1,2,3,4-tetrahydro-quinolin-4-yl)methanone | (DMSO-d₆, 400 MHz, ppm): δ 6.82(d, J = 7.2 Hz, 1H), 6.65(d, J = 7.2 Hz, 1H), 6.55(s, 2H), 6.37-6.33(m, 1H), 5.23(s, 1H), 5.06-5.04(m, 1H), 4.42(s, 2H), 3.83-3.80(m, 2H), 3.30-3.26(m, 2H), 2.62-2.59(m, 2H), 2.10-1.98(m, 5H). | 313 |
| Example 191 | 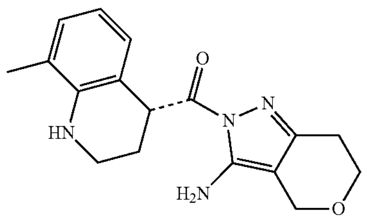 [SMILES: Cc1cccc2c1NCC[C@H]2C(=O)n1nc2c(c1N)COCC2] | (R*)-(3-amino-6,7-dihydropyrano[4,3-c]pyrazol-2(4H)-yl)(8-methyl-1,2,3,4-tetrahydro-quinolin-4-yl)methanone | (DMSO-d₆, 400 MHz, ppm): δ 6.82(d, J = 7.2 Hz, 1H), 6.65(d, J = 7.6 Hz, 1H), 6.55(s, 2H), 6.37-6.34(m, 1H), 5.23(s, 1H), 5.07-5.04(m, 1H), 4.42(s, 2H), 3.83-3.80(m, 2H), 3.30-3.26(m, 2H), 2.62-2.59(m, 2H), 2.10-1.98(m, 5H). | 313 |
| Example 192 | 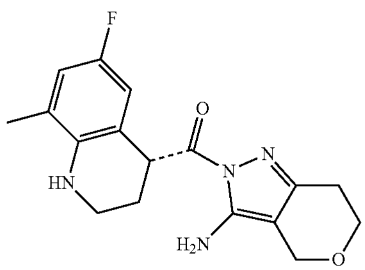 [SMILES: Cc1cc(F)cc2c1NCC[C@H]2C(=O)n1nc2c(c1N)COCC2] | (R*)-(3-amino-6,7-dihydropyrano[4,3-c]pyrazol-2(4H)-yl)(6-fluoro-8-methyl-1,2,3,4-tetrahydro-quinolin-4-yl)methanone | (DMSO-d₆, 300 MHz, ppm): δ 6.83-6.75(m, 1H), 6.59-6.56(m, 1H), 5.03-4.99(m, 1H), 4.40(s, 2H), 3.82-3.63(m, 2H), 3.28-3.25(m, 2H), 2.68-2.57(m, 2H), 2.12-2.00(m, 5H). | 331 |
| Example 193 | 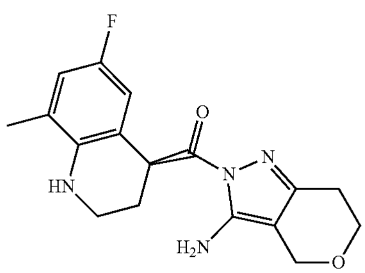 [SMILES: Cc1cc(F)cc2c1NCC[C@@H]2C(=O)n1nc2c(c1N)COCC2] | (S*)-(3-amino-6,7-dihydropyrano[4,3-c]pyrazol-2(4H)-yl)(6-fluoro-8-methyl-1,2,3,4-tetrahydro-quinolin-4-yl)methanone | (DMSO-d₆, 300 MHz, ppm): δ 6.77-6.74(m, 1H), 6.58-6.54(m, 1H), 5.08-5.01(m, 1H), 4.50(s, 2H), 3.85-3.82(m, 2H), 3.28-3.25(m, 2H), 2.68-2.57(m, 2H), 2.11-1.98(m, 5H). | 331 |
| Example 194 | 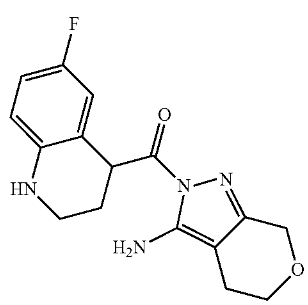 [SMILES: Nc1c2c(nn1C(=O)C1CCNc3ccc(F)cc31)COCC2] | (3-amino-4,5-dihydropyrano[3,4-c]pyrazol-2(7H)-yl)(6-fluoro-1,2,3,4-tetrahydro-quinolin-4-yl)methanone | (400 MHz, DMSO-d₆, ppm): δ 6.81-6.80(m, 1H), 6.79-7.78(m, 1H), 6.77-6.70(m, 2H), 6.57-6.49(m, 1H), 5.79(s, 1H), 4.98-4.95(m, 1H), 4.59-4.51(m, 2H), 3.32-3.14(m, 2H), 2.40-2.38(m, 2H), 2.01-1.96(m, 4H). | 317 |
| Example 195 | 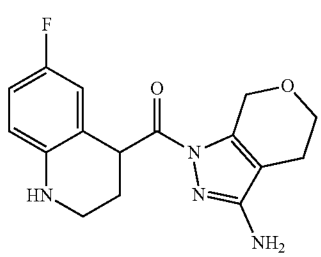 [SMILES: Nc1nn(C(=O)C2CCNc3ccc(F)cc32)c2c1CCOC2] | (3-amino-4,5-dihydropyrano[3,4-c]pyrazol-1(7H)-yl)(6-fluoro-1,2,3,4-tetrahydro-quinolin-4-yl)methanone | (400 MHz, DMSO-d₆, ppm): δ 6.79-6.66(m, 2H), 6.51-6.48(m, 1H), 5.78(s, 3H), 4.87-4.84(m, 1H), 4.74(s, 2H), 3.78-3.71(m, 2H), 3.32-3.14(m, 2H), 2.35-2.33(m, 2H), 2.07-1.95(m, 2H). | 317 |

TABLE 1-continued

List of the examples

| Example | Name | ¹HNMR | (ES, m/z) [M + H]⁺ |
|---|---|---|---|
| Example 196 | (S*)-(3-amino-4,5-dihydropyrano[3,4-c]pyrazol-2(7H)-yl)(6-fluoro-1,2,3,4-tetrahydroquinolin-4-yl)methanone | (400 MHz, DMSO-d₆, ppm): δ 6.81-6.78(m, 1H), 6.67-6.64(m, 1H), 6.58(s, 2H), 6.52-6.49(m, 1H), 5.80(s, 1H), 4.98-4.95(m, 1H), 4.55(s, 2H), 3.79-3.77(m, 2H), 3.25-3.16(m, 2H), 2.41-2.38(m, 2H), 2.07-1.96(m, 2H). | 317 |
| Example 197 | (R*)-(3-amino-4,5-dihydropyrano[3,4-c]pyrazol-2(7H)-yl)(6-fluoro-1,2,3,4-tetrahydroquinolin-4-yl)methanone | (400 MHz, DMSO-d₆, ppm): δ 6.81-6.76(m, 1H), 6.67-6.64(m, 1H), 6.58(s, 2H), 6.54-6.49(m, 1H), 5.81(s, 1H), 4.98-4.95(m, 1H), 4.55(m, 2H), 3.79-3.75(m, 2H), 3.25-3.15(m, 2H), 2.41-2.38(m, 2H), 2.09-2.01(m, 2H). | 317 |
| Example 198 | (S*)-(3-amino-4,5-dihydropyrano[3,4-c]pyrazol-2(7H)-yl)(8-methyl-1,2,3,4-tetrahydroquinolin-4-yl)methanone | (400 MHz, DMSO-d₆, ppm): δ 6.82(d, J = 7.2 Hz, 1H), 6.65(d, J = 7.2 Hz, 1H), 6.53(s, 2H), 6.37-6.33(m, 1H), 5.22(s, 1H), 5.04-5.01(m, 1H), 4.59-4.56(m, 2H), 3.79-3.77(m, 2H), 3.36-3.25(m, 2H), 2.50-2.41(m, 2H), 2.10-1.99(m, 5H). | 313 |
| Example 199 | (R*)-(3-amino-4,5-dihydropyrano[3,4-c]pyrazol-2(7H)-yl)(8-methyl-1,2,3,4-tetrahydroquinolin-4-yl)methanone | (400 MHz, DMSO-d₆, ppm): δ 6.82(d, J = 7.2 Hz, 1H), 6.65(d, J = 7.6 Hz, 1H), 6.53(s, 2H), 6.35-6.33(m, 1H), 5.20(s, 1H), 5.04-5.01(m, 1H), 4.59-4.54(m, 2H), 3.79-3.78(m, 2H), 3.36-3.25(m, 2H), 2.50-2.41(m, 2H), 2.10-1.99(m, 5H). | 313 |
| Example 200 | (3-amino-4,5-dihydropyrano[3,4-c]pyrazol-1(7H)-yl)(8-methyl-1,2,3,4-tetrahydroquinolin-4-yl)methanone | (400 MHz, DMSO-d₆, ppm): δ 6.81(d, J = 7.2 Hz, 1H), 6.66(d, J = 7.6 Hz, 1H), 6.35-6.32(m, 1H), 5.74(s, 2H), 5.20(s, 1H), 4.93-4.90(m, 1H), 4.77-4.68(m, 2H), 3.77-3.72(m, 2H), 3.34-3.21(m, 2H), 2.50-2.49(m, 2H), 2.07-1.96(m, 5H). | 313 |

TABLE 1-continued

List of the examples

| Example | Structure | Name | ¹HNMR | (ES, m/z) [M + H]⁺ |
|---|---|---|---|---|
| Example 201 | 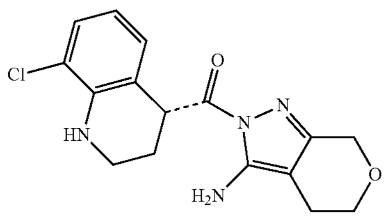 [SMILES: Nc1c2c(nn1C(=O)[C@@H]1CCNc3c(Cl)cccc31)COCC2] | (R*)-(3-amino-4,5-dihydropyrano[3,4-c]pyrazol-2(7H)-yl)(8-chloro-1,2,3,4-tetrahydro-quinolin-4-yl)methanone | (300 MHz, DMSO-$d_6$, ppm): δ 7.12-7.10(m, 1H), 6.81 (d, J = 7.5 Hz, 1H), 6.56(s, 2H), 6.46-6.41(m, 1H), 5.75(s, 1H), 5.06-5.02(m, 1H), 4.55(s, 2H), 3.80-3.76(m, 2H), 3.31-3.29(m, 2H), 2.41-2.38(m, 2H), 2.10-1.99(m, 2H). | 333 |
| Example 202 | 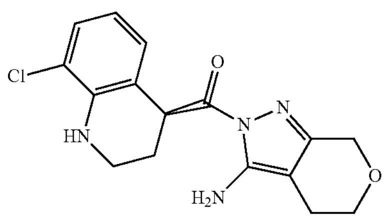 [SMILES: Nc1c2c(nn1C(=O)[C@H]1CCNc3c(Cl)cccc31)COCC2] | (S*)-(3-amino-4,5-dihydropyrano[3,4-c]pyrazol-2(7H)-yl)(8-chloro-1,2,3,4-tetrahydro-quinolin-4-yl)methanone | (300 MHz, DMSO-$d_6$, ppm): δ 7.13-7.10(m, 1H), 6.81(d, J = 7.5 Hz, 1H), 6.56(s, 2H), 6.46-6.41(m, 1H), 5.76(s, 1H), 5.06-5.02(m, 1H), 4.55(s, 2H), 3.80-3.76(m, 2H), 3.31-3.29(m, 2H), 2.41-2.38(m, 2H), 2.16-1.96(m, 2H). | 333 |
| Example 203 | 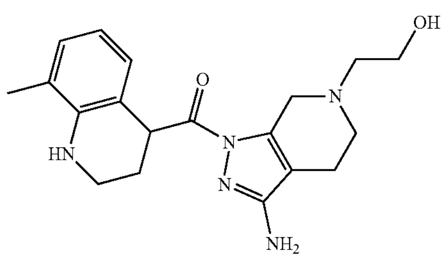 [SMILES: Cc1cccc2c1NCCC2C(=O)n1nc(N)c2c1CN(CCO)CC2] | (3-amino-6-(2-hydroxyethyl)-4,5,6,7-tetrahydro-1H-pyrazolo[3,4-c]pyridin-1-yl)(8-methyl-1,2,3,4-tetrahydro-quinolin-4-yl)methanone | (300 MHz, DMSO-$d_6$, ppm): δ 6.80 (d, J = 6.9, 1H), 6.65 (d, J = 7.2, 1H), 6.36-6.31 (s, 1H), 5.63 (s, 2H), 5.17 (s, 1H), 4.96-4.92 (m, 1H), 4.45-4.42 (m, 1H), 3.72 (s, 2H), 3.54-3.49 (m, 2H), 3.34-3.31 (m, 1H), 3.24-3.23 (m, 1H), 2.69-2.55 (m, 4H), 2.36-2.33 (m, 2H), 2.06-1.93 (m, 5H). | 356 |
| Example 204 | 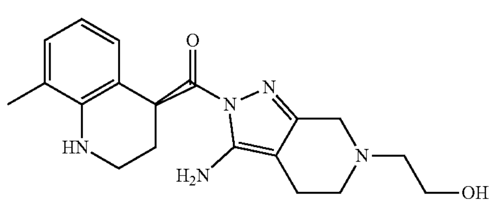 [SMILES: Cc1cccc2c1NCC[C@@H]2C(=O)n1nc2c(c1N)CCN(CCO)C2] | (S*)-(3-amino-6-(2-hydroxyethyl)-4,5,6,7-tetrahydro-2H-pyrazolo[3,4-c]pyridin-2-yl)(8-methyl-1,2,3,4-tetrahydro-quinolin-4-yl)methanone | (DMSO-$d_6$, 300 MHz, ppm): δ 6.82 (d, J = 6.9, 1H), 6.64 (d, J = 7.2, 1H), 6.45 (s, 2H), 6.37-6.32 (m, 1H), 5.21 (s, 1H), 5.05-5.01 (m, 1H), 4.47 (s, 1H), 3.59-3.56 (m, 2H), 3.55-3.45 (m, 2H), 3.27-3.25 (m, 2H), 2.72-2.59 (m, 4H), 2.36-2.33 (m, 2H), 2.06-1.98 (m, 5H). | 356 |
| Example 205 | 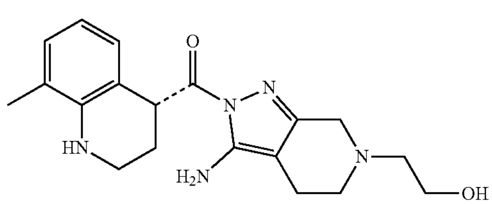 [SMILES: Cc1cccc2c1NCC[C@H]2C(=O)n1nc2c(c1N)CCN(CCO)C2] | (R*)-(3-amino-6-(2-hydroxyethyl)-4,5,6,7-tetrahydro-2H-pyrazolo[3,4-c]pyridin-2-yl)(8-methyl-1,2,3,4-tetrahydro-quinolin-4-yl)methanone | (DMSO-$d_6$, 300 MHz, ppm): δ 6.82 (d, J = 6.9, 1H), 6.64 (d, J = 7.5, 1H), 6.44 (s, 2H), 6.37-6.32 (m, 1H), 5.21 (s, 1H), 5.04-5.02 (m, 1H), 4.47 (s, 1H), 3.59-3.56 (m, 2H), 3.55-3.45 (m, 2H), 3.27-3.25 (m, 2H), 2.72-2.59 (m, 4H), 2.36-2.33 (m, 2H), 2.02-2.00 (m, 5H). | 356 |

The following additional species of the invention may be prepared by methods analogous to those described above.
| compound | |
|---|---|
| 301 | 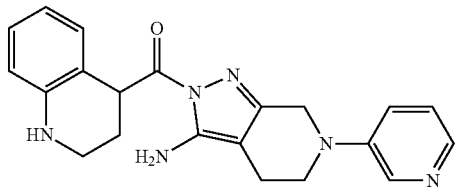 [SMILES: Nc1c2c(nn1C(=O)C1CCNc3ccccc31)CN(c1cccnc1)CC2] |
| 302 | 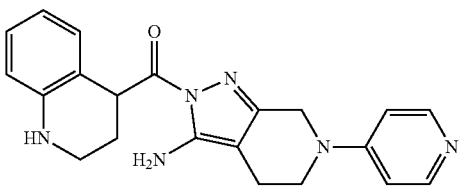 [SMILES: Nc1c2c(nn1C(=O)C1CCNc3ccccc31)CN(c1ccncc1)CC2] |
| 303 | 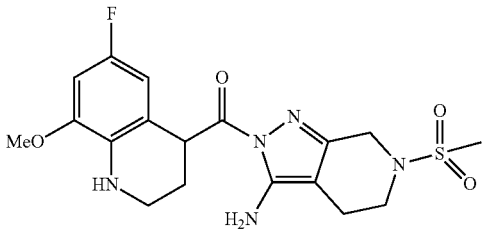 [SMILES: COc1cc(F)cc2c1NCCC2C(=O)n1nc2c(c1N)CCN(S(C)(=O)=O)C2] |
| 304 | 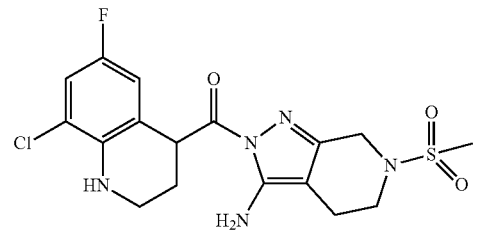 [SMILES: CS(=O)(=O)N1CCc2c(nn(C(=O)C3CCNc4c(Cl)cc(F)cc43)c2N)C1] |
| 305 | 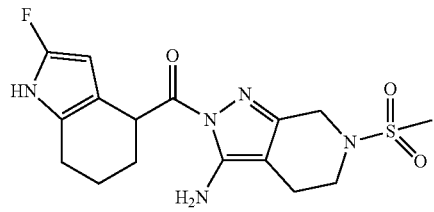 [SMILES: CS(=O)(=O)N1CCc2c(nn(C(=O)C3CCCc4[nH]c(F)cc43)c2N)C1] |
| 306 | 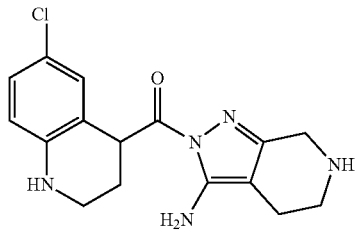 [SMILES: Nc1c2c(nn1C(=O)C1CCNc3ccc(Cl)cc31)CNCC2] |
-continued
| compound | |
|---|---|
| 307 | 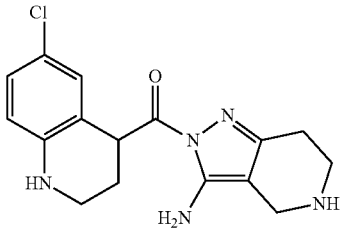 [SMILES: Nc1c2c(nn1C(=O)C1CCNc3ccc(Cl)cc31)CCNC2] |
| 308 | 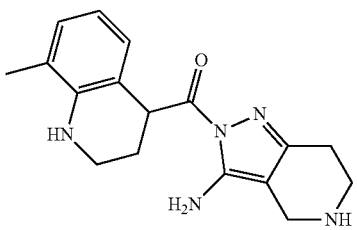 [SMILES: Cc1cccc2c1NCCC2C(=O)n1nc2c(c1N)CNCC2] |
| 309 | 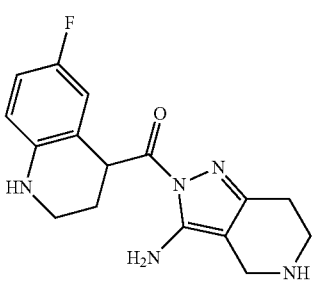 [SMILES: Nc1c2c(nn1C(=O)C1CCNc3ccc(F)cc31)CCNC2] |
| 310 | 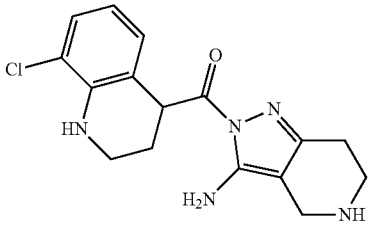 [SMILES: Nc1c2c(nn1C(=O)C1CCNc3c(Cl)cccc31)CCNC2] |
| 311 | 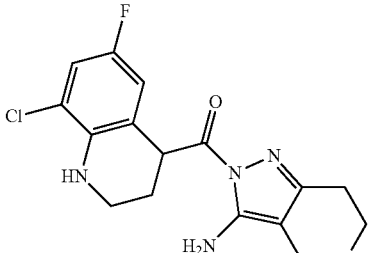 |
| 312 | 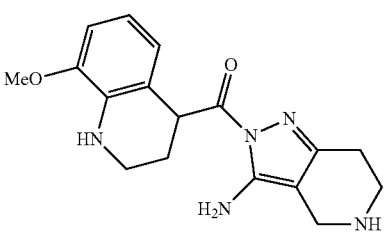 [SMILES: COc1cccc2c1NCCC2C(=O)n1nc2c(c1N)CNCC2] |

| | 189-continued | | 190-continued |
|---|---|---|---|
| | compound | | compound |
| 313 | 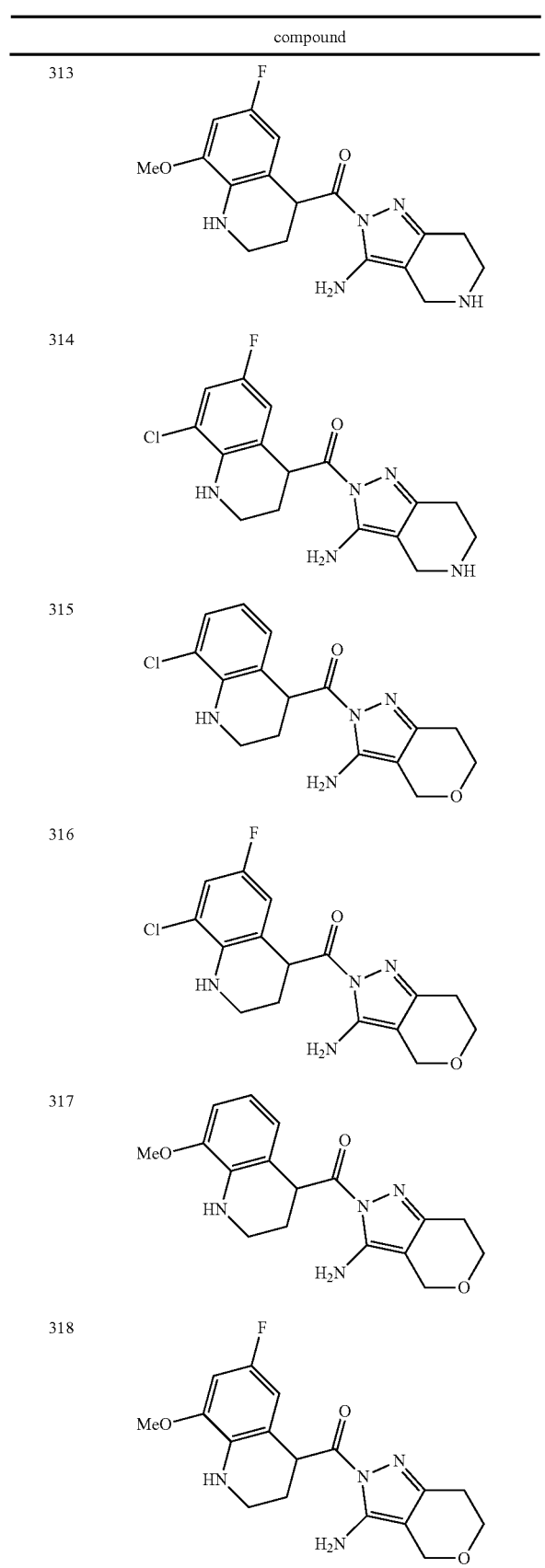 | 319 | 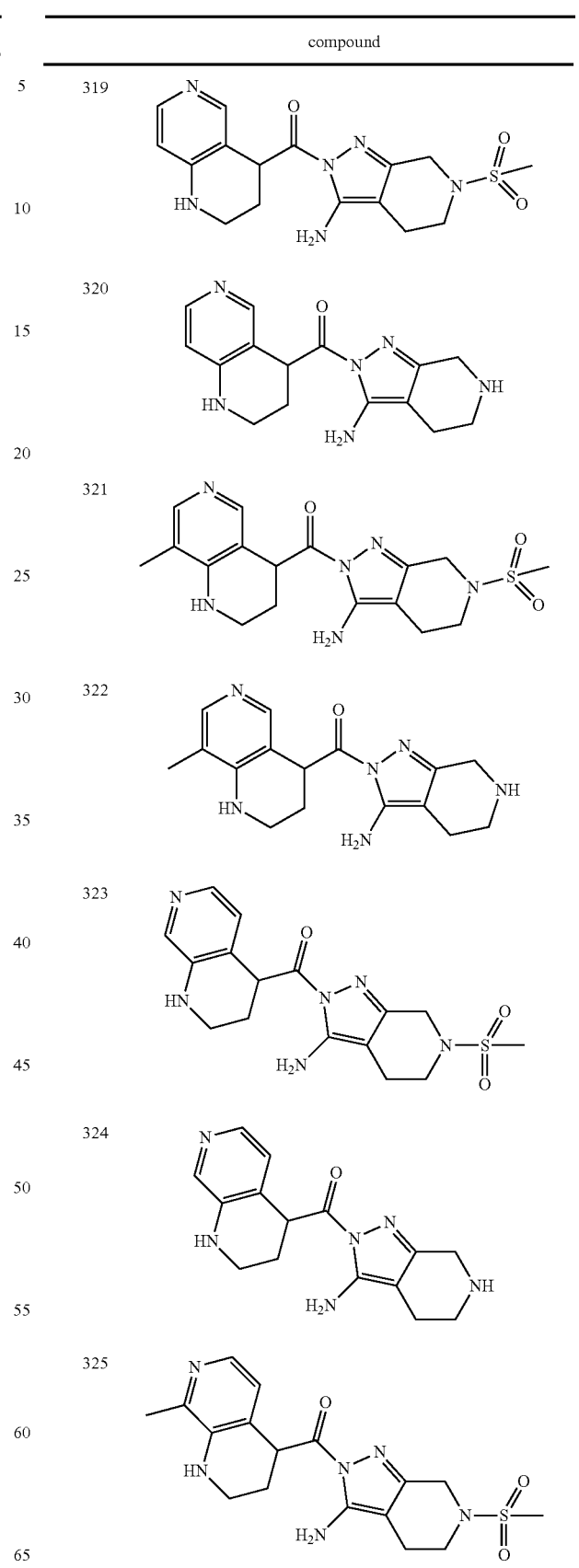 |
| 314 | | 320 | |
| 315 | | 321 | |
| 316 | | 322 | |
| 317 | | 323 | |
| 318 | | 324 | |
| | | 325 | |

| compound | | compound | |
|---|---|---|---|
| 326 | 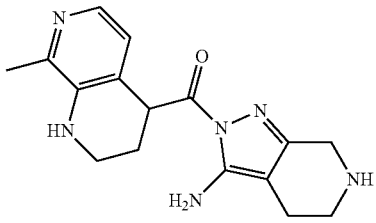 [SMILES: Cc1nccc2c1NCCC2C(=O)n1nc2c(c1N)CCNC2] | 332 | 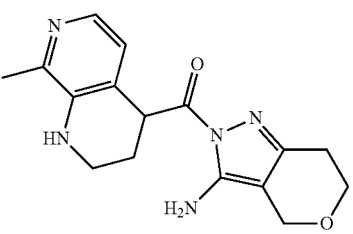 |
| 327 | 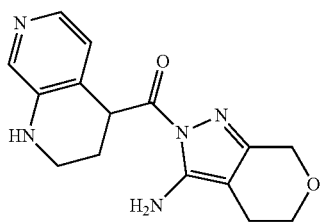 [SMILES: Nc1c2c(nn1C(=O)C1CCNc3cnccc31)COCC2] | 333 | 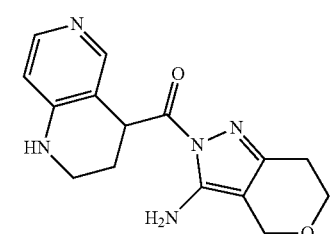 |
| 328 | 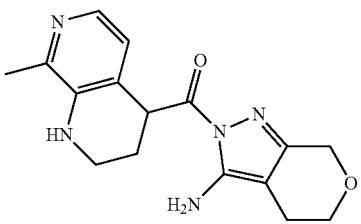 [SMILES: Cc1nccc2c1NCCC2C(=O)n1nc2c(c1N)CCOC2] | 334 | 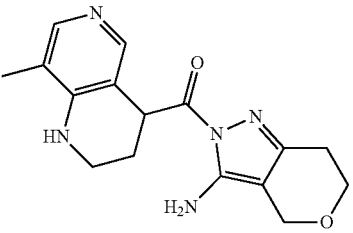 |
| 329 | 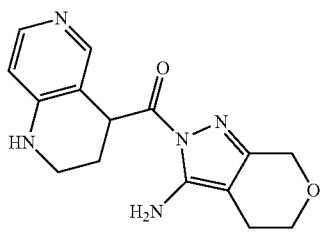 [SMILES: Nc1c2c(nn1C(=O)C1CCNc3ccncc31)COCC2] | 335 | 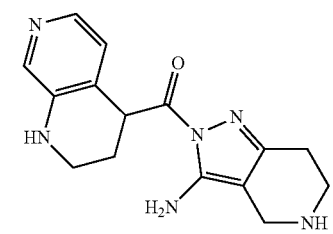 |
| 330 | 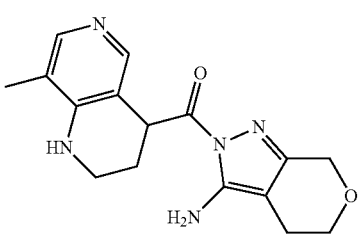 [SMILES: Cc1cncc2c1NCCC2C(=O)n1nc2c(c1N)CCOC2] | 336 | 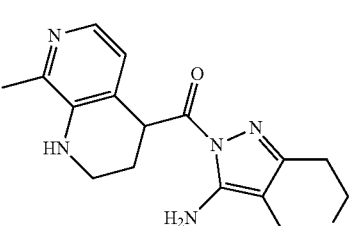 |
| 331 | 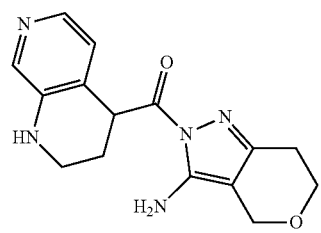 [SMILES: Nc1c2c(nn1C(=O)C1CCNc3cnccc31)CCOC2] | 337 | 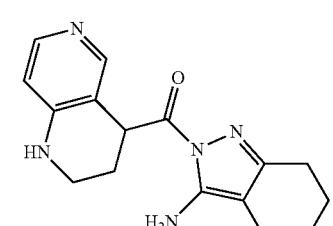 |

| compound | |
|---|---|
| 338 | (structure) |
| 339 | (structure) |
| 340 | (structure) |
| 341 | (structure) |
| 342 | (structure) |
| 343 | (structure) |
| 344 | (structure) |

| compound | |
|---|---|
| 345 | (structure) |
| 346 | (structure) |
| 347 | (structure) |
| 348 | (structure) |
| 349 | (structure) |
| 350 | (structure) |
| 351 | (structure) |

| compound |
|---|
| 352 |
| 353 |
| 354 |
| 355 |
| 356 |
| 357 |
| 358 |
| 359 |
| 360 |
| 361 |
| 362 |
| 363 |

| compound | |
|---|---|
| 364 | 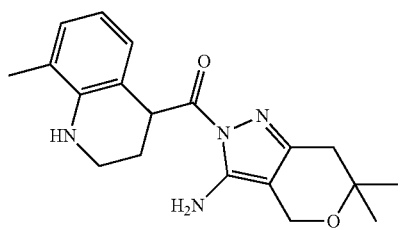 |
| 365 | 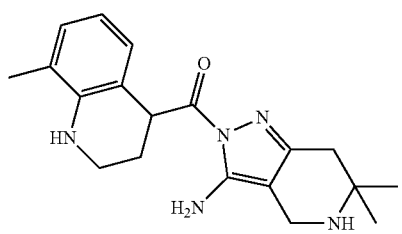 |
| 366 | 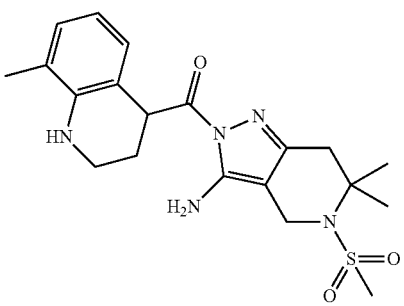 [SMILES: Cc1cccc2c1NCCC2C(=O)n1nc2c(c1N)CN(S(C)(=O)=O)C(C)(C)C2] |
| 367 | 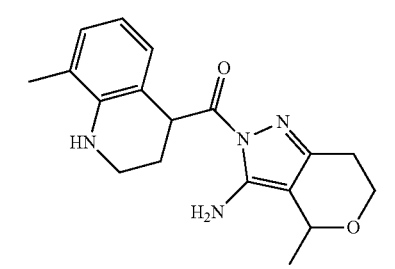 [SMILES: Cc1cccc2c1NCCC2C(=O)n1nc2c(c1N)C(C)OCC2] |
| 368 | 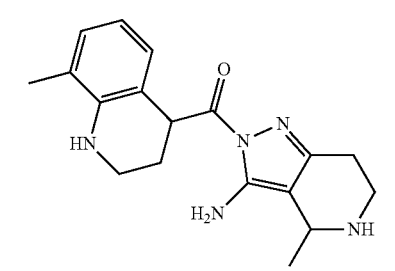 [SMILES: Cc1cccc2c1NCCC2C(=O)n1nc2c(c1N)C(C)NCC2] |
| 369 | 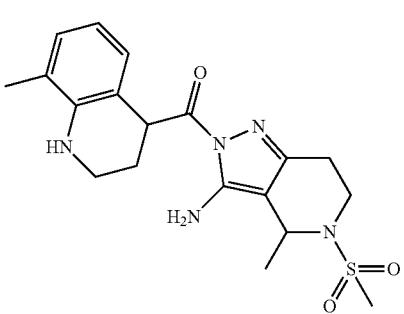 [SMILES: Cc1cccc2c1NCCC2C(=O)n1nc2c(c1N)C(C)N(S(C)(=O)=O)CC2] |
| compound | |
|---|---|
| 370 | 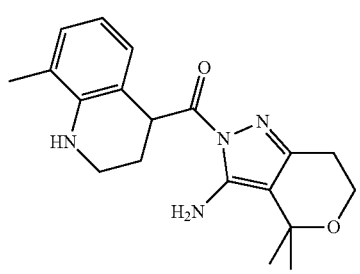 [SMILES: Cc1cccc2c1NCCC2C(=O)n1nc2c(c1N)C(C)(C)OCC2] |
| 371 | 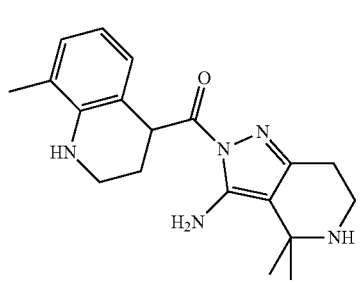 [SMILES: Cc1cccc2c1NCCC2C(=O)n1nc2c(c1N)C(C)(C)NCC2] |
| 372 | 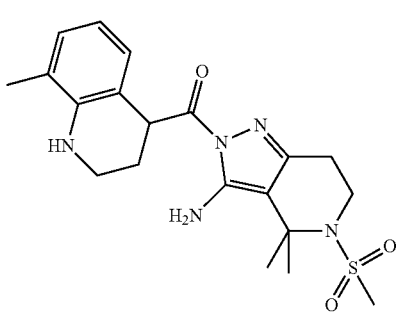 [SMILES: Cc1cccc2c1NCCC2C(=O)n1nc2c(c1N)C(C)(C)N(S(C)(=O)=O)CC2] |
| 373 | 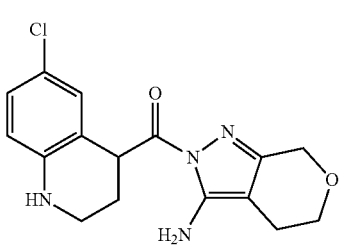 [SMILES: Nc1c2c(nn1C(=O)C1CCNc3ccc(Cl)cc31)COCC2] |
| 374 | 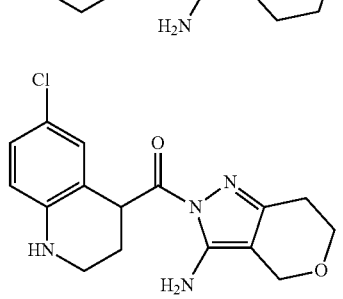 |
| 375 | 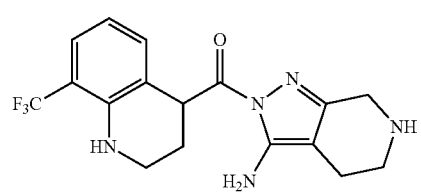 [SMILES: Nc1c2c(nn1C(=O)C1CCNc3c1cccc3C(F)(F)F)CNCC2] |

-continued compound

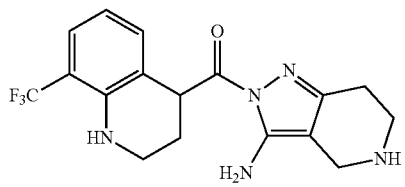 [SMILES: Nc1c2c(nn1C(=O)C1CCNc3c1cccc3C(F)(F)F)CCNC2]

376

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Also provided herein is a pharmaceutical composition comprising a compound disclosed above, or a pharmaceutically acceptable salt form thereof, and a pharmaceutically acceptable carrier or diluent.

While it may be possible for the compounds of formula I or formula II to be administered as the raw chemical, it is preferable to present them as a pharmaceutical composition. According to a further aspect, the present invention provides a pharmaceutical composition comprising a compound of formula I or formula II, or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or formula II, or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Compounds that inhibit Coagulation Factor XIIa are useful for treating diseases and conditions that commonly benefit from an anticoagulant, such as venous thrombosis. Those compounds that selectively inhibit Coagulation Factor XIIa in the presence of thrombin and other coagulation factors are additionally useful to treat non-thrombotic diseases and conditions that have an inflammatory component. Thus the compounds provided herein can be used for treating inflammation, for treating an immunological disorder, for treating pathologies associated with vasodilatation, or for treating thrombosis. The method includes, for example, administering to a patient a therapeutically effective amount of a compound of formula I or formula II.

The compounds of the invention were tested in the following screens.

Factor XIIa (FXIIa) Inhibitory Activity:

In a 96-well clear bottom plate, 80 μl of assay buffer was added to each well. Assay buffer consists of 0.5× Hank's Balanced Salt Solution (Invitrogen), buffered with 25 mM HEPES pH 7.4 (Invitrogen) and 0.5× Tris-buffered saline with Tween-20 0.05% (Santa Cruz Biotechnology). Test compounds were first dissolved in DMSO (Sigma) and then 4 μl were added to test wells containing assay buffer. Serial dilutions using an automated multi-channel pipette were used to generate a concentration range of approximately 1-100 μM. Human FXIIa (Enzyme Research Labs) was diluted in assay buffer to a final concentration of 12.5 nM. 80 μl of this enzyme solution was added to the assay wells. The enzyme/compound mixtures were incubated for 10 minutes at room temperature. Chromogenic substrate (Pefachrome XIIa; Enzyme Research Labs) was added to assay wells at a final concentration of 400 μM. The assay plate was spun for 1 minute at 1500 g and then read at 37° C. in a SpectraMax M2 plate reader ($\lambda$=405 nm). Activity was quantified as the rate of change in absorbance, which corresponds to the rate of substrate cleavage. $IC_{50}$ values were determined as the concentration of inhibitor that produced 50% of the rate of change of control wells without any inhibitor. For compounds with activity <1 μM, the assay was repeated with a lower concentration range, typically from 10-1000 nM.

Counterscreens for Selectivity:

Thrombin. In a 96-well white opaque plate, 80 μl of assay buffer was added to each well. Test compounds were added, and serially diluted as above, to generate a concentration range of approximately 1-100 μM. Human alpha-thrombin (Enzyme Research Labs) was diluted in assay buffer to a final concentration of 12.5 nM. 80 μl of this enzyme solution was added to the assay wells. The enzyme/compound mixtures were incubated for 10 minutes at room temperature. Fluorogenic substrate (Boc-Val-Pro-Arg-7-amido-4-methylcoumarin; Sigma) was added to assay wells at a final concentration of 20 μM. The assay plate was spun for 1 minute at 1500 g and then read at 37° C. in a SpectraMax M2 plate reader ($\lambda_{ex}$=380 nm and $\lambda_{em}$=460 nm). Activity was quantified as the rate of change in fluorescence, which corresponds to the rate of substrate cleavage. $IC_{50}$ values were determined as the concentration of inhibitor that produced 50% of the rate of change of control wells without any inhibitor. For compounds with activity <1 μM, the assay was repeated with a lower concentration range, typically from 10-1000 nM.

Factor Xa. In a 96-well white opaque plate, 80 μl of assay buffer was added to each well. Test compounds were added, and serially diluted as above, to generate a concentration range of approximately 1-100 μM. Human FXa (Enzyme Research Labs) was diluted in assay buffer to a final concentration of 12.5 nM. 80 μl of this enzyme solution was added to the assay wells. The enzyme/compound mixtures were incubated for 10 minutes at room temperature. Fluorogenic substrate (Pefafluor FXa; Enzyme Research Labs) was added to assay wells at a final concentration of 80 μM. The assay plate was spun for 1 minute at 1500 g and then read at 37° C. in a SpectraMax M2 plate reader ($\lambda_{ex}$=380 nm and $\lambda_{em}$=460 nm). Activity was quantified as the rate of change in fluorescence, which corresponds to the rate of substrate cleavage. $IC_{50}$ values were determined as the concentration of inhibitor that produced 50% of the rate of change of control wells without any inhibitor.

Factor XIa. In a 96-well clear-bottom plate, 80 μl of assay buffer was added to each well. Test compounds were added, and serially diluted as above, to generate a concentration range of approximately 1-100 μM. Human FXIa (Enzyme Research Labs) was diluted in assay buffer to a final concentration of 12.5 nM. 80 μl of this enzyme solution was added to the assay wells. The enzyme/compound mixtures were incubated for 10 minutes at room temperature. Chromogenic substrate (Pefachrome FXIa 3371; Enzyme Research Labs) was added to assay wells at a final concentration of 100 μM. The assay plate was spun for 1 minute at 1500 g and then read at 37° C. in a SpectraMax M2 plate reader ($\lambda$=405). Activity was quantified as the rate of change in absorbance, which corresponds to the rate of substrate cleavage. $IC_{50}$ values were determined as the concentration of inhibitor that produced 50% of the rate of change of control wells without any inhibitor.

Plasma Kallikrein. In a 96-well white opaque plate, 80 μl of assay buffer was added to each well. Test compounds were added, and serially diluted as above, to generate a concentration range of approximately 1-100 μm. Human plasma kallikrein (Enzyme Research Labs) was diluted in assay buffer to a final concentration of 12.5 nM. 80 μl of this enzyme solution was added to the assay wells. The enzyme/compound mixtures were incubated for 10 minutes at room temperature. Fluorogenic substrate (Z-Phe-Arg 7-amido-4-methylcoumarin; Sigma) was added to assay wells at a final concentration of 50 μM. The assay plate was spun for 1 minute at 1500 g and then read at 37° C. in a SpectraMax M2 plate reader ($\lambda_{ex}$=380 nm and $\lambda_{em}$=460 nm). Activity was quantified as the rate of change in fluorescence, which corresponds to the rate of substrate cleavage. $IC_{50}$ values were determined as the concentration of inhibitor that produced 50% of the rate of change of control wells without any inhibitor.

Results of testing of some embodiments in the foregoing screens are shown in Table 2, wherein the $IC_{50}$s are given in μM:

TABLE 2

| example number | Factor XIIa IC50 uM | Thrombin IC50 uM |
|---|---|---|
| 1 | 0.08 | |
| 2 | 0.06 | |
| 3 | 0.35 | >35 |
| 4 | 0.3 | >25 |
| 5 | >40 | |
| 6 | 0.25 | >50 |
| 7 | 0.07 | >25 |
| 8 | 50 | |
| 9 | 0.15 | >150 |
| 10 | 0.03 | |
| 11 | 50 | |
| 12 | 0.3 | >55 |
| 13 | >90 | |
| 14 | 0.04 | 20 |
| 15 | >65 | >70 |
| 16 | 0.06 | 20 |
| 17 | 30 | |
| 18 | 0.03 | 12.5 |
| 19 | 11 | |
| 20 | 0.15 | >40 |
| 21 | 1.5 | >50 |
| 22 | 1.4 | |
| 23 | >60 | |
| 24 | 0.1 | 25 |
| 25 | 40 | >70 |
| 26 | 0.15 | 4.5 |
| 27 | 75 | |
| 28 | 0.16 | >35 |
| 29 | >60 | |
| 30 | 0.05 | 22 |
| 31 | 40 | |
| 32 | 0.02 | |
| 33 | 10 | |
| 34 | 0.04 | 23 |
| 35 | 0.02 | 18 |
| 36 | 17 | |

TABLE 2-continued

| example number | Factor XIIa IC50 uM | Thrombin IC50 uM |
|---|---|---|
| 37 | 0.1 | 25 |
| 38 | 70 | |
| 39 | 0.15 | 45 |
| 40 | no data | |
| 41 | 1.7 | 4.4 |
| 42 | >80 | |
| 43 | 4 | |
| 44 | no data | |
| 45 | 2.2 | 45 |
| 46 | >80 | |
| 47 | 8.5 | |
| 48 | >30 | |
| 49 | 11 | 17 |
| 50 | >80 | |
| 51 | 0.02 | 15 |
| 52 | 32 | |
| 53 | 0.01 | 9 |
| 54 | 2.5 | |
| 55 | 0.04 | >70 |
| 56 | >65 | |
| 57 | 0.05 | 16 |
| 58 | 60 | |
| 59 | 35 | |
| 60 | 0.03 | >60 |
| 61 | 0.1 | 20 |
| 62 | >65 | |
| 63 | 0.14 | 35 |
| 64 | 35 | |
| 65 | 0.09 | |
| 66 | >100 | |
| 67 | 0.15 | >70 |
| 68 | >90 | |
| 69 | 0.01 | 40 |
| 70 | 5 | |
| 71 | 5 | |
| 72 | 0.07 | |
| 73 | 7 | |
| 74 | 0.08 | 50 |
| 75 | 25 | |
| 76 | 0.05 | >100 |
| 77 | 70 | |
| 78 | >80 | |
| 79 | 3 | |
| 80 | no data | |
| 81 | no data | |
| 82 | 0.07 | |
| 83 | no data | |
| 84 | no data | |
| 85 | 0.03 | 60 |
| 86 | 1.25 | |
| 87 | 0.8 | >100 |
| 88 | 80 | |
| 89 | 0.8 | >80 |
| 90 | 1.5 | 12 |
| 91 | 1.5 | >70 |
| 92 | no data | |
| 93 | 1.3 | >100 |
| 94 | >50 | >80 |
| 95 | 0.7 | >50 |
| 96 | no data | |
| 97 | 8.5 | >80 |
| 98 | 20 | 70 |
| 99 | 0.04 | >50 |
| 100 | no data | |
| 101 | 0.02 | 10 |
| 102 | 1.2 | |
| 103 | 0.35 | 30 |
| 104 | 80 | >85 |
| 105 | 1 | >100 |
| 106 | 50 | 70 |
| 107 | 1.8 | >40 |
| 108 | 80 | >150 |
| 109 | 0.8 | >75 |
| 110 | 60 | >65 |
| 111 | 2 | >50 |
| 112 | >70 | >70 |
| 113 | 95 | >100 |
| 114 | 0.45 | >80 |
| 115 | 30 | |
| 116 | 1 | 17 |
| 117 | 45 | 5 |
| 118 | 0.6 | >100 |
| 119 | 0.45 | >85 |
| 120 | 15 | >75 |
| 121 | 0.4 | >80 |
| 122 | no data | |
| 123 | 0.35 | >80 |
| 124 | no data | |
| 125 | 0.25 | 100 |
| 126 | 32 | >70 |
| 127 | 0.2 | >70 |
| 128 | 28 | >65 |
| 129 | 0.25 | >75 |
| 130 | no data | |
| 131 | 0.03 | 1.5 |
| 132 | 3 | |
| 133 | 45 | |
| 134 | 28 | |
| 135 | 0.08 | 28 |
| 136 | 0.08 | >55 |
| 137 | 7 | |
| 138 | 0.08 | >100 |
| 139 | 55 | |
| 140 | 0.13 | 60 |
| 141 | 31 | |
| 142 | 0.2 | 40 |
| 143 | 17 | |
| 144 | 0.23 | >80 |
| 145 | no data | |
| 146 | 0.07 | >90 |
| 147 | 10 | |
| 148 | 20 | |
| 149 | 0.05 | 64 |
| 150 | >70 | |
| 151 | 0.04 | >70 |
| 152 | 60 | |
| 153 | 0.05 | >100 |
| 154 | 18 | |
| 155 | 1.2 | |
| 156 | 14 | |
| 157 | 0.7 | 15 |
| 158 | 37 | |
| 159 | 0.13 | 70 |
| 160 | 16 | |
| 161 | 0.05 | 20 |
| 162 | 21 | |
| 163 | 0.03 | >100 |
| 164 | 12 | |
| 165 | 0.03 | >75 |
| 166 | 10 | |
| 167 | 60 | >120 |
| 168 | 2 | 3.5 |
| 169 | 15 | 15 |
| 170 | 0.01 | >90 |
| 171 | 4.5 | |
| 172 | 4.5 | |
| 173 | 0.02 | >100 |
| 174 | 8 | |
| 175 | 50 | |

TABLE 2-continued

| example number | Factor XIIa IC50 uM | Thrombin IC50 uM |
|---|---|---|
| 176 | 0.1 | >90 |
| 177 | 30 | |
| 178 | 60 | |

TABLE 2-continued

| example number | Factor XIIa IC50 uM | Thrombin IC50 uM |
|---|---|---|
| 179 | no data | |
| 180 | 0.04 | |
| 181 | no data | |
| 182 | 0.04 | |
| 183 | 35 | |
| 184 | 11 | |
| 185 | 0.2 | |
| 186 | 40 | |
| 187 | 35 | |
| 188 | 0.17 | >80 |
| 189 | 40 | |
| 190 | 0.05 | |
| 191 | no data | |
| 192 | 12.5 | |
| 193 | 0.04 | |
| 194 | 0.16 | 70 |
| 195 | no data | |
| 196 | 0.08 | 95 |
| 197 | 40 | |
| 198 | 0.09 | >150 |
| 199 | 80 | |
| 200 | >100 | |
| 201 | 16 | |
| 202 | 0.09 | |
| 203 | no data | |
| 204 | 0.04 | |
| 205 | >25 | |

For in vivo confirmation of efficacy, Example 35 was studied in a model of rheumatoid arthritis. Collagen-Induced Arthritis (CIA) in DBA/1 Mice is one of the most commonly used animal models of human rheumatoid arthritis. The joint inflammation which develops in CIA resembles inflammation in human patients with rheumatoid arthritis. Therapeutic agents that reduce rheumatoid arthritis in people (e.g. NSAIDs, corticosteroids, methotrexate, etc) are also efficacious in CIA, and efficacy in the mouse CIA model has excellent predictive value for efficacy in rheumatoid arthritis. CIA is induced by immunization with type II collagen emulsified in Complete Freund's Adjuvant, followed by a booster immunization with type II collagen emulsified in incomplete Freund's Adjuvant. Three to four weeks after immunization, inflammation develops in mouse paws, Treatment is initiated at, the time of immunization and continues for 6 weeks. Mice are assigned to groups in a balanced manner to achieve similar weight at the time of immunization. CIA is scored blind, by a person unaware of both treatment and of previous scores for each animal. The animal's score is the total of all four paw scores on scale of 0-16, where each paw is scored as follows: 0 Normal paw; 1 One toe inflamed and swollen; 2 More than one toe, but not entire paw, inflamed and swollen, or mild swelling of entire paw; 3 Entire paw inflamed and swollen; 4 Very inflamed and swollen paw or ankylosed paw.

The compound of Example 35 significantly ameliorated the disease phenotype compared to placebo:

| | Mean day of CIA onset ± SD | Score at CIA onset ± SD | Maximum CIA score ± SD | p value | End CIA score ± SD | p value | (%) Relative body weight at the end of study ± SD | p value |
|---|---|---|---|---|---|---|---|---|
| Vehicle | 24.3 ± 1.4 | 2.3 ± 1.8 | 9.3 ± 3.8 | | 9.2 ± 3.7 | | 99.6% ± 4.1% | |
| Ex 35 | 24.4 ± 1.4 | 2.3 ± 1.5 | 5.6 ± 3.7 | 0.0175 | 4.4 ± 4.4 | 0.0062 | 99.6% ± 6.0% | 0.9956 |

What is claimed is:

1. A compound of formula I or formula II:

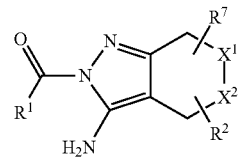

Formula I

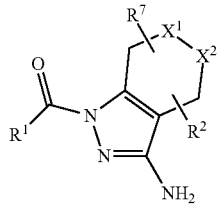

Formula II wherein
  $R^1$ is an optionally substituted bicyclic ring system;
  $R^2$ is chosen from hydrogen, halogen, hydroxy, amino, cyano, $(C_1-C_4)$alkyl, $(C_1-C_4)$alkoxy, $(C_1-C_4)$alkylamino, di$(C_1-C_4)$alkylamino, $(C_1-C_4)$acylamino, $(C_1-C_4)$fluoroalkyl, $C_1-C_4$)fluoroalkoxy, and $(C_1-C_6)$oxaalkyl;
  one of $X^1$ and $X^2$ is —N(QR$^5$)—, and the other is —CR$^3$R$^4$—;
  Q is chosen from —SO$_2$—, and —SO$_2$NR$^6$—;
  $R^3$, $R^4$, $R^6$ and $R^7$ are independently chosen from hydrogen and $(C_1-C_6)$alkyl; and
  $R^5$ is chosen from hydrogen, $(C_1-C_6)$alkyl, hydroxy $(C_2-C_6)$alkyl, a three- to seven-membered carbocycle, and a three- to seven-membered heterocycle.

2. A compound according to claim 1 wherein $R^1$ is a 6:6 or 6:5 bicycle optionally substituted with one to three substituents chosen from halogen, hydroxy, amino, cyano, oxo, $(C_1-C_6)$aliphatic hydrocarbyl, $(C_1-C_4)$alkoxy, $(C_1-C_4)$alkylamino, di$(C_1-C_4)$alkylamino, $(C_1-C_4)$acylamino, $(C_1-C_4)$alkylsulfonyl, [$C_1-C_4$)alkylsulfonyl]amino, $(C_1-C_4)$fluoroalkyl, $(C_1-C_4)$fluoroalkoxy, $(C_1-C_6)$oxaalkyl, aryl, and heteroaryl.

3. A compound according to claim 2, wherein the optionally substituted bicyclic ring system is chosen from an optionally substituted indole, isoindole, oxindole, tetrahydroindole, tetralin, indoline, isoindoline, tetrahydroquinoline, tetrahydroisoquinoline, 3,4-dihydro-1H-isochromene, 3,4-dihydro-2H-chromene, benzofuran, dihydrobenzofuran, tetrahydrobenzofuran, benzothiophene, tetrahydrobenzothiophene, indazole, tetrahydroindazole, 2,3-dihydro-1H-indene, naphthalene, tetrahydronaphthalene, naphthyridine, tetrahydronaphthyridine, and isochroman.

4. A compound according to claim 2 wherein $R^1$ is a nitrogenous bicycle.

5. A compound according to claim 4 wherein $R^1$ is optionally substituted tetrahydroquinoline, indole, or tetrahydroindole.

6. A compound according to claim 3 wherein $R^1$ is optionally substituted with one or more of halogen, $(C_1-C_6)$ aliphatic hydrocarbyl, $(C_1-C_4)$fluoroalkyl, $(C_1-C_4)$alkoxy, $(C_1-C_4)$acylamino, $(C_1-C_4)$alkylsulfonyl, phenyl, and pyridinyl.

7. A compound according to claim 6 wherein $R^1$ is optionally substituted with one or two fluoro, chloro, bromo, methyl, ethyl, propyl, trifluoromethyl, methoxy, methanesulfonyl, acetamido, phenyl, and pyridinyl.

8. A compound according to claim 2, wherein $R^1$ is chosen from

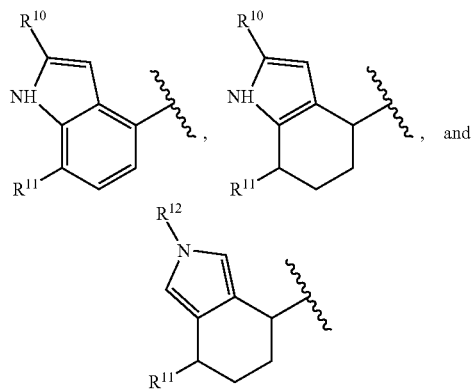

wherein
$R^{10}$ is chosen from H, halogen, $(C_1-C_4)$alkyl, and $(C_3-C_6)$cycloalkyl;
$R^{11}$ is chosen from H and methoxy; and
$R^{12}$ is chosen from H and $(C_1-C_4)$alkyl.

9. A compound according to claim 2, wherein $R^1$ is

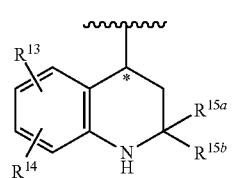

wherein
$R^{13}$ and $R^{14}$ are chosen independently from H, halogen, $(C_1-C_4)$alkyl, fluoro$(C_1-C_4)$alkyl, $(C_1-C_4)$alkoxy, $(C_1-C_4)$acylamino $(C_1-C_4)$alkylsulfonyl, phenyl, and pyridinyl; and
$R^{15a}$ and $R^{15b}$ are chosen independently from —H, and —$(C_1-C_4)$alkyl or, taken together, $R^{15a}$ and $R^{15b}$ are oxo.

10. A compound according to claim 9, wherein the carbon marked with an asterisk is >90% e.e. in the (R) absolute configuration.

11. A compound according to claim 9, wherein the carbon marked with an asterisk is >90% e.e. in the (S) absolute configuration.

12. A compound according to claim 6, wherein $R^1$ is an optionally substituted tetrahydro-1,8-naphthyridine.

13. A compound according to claim 1 wherein $X^1$ is —$CR^3R^4$— and $X^2$ is —$N(QR^5)$—.

14. A compound according to claim 1 wherein $X^1$ is —$N(QR^5)$— and $X^2$ is —$CR^3R^4$—.

15. A compound according to claim 14 wherein $R^3$ and $R^4$ are both hydrogen.

16. A compound according to claim 1 wherein $R^6$ is hydrogen or methyl.

17. A compound according to claim 16 wherein $R^5$ is chosen from H, $(C_1-C_4)$alkyl, $(C_3-C_6)$cycloalkyl, hydroxy $(C_2-C_6)$alkyl, fluoromethyl, difluoromethyl, phenyl, pyridinyl, oxetanyl, tetrahydrofuranyl, and tetrahydropyranyl.

18. A compound according to claim 1 of formula I:

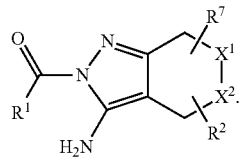

19. A compound according to claim 18 wherein $R^3$ and $R^4$ are both hydrogen; $R^6$ and $R^7$ are hydrogen or methyl and $R^5$ is chosen from H, $(C_1-C_4)$alkyl, $(C_3-C_6)$cycloalkyl, fluoromethyl, difluoromethyl, phenyl, pyridinyl, oxetanyl, tetrahydrofuranyl, and tetrahydropyranyl.

20. A method for inhibiting Factor XIIa in a subject comprising administering to said subject an inhibitory amount of a compound according to claim 1.

21. A method for selectively inhibiting Factor XIIa in the presence of thrombin and kallikrein, said method comprising contacting an inhibitory amount of a compound according claim 1 with Factor XIIa.

22. A method for treating inflammation in a patient, said method comprising administering to said patient a therapeutically effective amount of a compound according to claim 1.

23. A compound according to claim 9 of formula

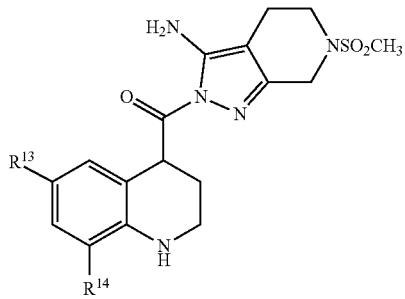

wherein $R^{13}$ and $R^{14}$ are chosen independently from H, halogen, $(C_1-C_4)$alkyl, fluoro$(C_1-C_4)$alkyl, and $(C_1-C_4)$alkoxy.

* * * * *